US009999620B2

(12) United States Patent
McDonnell et al.

(10) Patent No.: US 9,999,620 B2
(45) Date of Patent: Jun. 19, 2018

(54) CAMKK-β AS A TARGET FOR TREATING CANCER

(71) Applicant: Duke University, Durham, NC (US)

(72) Inventors: Donald P. McDonnell, Chapel Hill, NC (US); Daniel Frigo, Houston, TX (US); Anthony R. Means, Boerne, TX (US)

(73) Assignee: Duke University, Durham, NC (US)

( * ) Notice: Subject to any disclaimer, the term of this patent is extended or adjusted under 35 U.S.C. 154(b) by 0 days. days.

(21) Appl. No.: 15/185,853

(22) Filed: Jun. 17, 2016

(65) Prior Publication Data

US 2017/0027928 A1    Feb. 2, 2017

Related U.S. Application Data

(63) Continuation of application No. 13/817,382, filed as application No. PCT/US2011/047846 on Aug. 16, 2011, now abandoned.

(60) Provisional application No. 61/374,106, filed on Aug. 16, 2010, provisional application No. 61/379,226, filed on Sep. 1, 2010.

(51) Int. Cl.

| C07D 471/04 | (2006.01) |
|---|---|
| C07K 16/40 | (2006.01) |
| A61K 31/4745 | (2006.01) |
| C12Q 1/48 | (2006.01) |
| C12Q 1/68 | (2018.01) |
| G01N 33/574 | (2006.01) |
| A61K 31/437 | (2006.01) |
| A61K 31/7088 | (2006.01) |
| G01N 33/68 | (2006.01) |
| C07K 16/30 | (2006.01) |
| C12N 15/113 | (2010.01) |

(52) U.S. Cl.
CPC ........ *A61K 31/4745* (2013.01); *A61K 31/437* (2013.01); *A61K 31/7088* (2013.01); *C07K 16/3069* (2013.01); *C07K 16/40* (2013.01); *C12N 15/1137* (2013.01); *C12Q 1/485* (2013.01); *C12Q 1/6886* (2013.01); *C12Y 207/11017* (2013.01); *G01N 33/57434* (2013.01); *G01N 33/6893* (2013.01); *C07K 2317/76* (2013.01); *C12N 2310/14* (2013.01); *C12N 2320/30* (2013.01); *C12Q 2600/106* (2013.01); *C12Q 2600/112* (2013.01); *C12Q 2600/136* (2013.01); *C12Q 2600/158* (2013.01); *G01N 2333/912* (2013.01); *G01N 2500/04* (2013.01); *G01N 2500/10* (2013.01); *G01N 2500/20* (2013.01); *G01N 2800/52* (2013.01)

(58) Field of Classification Search
USPC ........... 435/6.1, 6.11, 69.1, 91.1, 91.31, 455, 435/6.12; 514/1, 2, 44, 283; 530/300, 530/350; 536/23.1, 24.5; 436/501
See application file for complete search history.

(56) References Cited

U.S. PATENT DOCUMENTS

| 2,820,037 | A | 1/1958 | Schmidt-Nickels |
|---|---|---|---|
| 2,835,674 | A | 5/1958 | Eckert et al. |
| 2,949,467 | A | 8/1960 | Staeuble |
| 2,965,644 | A | 12/1960 | Eckert et al. |
| 3,953,452 | A | 4/1976 | Kruckenberg |
| 3,960,867 | A | 6/1976 | Dokunikhin et al. |
| 4,239,868 | A | 12/1980 | Bonnet et al. |
| 4,336,383 | A | 6/1982 | Vorozhtsov et al. |
| 5,545,806 | A | 8/1996 | Lonberg et al. |
| 5,545,807 | A | 8/1996 | Surani et al. |
| 5,569,825 | A | 10/1996 | Lonberg et al. |
| 5,625,126 | A | 4/1997 | Lonberg et al. |
| 5,633,425 | A | 5/1997 | Lonberg et al. |
| 5,661,016 | A | 8/1997 | Lonberg et al. |
| 5,770,429 | A | 6/1998 | Lonberg et al. |
| 5,789,650 | A | 8/1998 | Lonberg et al. |
| 5,814,318 | A | 9/1998 | Lonberg et al. |
| 5,874,299 | A | 2/1999 | Lonberg et al. |
| 5,877,397 | A | 3/1999 | Lonberg et al. |
| 7,105,312 | B2 | 9/2006 | Means |
| 7,527,936 | B2 | 5/2009 | Xu et al. |
| 7,737,125 | B2 * | 6/2010 | Worm ................ C12N 15/1137 514/44 R |
| 2005/0208472 | A1 | 9/2005 | Xu et al. |
| 2006/0147947 | A1 | 7/2006 | Apfeld et al. |

(Continued)

FOREIGN PATENT DOCUMENTS

| EP | 2000543 | * 12/2008 |
|---|---|---|
| JP | 2003-012516 | 1/2003 |

(Continued)

OTHER PUBLICATIONS

Li et al, J. Integrative Biology, vol. 10, No. 3, pp. 261-275 (2005).*
Hawley et al, Cell Metabolism, vol. 2, pp. 9-19 (2005).*
"Cancer Facts and Figures" American Cancer Society; Feb. 28, 2007, 3-4.
Allard, W.J., et al., "Tumor Cells Circulate in the Peripheral Blood of All Major Carcinomas but not in Healthy Subjects or Patients With Nonmalignant Diseases," Clin Can Res (2004); 10:6897-6904.
Anderson et al. "Component of a Calmodulin-dependent Protein Kinase Cascade"; JBC; Nov. 27, 1998; vol. 273, No. 48; p. 31880-31889.
Attar RM, Takimoto CH, Gottardis MM. "Castration-resistant prostate cancer: locking up the molecular escape routes." Clin Cancer Res 2009; 15: 3251-3255.

(Continued)

*Primary Examiner* — Jane Zara
(74) *Attorney, Agent, or Firm* — Michael Best & Friedrich LLP

(57) ABSTRACT

Provided herein are compounds, compositions, including pharmaceutical compositions, having anti-cancer activity. Also provided are methods for diagnosing, detecting, and treating cancer in a subject, as well as a method for evaluating cancer stage in a subject, wherein the methods include determining the amount of a $Ca^{2+}$/calmodulin dependent kinase kinase (CaMKK) in a sample. Further provided are methods of screening and identifying a compound that inhibits CaMKK.

12 Claims, 39 Drawing Sheets

(56) References Cited

U.S. PATENT DOCUMENTS

| | | | |
|---|---|---|---|
| 2006/0211025 | A1 | 9/2006 | Su et al. |
| 2007/0128639 | A1 | 6/2007 | Chinnaiyan et al. |
| 2008/0063640 | A1* | 3/2008 | Nakamura ......... A61K 39/0011 424/138.1 |
| 2008/0146555 | A1 | 6/2008 | Caligiuri et al. |
| 2009/0163545 | A1* | 6/2009 | Goldfarb .............. A61K 31/122 514/312 |
| 2009/0269281 | A1* | 10/2009 | Grant ................. A61K 31/4745 424/9.2 |
| 2010/0105716 | A1 | 4/2010 | Means |
| 2010/0137164 | A1 | 6/2010 | Rubin et al. |

FOREIGN PATENT DOCUMENTS

| | | |
|---|---|---|
| WO | WO 92/03918 | 3/1992 |
| WO | WO 92/22646 | 12/1992 |
| WO | WO 93/12227 | 6/1993 |
| WO | WO 2004/031414 | 4/2004 |
| WO | WO 2008/045273 | 4/2008 |
| WO | WO 2012/024255 | 2/2012 |

OTHER PUBLICATIONS

Balk, et al., "AR, the cell cycle, and prostate cancer," Nucl Recept Signal 2008; 6, pp. 1-12.

Ben Sahra et al., "The antidiabetic drug metformin exerts an antitumoral effect in vitro and in vivo through a decrease of cyclin D1 level." Oncogene 2008; 27: 3576-3586.

Berglund L, Bjorling E, Oksvold P, et al. "A genecentric Human Protein Atlas for expression profiles based on antibodies." Mol Cell Proteomics 2008; 7: 2019-27.

Bolla, et al., "Long-term results with immediate androgen suppression and external irradiation in patients with locally advanced prostate cancer (an EORTC study): a phase III randomised trial." The Lancet 2002; 360: 103-108.

Budd G., et al., "Circulating Tumor Cells versus Imaging—Predicting Overall Survival in Metastatic Breast Cancer," Clin Can Res (2006); 12:6404-6409.

Butler et al., "Calcium intake increases risk of prostate cancer among Singapore Chinese." Cancer Res 2010; 70: 4941-8.

CellSearch system ("Veridex CellSearch Website". Mar. 2010. http://veridex.com/CellSearch/CellSearchHCP.aspx. Retrieved Mar. 14, 2010.).

Chen C.D., et al., "Molecular determinants of resistance to antiandrogen therapy," Nature Med2004; 10:33-39.

Chen et al., "Immunoglobulin gene rearrangement in B cell deficient mice generated by targeted deletion of the JH locus," International Immunology (1993); 5:647-656.

Cohen, S.J., et al., "Relationship of Circulating Tumor Cells to Tumor Response, Progression-Free Survival, and Overall Survival in Patients With Metastatic Colorectal Cancer," JCO (2008); 26:3213-3221.

Corcoran et al., "Defining Ca2 + /Calmodulindependent Protein Kinase Cascades in Transcriptional Regulation," J Biol Chem, (Feb. 2, 2001); 276(5):2975-2978.

Cristofanilli M., et al., "Circulating Tumor Cells, Disease Progression, and Survival in Metastatic Breast Cancer," NEJM (2004); 351:781-791.

DeBono, J.S., et al., "Circulating Tumor Cells Predict Survival Benefit fromTreatment in Metastatic Castration-Resistant Prostate Cancer," Clin Can Res (2008); 14:6302-6309.

Fidler, "The pathogenesis of cancer metastasis: the'seed and soil' hypothesis revisited," Nat Rev Cancer (2003); 3:453-458.

Fishwild et al., "High-avidity hutnan IgGK tnonoclonal antibodies from a novel strain of minilocus transgenic mice," Nature Biotechnology (1996); 14:845-851.

Frigo D.E. et al., "CaM Kinase Kinase-Mediated Activation of the Growth Regulatory Kinase AMPK is Required for Androgen-Dependent Migration of Prostate Cancer Cells" Cancer Research (2010) vol. 71, No. 2, 528-537.

Frigo DE, McDonnell DP. "Differential effects of prostate cancer therapeutics on neuroendocrine transdifferentiation." Mol Cancer Ther 2008; 7: 659-669.

Frigo, et al., "Induction of Kruppel-like factor 5 expression by androgens results in increased CXCR4-dependent migration of prostate cancer cells in vitro." Mol Endocrinol 2009.

Gerbino, "Remington: The Science and Practice of Pharmacy," American Journal of Pharmaceutical Education, 70(3) Article 71, 2006, p. 3.

Harding & Lonberg, "Class Switching in Human Immunoglobulin Transgenic Mice," Ann. N.Y. Acad. Sci (1995); 764:536-546.

Hawley, et al., "Calmodulin-dependent protein kinase kinasebeta is an alternative upstream kinase for AMP-activated protein kinase." Cell Metab 2005; 2: 9-1.9.

Hayes D.F., and Smerage J., "Is There a Role for Circulating Tumor Cells in the Management of Breast Cancer?," Clin Cancer Res (2008); 14:3646-3650.

Hsu et al., "Human Ca2+/calmodulindependent protein kinase kinase beta gene encodes multiple isoforms that display distinct kinase activity." J Biol Chem 2001; 276: 31113-31123.

Hurley et al., "The Ca2+/calmodulin-dependent protein kinase kinases are AMP-activated protein kinase kinases." J Bioi Chem 2005; 280: 29060-29066.

Isaacs, et al., "Androgen receptor outwits prostate cancer drugs," Nat Med 2004; 10:26-27.

Jaffe AB, Hall A. "Rho GTPases: biochemistry and biology." Annu Rev Cell Dev Biol 2005; 21: 247-269.

Kampa et al., "The opioid agonist ethylketocyclazocine reverts the rapid, non-genomic effects of membrane testosterone receptors in the human prostate LNCaP cell line." Exp Cell Res 2004; 294: 434-445.

Kazmin, et al., "Linking ligand-induced alterations in androgen receptor structure to differential gene expression: a first step in the rational design of selective androgen receptor modulators." Mol Endocrinol 2006; 20: 1201-17.

Knight-Krajewski S, Welsh CF, Liu Y, et al. "Deregulation of the Rho GTPase, Racl, suppresses cyclin-dependent kinase inhibitor p21 CIP1 levels in androgen-independent human prostate cancer cells," Oncogene 2004; 23: 5513-5522.

Kobayashi, et al., "Activation of Racl ts closely related to androgen-independent cell proliferation of prostate cancer cells both in vitro and in vivo." Mol Endocrinol 2010; 24: 722-734.

Kohler and Milstein. "Continuous cultures of fused cells secreting antibody of predefined specificity," Nature (1975); 256:495-497.

Kokubo et al., "BDNF-mediated cerebellar granule cell development is impaired in mice null for CaMKK2 or CaMKIV." J Neurosci 2009; 29: 8901-8913.

Kou et al., "Regulation of Racl by simvastatin in endothelial cells: differential roles of AMP-activated protein kinase and calmodulin-dependent kinase kinase-beta." J Biol Chem 2009; 284: 14734-43.

Lapointe J, Li C, Higgins JP, et al. "Gene expression profiling identifies clinically relevant subtypes of prostate cancer." Proc Natl Acad Sci USA 2004; 101: 811-816.

Lawton et al., "Updated results of the phase III radiation therapy oncology group (R TOG) trial 85-31 evaluating the potential benefit of androgen suppression following standard radiation therapy for unfavorable prognosis carcinoma of the prostate." Int J Radiation Oncology Bioi Phys 2001; 49: 937-946.

Levine et al., "Agonist-modulated regulation of AMP-activated protein kinase (AMPK) in endothelial cells. Evidence for an AMPK-> Racl-> Akt-> endothelial nitric-oxide synthase pathway." J Biol Chem 2007; 282: 20351-20364.

Li, S. et al., "Application of genomic technologies to human prostate cancer" Omics a Journal of Integrative Biology (2006) vol. 10, No. 3, 261-275.

Liao et al., "Androgen stimulates matrix metalloproteinase-2 expression in human prostate cancer." Endocrinology 2003; 144: 1656-63.

Lonberg & Huszar, "Human Antibodies from Transgenic Mice," Intern. Rev. Immunol. (1995); 13:65-93.

Lonberg et al., "Antigen-specific human antibodies from mice comprising four distinct genetic modifications," Nature (1994); 368:856-859.

(56) References Cited

OTHER PUBLICATIONS

Lonberg, "Transgenic Approaches to Human Monoclonal Antibodies," Handbook of Exp. Pharmacology (1994); 113:49-101.
Massie, C. E. et al., "The androgen receptor fuels prostate cancer by regulating central metabolism and biosynthesis" The Embo Journal (2011) vol. 30, No. 13, 2719-2733.
Means AR. "The Year in Basic Science: calmodulin kinase cascades." Mol Endocrinol 2008; 22: 2759-2765.
Migita et al., "Fatty acid synthase: a metabolic enzyme and candidate oncogene in prostate cancer." J Natl Cancer Inst 2009; 101: 519-532.
Miller, M.C., et al., "Significance of Circulating Tumor Cells Detected by the Cell.Search System in Patients with Metastatic Breast Colorectal and Prostate Cancer," J of Oncology, 2010 (8 pages).
Monet, et al., "Role of cationic channel TRPV2 in promoting prostate cancer migration and progression to androgen resistance." Cancer Res 2010; 70: 1225-1235.
Nagata et al., "AMP-activated protein kinase (AMPK) signaling in endothelial cells is essential for angiogenesis in response to hypoxic stress." J Biol Chem 2003; 278: 31000-31006.
Pantel K, et al., "Cancer micrometastases," Nat Rev Clin Oneal (2009); 6:339-351.
Pantel K., and Riethdorf S., "Are circulating tumor cells predictive of overall survival?," Nat Rev Clin Oncol. (2009); 6:190-191.
Panteleakou Z., et al., "Detection of Circulating Tumor Cells in Prostate Cancer Patients: Methodological Pitfalls and Clinical Relevance," Mol Med (2009); 15:101-114.
Papakonstanti et al., "A rapid, nongenomic, signaling pathway regulates the actin reorganization induced by activation of membrane testosterone receptors." Mol Endocrinol2003; 17: 870-881.
Park et al., "AMP-activated protein kinase promotes human prostate cancer cell grmvth and survival." Mol Cancer Ther 2009; 8: 733-741.
Paterlini-Brechot P, and Benali N. L., "Circulating tumor cells ( CTC) detection: Clinical impact and future directions," Cancer Lett. (2007); 253:180-204.
Riethdorf et al., "Detection of Circulating Tumor Cells in Peripheral Blood of Patients with Met astatic Breast Cancer: A Validation Study of the CellSearch System," Clin Cancer Res (2007); 13:920-928.
Salt, et al., "AMP-activated protein kinase: greater AMP dependence, and preferential nuclear localization, of complexes containing the alpha2 isoform." Biochem J 1998; 334 ( Pt 1 ): 177-187.
Saneyoshi, et al., "Activity-dependent synaptogenesis: regulation by a CaM-kinase kinase/CaM-kinase I/betaPIX signaling complex." Neuron 2008; 57: 94-107.
Scher et al., "Antitumour activity of MDV3100 in castration-resistant prostate cancer: a phase 1-2 study." Lancet 2010; 375: 1437-1446.
Sherk et al., "Development of a small molecule serum and glucocorticoid-regulated kinase 1 antagonist and its evaluation as a prostate cancer therapeutic." Cancer Res 2008; 68: 1-9.
Sleijfe et al., "Circulating tumour cell detection on its way to routine diagnostic imp Iemen tation?," Eur J Cancer (2007); 43:2645-2650.
Su et al., "Molecular classification of human carcinomas by use of gene expression signatures." Cancer Res 2001; 61: 7388-7393.
Taylor et al., "Human immunoglobulin transgenes undergo rearrangement, somatic mutation and class switching in mice that lack endogenous IgM," International Immunology (1994); 6:579-591.
Taylor et al., "A transgenic mouse that expresses a diversity of human sequence heavy and light chain immunoglobulins," Nucleic Acids Res. (1992); 20:6287-6295.

Tokumitsu et al., "ST0-609, a Specific Inhibitor of the Ca2+/Calmodulin-dependent Protein Kinase Kinase," vol. 277, No. 18, Issue of May 3, 2002, pp. 15813-15818.
Tuaillon et al., "Biased Utilization of DHQs2 and JH4 Gene Segments in a Human lg Transgenic Minilocus Is Independent of Antigenic Selection," J. Immunol. (1994); 152:2912-2920.
Varambally et al., "Integrative genomic and proteomic analysis of prostate cancer reveals signatures of metastatic progression." Cancer Cell 2005; 8: 393-406.
Veridex, LLC, "Section 3 510(k) Summary" CellSearch Circulating Tumor Cell Kit, Feb. 26, 2003 (20 pages).
Wang et al., "A hierarchical network of transcription factors governs androgen receptor-dependent prostate cancer growth." Mol Cell 2007; 27: 380-392.
Wang et al., "Androgen receptor regulates a distinct transcription program in androgen-independent prostate cancer." Cell 2009; 138: 245-256.
Wayman et al., "Calmodulin-kinases: modulators of neuronal development and plasticity." Neuron 2008; 59: 914-931.
Welsh et al., "Analysis of gene expression identifies candidate markers and pharmacological targets in prostate cancer." Cancer Res 2001; 61: 5974-5978.
Woods et al., "Ca2+/calmodulin-dependent protein kinase kinase-beta acts upstream of AMP-activated protein kinase in mammalian cells." Cell Metab 2005; 2: 21-33.
Xiang et al., "AMP-activated protein kinase activators can inhibit the growth of prostate cancer cells by multiple mechanisms." Biochem Biophys Res Commun 2004; 321: 161-167.
Xu et al., "Androgens induce prostate cancer cell proliferation through mammalian target of rapamycin activation and post-transcriptional increases in cyclin D proteins." Cancer Res 2006; 66: 7783-7792.
Yang et al., "Orail and STIM1 are critical for breast tumor cell migration and metastasis." Cancer Cell2009; 15: 124-134.
Yu et al., "Gene expression alterations in prostate cancer predicting tumor aggression and preceding development of malignancy." J Clin Oncol 2004; 22: 2790-2799.
Zhou et al., "Inactivation of AMPK alters gene expression and promotes growth of prostate cancer cells." Oncogene 2009; 28: 1993-2002.
"Structure Search Results," in Office action dated Feb. 26, 2015 for U.S. Appl. No. 13/817,382.
PCT/US2011/047846 International Preliminary Report on Patentability and Written Opinion dated Feb. 28, 2013 (9 pages).
PCT/US2011/047846 International Search Report dated Mar. 7, 2012 (5 pages).
Extended European Search Report for Application No. 11818636.0 dated Dec. 13, 2013 (13 pages).
European Patent Office Action for Application No. 11818636.0 dated Dec. 4, 2014 (5 pages).
European Patent Office Action for Application No. 11818636.0 dated Jul. 23, 2015 (4 pages).
United States Patent Office Action for U.S. Appl. No. 13/817,382 dated Feb. 26, 2015 (9 pages).
United States Patent Office Final Office Action for U.S. Appl. No. 13/817,382 dated Jun. 24, 2015 (11 pages).
United States Patent Office Final Office Action for U.S. Appl. No. 13/817,382 dated Dec. 8, 2015 (14 pages).
United States Patent Office Notice of Allowance for U.S. Appl. No. 13/817,382 dated Mar. 18, 2016 (7 pages).
European Examination Report for Application No. 11818636.0 dated Dec. 8, 2016 (5 pages).
European Patent Office Action for Application No. 11818636.0 dated Jan. 15, 2018 (5 pages).

* cited by examiner

B

B

```
                         SEQUENCE LISTING

<160> NUMBER OF SEQ ID NOS: 119

<210> SEQ ID NO 1
<211> LENGTH: 5620
<212> TYPE: DNA
<213> ORGANISM: Artificial Sequence
<220> FEATURE:
<223> OTHER INFORMATION: Synthetic

<400> SEQUENCE: 1
gagcctgggg aggtcgaggg tgcagcgagc cgtgatcgtg ctactgcact ccagcctggg      60
caacacagag agaccctgtc tcaaaacaaa caaacaaaca aacaaacaaa caaacaaaaa     120
aaacaaagaa aaaaaaatgg gagtgggccg ggcgcggtga ctcacacctg taatcccagc     180
actttcggag gccaaggcgg gtggatcacg aggtcaggaa ttcaagatta gcctggacaa     240
catggtgaaa ccccatctct acgaaaaata caaaaattag ccaagtatgg tggccggcgc     300
ctgtaatccc agctactcgg gagactgagg cagagaactg cttgaacctg ggaggcagag     360
gttgcagtga tccgagatcg cgtcactgca ctccagcgtg ggcgacagag cgagactccg     420
tttcagaaaa gaaaaaaaaa aaaaaaaaaa agggagtcgg ggtggagctc tcattggctc     480
gttgcatgtg agtgtcccta cggcctagaa atacaagaga agcacatcgg aacgggctgg     540
aaatccaccc agttaactag agggctttga accttttatt aacttggagg ttgactctcc     600
tgtcaactcg attcccttt ggctgtttgg cagggtcagt gagacatccc ctgggtcgct      660 cgacccgta ggacggttca gggagccctc caggtcttcg tttctcctct tccccgcaca      720
gtgctgttat ccagctgggg gatccaacgc acacttaagg ctccagcaaa gtggctccgc     780
tgccggatgg gagtgcccca gtgtgctgga tgaagctggc gcatgcacca tgtcatcatg     840
tgtctctagc cagcccagca gcaaccgggc cgcccccag gatgagctgg ggggcagggg      900
cagcagcagc agcgaaagcc agaagccctg tgaggccctg cggggcctct catccttgag     960
catccacctg ggcatggagt ccttcattgt ggtcaccgag tgtgagccgg gctgtgctgt    1020
ggacctcggc ttggcgcggg accggcccct ggaggccgat ggccaagagg tccccttga    1080
```

```
cacctccggg tcccaggccc ggccccacct ctccggtcgc aagctgtctc tgcaagagcg    1140
gtcccagggt gggctggcag ccggtggcag cctggacatg aacggacgct gcatctgccc    1200
gtccctgccc tactcacccg tcagctcccc gcagtcctcg cctcggctgc cccggcggcc    1260
gacagtggag tctcaccacg tctccatcac gggtatgcag gactgtgtgc agctgaatca    1320
gtataccctg aaggatgaaa ttggaaaggg ctcctatggt gtcgtcaagt tggcctacaa    1380
tgaaaatgac aatacctact atgcaatgaa ggtgctgtcc aaaagaagc tgatccggca    1440 ggccggcttt ccacgtcgcc ctccaccccg aggcacccgg ccagctcctg gaggctgcat    1500
ccagcccagg ggcccattg agcaggtgta ccaggaaatt gccatcctca agaagctgga    1560
ccaccccaat gtggtgaagc tggtggaggt cctggatgac cccaatgagg accatctgta    1620
catggtgttc gaactggtca accaagggcc cgtgatggaa gtgccaccc tcaaaccact    1680 ctctgaagac caggcccgtt tctacttcca ggatctgatc aaaggcatcg agtacttaca    1740
ctaccagaag atcatccacc gtgacatcaa accttccaac ctcctggtcg agaagatgg    1800 gcacatcaag atcgctgact ttggtgtgag caatgaattc aagggcagtg acgcgctcct    1860
ctccaacacc gtgggcacgc ccgccttcat ggcacccgag tcgctctctg agacccgcaa    1920
gatcttctct gggaaggcct tggatgtttg gccatgggt gtgacactat actgctttgt    1980
ctttggccag tgcccattca tggacgagcg gatcatgtgt ttacacgta agatcaagag    2040 tcaggccctg gaatttccag accagcccga catagctgag gacttgaagg acctgatcac    2100
ccgtatgctg gacaagaacc ccgagtcgag gatcgtggtg ccggaaatca gctgcaccc    2160 ctgggtcacg aggcatgggg cggagccgtt gccgtcggag gatgagaact gcacgctggt    2220
cgaagtgact gaagaggagg tcgagaactc agtcaaacac attcccagct tggcaaccgt    2280
gatcctggtg aagaccatga tacgtaaacg ctcctttggg aacccattcg agggcagccg    2340 gcggaggaa cgctcactgt cagcgcctgg aaacttgctc accaaaaaac caaccaggga    2400
atgtgagtcc ctgtctgagc tcaaggaagc aaggcagcga agacaacctc cagggcaccg    2460 accccgccccc cgtgggggag gaggaagtgc tcttgtgaga ggcagtccct gcgtggaaag    2520
ttgctgggcc ccgccccccg gctccccgc acgcatgcat ccactgcggc cggaggaggc    2580
catggagccc gagtagctgc ctggatcgct cgacctcgca tgcgcgccgc gtcgcctctg    2640 ggggggctgct gcaccgcgtt tccatagcag catgtcctac ggaaacccag cacgtgtgta    2700
gagcctcgat cgtcatctct ggttatttgt tttttccttt gttgttttaa agggacaaa    2760 aaaaaaaaaa ggacttgact ccatgacgtc gaccgtggcc gctggctggc tggacaggcg    2820
ggtgtgagga gttgcagacc caaacccacg tgcattttgg gacaattgct ttttaaaacg    2880 ttttatgcc aaaaatcctt cattgtgatt ttcagaacca cgtcagatat accaagtgac    2940
tgtgtgtggg gtttgacaac tgtggaaagg cgagcagaaa actccggcgg tctgaggcca    3000
tggaggtggt gctgcatttt gagagggagt aggggggctag atgtggctcc tagtgcaaac    3060
cggaaaccat ggcaccttcc agagccgtgg tctcaaggag tcagagcagg gctggccctc    3120
agtagctgca gggagctttg atgcaactta tttgtaagaa ggattttta atttttatg    3180 ggtagaattg tagtcaggaa aacagaaagg gcttgaaatt taataagtgc tgctggaagg    3240
ggatttccca agcctggaag ggtattcagc agctgtggtg gggaaacatt tctcctgaaa    3300
gactgaacgt gtttcttcat gacagctgct caaagcaggt ttctgagata gctgaccgag    3360
ctctggtaaa tctctttgtc aaattacgaa aacttcaggg tgaaatccta tgcttccatg    3420
```

```
tacattacat ggcttaagat taaacaaaaa cattttttcaa gtctctaact agagtgaact    3480
ctagagcaca gtagttcaga aactatttag agcttccagg atatatttca cagcttcagg    3540
catgtgatca gttagagccg atgaaaccta tgcccgcctg tatatatatt agcagcttag    3600
ctagttcata acctgtatat tctaaagact gctaaggttt tgttttcatt ttaaatccta    3660
gctgattgtt gtggtcaatg aaatacccag tttctggagg gccaggtggg aaatgctttc    3720
actggaccaa cacacaaatg atcatcctga ggatctgagc ttccctagac tccacacaat    3780
aaccttgggg caccctttta gagaagactg ttgaaaccca cagcactcgt tggggtatga    3840
ggaaaccagg gcttggcaca ggaagttccc ctttgtagct aaaagtccag aaagaaaggg    3900
ttcatctttt tgacttccaa ctgatattgg gaagtttggt tgaggttcaa gtgtgactcc    3960
ttccagagcc acaggtaggg gagtgtgaag ttgaggggga ggaaagctgg aaggactctg    4020
ccttgggaga ttcccagctc tgctttccag cgcttggtgg aatctgggct ggggaaagac    4080
ggcaccggga aactctgctt ccccattgtt tccatctgat cagctgtggt gtgaggactt    4140
ctcagacaaa ggcaaggcct cgtgcccctg cccagcccat tcatggagcc ctgggccttc    4200
ttggcttcca tagatcctaa gctcttgact gtagtttagc cagacttgtt ttgctatctt    4260
ataagcagtt cagaattagg gaatgctggt tttgaagagc aaaggacagg tagtctagag    4320
agggtcgtct ggcctgcttg ctgggtcttt gtaacccagc acttcctctt gccctcctgg    4380
ctttatgttt atggggagag gactcaatag ctccacccct tctggcacca gatgggggctt    4440 ggttagtttg caataagcac cttgcagagg ttaaagccag cgggtcccta gtcttaggcc    4500
cagcctgctt gtgtgggctc tggcctggcc tggtggctgg cccagggggc agcagtgctt    4560
agagcttctg cagggcttct cttgtttaca cagctgcatc agacaatgcc atttctcccc    4620
accacggaac cttccatcta agatttcttc cagggaatgc cagcaatcag gcagcaccca    4680
gctgtggggg cagtggggtg ggggagaccc acattgatga cttttttttt ttcttttaat    4740
gaagaaacac caaagaaagc tgtggaaagg acctgcccca catgaaaagg ataagccaag    4800
atggctgtaa acacagagca tttgagctgc cactcttgga gcacattgat ttttcaaaag    4860
ccagctctgt caggaaagga ggtgctgtta tgagcagctc ttccagtggg caaagaggac    4920
gcccataatt tcttccattg ctagctcatc tgtgggacca atttggtgta agcaacctgt    4980
ggcctgcact tgtggcctcg aaggaagcac aaaccctcca tccacttccc atttcctctg    5040 ccctttttcca cctcccccctt ccatcccacc agctgccagt ggctcccaga aagccttatt    5100 gagcccttg ttgacacttg gggctgcgga ggctctctcc tactggtctg gccttttcctg    5160 agaggcaggt cttccgtcct cagagccttt ctggaacaag gagaatgcct gtgcaggtgg    5220
acacacaggc ctggcctgtc gctctcactt gtcttccagc ggggagcttc acgttgccga    5280
gtggaagaac catgacctcc acttgcttcc aaggtgctag ggaagtttca gggtacgctg    5340
gttcccctct ccagctggag gccgagtttc tgggactgc agattttttct actctgtgat    5400 cgattcaatg cccgatgctt ctgtttcatt cccgacccctt tctactatgc attttccttt    5460
tatcaggtgt ataaagttaa atactgtgta tttatcacta aaaagtacat gaacttaaga    5520
gacaactaag cctttcgtgt ttttccacag gtgtttaagc ttctctgtac agttgaaata    5580
aacagacagc aaaatggtgc caaaaaaaaa aaaaaaaaa                          5620
```

<210> SEQ ID NO 2
<211> LENGTH: 588
<212> TYPE: PRT
<213> ORGANISM: Artificial Sequence

```
<220> FEATURE:
<223> OTHER INFORMATION: Synthetic

<400> SEQUENCE: 2

Met Ser Ser Cys Val Ser Ser Gln Pro Ser Ser Asn Arg Ala Ala Pro
1               5                   10                  15

Gln Asp Glu Leu Gly Gly Arg Gly Ser Ser Ser Glu Ser Gln Lys
            20                  25                  30

Pro Cys Glu Ala Leu Arg Gly Leu Ser Ser Leu Ser Ile His Leu Gly
        35                  40                  45

Met Glu Ser Phe Ile Val Val Thr Glu Cys Glu Pro Gly Cys Ala Val
    50                  55                  60

Asp Leu Gly Leu Ala Arg Asp Arg Pro Leu Glu Ala Asp Gly Gln Glu
65                  70                  75                  80

Val Pro Leu Asp Thr Ser Gly Ser Gln Ala Arg Pro His Leu Ser Gly
                85                  90                  95

Arg Lys Leu Ser Leu Gln Glu Arg Ser Gln Gly Gly Leu Ala Ala Gly
                100                 105                 110

Gly Ser Leu Asp Met Asn Gly Arg Cys Ile Cys Pro Ser Leu Pro Tyr
            115                 120                 125

Ser Pro Val Ser Ser Pro Gln Ser Ser Pro Arg Leu Pro Arg Arg Pro
130                 135                 140

Thr Val Glu Ser His His Val Ser Ile Thr Gly Met Gln Asp Cys Val
145                 150                 155                 160

Gln Leu Asn Gln Tyr Thr Leu Lys Asp Glu Ile Gly Lys Gly Ser Tyr
                165                 170                 175

Gly Val Val Lys Leu Ala Tyr Asn Glu Asn Asp Asn Thr Tyr Tyr Ala
            180                 185                 190

Met Lys Val Leu Ser Lys Lys Lys Leu Ile Arg Gln Ala Gly Phe Pro
        195                 200                 205

Arg Arg Pro Pro Pro Arg Gly Thr Arg Pro Ala Pro Gly Gly Cys Ile
    210                 215                 220

Gln Pro Arg Gly Pro Ile Glu Gln Val Tyr Gln Glu Ile Ala Ile Leu
225                 230                 235                 240

Lys Lys Leu Asp His Pro Asn Val Val Lys Leu Val Glu Val Leu Asp
                245                 250                 255

Asp Pro Asn Glu Asp His Leu Tyr Met Val Phe Glu Leu Val Asn Gln
            260                 265                 270

Gly Pro Val Met Glu Val Pro Thr Leu Lys Pro Leu Ser Glu Asp Gln
        275                 280                 285

Ala Arg Phe Tyr Phe Gln Asp Leu Ile Lys Gly Ile Glu Tyr Leu His
    290                 295                 300

Tyr Gln Lys Ile Ile His Arg Asp Ile Lys Pro Ser Asn Leu Leu Val
305                 310                 315                 320

Gly Glu Asp Gly His Ile Lys Ile Ala Asp Phe Gly Val Ser Asn Glu
                325                 330                 335

Phe Lys Gly Ser Asp Ala Leu Leu Ser Asn Thr Val Gly Thr Pro Ala
            340                 345                 350

Phe Met Ala Pro Glu Ser Leu Ser Glu Thr Arg Lys Ile Phe Ser Gly
        355                 360                 365

Lys Ala Leu Asp Val Trp Ala Met Gly Val Thr Leu Tyr Cys Phe Val
    370                 375                 380

Phe Gly Gln Cys Pro Phe Met Asp Glu Arg Ile Met Cys Leu His Ser
385                 390                 395                 400
```

```
Lys Ile Lys Ser Gln Ala Leu Glu Phe Pro Asp Gln Pro Asp Ile Ala
                405                 410                 415

Glu Asp Leu Lys Asp Leu Ile Thr Arg Met Leu Asp Lys Asn Pro Glu
            420                 425                 430

Ser Arg Ile Val Val Pro Glu Ile Lys Leu His Pro Trp Val Thr Arg
        435                 440                 445

His Gly Ala Glu Pro Leu Pro Ser Glu Asp Glu Asn Cys Thr Leu Val
    450                 455                 460

Glu Val Thr Glu Glu Val Glu Asn Ser Val Lys His Ile Pro Ser
465                 470                 475                 480

Leu Ala Thr Val Ile Leu Val Lys Thr Met Ile Arg Lys Arg Ser Phe
                485                 490                 495

Gly Asn Pro Phe Glu Gly Ser Arg Arg Glu Glu Arg Ser Leu Ser Ala
            500                 505                 510

Pro Gly Asn Leu Leu Thr Lys Lys Pro Thr Arg Glu Cys Glu Ser Leu
        515                 520                 525

Ser Glu Leu Lys Glu Ala Arg Gln Arg Arg Gln Pro Pro Gly His Arg
    530                 535                 540

Pro Ala Pro Arg Gly Gly Gly Ser Ala Leu Val Arg Gly Ser Pro
545                 550                 555                 560

Cys Val Glu Ser Cys Trp Ala Pro Ala Pro Gly Ser Pro Ala Arg Met
                565                 570                 575

His Pro Leu Arg Pro Glu Glu Ala Met Glu Pro Glu
            580                 585
```

```
<210> SEQ ID NO 3
<211> LENGTH: 5577
<212> TYPE: DNA
<213> ORGANISM: Artificial Sequence
<220> FEATURE:
<223> OTHER INFORMATION: Synthetic

<400> SEQUENCE: 3
gagcctgggg aggtcgaggg tgcagcgagc cgtgatcgtg ctactgcact ccagcctggg      60
caacacagag agaccctgtc tcaaaacaaa caaacaaaca acaaacaaa caaacaaaaa      120 aaacaaagaa aaaaaaatgg gagtgggccg ggcgcggtga ctcacacctg taatcccagc    180
actttcggag gccaaggcgg gtggatcacg aggtcaggaa ttcaagatta gcctggacaa    240
catggtgaaa ccccatctct acgaaaaata caaaaattag ccaagtatgg tggccggcgc    300
ctgtaatccc agctactcgg gagactgagg cagagaactg cttgaacctg ggaggcagag    360
gttgcagtga tccgagatcg cgtcactgca ctccagcgtg ggcgacagag cgagactccg    420
tttcagaaaa gaaaaaaaaa aaaaaaaaa agggagtcgg ggtggagctc tcattggctc    480
gttgcatgtg agtgtcccta cggcctagaa atacaagaga agcacatcgg aacgggctgg    540
aaatccaccc agttaactag agggctttga acctttattt aacttggagg ttgactctcc    600
tgtcaactcg attcccttt ggctgtttgg cagggtcagt gagacatccc ctgggtcgct    660 cgacccgta ggacggttca gggagccctc caggtcttcg tttctcctct tcccgcaca    720 gtgctgttat ccagctgggg gatccaacgc acacttaagg ctccagcaaa gtggctccgc    780
tgccggatgg gagtgcccca gtgtgctgga tgaagctggc gcatgcacca tgtcatcatg    840
tgtctctagc cagcccagca gcaaccgggc cgcccccag gatgagctgg ggggcagggg    900
cagcagcagc agcgaaagcc agaagccctg tgaggccctg cggggcctct catccttgag    960
```

```
catccacctg ggcatggagt ccttcattgt ggtcaccgag tgtgagccgg gctgtgctgt    1020
ggacctcggc ttggcgcggg accggcccct ggaggccgat ggccaagagg tcccccttga    1080
cacctccggg tcccaggccc ggccccacct ctccggtcgc aagctgtctc tgcaagagcg    1140
gtcccagggt gggctggcag ccggtggcag cctggacatg aacggacgct gcatctgccc    1200
gtccctgccc tactcacccg tcagctcccc gcagtcctcg cctcggctgc cccggcggcc    1260
gacagtggag tctcaccacg tctccatcac gggtatgcag gactgtgtgc agctgaatca    1320
gtataccctg aaggatgaaa ttggaaaggg ctcctatggt gtcgtcaagt tggcctacaa    1380
tgaaaatgac aatacctact atgcaatgaa ggtgctgtcc aaaaagaagc tgatccggca    1440
ggccggcttt ccacgtcgcc ctccaccccg aggcacccgg ccagctcctg gaggctgcat    1500
ccagcccagg ggccccattg agcaggtgta ccaggaaatt gccatcctca agaagctgga    1560
ccaccccaat gtggtgaagc tggtggaggt cctggatgac cccaatgagg accatctgta    1620
catggtgttc gaactggtca accaagggcc cgtgatggaa gtgccccccc tcaaaccact    1680
ctctgaagac caggcccgtt tctacttcca ggatctgatc aaaggcatcg agtacttaca    1740
ctaccagaag atcatccacc gtgacatcaa accttccaac ctcctggtcg agaagatgg    1800 gcacatcaag atcgctgact tggtgtgag caatgaattc aagggcagtg acgcgctcct    1860
ctccaacacc gtgggcacgc ccgccttcat ggcacccgag tcgctctctg agacccgcaa    1920
gatcttctct gggaaggcct tggatgtttg gccatgggt gtgacactat actgctttgt    1980 cttggccag tgcccattca tggacgagcg gatcatgtgt ttacacagta agatcaagag    2040
tcaggccctg gaatttccag accagcccga catagctgag gacttgaagg acctgatcac    2100
ccgtatgctg gacaagaacc ccgagtcgag gatcgtggtg ccggaaatca gctgcaccc    2160 ctgggtcacg aggcatgggg cggagccgtt gccgtcggag gatgagaact gcacgctggt    2220
cgaagtgact gaagaggagg tcgagaactc agtcaaacac attcccagct ggcaaccgt    2280 gatcctggtg aagaccatga tacgtaaacg ctcctttggg aacccattcg agggcagccg    2340
gcgggaggaa cgctcactgt cagcgcctgg aaacttgctc acgaagcaag gcagcgaaga    2400
caacctccag ggcaccgacc cgcccccgt ggggaggag gaagtgctct tgtgagaggc    2460
agtccctgcg tggaaagttg ctgggcccc gcccccggct cccccgcacg catgcatcca    2520
ctgcggccgg aggaggccat ggagcccgag tagctgcctg gatcgctcga cctcgcatgc    2580
gcgccgcgtc gcctctgggg ggctgctgca ccgcgtttcc atagcagcat gtcctacgga    2640
aacccagcac gtgtgtagag cctcgatcgt catctctggt tatttgtttt ttcctttgtt    2700
gttttaaagg ggacaaaaaa aaaaaaagga cttgactcca tgacgtcgac cgtggccgct    2760
ggctggctgg acaggcgggt gtgaggagtt gcagacccaa acccacgtgc attttgggac    2820
aattgctttt taaaacgttt ttatgccaaa aatccttcat tgtgattttc agaaccacgt    2880
cagatatacc aagtgactgt gtgtggggtt tgacaactgt ggaaaggcga gcagaaaact    2940
ccggcggtct gaggccatgg aggtggttgc tgcatttgag agggagtagg gggctagatg    3000
tggctcctag tgcaaaccgg aaaccatggc accttccaga gccgtggtct caaggagtca    3060
gagcagggct ggccctcagt agctgcaggg agctttgatg caacttattt gtaagaagga    3120 ttttaaatt ttttatgggt agaattgtag tcaggaaaac agaaagggct tgaaatttaa    3180
taagtgctgc tggaagggga ttttccaagc ctggaagggt attcagcagc tgtggtgggg    3240
aaacatttct cctgaaagac tgaacgtgtt tcttcatgac agctgctcaa agcaggtttc    3300
tgagatagct gaccgagctc tggtaaatct ctttgtcaaa ttacgaaaac ttcagggtga    3360
```

```
aatcctatgc ttccatgtac attacatggc ttaagattaa acaaaaacat ttttcaagtc    3420
tctaactaga gtgaactcta gagcacagta gttcagaaac tatttagagc ttccaggata    3480
tatttcacag cttcaggcat gtgatcagtt agagccgatg aaacctatgc ccgcctgtat    3540
atatattagc agcttagcta gttcataacc tgtatattct aaagactgct aaggttttgt    3600 tttcattttta aatcctagct gattgttgtg gtcaatgaaa tacccagttt ctggagggcc    3660
aggtgggaaa tgctttcact ggaccaacac acaaatgatc atcctgagga tctgagcttc    3720
cctagactcc acacaataac cttggggcac cctttagag aagactgttg aaacccacag    3780
cactcgttgg ggtatgagga accagggct tggcacagga agttcccctt tgtagctaaa    3840
agtccagaaa gaaagggttc atcttttga cttccaactg atattgggaa gtttggttga    3900
ggttcaagtg tgactccttc cagagccaca ggtaggggag tgtgaagttg aggggggagga    3960 aagctggaag gactctgcct tgggagattc ccagctctgc tttccagcgc ttggtggaat    4020
ctgggctggg gaaagacggc accgggaaac tctgcttccc cattgtttcc atctgatcag    4080
ctgtggtgtg aggacttctc agacaaaggc aaggcctcgt gccctgccc agcccattca    4140 tggagccctg ggccttcttg gcttccatag atcctaagct cttgactgta gtttagccag    4200
acttgttttg ctatcttata agcagttcag aattagggaa tgctggtttt gaagagcaaa    4260
ggacaggtag tctagagagg gtcgtctggc ctgcttgctg ggtctttgta acccagcact    4320
tcctcttgcc ctcctggctt tatgtttatg gggagaggac tcaatagctc caccccttct    4380
ggcaccagat ggggcttggt tagtttgcaa taagcacctt gcagaggtta aagccagcgg    4440
gtccctagtc ttaggcccag cctgcttgtg tgggctctgg cctggcctgg tggctggccc    4500 aggggggcagc agtgcttaga gcttctgcag ggcttctctt gtttacacag ctgcatcaga    4560
caatgccatt tctccccacc acggaacctt ccatctaaga tttcttccag ggaatgccag    4620
caatcaggca gcacccagct gtggggggcag tggggtgggg gagacccaca ttgatgactt    4680
tttttttttc ttttaatgaa gaaacaccaa agaaagctgt ggaaaggacc tgccccacat    4740
gaaaaggata agccaagatg gctgtaaaca cagagcattt gagctgccac tcttggagca    4800
cattgatttt tcaaaagcca gctctgtcag gaaaggaggt gctgttatga gcagctcttc    4860
cagtgggcaa agaggacgcc cataatttct tccattgcta gctcatctgt gggaccaatt    4920
tggtgtaagc aacctgtggc ctgcacttgt ggcctcgaag gaagcacaaa ccctccatcc    4980
acttcccatt tcctctgccc ttttccacct ccccctccca tcccaccagc tgccagtggc    5040
tcccagaaag cctattgag ccccttgttg acacttgggg ctgcggaggc ctctccctac    5100
tggtctggcc tttcctgaga ggcaggtctt ccgtcctcag agcctttctg gaacaaggag    5160
aatgcctgtg caggtggaca cacaggcctg gcctgtcgct ctcacttgtc ttccagcggg    5220
gagcttcacg ttgccgagtg gaagaaccat gacctccact tgcttccaag gtgctaggga    5280
agttcagggg tacgctggtt cccctctcca gctggaggcc gagttctgg ggactgcaga    5340 ttttttctact ctgtgatcga ttcaatgccc gatgcttctg tttcattccc gacccttct    5400 actatgcatt ttcctttat caggtgtata aagttaaata ctgtgtattt atcactaaaa    5460
agtacatgaa cttaagagac aactaagcct ttcgtgtttt tccacaggtg tttaagcttc    5520
tctgtacagt tgaaataaac agacagcaaa atggtgccaa aaaaaaaaaa aaaaaaa     5577
```

<210> SEQ ID NO 4
<211> LENGTH: 541
<212> TYPE: PRT

<213> ORGANISM: Artificial Sequence
<220> FEATURE:
<223> OTHER INFORMATION: Synthetic

<400> SEQUENCE: 4

Met Ser Ser Cys Val Ser Ser Gln Pro Ser Ser Asn Arg Ala Ala Pro
1               5                   10                  15

Gln Asp Glu Leu Gly Gly Arg Gly Ser Ser Ser Glu Ser Gln Lys
            20                  25                  30

Pro Cys Glu Ala Leu Arg Gly Leu Ser Leu Ser Ile His Leu Gly
        35                  40                  45

Met Glu Ser Phe Ile Val Val Thr Glu Cys Glu Pro Gly Cys Ala Val
50                  55                  60

Asp Leu Gly Leu Ala Arg Asp Arg Pro Leu Glu Ala Asp Gly Gln Glu
65                  70                  75                  80

Val Pro Leu Asp Thr Ser Gly Ser Gln Ala Arg Pro His Leu Ser Gly
                85                  90                  95

Arg Lys Leu Ser Leu Gln Glu Arg Ser Gln Gly Gly Leu Ala Ala Gly
            100                 105                 110

Gly Ser Leu Asp Met Asn Gly Arg Cys Ile Cys Pro Ser Leu Pro Tyr
        115                 120                 125

Ser Pro Val Ser Ser Pro Gln Ser Ser Pro Arg Leu Pro Arg Arg Pro
130                 135                 140

Thr Val Glu Ser His His Val Ser Ile Thr Gly Met Gln Asp Cys Val
145                 150                 155                 160

Gln Leu Asn Gln Tyr Thr Leu Lys Asp Glu Ile Gly Lys Gly Ser Tyr
                165                 170                 175

Gly Val Val Lys Leu Ala Tyr Asn Glu Asn Asp Asn Thr Tyr Tyr Ala
            180                 185                 190

Met Lys Val Leu Ser Lys Lys Lys Leu Ile Arg Gln Ala Gly Phe Pro
        195                 200                 205

Arg Arg Pro Pro Pro Arg Gly Thr Arg Pro Ala Pro Gly Gly Cys Ile
210                 215                 220

Gln Pro Arg Gly Pro Ile Glu Gln Val Tyr Gln Glu Ile Ala Ile Leu
225                 230                 235                 240

Lys Lys Leu Asp His Pro Asn Val Val Lys Leu Val Glu Val Leu Asp
                245                 250                 255

Asp Pro Asn Glu Asp His Leu Tyr Met Val Phe Glu Leu Val Asn Gln
            260                 265                 270

Gly Pro Val Met Glu Val Pro Thr Leu Lys Pro Leu Ser Glu Asp Gln
        275                 280                 285

Ala Arg Phe Tyr Phe Gln Asp Leu Ile Lys Gly Ile Glu Tyr Leu His
290                 295                 300

Tyr Gln Lys Ile Ile His Arg Asp Ile Lys Pro Ser Asn Leu Leu Val
305                 310                 315                 320

Gly Glu Asp Gly His Ile Lys Ile Ala Asp Phe Gly Val Ser Asn Glu
                325                 330                 335

Phe Lys Gly Ser Asp Ala Leu Leu Ser Asn Thr Val Gly Thr Pro Ala
            340                 345                 350

Phe Met Ala Pro Glu Ser Leu Ser Glu Thr Arg Lys Ile Phe Ser Gly
        355                 360                 365

Lys Ala Leu Asp Val Trp Ala Met Gly Val Thr Leu Tyr Cys Phe Val
370                 375                 380

Phe Gly Gln Cys Pro Phe Met Asp Glu Arg Ile Met Cys Leu His Ser

```
                385                 390                 395                 400
Lys Ile Lys Ser Gln Ala Leu Glu Phe Pro Asp Gln Pro Asp Ile Ala
                    405                 410                 415

Glu Asp Leu Lys Asp Leu Ile Thr Arg Met Leu Asp Lys Asn Pro Glu
            420                 425                 430

Ser Arg Ile Val Val Pro Glu Ile Lys Leu His Pro Trp Val Thr Arg
        435                 440                 445

His Gly Ala Glu Pro Leu Pro Ser Glu Asp Asn Cys Thr Leu Val
    450                 455                 460

Glu Val Thr Glu Glu Val Glu Asn Ser Val Lys His Ile Pro Ser
465                 470                 475                 480

Leu Ala Thr Val Ile Leu Val Lys Thr Met Ile Arg Lys Ser Phe
                485                 490                 495

Gly Asn Pro Phe Glu Gly Ser Arg Arg Glu Glu Arg Ser Leu Ser Ala
                    500                 505                 510

Pro Gly Asn Leu Leu Thr Lys Gln Gly Ser Glu Asp Asn Leu Gln Gly
        515                 520                 525

Thr Asp Pro Pro Val Gly Glu Glu Val Leu Leu
    530                 535                 540

<210> SEQ ID NO 5
<211> LENGTH: 5491
<212> TYPE: DNA
<213> ORGANISM: Artificial Sequence
<220> FEATURE:
<223> OTHER INFORMATION: Synthetic

<400> SEQUENCE: 5
gagcctgggg aggtcgaggg tgcagcgagc cgtgatcgtg ctactgcact ccagcctggg      60
caacacagag agaccctgtc tcaaaacaaa caaacaaaca acaaacaaa caaacaaaaa     120 aaacaaagaa aaaaaaatgg gagtgggccg ggcgcggtga ctcacacctg taatcccagc    180
actttcggag gccaaggcgg gtggatcacg aggtcaggaa ttcaagatta gcctggacaa    240
catggtgaaa ccccatctct acgaaaaata caaaaattag ccaagtatgg tggccggcgc    300
ctgtaatccc agctactcgg gagactgagg cagagaactg cttgaacctg ggaggcagag    360
gttgcagtga tccgagatcg cgtcactgca ctccagcgtg ggcgacagag cgagactccg    420
tttcagaaaa gaaaaaaaaa aaaaaaaaaa agggagtcgg ggtggagctc tcattggctc    480
gttgcatgtg agtgtcccta cggcctagaa atacaagaga agcacatcgg aacgggctgg    540
aaatccaccc agttaactag agggctttga acctttttatt aacttggagg ttgactctcc    600
tgtcaactcg attcccttttt ggctgtttgg cagggtcagt gagacatccc ctgggtcgct    660
cgaccccgta ggacggttca gggagccctc caggtcttcg tttctcctct tccccgcaca    720
gtgctgttat ccagctgggg gatccaacgc acacttaagg ctccagcaaa gtggctccgc    780
tgccggatgg gagtgcccca gtgtgctgga tgaagctggc gcatgcacca tgtcatcatg    840
tgtctctagc cagcccagca gcaaccgggc cgccccccag gatgagctgg ggggcagggg    900
cagcagcagc agcgaaagcc agaagccctg tgaggccctg cggggcctct catccttgag    960
catccacctg gcatggagt ccttcattgt ggtcaccgag tgtgagccgg gctgtgctgt   1020
ggacctcggc ttggcgcggg accggcccct ggaggccgat ggccaagagg tcccccttga   1080
cacctccggg tcccaggccc ggccccacct tccggtcgc aagctgtctc tgcaagagcg    1140
gtcccagggt gggctggcag ccggtggcag cctggacatg aacggacgct gcatctgccc   1200
```

-continued

```
gtccctgccc tactcacccg tcagctcccc gcagtcctcg cctcggctgc cccggcggcc   1260
gacagtggag tctccaccacg tctccatcac gggtatgcag gactgtgtgc agctgaatca   1320
gtataccctg aaggatgaaa ttggaaaggg ctcctatggt gtcgtcaagt tggcctacaa   1380
tgaaaatgac aatacctact atgcaatgaa ggtgctgtcc aaaaagaagc tgatccggca   1440
ggccggcttt ccacgtcgcc ctccacccg aggcacccgg ccagctcctg gaggctgcat    1500
ccagcccagg ggccccattg agcaggtgta ccaggaaatt gccatcctca agaagctgga   1560
ccaccccaat gtggtgaagc tggtggaggt cctggatgac cccaatgagg accatctgta   1620
catggtgttc gaactggtca accaagggcc cgtgatggaa gtgcccaccc tcaaaccact   1680
ctctgaagac caggcccgtt tctacttcca ggatctgatc aaaggcatcg agtacttaca   1740
ctaccagaag atcatccacc gtgacatcaa accttccaac ctcctggtcg agaagatgg    1800
gcacatcaag atcgctgact tggtgtgag caatgaattc aagggcagtg acgcgctcct    1860
ctccaacacc gtgggcacgc cgccttcat ggcacccgag tcgctctctg agacccgcaa    1920
gatcttctct gggaaggcct tggatgtttg gccatgggt gtgacactat actgctttgt    1980
ctttggccag tgcccattca tggacgagcg gatcatgtgt ttacacagta agatcaagag   2040
tcaggccctg gaatttccag accagcccga catagctgag gacttgaagg acctgatcac   2100
ccgtatgctg gacaagaacc ccgagtcgag gatcgtggtg ccggaaatca agatcctggt   2160
gaagaccatg atacgtaaac gctcctttgg gaacccattc gagggcagcc ggcgggagga   2220
acgctcactg tcagcgcctg gaaacttgct caccaaaaaa ccaaccaggg aatgtgagtc   2280
cctgtctgag ctcaaggaag caaggcagcg aagacaacct ccaggcacc gacccgcccc    2340
ccgtggggga ggaggaagtg ctcttgtgag aggcagtccc tgcgtggaaa gttgctgggc   2400
ccccgcccc ggctcccccg cacgcatgca tccactgcgg ccgaggagg ccatggagcc     2460
cgagtagctg cctggatcgc tcgacctcgc atgcgcgccg cgtcgcctct gggggggctgc  2520
tgcaccgcgt ttccatagca gcatgtccta cggaaaccca gcacgtgtgt agagcctcga   2580
tcgtcatctc tggttatttg ttttttcctt tgttgtttta aaggggacaa aaaaaaaaa    2640
aggacttgac tccatgacgt cgaccgtggc cgctggctgg ctggacaggc gggtgtgagg   2700
agttgcagac ccaaacccac gtgcattttg ggacaattgc ttttttaaaac gtttttatgc   2760
caaaaatcct tcattgtgat tttcagaacc acgtcagata taccaagtga ctgtgtgtgg   2820
ggtttgacaa ctgtggaaag gcgagcagaa aactccggcg gtctgaggcc atggaggtgg   2880
ttgctgcatt tgagagggag tagggggcta gatgtggctc ctagtgcaaa ccggaaacca   2940
tggcaccttc cagagccgtg gtctcaagga gtcagagcag ggctggccct cagtagctgc   3000
agggagcttt gatgcaactt atttgtaaga aggattttta aatttttat gggtagaatt    3060
gtagtcagga aaacagaaag ggcttgaaat ttaataagtg ctgctggaag gggattttcc   3120
aagcctggaa gggtattcag cagctgtggt gggaaacat ttctcctgaa agactgaacg    3180
tgtttcttca tgacagctgc tcaaagcagg tttctgagat agctgaccga gctctggtaa   3240
atctctttgt caaattacga aaacttcagg gtgaaatcct atgcttccat gtacattaca   3300
tggcttaaga ttaaacaaaa acattttca agtctctaac tagagtgaac tctagagcac    3360
agtagttcag aaactattta gagcttccag gatatatttc acagcttcag gcatgtgatc   3420
agttagagcc gatgaaacct atgcccgcct gtatatatat tagcagctta gctagttcat   3480
aacctgtata ttctaaagac tgctaaggtt ttgttttcat tttaaatcct agctgattgt   3540
tgtggtcaat gaaatacccca gtttctggag ggccaggtgg gaaatgcttt cactggacca   3600
```

```
acacacaaat gatcatcctg aggatctgag cttccctaga ctccacacaa taaccttggg    3660 gcacccttt  agagaagact gttgaaaccc acagcactcg ttggggtatg aggaaaccag    3720
ggcttggcac aggaagttcc cctttgtagc taaaagtcca gaaagaaagg gttcatcttt    3780
ttgacttcca actgatattg ggaagtttgg ttgaggttca agtgtgactc cttccagagc    3840
cacaggtagg ggagtgtgaa gttgaggggg aggaaagctg aaggactct  gccttgggag    3900 attcccagct ctgctttcca gcgcttggtg gaatctgggc tggggaaaga cggcaccggg    3960
aaactctgct tccccattgt ttccatctga tcagctgtgg tgtgaggact tctcagacaa    4020
aggcaaggcc tcgtgcccct gcccagccca ttcatggagc cctgggcctt cttggcttcc    4080
atagatccta agctcttgac tgtagtttag ccagacttgt tttgctatct tataagcagt    4140
tcagaattag ggaatgctgg ttttgaagag caaaggacag gtagtctaga gagggtcgtc    4200
tggcctgctt gctgggtctt tgtaacccag cacttcctct tgccctcctg gctttatgtt    4260
tatggggaga ggactcaata gctccacccc ttctggcacc agatgggggct tggttagttt    4320 gcaataagca ccttgcagag gttaaagcca gcgggtccct agtcttaggc ccagcctgct    4380
tgtgtgggct ctggcctggc ctggtggctg gcccaggggg cagcagtgct tagagcttct    4440
gcagggcttc tcttgtttac acagctgcat cagacaatgc catttctccc caccacggaa    4500
ccttccatct aagatttctt ccagggaatg ccagcaatca ggcagcaccc agctgtgggg    4560 gcagtgggt ggggagacc cacattgatg actttttttt tttcttttaa tgaagaaaca     4620
ccaaagaaag ctgtggaaag gacctgcccc acatgaaaag gataagccaa gatggctgta    4680
aacacagagc atttgagctg ccactcttgg agcacattga tttttcaaaa gccagctctg    4740
tcaggaaagg aggtgctgtt atgagcagct cttccagtgg gcaaagagga cgcccataat    4800
ttcttccatt gctagctcat ctgtgggacc aatttggtgt aagcaacctg tggcctgcac    4860
ttgtggcctc gaaggaagca caaaccctcc atccacttcc catttcctct gccctttcc    4920 acctcccccct tccatcccac cagctgccag tggctcccag aaagccttat tgagcccctt    4980
gttgacactt ggggctgcgg aggcctctcc ctactggtct ggcctttcct gagaggcagg    5040
tcttccgtcc tcagagcctt tctggaacaa ggagaatgcc tgtgcaggtg acacacagg     5100 cctggcctgt cgctctcact tgtcttccag cggggagctt cacgttgccg agtggaagaa    5160
ccatgacctc cacttgcttc caaggtgcta gggaagtttc agggtacgct ggttcccctc    5220
tccagctgga ggccgagttt ctggggactg cagattttc  tactctgtga tcgattcaat    5280
gcccgatgct tctgtttcat tcccgacccc ttctactatg cattttcctt ttatcaggtg    5340
tataaagtta aatactgtgt atttatcact aaaaagtaca tgaacttaag agacaactaa    5400
gcctttcgtg ttttccaca  ggtgtttaag cttctctgta cagttgaaat aaacagacag    5460
caaaatggtg ccaaaaaaa  aaaaaaaaa  a                                   5491
```

<210> SEQ ID NO 6
<211> LENGTH: 545
<212> TYPE: PRT
<213> ORGANISM: Artificial Sequence
<220> FEATURE:
<223> OTHER INFORMATION: Synthetic

<400> SEQUENCE: 6

Met Ser Ser Cys Val Ser Ser Gln Pro Ser Ser Asn Arg Ala Ala Pro
1               5                   10                  15

Gln Asp Glu Leu Gly Gly Arg Gly Ser Ser Ser Ser Glu Ser Gln Lys

```
            20                  25                  30
Pro Cys Glu Ala Leu Arg Gly Leu Ser Ser Leu Ser Ile His Leu Gly
            35                  40                  45
Met Glu Ser Phe Ile Val Val Thr Glu Cys Glu Pro Gly Cys Ala Val
 50                  55                  60
Asp Leu Gly Leu Ala Arg Asp Arg Pro Leu Glu Ala Asp Gly Gln Glu
 65                  70                  75                  80
Val Pro Leu Asp Thr Ser Gly Ser Gln Ala Arg Pro His Leu Ser Gly
                 85                  90                  95
Arg Lys Leu Ser Leu Gln Glu Arg Ser Gln Gly Gly Leu Ala Ala Gly
            100                 105                 110
Gly Ser Leu Asp Met Asn Gly Arg Cys Ile Cys Pro Ser Leu Pro Tyr
            115                 120                 125
Ser Pro Val Ser Ser Pro Gln Ser Ser Pro Arg Leu Pro Arg Arg Pro
            130                 135                 140
Thr Val Glu Ser His His Val Ser Ile Thr Gly Met Gln Asp Cys Val
145                 150                 155                 160
Gln Leu Asn Gln Tyr Thr Leu Lys Asp Glu Ile Gly Lys Gly Ser Tyr
                165                 170                 175
Gly Val Val Lys Leu Ala Tyr Asn Glu Asn Asp Asn Thr Tyr Tyr Ala
                180                 185                 190
Met Lys Val Leu Ser Lys Lys Leu Ile Arg Gln Ala Gly Phe Pro
                195                 200                 205
Arg Arg Pro Pro Pro Arg Gly Thr Arg Pro Ala Pro Gly Gly Cys Ile
            210                 215                 220
Gln Pro Arg Gly Pro Ile Glu Gln Val Tyr Gln Glu Ile Ala Ile Leu
225                 230                 235                 240
Lys Lys Leu Asp His Pro Asn Val Val Lys Leu Val Glu Val Leu Asp
                245                 250                 255
Asp Pro Asn Glu Asp His Leu Tyr Met Val Phe Glu Leu Val Asn Gln
                260                 265                 270
Gly Pro Val Met Glu Val Pro Thr Leu Lys Pro Leu Ser Glu Asp Gln
            275                 280                 285
Ala Arg Phe Tyr Phe Gln Asp Leu Ile Lys Gly Ile Glu Tyr Leu His
            290                 295                 300
Tyr Gln Lys Ile Ile His Arg Asp Ile Lys Pro Ser Asn Leu Leu Val
305                 310                 315                 320
Gly Glu Asp Gly His Ile Lys Ile Ala Asp Phe Gly Val Ser Asn Glu
                325                 330                 335
Phe Lys Gly Ser Asp Ala Leu Leu Ser Asn Thr Val Gly Thr Pro Ala
                340                 345                 350
Phe Met Ala Pro Glu Ser Leu Ser Glu Thr Arg Lys Ile Phe Ser Gly
            355                 360                 365
Lys Ala Leu Asp Val Trp Ala Met Gly Val Thr Leu Tyr Cys Phe Val
            370                 375                 380
Phe Gly Gln Cys Pro Phe Met Asp Glu Arg Ile Met Cys Leu His Ser
385                 390                 395                 400
Lys Ile Lys Ser Gln Ala Leu Glu Phe Pro Asp Gln Pro Asp Ile Ala
                405                 410                 415
Glu Asp Leu Lys Asp Leu Ile Thr Arg Met Leu Asp Lys Asn Pro Glu
            420                 425                 430
Ser Arg Ile Val Val Pro Glu Ile Lys Ile Leu Val Lys Thr Met Ile
            435                 440                 445
```

```
Arg Lys Arg Ser Phe Gly Asn Pro Phe Glu Gly Ser Arg Arg Glu Glu
    450                 455                 460

Arg Ser Leu Ser Ala Pro Gly Asn Leu Leu Thr Lys Lys Pro Thr Arg
465                 470                 475                 480

Glu Cys Glu Ser Leu Ser Glu Leu Lys Glu Ala Arg Gln Arg Gln
                485                 490                 495

Pro Pro Gly His Arg Pro Ala Pro Arg Gly Gly Gly Ser Ala Leu
            500                 505                 510

Val Arg Gly Ser Pro Cys Val Glu Ser Cys Trp Ala Pro Ala Pro Gly
            515                 520             525

Ser Pro Ala Arg Met His Pro Leu Arg Pro Glu Glu Ala Met Glu Pro
            530                 535                 540

Glu
545

<210> SEQ ID NO 7
<211> LENGTH: 5448
<212> TYPE: DNA
<213> ORGANISM: Artificial Sequence
<220> FEATURE:
<223> OTHER INFORMATION: Synthetic

<400> SEQUENCE: 7
gagcctgggg aggtcgaggg tgcagcgagc cgtgatcgtg ctactgcact ccagcctggg      60
caacacagag agaccctgtc tcaaaacaaa caaacaaaca aacaaacaaa caaacaaaaa     120
aaacaaagaa aaaaaaatgg gagtgggccg ggcgcggtga ctcacacctg taatcccagc     180
actttcggag gccaaggcgg gtggatcacg aggtcaggaa ttcaagatta gcctggacaa     240
catggtgaaa ccccatctct acgaaaaata caaaaattag ccagtatggt ggccggcgc      300 ctgtaatccc agctactcgg gagactgagg cagagaactg cttgaacctg ggaggcagag     360
gttgcagtga tccgagatcg cgtcactgca ctccagcgtg ggcgacagag cgagactccg     420
tttcagaaaa gaaaaaaaaa aaaaaaaaaa agggagtcgg ggtggagctc tcattggctc     480
gttgcatgtg agtgtcccta cggcctagaa atacaagaga agcacatcgg aacgggctgg     540
aaatccaccc agttaactag agggctttga accttttatt aacttggagg ttgactctcc     600
tgtcaactcg attcccttt ggctgtttgg cagggtcagt gagacatccc tgggtcgct      660 cgaccccgta ggacggttca gggagccctc caggtcttcg tttctcctct tccccgcaca     720
gtgctgttat ccagctgggg gatccaacgc acacttaagg ctccagcaaa gtggctccgc     780
tgccggatgg gagtgcccca gtgtgctgga tgaagctggc gcatgcacca tgtcatcatg     840
tgtctctagc cagcccagca gcaaccgggc cgccccccag gatgagctgg ggggcagggg     900
cagcagcagc agcgaaagcc agaagccctg tgaggccctg cggggcctct catccttgag     960
catccacctg ggcatggagt ccttcattgt ggtcaccgag tgtgagccgg gctgtgctgt    1020
ggacctcggc ttggcgcggg accggcccct ggaggccgat ggccaagagg tccccttga    1080 cacctccggg tcccaggccc ggccccacct ctccggtcgc aagctgtctc tgcaagagcg    1140
gtcccagggt gggctggcag ccggtggcag cctggacatg aacggacgct gcatctgccc    1200
gtccctgccc tactcacccg tcagctcccc gcagtcctcg cctcggctgc ccggcggcc     1260 gacagtggag tctcaccacg tctccatcac gggtatgcag actgtgtgc agctgaatca    1320 gtataccctg aaggatgaaa ttggaaaggg ctccctatgg gtcgtcaagt ggcctacaa    1380 tgaaaatgac aatacctact atgcaatgaa ggtgctgtcc aaaaagaagc tgatccggca    1440
```

```
ggccggcttt ccacgtcgcc ctccacccccg aggcacccgg ccagctcctg gaggctgcat    1500
ccagcccagg ggccccattg agcaggtgta ccaggaaatt gccatcctca agaagctgga    1560
ccaccccaat gtggtgaagc tggtggaggt cctggatgac cccaatgagg accatctgta    1620
catggtgttc gaactggtca accaagggcc cgtgatggaa gtgcccaccc tcaaaccact    1680
ctctgaagac caggcccgtt tctacttcca ggatctgatc aaaggcatcg agtacttaca    1740
ctaccagaag atcatccacc gtgacatcaa accttccaac ctcctggtcg agaagatgg     1800 gcacatcaag atcgctgact tggtgtgag caatgaattc aagggcagtg acgcgctcct    1860
ctccaacacc gtgggcacgc ccgccttcat ggcacccgag tcgctctctg agacccgcaa    1920
gatcttctct gggaaggcct tggatgtttg ggccatgggt gtgacactat actgctttgt    1980
ctttggccag tgcccattca tggacgagcg gatcatgtgt ttacacagta agatcaagag    2040
tcaggccctg gaatttccag accagcccga catagctgag gacttgaagg acctgatcac    2100
ccgtatgctg gacaagaacc ccgagtcgag gatcgtggtg ccggaaatca agatcctggt    2160
gaagaccatg atacgtaaac gctcctttgg gaacccattc gagggcagcc ggcgggagga    2220
acgctcactg tcagcgcctg gaaacttgct cacgaagcaa ggcagcgaag acaacctcca    2280
gggcaccgac ccgccccccg tgggggagga ggaagtgctc ttgtgagagg cagtccctgc    2340
gtggaaagtt gctgggcccc cgccccggc tccccgcac gcatgcatcc actgcggccg    2400
gaggaggcca tggagcccga gtagctgcct ggatcgctcg acctcgcatg cgcgccgcgt    2460
cgcctctggg gggctgctgc accgcgtttc catagcagca tgtcctacgg aaacccagca    2520
cgtgtgtaga gcctcgatcg tcatctctgg ttatttgttt tttcctttgt tgttttaaag    2580
gggacaaaaa aaaaaaaagg acttgactcc atgacgtcga ccgtggccgc tggctggctg    2640
gacaggcggg tgtgaggagt tgcagaccca aacccacgtg cattttggga caattgcttt    2700
ttaaaacgtt tttatgccaa aaatccttca ttgtgatttt cagaaccacg tcagatatac    2760
caagtgactg tgtgtggggt ttgacaactg tggaaaggcg agcagaaaac tccggcggtc    2820
tgaggccatg gaggtggttg ctgcatttga gagggagtag ggggctagat gtggctccta    2880
gtgcaaaccg gaaaccatgg caccttccag agccgtggtc tcaaggagtc agagcagggc    2940
tggccctcag tagctgcagg gagctttgat gcaacttatt tgtaagaagg attttttaaat    3000 tttttatggg tagaattgta gtcaggaaaa cagaaagggc ttgaaattta ataagtgctg    3060
ctggaagggg attttccaag cctggaaggg tattcagcag ctgtggtggg gaaacatttc    3120
tcctgaaaga ctgaacgtgt tcttcatga cagctgctca aagcaggttt ctgagatagc     3180
tgaccgagct ctggtaaatc tctttgtcaa attacgaaaa cttcagggtg aaatcctatg    3240
cttccatgta cattacatgg cttaagatta acaaaaaca ttttcaagt ctctaactag      3300 agtgaactct agagcacagt agttcagaaa ctatttagag cttccaggat atatttcaca    3360
gcttcaggca tgtgatcagt tagagccgat gaaacctatg cccgcctgta tatattag      3420 cagcttagct agttcataac ctgtatattc taaagactgc taaggttttg ttttcatttt    3480
aaatcctagc tgattgttgt ggtcaatgaa atacccagtt tctggagggc caggtgggaa    3540
atgctttcac tggaccaaca cacaaatgat catcctgagg atctgagctt ccctagactc    3600
cacacaataa ccttggggca ccctttagga gaagactgtt gaaacccaca gcactcgttg    3660
gggtatgagg aaaccagggc ttggcacagg aagttcccct ttgtagctaa agtccagaa     3720 agaaagggtt catcttttg acttccaact gatattggga agtttggttg aggttcaagt    3780
```

```
gtgactccttccagagccacaggtaggggagtgtgaagttgaggggganggaaagctggaa  3840
ggactctgccttgggagattcccagctctgcttttccagcgcttggtggaatctgggctgg  3900
ggaaagacggcaccgggaaactctgcttccccattgtttccatctgatcagctgtggtgt  3960
gaggacttctcagacaaaggcaaggcctcgtgccctgcccagcccattcatggagccct   4020
gggccttcttggcttccatagatcctaagctcttgactgtagtttagccagacttgtttt   4080
gctatcttataagcagttcagaattagggaatgctggttttgaagagcaaggacaggta   4140
gtctagagaggtcgtctggcctgcttgctgggtctttgtaacccagcacttcctcttgc   4200
cctcctggctttatgtttatggggagaggactcaatagctccaccccttctggcaccaga   4260
tggggcttggttagtttgcaataagcacctgcagaggttaaagccagcggtccctagt    4320
cttaggcccagcctgcttgtgtgggctctgcctggcctggtggctggcccaggggcag    4380
cagtgcttagagcttctgcagggcttctcttgtttacacagctgcatcagacaatgccat   4440
ttctccccaccacggaacctccatctaagatttcttccagggaatgccagcaatcaggc   4500
agcacccagctgtgggggcagtggggtgggggagacccacattgatgacttttttttttt   4560
cttttaatgaagaaacaccaaagaaagctgtggaaaggactgcccccacatgaaaaggat   4620
aagccaagatggctgtaaacacagagcattgagctgccactcttggagcacattgatttt   4680
ttcaaaagccagctctgtcaggaaaggaggtgctgttatgagcagctcttccagtgggca   4740
aagaggacgccataatttcttccattgctagctcatctgtgggaccaattggtgtaag    4800
caacctgtggcctgcacttgtggcctcgaaggaagcacaaaccctccatccacttcccat   4860
ttcctctgccctttttccacctcccccttccatcccaccagctgccagtggctcccagaaa   4920
gccttattgagccccttgttgacacttgggggctgcggaggcctctcccctactggtctggc   4980
cttttcctgagaggcaggtcttccgtcctcagagcctttctggaacaaggagaatgctgt   5040
gcaggtggacacacaggcctggcctgtcgctctcacttgtcttccagcggggagcttcac   5100
gttgccgagtggaagaaccatgacctccacttgcttccaaggtgctagggaagtttcagg   5160
gtacgctggttccctctccagctggagccgagtttctgggactgcagattttctac     5220
tctgtgatcgattcaatgccgatgcttctgtttcattcccgacctttctactatgcat    5280
tttccttttatcaggtgtataagttaaatactgtgtatttatcactaaaaagtacatga   5340
acttaagagacaactaagcctttcgtgttttccacaggtgtttaagcttctctgtacag   5400
ttgaaataaacagacagcaaaatggtgccaaaaaaaaaaaaaaaaaa              5448
```

<210> SEQ ID NO 8
<211> LENGTH: 498
<212> TYPE: PRT
<213> ORGANISM: Artificial Sequence
<220> FEATURE:
<223> OTHER INFORMATION: Synthetic

<400> SEQUENCE: 8

Met Ser Ser Cys Val Ser Ser Gln Pro Ser Ser Asn Arg Ala Ala Pro
1               5                   10                  15

Gln Asp Glu Leu Gly Gly Arg Gly Ser Ser Ser Glu Ser Gln Lys
        20                  25                  30

Pro Cys Glu Ala Leu Arg Gly Leu Ser Ser Leu Ser Ile His Leu Gly
        35                  40                  45

Met Glu Ser Phe Ile Val Val Thr Glu Cys Glu Pro Gly Cys Ala Val
    50                  55                  60

Asp Leu Gly Leu Ala Arg Asp Arg Pro Leu Glu Ala Asp Gly Gln Glu

-continued

```
                65                  70                  75                  80
Val Pro Leu Asp Thr Ser Gly Ser Gln Ala Arg Pro His Leu Ser Gly
                    85                  90                  95

Arg Lys Leu Ser Leu Gln Glu Arg Ser Gln Gly Gly Leu Ala Ala Gly
                    100                 105                 110

Gly Ser Leu Asp Met Asn Gly Arg Cys Ile Cys Pro Ser Leu Pro Tyr
                    115                 120                 125

Ser Pro Val Ser Ser Pro Gln Ser Ser Pro Arg Leu Pro Arg Arg Pro
                    130                 135                 140

Thr Val Glu Ser His His Val Ser Ile Thr Gly Met Gln Asp Cys Val
145                 150                 155                 160

Gln Leu Asn Gln Tyr Thr Leu Lys Asp Glu Ile Gly Lys Gly Ser Tyr
                    165                 170                 175

Gly Val Val Lys Leu Ala Tyr Asn Glu Asn Asp Asn Thr Tyr Tyr Ala
                    180                 185                 190

Met Lys Val Leu Ser Lys Lys Leu Ile Arg Gln Ala Gly Phe Pro
                    195                 200                 205

Arg Arg Pro Pro Pro Arg Gly Thr Arg Pro Ala Pro Gly Gly Cys Ile
                    210                 215                 220

Gln Pro Arg Gly Pro Ile Glu Gln Val Tyr Gln Glu Ile Ala Ile Leu
225                 230                 235                 240

Lys Lys Leu Asp His Pro Asn Val Val Lys Leu Val Glu Val Leu Asp
                    245                 250                 255

Asp Pro Asn Glu Asp His Leu Tyr Met Val Phe Glu Leu Val Asn Gln
                    260                 265                 270

Gly Pro Val Met Glu Val Pro Thr Leu Lys Pro Leu Ser Glu Asp Gln
                    275                 280                 285

Ala Arg Phe Tyr Phe Gln Asp Leu Ile Lys Gly Ile Glu Tyr Leu His
                    290                 295                 300

Tyr Gln Lys Ile Ile His Arg Asp Ile Lys Pro Ser Asn Leu Leu Val
305                 310                 315                 320

Gly Glu Asp Gly His Ile Lys Ile Ala Asp Phe Gly Val Ser Asn Glu
                    325                 330                 335

Phe Lys Gly Ser Asp Ala Leu Leu Ser Asn Thr Val Gly Thr Pro Ala
                    340                 345                 350

Phe Met Ala Pro Glu Ser Leu Ser Glu Thr Arg Lys Ile Phe Ser Gly
                    355                 360                 365

Lys Ala Leu Asp Val Trp Ala Met Gly Val Thr Leu Tyr Cys Phe Val
                    370                 375                 380

Phe Gly Gln Cys Pro Phe Met Asp Glu Arg Ile Met Cys Leu His Ser
385                 390                 395                 400

Lys Ile Lys Ser Gln Ala Leu Glu Phe Pro Asp Gln Pro Asp Ile Ala
                    405                 410                 415

Glu Asp Leu Lys Asp Leu Ile Thr Arg Met Leu Asp Lys Asn Pro Glu
                    420                 425                 430

Ser Arg Ile Val Val Pro Glu Ile Lys Ile Leu Val Lys Thr Met Ile
                    435                 440                 445

Arg Lys Arg Ser Phe Gly Asn Pro Phe Glu Gly Ser Arg Arg Glu Glu
                    450                 455                 460

Arg Ser Leu Ser Ala Pro Gly Asn Leu Leu Thr Lys Gln Gly Ser Glu
465                 470                 475                 480

Asp Asn Leu Gln Gly Thr Asp Pro Pro Val Gly Glu Glu Val
                    485                 490                 495
```

Leu Leu

<210> SEQ ID NO 9
<211> LENGTH: 2981
<212> TYPE: DNA
<213> ORGANISM: Artificial Sequence
<220> FEATURE:
<223> OTHER INFORMATION: Synthetic

<400> SEQUENCE: 9

```
gagcctgggg aggtcgaggg tgcagcgagc cgtgatcgtg ctactgcact ccagcctggg      60
caacacagag agaccctgtc tcaaaacaaa caaacaaaca acaaacaaa caaacaaaaa     120
aaacaaagaa aaaaaaatgg gagtgggccg ggcgcggtga ctcacacctg taatcccagc    180
actttcggag gccaaggcgg gtggatcacg aggtcaggaa ttcaagatta gcctggacaa    240
catggtgaaa ccccatctct acgaaaaata caaaaattag ccaagtatgg tggccggcgc    300
ctgtaatccc agctactcgg gagactgagg cagagaactg cttgaacctg ggaggcagag    360
gttgcagtga tccgagatcg cgtcactgca ctccagcgtg ggcgacagag cgagactccg    420
tttcagaaaa gaaaaaaaaa aaaaaaaaaa agggagtcgg ggtggagctc tcattggctc    480
gttgcatgtg agtgtcccta cggcctagaa atacaagaga agcacatcgg aacgggctgg    540
aaatccaccc agttaactag agggctttga acctttatt aacttggagg ttgactctcc    600
tgtcaactcg attcccttt ggctgtttgg cagggtcagt gagacatccc ctgggtcgct    660
cgaccccgta ggacggttca gggagccctc caggtcttcg tttctcctct tccccgcaca    720
gtgctgttat ccagctgggg gatccaacgc acacttaagg ctccagcaaa gtggctccgc    780
tgccggatgg gagtgcccca gtgtgctgga tgaagctggc gcatgcacca tgtcatcatg    840
tgtctctagc cagcccagca gcaaccgggc cgcccccag gatgagctgg ggggcagggg    900
cagcagcagc agcgaaagcc agaagccctg tgaggcctg cggggcctct catccttgag    960
catccacctg gcatggagt ccttcattgt ggtcaccgag tgtgagccgg gctgtgctgt    1020
ggacctcggc ttggcgcggg accgcccct ggaggccgat ggccaagagg tccccttga    1080
cacctccggg tcccaggccc ggccccacct ctccggtcgc aagctgtctc tgcaagagcg    1140
gtcccagggt gggctggcag ccggtggcag cctggacatg aacggacgct gcatctgccc    1200
gtccctgccc tactcacccg tcagctcccc gcagtcctcg cctcggctgc ccggcggcc    1260
gacagtggag tctcaccacg tctccatcac gggtatgcag gactgtgtgc agctgaatca    1320
gtataccctg aaggatgaaa ttggaaaggg ctcctatggt gtcgtcaagt tggcctacaa    1380
tgaaaatgac aatacctact atgcaatgaa ggtgctgtcc aaaagaagc tgatccggca    1440
ggccggcttt ccacgtcgcc ctccaccccg aggcaccgg ccagctcctg gaggctgcat    1500
ccagcccagg ggccccattg agcaggtgta ccaggaaatt gccatcctca gaagctggac    1560
ccaccccaat gtggtgaagc tgtggaggt cctggatgac cccaatgagg accatctgta    1620
catggtgttc gaactggtca accaagggcc cgtgatggaa gtgcccaccc tcaaaccact    1680
ctctgaagac caggcccgtt tctacttcca ggatctgatc aaaggcatcg agtacttaca    1740
ctaccagaag atcatccacc gtgacatcaa accttccaac ctcctggtcg agaagatgg    1800
gcacatcaag atcgctgact ttggtgtgag caatgaattc aagggcagtg acgcgctcct    1860
ctccaacacc gtgggcacgc ccgccttcat ggcacccgag tcgctctctg agacccgcaa    1920
gatcttctct gggaaggcct tggatgtttg ggccatgggt gtgacactat actgctttgt    1980
```

-continued

```
ctttggccag tgcccattca tggacgagcg gatcatgtgt ttacacagta agatcaagag   2040
tcaggccctg gaatttccag accagcccga catagctgag gacttgaagg acctgatcac   2100
ccgtatgctg gacaagaacc ccgagtcgag gatcgtggtg ccggaaatca agctgcaccc   2160
ctgggtcacg aggcatgggg cggagccgtt gccgtcggag gatgagaact gcacgctggt   2220
cgaagtgact gaagaggagg tcgagaactc agtcaaacac attcccagct ggcaaccgt    2280 gatcctggtg aagaccatga tacgtaaacg ctcctttggg aacccattcg agggcagccg   2340
gcgggaggaa cgctcactgt cagcgcctgg aaacttgctc accaaaaaac caaccaggga   2400
atgtgagtcc ctgtctgagc tcaagaccta gaaaataagt cccctccctg cctgttgcaa   2460
agtaacgtaa gagttccctc acccgagtgg atgcagacct tcttgctgtc agccacccct   2520
ccttcataca catagccagc ccaggtgacc agaacctccc aggacagatg aggctttgtg   2580
tccttatgag actgggagaa cctgctgggc accctgctg caggtgctgt ggtgggtggg    2640
gaccccactg cccttcccac tgagcacatc atggctacct gacttggtgg gagctccagg   2700
cagtcacttc tgtttcttaa acatagcttt actgaggtac aattcacata ccatgtaatt   2760
cacccacggg aagtgtatga ttcagtggtt tctaatacag acttctgcag ccattaccac   2820
cgtcaacttt acgacatttt catcagccca agaagacacc ctacactcct tagctgtccc   2880
catccaactc ccccaccca gtaaccactc agaataggta tggatttgcc tattctggac    2940
gtttcgtata aatggcgtca tacactaaaa aaaaaaaaa a                        2981
```

<210> SEQ ID NO 10
<211> LENGTH: 533
<212> TYPE: PRT
<213> ORGANISM: Artificial Sequence
<220> FEATURE:
<223> OTHER INFORMATION: Synthetic

<400> SEQUENCE: 10

```
Met Ser Ser Cys Val Ser Ser Gln Pro Ser Ser Asn Arg Ala Ala Pro
1               5                   10                  15

Gln Asp Glu Leu Gly Gly Arg Gly Ser Ser Ser Glu Ser Gln Lys
            20                  25                  30

Pro Cys Glu Ala Leu Arg Gly Leu Ser Ser Leu Ser Ile His Leu Gly
        35                  40                  45

Met Glu Ser Phe Ile Val Val Thr Glu Cys Glu Pro Gly Cys Ala Val
    50                  55                  60

Asp Leu Gly Leu Ala Arg Asp Arg Pro Leu Glu Ala Asp Gly Gln Glu
65                  70                  75                  80

Val Pro Leu Asp Thr Ser Gly Ser Gln Ala Arg Pro His Leu Ser Gly
                85                  90                  95

Arg Lys Leu Ser Leu Gln Glu Arg Ser Gln Gly Gly Leu Ala Ala Gly
            100                 105                 110

Gly Ser Leu Asp Met Asn Gly Arg Cys Ile Cys Pro Ser Leu Pro Tyr
        115                 120                 125

Ser Pro Val Ser Ser Pro Gln Ser Ser Pro Arg Leu Pro Arg Arg Pro
    130                 135                 140

Thr Val Glu Ser His His Val Ser Ile Thr Gly Met Gln Asp Cys Val
145                 150                 155                 160

Gln Leu Asn Gln Tyr Thr Leu Lys Asp Glu Ile Gly Lys Gly Ser Tyr
                165                 170                 175

Gly Val Val Lys Leu Ala Tyr Asn Glu Asn Asp Asn Thr Tyr Tyr Ala
            180                 185                 190
```

```
Met Lys Val Leu Ser Lys Lys Leu Ile Arg Gln Ala Gly Phe Pro
        195                 200                 205
Arg Arg Pro Pro Arg Gly Thr Arg Pro Ala Pro Gly Gly Cys Ile
    210                 215                 220
Gln Pro Arg Gly Pro Ile Glu Gln Val Tyr Gln Glu Ile Ala Ile Leu
225                 230                 235                 240
Lys Lys Leu Asp His Pro Asn Val Val Lys Leu Val Glu Val Leu Asp
                245                 250                 255
Asp Pro Asn Glu Asp His Leu Tyr Met Val Phe Glu Leu Val Asn Gln
            260                 265                 270
Gly Pro Val Met Glu Val Pro Thr Leu Lys Pro Leu Ser Glu Asp Gln
        275                 280                 285
Ala Arg Phe Tyr Phe Gln Asp Leu Ile Lys Gly Ile Glu Tyr Leu His
    290                 295                 300
Tyr Gln Lys Ile Ile His Arg Asp Ile Lys Pro Ser Asn Leu Leu Val
305                 310                 315                 320
Gly Glu Asp Gly His Ile Lys Ile Ala Asp Phe Gly Val Ser Asn Glu
                325                 330                 335
Phe Lys Gly Ser Asp Ala Leu Leu Ser Asn Thr Val Gly Thr Pro Ala
            340                 345                 350
Phe Met Ala Pro Glu Ser Leu Ser Glu Thr Arg Lys Ile Phe Ser Gly
        355                 360                 365
Lys Ala Leu Asp Val Trp Ala Met Gly Val Thr Leu Tyr Cys Phe Val
    370                 375                 380
Phe Gly Gln Cys Pro Phe Met Asp Glu Arg Ile Met Cys Leu His Ser
385                 390                 395                 400
Lys Ile Lys Ser Gln Ala Leu Glu Phe Pro Asp Gln Pro Asp Ile Ala
                405                 410                 415
Glu Asp Leu Lys Asp Leu Ile Thr Arg Met Leu Asp Lys Asn Pro Glu
            420                 425                 430
Ser Arg Ile Val Val Pro Glu Ile Lys Leu His Pro Trp Val Thr Arg
        435                 440                 445
His Gly Ala Glu Pro Leu Pro Ser Glu Asp Glu Asn Cys Thr Leu Val
    450                 455                 460
Glu Val Thr Glu Glu Glu Val Glu Asn Ser Val Lys His Ile Pro Ser
465                 470                 475                 480
Leu Ala Thr Val Ile Leu Val Lys Thr Met Ile Arg Lys Arg Ser Phe
                485                 490                 495
Gly Asn Pro Phe Glu Gly Ser Arg Arg Glu Glu Arg Ser Leu Ser Ala
            500                 505                 510
Pro Gly Asn Leu Leu Thr Lys Lys Pro Thr Arg Glu Cys Glu Ser Leu
        515                 520                 525
Ser Glu Leu Lys Thr
    530

<210> SEQ ID NO 11
<211> LENGTH: 2852
<212> TYPE: DNA
<213> ORGANISM: Artificial Sequence
<220> FEATURE:
<223> OTHER INFORMATION: Synthetic

<400> SEQUENCE: 11
gagcctgggg aggtcgaggg tgcagcgagc cgtgatcgtg ctactgcact ccagcctggg    60
```

-continued

| | |
|---|---|
| caacacagag agaccctgtc tcaaaacaaa caaacaaaca aacaaacaaa caaacaaaaa | 120 |
| aaacaaagaa aaaaaaatgg gagtgggccg ggcgcggtga ctcacacctg taatcccagc | 180 |
| actttcggag gccaaggcgg gtggatcacg aggtcaggaa ttcaagatta gcctggacaa | 240 |
| catggtgaaa ccccatctct acgaaaaata caaaaattag ccaagtatgg tggccggcgc | 300 |
| ctgtaatccc agctactcgg gagactgagg cagagaactg cttgaacctg ggaggcagag | 360 |
| gttgcagtga tccgagatcg cgtcactgca ctccagcgtg ggcgacagag cgagactccg | 420 |
| tttcagaaaa gaaaaaaaaa aaaaaaaaaa agggagtcgg ggtggagctc tcattggctc | 480 |
| gttgcatgtg agtgtcccta cggcctagaa atacaagaga agcacatcgg aacgggctgg | 540 |
| aaatccaccc agttaactag agggctttga acctttatt aacttggagg ttgactctcc | 600 |
| tgtcaactcg attcccttt ggctgtttgg cagggtcagt gagacatccc ctgggtcgct | 660 |
| cgaccccgta ggacggttca gggagccctc caggtcttcg tttctcctct tccccgcaca | 720 |
| gtgctgttat ccagctgggg gatccaacgc acacttaagg ctccagcaaa gtggctccgc | 780 |
| tgccggatgg gagtgcccca gtgtgctgga tgaagctggc gcatgcacca tgtcatcatg | 840 |
| tgtctctagc cagcccagca gcaaccgggc cgccccccag gatgagctgg ggggcagggg | 900 |
| cagcagcagc agcgaaagcc agaagccctg tgaggccctg cggggcctct catccttgag | 960 |
| catccacctg ggcatggagt ccttcattgt ggtcaccgag tgtgagccgg gctgtgctgt | 1020 |
| ggacctcggc ttggcgcggg accggcccct ggaggccgat ggccaagagg tcccccttga | 1080 |
| cacctccggg tcccaggccc ggccccacct ctccggtcgc aagctgtctc tgcaagagcg | 1140 |
| gtcccagggt gggctggcag ccggtggcag cctggacatg aacggacgct gcatctgccc | 1200 |
| gtccctgccc tactcacccg tcagctcccc gcagtcctcg cctcggctgc cccggcggcc | 1260 |
| gacagtggag tctcaccacg tctccatcac gggtatgcag gactgtgtgc agctgaatca | 1320 |
| gtataccctg aaggatgaaa ttggaaaggg ctcctatggt gtcgtcaagt tggcctacaa | 1380 |
| tgaaaatgac aatacctact atgcaatgaa ggtgctgtcc aaaaagaagc tgatccggca | 1440 |
| ggccggcttt ccacgtcgcc ctccaccccg aggcacccgg ccagctcctg gaggctgcat | 1500 |
| ccagcccagg ggccccattg agcaggtgta ccaggaaatt gccatcctca agaagctgga | 1560 |
| ccaccccaat gtggtgaagc tggtggaggt cctggatgac cccaatgagg accatctgta | 1620 |
| catggtgttc gaactggtca accaagggcc cgtgatggaa gtgcccaccc tcaaaccact | 1680 |
| ctctgaagac caggcccgtt tctacttcca ggatctgatc aaaggcatcg agtacttaca | 1740 |
| ctaccagaag atcatccacc gtgacatcaa accttccaac ctcctggtcg agaagatgg | 1800 |
| gcacatcaag atcgctgact tggtgtgag caatgaattc aagggcagtg acgcgctcct | 1860 |
| ctccaacacc gtgggcacgc ccgccttcat ggcacccgag tcgctctctg agacccgcaa | 1920 |
| gatcttctct gggaaggcct tggatgtttg gccatgggt gtgacactat actgctttgt | 1980 |
| ctttggccag tgcccattca tggacgagcg gatcatgtgt ttacacagta agatcaagag | 2040 |
| tcaggccctg gaatttccag accagcccga catagctgag gacttgaagg acctgatcac | 2100 |
| ccgtatgctg gacaagaacc ccgagtcgag gatcgtggtg ccggaaatca gatcctggt | 2160 |
| gaagaccatg atacgtaaac gctcctttg gaacccattc gagggcagcc ggcgggagga | 2220 |
| acgctcactg tcagcgcctg gaaacttgct caccaaaaaa ccaaccaggg aatgtgagtc | 2280 |
| cctgtctgag ctcaagacct agaaaataag tccccttcct gcctgttgca agtaacgta | 2340 |
| agagttccct cacccgagtg gatgcagacc ttcttgctgt cagccaccct tccttcatac | 2400 |
| acatagccag cccaggtgac cagaacctcc caggacagat gaggctttgt gtccttatga | 2460 |

```
gactgggaga acctgctggg caccoctgct gcaggtgctg tggtgggtgg ggacoccact    2520 gcccttccca ctgagcacat catggctacc tgacttggtg ggagctccag gcagtcactt    2580
ctgtttctta aacatagctt tactgaggta caattcacat accatgtaat tcacccacgg    2640
gaagtgtatg attcagtggt ttctaataca gacttctgca gccattacca ccgtcaactt    2700
tacgacattt tcatcagccc aagaagacac cctacactcc ttagctgtcc ccatccaact    2760
cccccacccc agtaaccact cagaataggt atggatttgc ctattctgga cgtttcgtat    2820
aaatggcgtc atacactaaa aaaaaaaaaa aa                                  2852
```

```
<210> SEQ ID NO 12
<211> LENGTH: 490
<212> TYPE: PRT
<213> ORGANISM: Artificial Sequence
<220> FEATURE:
<223> OTHER INFORMATION: Synthetic

<400> SEQUENCE: 12

Met Ser Ser Cys Val Ser Ser Gln Pro Ser Asn Arg Ala Ala Pro
1               5                   10                  15

Gln Asp Glu Leu Gly Gly Arg Gly Ser Ser Ser Glu Ser Gln Lys
                20                  25                  30

Pro Cys Glu Ala Leu Arg Gly Leu Ser Ser Leu Ser Ile His Leu Gly
                35                  40                  45

Met Glu Ser Phe Ile Val Val Thr Glu Cys Glu Pro Gly Cys Ala Val
            50                  55                  60

Asp Leu Gly Leu Ala Arg Asp Arg Pro Leu Glu Ala Asp Gly Gln Glu
65                  70                  75                  80

Val Pro Leu Asp Thr Ser Gly Ser Gln Ala Arg Pro His Leu Ser Gly
                85                  90                  95

Arg Lys Leu Ser Leu Gln Glu Arg Ser Gln Gly Gly Leu Ala Ala Gly
                100                 105                 110

Gly Ser Leu Asp Met Asn Gly Arg Cys Ile Cys Pro Ser Leu Pro Tyr
            115                 120                 125

Ser Pro Val Ser Ser Pro Gln Ser Ser Pro Arg Leu Pro Arg Arg Pro
        130                 135                 140

Thr Val Glu Ser His His Val Ser Ile Thr Gly Met Gln Asp Cys Val
145                 150                 155                 160

Gln Leu Asn Gln Tyr Thr Leu Lys Asp Glu Ile Gly Lys Gly Ser Tyr
                165                 170                 175

Gly Val Val Lys Leu Ala Tyr Asn Glu Asn Asp Asn Thr Tyr Tyr Ala
            180                 185                 190

Met Lys Val Leu Ser Lys Lys Leu Ile Arg Gln Ala Gly Phe Pro
                195                 200                 205

Arg Arg Pro Pro Arg Gly Thr Arg Pro Ala Pro Gly Gly Cys Ile
        210                 215                 220

Gln Pro Arg Gly Pro Ile Glu Gln Val Tyr Gln Glu Ile Ala Ile Leu
225                 230                 235                 240

Lys Lys Leu Asp His Pro Asn Val Val Lys Leu Val Glu Val Leu Asp
                245                 250                 255

Asp Pro Asn Glu Asp His Leu Tyr Met Val Phe Glu Leu Val Asn Gln
            260                 265                 270

Gly Pro Val Met Glu Val Pro Thr Leu Lys Pro Leu Ser Glu Asp Gln
        275                 280                 285
```

```
Ala Arg Phe Tyr Phe Gln Asp Leu Ile Lys Gly Ile Glu Tyr Leu His
        290                 295                 300

Tyr Gln Lys Ile Ile His Arg Asp Ile Lys Pro Ser Asn Leu Leu Val
305                 310                 315                 320

Gly Glu Asp Gly His Ile Lys Ile Ala Asp Phe Gly Val Ser Asn Glu
                325                 330                 335

Phe Lys Gly Ser Asp Ala Leu Leu Ser Asn Thr Val Gly Thr Pro Ala
            340                 345                 350

Phe Met Ala Pro Glu Ser Leu Ser Glu Thr Arg Lys Ile Phe Ser Gly
        355                 360                 365

Lys Ala Leu Asp Val Trp Ala Met Gly Val Thr Leu Tyr Cys Phe Val
370                 375                 380

Phe Gly Gln Cys Pro Phe Met Asp Glu Arg Ile Met Cys Leu His Ser
385                 390                 395                 400

Lys Ile Lys Ser Gln Ala Leu Glu Phe Pro Asp Gln Pro Asp Ile Ala
                405                 410                 415

Glu Asp Leu Lys Asp Leu Ile Thr Arg Met Leu Asp Lys Asn Pro Glu
            420                 425                 430

Ser Arg Ile Val Val Pro Glu Ile Lys Ile Leu Val Lys Thr Met Ile
        435                 440                 445

Arg Lys Arg Ser Phe Gly Asn Pro Phe Glu Gly Ser Arg Arg Glu Glu
450                 455                 460

Arg Ser Leu Ser Ala Pro Gly Asn Leu Leu Thr Lys Lys Pro Thr Arg
465                 470                 475                 480

Glu Cys Glu Ser Leu Ser Glu Leu Lys Thr
                485                 490

<210> SEQ ID NO 13
<211> LENGTH: 4923
<212> TYPE: DNA
<213> ORGANISM: Artificial Sequence
<220> FEATURE:
<223> OTHER INFORMATION: Synthetic

<400> SEQUENCE: 13
gcgcgcccgc cgcccgggcg gaggagagga gcgcgcggcc gcgcagagca agctgagccg      60
agccgagccg agctgggggc gcagagcgcg ggaggcggcg gcggcgcgga gcccaggtgg     120
ctccgctgcc ggatgggagt gccccagtgt gctggatgaa gctggcgcat gcaccatgtc     180
atcatgtgtc tctagccagc ccagcagcaa ccgggccgcc ccccaggatg agctgggggg     240
caggggcagc agcagcagcg aaagccagaa gccctgtgag gccctgcggg gcctctcatc     300
cttgagcatc cacctgggca tggagtcctt cattgtggtc accgagtgtg agccgggctg     360
tgctgtggac ctcggcttgg cgcgggaccg gcccctggag gccgatggcc aagaggtccc     420
ccttgacacc tccgggtccc aggcccggcc ccacctctcc ggtcgcaagc tgtctctgca     480
agagcggtcc cagggtgggc tggcagccgg tggcagcctg acatgaacg dacgctgcat      540 ctgcccgtcc ctgccctact caccccgtcag ctccccgcag tcctcgcctc ggctgccccg     600
gcggccgaca gtggagtctc accacgtctc catcacgggt atgcaggact gtgtgcagct     660
gaatcagtat accctgaagg atgaaattgg aaagggctcc tatggtgtcg tcaagttggc     720
ctacaatgaa aatgacaata cctactatgc aatgaaggtg ctgtccaaaa agaagctgat     780
ccggcaggcc ggctttccac gtcgccctcc accccgaggc accggccag ctcctggagg      840 ctgcatccag cccaggggcc ccattgagca ggtgtaccag gaaattgcca tcctcaagaa     900
```

```
gctggaccac cccaatgtgg tgaagctggt ggaggtcctg gatgacccca atgaggacca    960
tctgtacatg gtgttcgaac tggtcaacca agggcccgtg atggaagtgc ccaccctcaa   1020
accactctct gaagaccagg cccgtttcta cttccaggat ctgatcaaag gcatcgagta   1080
cttacactac cagaagatca tccaccgtga catcaaacct tccaacctcc tggtcggaga   1140
agatgggcac atcaagatcg ctgactttgg tgtgagcaat gaattcaagg gcagtgacgc   1200
gctcctctcc aacaccgtgg gcacgcccgc cttcatggca cccgagtcgc tctctgagac   1260
ccgcaagatc ttctctggga aggccttgga tgtttgggcc atgggtgtga cactatactg   1320
cttttgtcttt ggccagtgcc cattcatgga cgagcggatc atgtgtttac acagtaagat   1380
caagagtcag gccctggaat tccagacca gcccgacata gctgaggact tgaaggacct   1440
gatcacccgt atgctggaca gaacccccga gtcgaggatc gtggtgccgg aaatcaagct   1500
gcacccctgg gtcacgaggc atgggcgga gccgttgccg tcggaggatg agaactgcac   1560
gctggtcgaa gtgactgaag aggaggtcga gaactcagtc aaacacattc ccagcttggc   1620
aaccgtgatc ctggtgaaga ccatgatacg taaacgctcc tttgggaacc cattcgaggg   1680
cagccggcgg gaggaacgct cactgtcagc gcctggaaac ttgctcacga agcaaggcag   1740
cgaagacaac ctccagggca ccgacccgcc ccccgtgggg gaggaggaag tgctcttgtg   1800
agaggcagtc cctgcgtgga aagttgctgg gccccgccc ccggctcccc cgcacgcatg   1860
catccactgc ggccggagga ggccatggag cccgagtagc tgcctggatc gctcgacctc   1920
gcatgcgcgc cgcgtcgcct ctgggggct gctgcaccgc gtttccatag cagcatgtcc   1980
tacgaaaacc cagcacgtgt gtagagcctc gatcgtcatc tctggttatt tgtttttttcc   2040
tttgttgttt taaaggggac aaaaaaaaaa aaaggacttg actccatgac gtcgaccgtg   2100
gccgctggct ggctggacag gcgggtgtga ggagttgcag acccaaaccc acgtgcattt   2160
tgggacaatt gcttttttaaa acgttttttat gccaaaaatc cttcattgtg attttcagaa   2220
ccacgtcaga tataccaagt gactgtgtgt ggggtttgac aactgtggaa aggcgagcag   2280
aaaactccgg cggtctgagg ccatggaggt ggttgctgca tttgagaggg agtaggggc   2340
tagatgtggc tccagtgtca aaccggaaac catggcacct tccagagccg tggtctcaag   2400
gagtcagagc agggctggcc ctcagtagct gcagggagct ttgatgcaac ttatttgtaa   2460
gaaggatttt taaattttt atgggtagaa ttgtagtcag gaaaacagaa agggcttgaa   2520
atttaataag tgctgctgga aggggatttt ccaagcctgg aagggtattc agcagctgtg   2580
gtggggaaac atttctcctg aaagactgaa cgtgttttctt catgcagct gctcaaagca   2640
ggtttctgag atagctgacc gagctctggt aaatctcttt gtcaaattac gaaaacttca   2700
gggtgaaatc ctatgcttcc atgtacatta catggcttaa gattaaacaa aaacattttt   2760
caagtctcta actagagtga actctagagc acagtagttc agaaactatt tagagcttcc   2820
aggatatatt tcacagcttc aggcatgtga tcagttagag ccgatgaaac ctatgcccgc   2880
ctgtatatat attagcagct tagctagttc ataacctgta tattctaaag actgctaagg   2940
ttttgttttc atttttaaatc ctagctgatt gttgtggtca atgaaatacc cagtttctgg   3000
agggccaggt gggaaatgct ttcactgac caacacacaa atgatcatcc tgaggatctg   3060
agcttcccta gactccacac aataaccttg gggcacccctt ttagagaaga ctgttgaaac   3120
ccacagcact cgttgggta tgaggaaacc agggcttggc acaggaagtt cccctttgta   3180
gctaaaagtc cagaaagaaa gggttcatct ttttgacttc caactgatat tgggaagttt   3240
ggttgaggtt caagtgtgac tccttccaga gccacaggta ggggagtgtg aagttgaggg   3300
```

-continued

```
ggaggaaagc tggaaggact ctgccttggg agattcccag ctctgctttc cagcgcttgg    3360
tggaatctgg gctggggaaa gacggcaccg ggaaactctg cttccccatt gtttccatct    3420
gatcagctgt ggtgtgagga cttctcagac aaaggcaagg cctcgtgccc ctgcccagcc    3480
cattcatgga gccctgggcc ttcttggctt ccatagatcc taagctcttg actgtagttt    3540
agccagactt gttttgctat cttataagca gttcagaatt agggaatgct ggttttgaag    3600
agcaaaggac aggtagtcta gagagggtcg tctggcctgc ttgctgggtc tttgtaaccc    3660
agcacttcct cttgccctcc tggctttatg tttatgggga gaggactcaa tagctccacc    3720
ccttctggca ccagatgggg cttggttagt ttgcaataag caccttgcag aggttaaagc    3780
cagcgggtcc ctagtcttag gcccagcctg cttgtgtggg ctctggcctg gcctggtggc    3840
tggcccaggg ggcagcagtg cttagagctt ctgcagggct tctcttgttt acacagctgc    3900
atcagacaat gccatttctc cccaccacgg aaccttccat ctaagatttc ttccagggaa    3960
tgccagcaat caggcagcac ccagctgtgg gggcagtggg gtgggggaga cccacattga    4020
tgactttttt ttttctttt aatgaagaaa caccaaagaa agctgtggaa aggacctgcc      4080
ccacatgaaa aggataagcc aagatggctg taaacacaga gcatttgagc tgccactctt    4140
ggagcacatt gattttcaa aagccagctc tgtcaggaaa ggaggtgctg ttatgagcag      4200
ctcttccagt gggcaaagag gacgcccata atttcttcca ttgctagctc atctgtggga    4260
ccaatttggt gtaagcaacc tgtggcctgc acttgtggcc tcgaaggaag cacaaaccct    4320
ccatccactt cccatttcct ctgccctttt ccacctcccc cttccatccc accagctgcc    4380
agtggctccc agaaagcctt attgagcccc ttgttgacac ttggggctgc ggaggcctct    4440
ccctactggt ctggcctttc ctgagaggca ggtcttccgt cctcagagcc tttctggaac    4500
aaggagaatg cctgtgcagg tggacacaca ggcctggcct gtcgctctca cttgtcttcc    4560
agcggggagc ttcacgttgc cgagtggaag aaccatgacc tccacttgct tccaaggtgc    4620
tagggaagtt tcagggtacg ctggttcccc tctccagctg gaggccgagt ttctggggac    4680
tgcagatttt tctactctgt gatcgattca atgcccgatg cttctgtttc attcccgacc    4740 cttttctacta tgcattttcc ttttatcagg tgtataaagt taaatactgt gtatttatca    4800
ctaaaaagta catgaactta agagacaact aagcctttcg tgtttttcca caggtgttta    4860
agcttctctg tacagttgaa ataaacagac agcaaaatgg tgccaaaaaa aaaaaaaaa    4920 aaa    4923
```

<210> SEQ ID NO 14
<211> LENGTH: 541
<212> TYPE: PRT
<213> ORGANISM: Artificial Sequence
<220> FEATURE:
<223> OTHER INFORMATION: Synthetic

<400> SEQUENCE: 14

```
Met Ser Ser Cys Val Ser Ser Gln Pro Ser Ser Asn Arg Ala Ala Pro
1               5                   10                  15

Gln Asp Glu Leu Gly Gly Arg Gly Ser Ser Ser Glu Ser Gln Lys
        20                  25                  30

Pro Cys Glu Ala Leu Arg Gly Leu Ser Ser Leu Ser Ile His Leu Gly
        35                  40                  45

Met Glu Ser Phe Ile Val Val Thr Glu Cys Glu Pro Gly Cys Ala Val
    50                  55                  60
```

```
Asp Leu Gly Leu Ala Arg Asp Arg Pro Leu Glu Ala Asp Gly Gln Glu
 65                  70                  75                  80

Val Pro Leu Asp Thr Ser Gly Ser Gln Ala Arg Pro His Leu Ser Gly
                 85                  90                  95

Arg Lys Leu Ser Leu Gln Glu Arg Ser Gln Gly Gly Leu Ala Ala Gly
            100                 105                 110

Gly Ser Leu Asp Met Asn Gly Arg Cys Ile Cys Pro Ser Leu Pro Tyr
        115                 120                 125

Ser Pro Val Ser Ser Pro Gln Ser Ser Pro Arg Leu Pro Arg Arg Pro
    130                 135                 140

Thr Val Glu Ser His His Val Ser Ile Thr Gly Met Gln Asp Cys Val
145                 150                 155                 160

Gln Leu Asn Gln Tyr Thr Leu Lys Asp Glu Ile Gly Lys Gly Ser Tyr
                165                 170                 175

Gly Val Val Lys Leu Ala Tyr Asn Glu Asn Asp Asn Thr Tyr Tyr Ala
            180                 185                 190

Met Lys Val Leu Ser Lys Lys Leu Ile Arg Gln Ala Gly Phe Pro
        195                 200                 205

Arg Arg Pro Pro Pro Arg Gly Thr Arg Pro Ala Pro Gly Gly Cys Ile
210                 215                 220

Gln Pro Arg Gly Pro Ile Glu Gln Val Tyr Gln Glu Ile Ala Ile Leu
225                 230                 235                 240

Lys Lys Leu Asp His Pro Asn Val Val Lys Leu Val Glu Val Leu Asp
                245                 250                 255

Asp Pro Asn Glu Asp His Leu Tyr Met Val Phe Glu Leu Val Asn Gln
            260                 265                 270

Gly Pro Val Met Glu Val Pro Thr Leu Lys Pro Leu Ser Glu Asp Gln
        275                 280                 285

Ala Arg Phe Tyr Phe Gln Asp Leu Ile Lys Gly Ile Glu Tyr Leu His
    290                 295                 300

Tyr Gln Lys Ile Ile His Arg Asp Ile Lys Pro Ser Asn Leu Leu Val
305                 310                 315                 320

Gly Glu Asp Gly His Ile Lys Ile Ala Asp Phe Gly Val Ser Asn Glu
                325                 330                 335

Phe Lys Gly Ser Asp Ala Leu Leu Ser Asn Thr Val Gly Thr Pro Ala
            340                 345                 350

Phe Met Ala Pro Glu Ser Leu Ser Glu Thr Arg Lys Ile Phe Ser Gly
        355                 360                 365

Lys Ala Leu Asp Val Trp Ala Met Gly Val Thr Leu Tyr Cys Phe Val
    370                 375                 380

Phe Gly Gln Cys Pro Phe Met Asp Glu Arg Ile Met Cys Leu His Ser
385                 390                 395                 400

Lys Ile Lys Ser Gln Ala Leu Glu Phe Pro Asp Gln Pro Asp Ile Ala
                405                 410                 415

Glu Asp Leu Lys Asp Leu Ile Thr Arg Met Leu Asp Lys Asn Pro Glu
            420                 425                 430

Ser Arg Ile Val Val Pro Glu Ile Lys Leu His Pro Trp Val Thr Arg
        435                 440                 445

His Gly Ala Glu Pro Leu Pro Ser Glu Asp Glu Asn Cys Thr Leu Val
    450                 455                 460

Glu Val Thr Glu Glu Glu Val Glu Asn Ser Val Lys His Ile Pro Ser
465                 470                 475                 480

Leu Ala Thr Val Ile Leu Val Lys Thr Met Ile Arg Lys Arg Ser Phe
```

|   |   | 485 |   |   | 490 |   |   |   | 495 |   |   |
|---|---|---|---|---|---|---|---|---|---|---|---|
| Gly | Asn | Pro | Phe | Glu | Gly | Ser | Arg | Arg | Glu | Glu | Arg | Ser | Leu | Ser | Ala |
|   |   |   |   | 500 |   |   |   | 505 |   |   |   |   | 510 |   |   |

| Pro | Gly | Asn | Leu | Leu | Thr | Lys | Gln | Gly | Ser | Glu | Asp | Asn | Leu | Gln | Gly |
|---|---|---|---|---|---|---|---|---|---|---|---|---|---|---|---|
|   |   |   | 515 |   |   |   |   | 520 |   |   |   | 525 |   |   |   |

| Thr | Asp | Pro | Pro | Pro | Val | Gly | Glu | Glu | Val | Leu | Leu |
|---|---|---|---|---|---|---|---|---|---|---|---|
|   | 530 |   |   |   |   | 535 |   |   |   | 540 |   |

<210> SEQ ID NO 15
<211> LENGTH: 3583
<212> TYPE: DNA
<213> ORGANISM: Artificial Sequence
<220> FEATURE:
<223> OTHER INFORMATION: Synthetic

<400> SEQUENCE: 15

| ctgggcccca | gcgaggcggt | ggggcggggc | ggggcggggc | ggggcgcgca | gcaggagcga | 60 |
|---|---|---|---|---|---|---|
| gtggggccgc | cgccgggcc | gcggacactg | tcgcccggcg | cccaggttcc | caacaaggct | 120 |
| acgcagaaga | accccttga | ctgaagcaat | ggaggggggt | ccagctgtct | gctgccagga | 180 |
| tcctcgggca | gagctggtag | aacggtggc | agccatcgat | gtgactcact | tggaggaggc | 240 |
| agatggtggc | ccagagccta | ctagaaacgg | tgtggacccc | ccaccacggg | ccagagctgc | 300 |
| ctctgtgatc | cctggcagta | cttcaagact | gctcccagcc | cggcctagcc | tctcagccag | 360 |
| gaagctttcc | ctacaggagc | ggccagcagg | aagctatctg | gaggcgcagg | ctgggcctta | 420 |
| tgccacgggg | cctgccagcc | acatctcccc | cggggcctgg | cggaggccca | ccatcgagtc | 480 |
| ccaccacgtg | gccatctcag | atgcagagga | ctgcgtgcag | ctgaaccagt | acaagctgca | 540 |
| gagtgagatt | ggcaagggtg | cctacggtgt | ggtgaggctg | gcctacaacg | aaagtgaaga | 600 |
| cagacactat | gcaatgaaag | tcctttccaa | aaagaagtta | ctgaagcagt | atggcttttc | 660 |
| acgtcgccct | cccccgagag | gtcccagcc | tgcccaggga | ggaccagcca | agcagctgct | 720 |
| gcccctggag | cgggtgtacc | aggagattgc | catcctgaag | aagctggacc | acgtgaatgt | 780 |
| ggtcaaactg | atcgaggtcc | tggatgaccc | agctgaggac | aacctctatt | tggtgtttga | 840 |
| cctcctgaga | aaggggcccg | tcatggaagt | gccctgtgac | aagcccttct | cggaggagca | 900 |
| agctcgcctc | tacctgcggg | acgtcatcct | gggcctcgag | tacttgcact | gccagaagat | 960 |
| cgtccacagg | gacatcaagc | catccaacct | gctcctgggg | gatgatgggc | acgtgaagat | 1020 |
| cgccgacttt | ggcgtcagca | accagttga | ggggaacgac | gctcagctgt | ccagcacggc | 1080 |
| gggaacccca | gcattcatgg | ccccgaggc | catttctgat | tccggccaga | gcttcagtgg | 1140 |
| gaaggccttg | gatgtatggg | ccactggcgt | cacgttgtac | tgctttgtct | atgggaagtg | 1200 |
| cccattcatc | gacgatttca | tcctggcccct | ccacaggaag | atcaagaatg | agcccgtggt | 1260 |
| gtttcctgag | gagccagaaa | tcagcgagga | gctcaaggac | ctgatcctga | agatgttaga | 1320 |
| caagaatccc | gagacgagaa | ttggggtgcc | agacatcaag | ttgcaccctt | gggtgaccaa | 1380 |
| gaacggggag | gagcccctc | cttcggagga | ggagcactgc | agcgtggtgg | aggtgacaga | 1440 |
| ggaggaggtt | aagaactcag | tcaggctcat | ccccagctgg | accacggtga | tcctggtgaa | 1500 |
| gtccatgctg | aggaagcgtt | cctttgggaa | cccgtttgag | cccaagcac | ggagggaaga | 1560 |
| gcgatccatg | tctgctccag | gaaacctact | ggtgaaagaa | gggtttggtg | aagggggcaa | 1620 |
| gagcccagag | ctccccggcg | tccaggaaga | cgaggctgca | tcctgagccc | ctgcatgcac | 1680 |
| ccagggccac | ccggcagcac | actcatcccg | cgcctccaga | ggcccacccc | tcatgcaaca | 1740 |

```
gccgccccg caggcagggg gctgggact gcagccccac tcccgcccct ccccatcgt    1800
gctgcatgac ctccacgcac gcacgtccag ggacagactg gaatgtatgt catttgggt    1860
cttggggca gggctcccac gaggccatcc tcctcttctt ggacctcctt ggcctgaccc    1920
attctgtggg gaaaccgggt gcccatggag cctcagaaat gccacccggc tggttggcat    1980
ggcctgggc aggaggcaga ggcaggagac caagatggca ggtggaggcc aggcttacca    2040
caacggaaga gacctcccgc tggggccggg caggcctggc tcagctgcca caggcatatg    2100
gtggagaggg gggtaccctg cccaccttgg ggtggtggca ccagagctct tgtctattca    2160
gacgctggta tggggctcg gaccctcac tggggacagg gccagtgttg gagaattctg    2220
attccttttt tgttgtcttt tactttttgtt tttaacctgg gggttcgggg agaggccctg    2280
cttgggaaca tctcacgagc tttcctacat cttccgtggt tcccagcaca gcccaagatt    2340
atttggcagc caagtggatg gaactaactt tcctggactg tgtttcgcat tcggcgttat    2400
ctggaaagtg gactgaacgg aatcaagctc tgagcagagg cctgaagcgg aagcaccaca    2460
tcgtccctgc ccatctcact ctctcccttg atgatgcccc tagagctgag gctggagaag    2520
acaccagggc tgactttgac cgagggccat ggacgcgaca ggcctgtggc cctgcgcatg    2580
ctgaaataac tggaacccag cctctcctcc tacaccggcc tacccatctg ggcccaagag    2640
ctgcactcac actcctacaa cgaaggacaa actgtccagg tcggagggat cacgagacac    2700
agaacctgga ggggtgtgca cgctggcagg tggcctctgc ggcaattgcc tcaccctgag    2760
gacatcagca gtcagcctgc tcagagcggg ggtgctggag cgcgtgcaga cacagctctt    2820
ccggagcagc cttcaccttc tctctgggat cagtgtccgg ctggccgacg tggcatttgc    2880
tgaccgaatg ctcatagagg ttgaccccca cagggtcacg caggactcgg acactgccct    2940
ggaaacatgg atggacaagg cttttggcc acaggtgtgg gtgtcctgtt ggaggaggc    3000
ttgtttggag aagggaggct ggctggggga gaaacccgga tcccgctgca tctccgcgcc    3060
tgtgggtgca tgtcgcgtgc tcatctgttg cacacagctc actcgtatgt cctgcactgg    3120
tacatgcatc tgtaatacag tttctacgtc tatttaaggc taggagccga atgtgcccca    3180
ttgtcagtgg gtccacgttt ctcccccggct cctctgggct aaggcagtgt ggcccgaagc    3240
ttaaaaagtt actcggtact gtttttaaga acactttta agagttagtg gaaggcaagt    3300
taagagccaa tcactgatcc ccaagtgttt cttgagcatc tggtctgggg gaccactttt    3360
gatcggaccc accccttggaa agctcagggg taggcccagg tgggatgctc accctgtcac    3420
tgagggtttt ggttggcatc gttgttttg aatgtagcac aagcgatgag caaactctat    3480
aagagtgttt taaaaattaa cttcccagga agtgagttaa aaacaataaa agcccctttct    3540
tgagttaaaa agaaaaaaaa aaaaaaaaa aaaaaaaaa aaa               3583
```

```
<210> SEQ ID NO 16
<211> LENGTH: 505
<212> TYPE: PRT
<213> ORGANISM: Artificial Sequence
<220> FEATURE:
<223> OTHER INFORMATION: Synthetic

<400> SEQUENCE: 16

Met Glu Gly Gly Pro Ala Val Cys Cys Gln Asp Pro Arg Ala Glu Leu
1               5                   10                  15

Val Glu Arg Val Ala Ala Ile Asp Val Thr His Leu Glu Glu Ala Asp
            20                  25                  30

Gly Gly Pro Glu Pro Thr Arg Asn Gly Val Asp Pro Pro Pro Arg Ala
```

```
            35                  40                  45
Arg Ala Ala Ser Val Ile Pro Gly Ser Thr Ser Arg Leu Leu Pro Ala
             50                  55                  60
Arg Pro Ser Leu Ser Ala Arg Lys Leu Ser Leu Gln Glu Arg Pro Ala
 65                  70                  75                  80
Gly Ser Tyr Leu Glu Ala Gln Ala Gly Pro Tyr Ala Thr Gly Pro Ala
                 85                  90                  95
Ser His Ile Ser Pro Arg Ala Trp Arg Arg Pro Thr Ile Glu Ser His
                100                 105                 110
His Val Ala Ile Ser Asp Ala Glu Asp Cys Val Gln Leu Asn Gln Tyr
            115                 120                 125
Lys Leu Gln Ser Glu Ile Gly Lys Gly Ala Tyr Gly Val Val Arg Leu
        130                 135                 140
Ala Tyr Asn Glu Ser Glu Asp Arg His Tyr Ala Met Lys Val Leu Ser
145                 150                 155                 160
Lys Lys Lys Leu Leu Lys Gln Tyr Gly Phe Pro Arg Arg Pro Pro Pro
                165                 170                 175
Arg Gly Ser Gln Ala Ala Gln Gly Gly Pro Ala Lys Gln Leu Leu Pro
            180                 185                 190
Leu Glu Arg Val Tyr Gln Glu Ile Ala Ile Leu Lys Lys Leu Asp His
        195                 200                 205
Val Asn Val Val Lys Leu Ile Glu Val Leu Asp Asp Pro Ala Glu Asp
210                 215                 220
Asn Leu Tyr Leu Val Phe Asp Leu Leu Arg Lys Gly Pro Val Met Glu
225                 230                 235                 240
Val Pro Cys Asp Lys Pro Phe Ser Glu Glu Gln Ala Arg Leu Tyr Leu
                245                 250                 255
Arg Asp Val Ile Leu Gly Leu Glu Tyr Leu His Cys Gln Lys Ile Val
            260                 265                 270
His Arg Asp Ile Lys Pro Ser Asn Leu Leu Leu Gly Asp Asp Gly His
        275                 280                 285
Val Lys Ile Ala Asp Phe Gly Val Ser Asn Gln Phe Glu Gly Asn Asp
290                 295                 300
Ala Gln Leu Ser Ser Thr Ala Gly Thr Pro Ala Phe Met Ala Pro Glu
305                 310                 315                 320
Ala Ile Ser Asp Ser Gly Gln Ser Phe Ser Gly Lys Ala Leu Asp Val
                325                 330                 335
Trp Ala Thr Gly Val Thr Leu Tyr Cys Phe Val Tyr Gly Lys Cys Pro
            340                 345                 350
Phe Ile Asp Asp Phe Ile Leu Ala Leu His Arg Lys Ile Lys Asn Glu
        355                 360                 365
Pro Val Val Phe Pro Glu Glu Pro Glu Ile Ser Glu Glu Leu Lys Asp
    370                 375                 380
Leu Ile Leu Lys Met Leu Asp Lys Asn Pro Glu Thr Arg Ile Gly Val
385                 390                 395                 400
Pro Asp Ile Lys Leu His Pro Trp Val Thr Lys Asn Gly Glu Glu Pro
                405                 410                 415
Leu Pro Ser Glu Glu Glu His Cys Ser Val Val Glu Val Thr Glu Glu
            420                 425                 430
Glu Val Lys Asn Ser Val Arg Leu Ile Pro Ser Trp Thr Thr Val Ile
        435                 440                 445
Leu Val Lys Ser Met Leu Arg Lys Arg Ser Phe Gly Asn Pro Phe Glu
    450                 455                 460
```

```
Pro Gln Ala Arg Arg Glu Glu Arg Ser Met Ser Ala Pro Gly Asn Leu
465                 470                 475                 480

Leu Val Lys Glu Gly Phe Gly Glu Gly Gly Lys Ser Pro Glu Leu Pro
                485                 490                 495

Gly Val Gln Glu Asp Glu Ala Ala Ser
            500                 505

<210> SEQ ID NO 17
<211> LENGTH: 3529
<212> TYPE: DNA
<213> ORGANISM: Artificial Sequence
<220> FEATURE:
<223> OTHER INFORMATION: Synthetic

<400> SEQUENCE: 17
```

| | | | | | |
|---|---|---|---|---|---|
| agcagaacag | agtatgcaat | ttgggaagct | gtggtgtggc | tgcagtggag | agttcccaac | 60 |
| aaggctacgc | agaagaaccc | ccttgactga | agcaatggag | ggggtccag | ctgtctgctg | 120 |
| ccaggatcct | cgggcagagc | tggtagaacg | ggtggcagcc | atcgatgtga | ctcacttgga | 180 |
| ggaggcagat | ggtggcccag | agcctactag | aaacggtgtg | acccccac | cacgggccag | 240 |
| agctgcctct | gtgatccctg | gcagtacttc | aagactgctc | ccagcccggc | ctagcctctc | 300 |
| agccaggaag | ctttccctac | aggagcggcc | agcaggaagc | tatctggagg | cgcaggctgg | 360 |
| gccttatgcc | acgggcctg | ccagccacat | ctccccccgg | gctggcgga | ggcccaccat | 420 |
| cgagtcccac | cacgtggcca | tctcagatgc | agaggactgc | gtgcagctga | ccagtacaa | 480 |
| gctgcagagt | gagattggca | agggtgccta | cggtgtggtg | aggctggcct | acaacgaaag | 540 |
| tgaagacaga | cactatgcaa | tgaaagtcct | ttccaaaaag | aagttactga | agcagtatgg | 600 |
| cttttccacgt | cgccctcccc | cgagagggtc | ccaggctgcc | cagggaggac | cagccaagca | 660 |
| gctgctgccc | ctggagcggg | tgtaccagga | gattgccatc | ctgaagaagc | tggaccacgt | 720 |
| gaatgtggtc | aaactgatcg | aggtcctgga | tgcccagct | gaggacaacc | tctatttggt | 780 |
| gtttgacctc | ctgagaaagg | ggcccgtcat | ggaagtgccc | tgtgacaagc | ccttctcgga | 840 |
| ggagcaagct | cgcctctacc | tgcgggacgt | catcctgggc | ctcgagtact | tgcactgcca | 900 |
| gaagatcgtc | cacagggaca | tcaagccatc | caacctgctc | ctgggggatg | atgggcacgt | 960 |
| gaagatcgcc | gactttggcg | tcagcaacca | gtttgagggg | aacgacgctc | agctgtccag | 1020 |
| cacggcggga | accccagcat | tcatggcccc | cgaggccatt | tctgattccg | ccagagcttc | 1080 |
| cagtgggaag | gccttggatg | tatgggccac | tggcgtcacg | ttgtactgct | ttgtctatgg | 1140 |
| gaagtgccca | ttcatcgacg | atttcatcct | ggccctccac | aggaagatca | gaatgagcc | 1200 |
| cgtggtgttt | cctgaggagc | cagaaatcag | cgaggagctc | aaggacctga | tcctgaagat | 1260 |
| gttagacaag | aatcccgaga | cgagaattgg | ggtgccagac | atcaagttgc | acccttgggt | 1320 |
| gaccaagaac | ggggaggagc | ccttccttc | ggaggaggag | cactgcagcg | tggtggaggt | 1380 |
| gacagaggag | gaggttaaga | actcagtcag | gctcatcccc | agctggacca | cggtgatcct | 1440 |
| ggtgaagtcc | atgctgagga | agcgttcctt | tgggaacccg | tttgagcccc | aagcacggag | 1500 |
| ggaagagcga | tccatgtctg | ctccaggaaa | cctactggtg | aaagaagggt | ttggtgaagg | 1560 |
| gggcaagagc | ccagagctcc | ccggcgtcca | ggaagacgag | gctgcatcct | gagcccctgc | 1620 |
| atgcacccag | ggccacccgg | cagcacactc | atccgcgcc | tccagaggcc | cacccctcat | 1680 |
| gcaacagccg | ccccgcagg | cagggggctg | gggactgcag | ccccactccc | gcccctccc | 1740 |
| catcgtgctg | catgacctcc | acgcacgcac | gtccagggac | agactggaat | gtatgtcatt | 1800 |

```
tggggtcttg ggggcagggc tcccacgagg ccatcctcct cttcttggac ctccttggcc    1860
tgacccattc tgtggggaaa ccgggtgccc atggagcctc agaaatgcca cccggctggt    1920
tggcatggcc tggggcagga ggcagaggca ggagaccaag atggcaggtg gaggccaggc    1980
ttaccacaac ggaagagacc tcccgctggg gccgggcagg cctggctcag ctgccacagg    2040
catatggtgg agagggggt accctgccca ccttggggtg gtggcaccag agctcttgtc     2100
tattcagacg ctggtatggg ggctcggacc cctcactggg gacagggcca gtgttggaga    2160
attctgattc ctttttttgtt gtcttttact tttgttttta acctgggggt cggggagag    2220 gccctgcttg ggaacatctc acgagctttc ctacatcttc cgtggttccc agcacagccc    2280
aagattattt ggcagccaag tggatggaac taactttcct ggactgtgtt tcgcattcgg    2340
cgttatctgg aaagtggact gaacggaatc aagctctgag cagaggcctg aagcggaagc    2400
accacatcgt ccctgcccat ctcactctct cccttgatga tgcccctaga gctgaggctg    2460
gagaagacac cagggctgac tttgaccgag ggccatggac gcgacaggcc tgtggccctg    2520
cgcatgctga ataactgga acccagcctc tcctcctaca ccggcctacc catctgggcc     2580
caagagctgc actcacactc ctacaacgaa ggacaaactg tccaggtcgg agggatcacg    2640
agacacagaa cctggagggg tgtgcacgct ggcaggtggc ctctgcggca attgcctcac    2700
cctgaggaca tcagcagtca gcctgctcag agcggggtg ctggagcgcg tgcagacaca     2760
gctcttccgg agcagccttc accttctctc tgggatcagt gtccggctgg ccgacgtggc    2820
atttgctgac cgaatgctca tagaggttga ccccacagg gtcacgcagg actcggacac     2880
tgccctggaa acatggatgg acaagggctt ttggccacag gtgtgggtgt cctgttggag    2940
gagggcttgt ttggagaagg gaggctggct ggggagaaa cccggatccc gctgcatctc     3000
cgcgcctgtg ggtgcatgtc gcgtgctcat ctgttgcaca cagctcactc gtatgtcctg    3060
cactggtaca tgcatctgta atacagtttc tacgtctatt taaggctagg agccgaatgt    3120
gccccattgt cagtgggtcc acgtttctcc ccggctcctc tgggctaagg cagtgtggcc    3180
cgaagcttaa aaagttactc ggtactgttt ttaagaacac ttttatagag ttagtggaag    3240
gcaagttaag agccaatcac tgatccccaa gtgtttcttg agcatctggt ctgggggac     3300 cactttgatc ggacccaccc ttggaaagct caggggtagg cccaggtggg atgctcaccc    3360
tgtcactgag ggttttggtt ggcatcgttg tttttgaatg tagcacaagc gatgagcaaa    3420
ctctataaga gtgttttaaa aattaacttc ccaggaagtg agttaaaaac aataaaagcc    3480
ctttcttgag ttaaaagaa aaaaaaaaa aaaaaaaaa aaaaaaaa                    3529
```

<210> SEQ ID NO 18
<211> LENGTH: 505
<212> TYPE: PRT
<213> ORGANISM: Artificial Sequence
<220> FEATURE:
<223> OTHER INFORMATION: Synthetic

<400> SEQUENCE: 18

Met Glu Gly Gly Pro Ala Val Cys Cys Gln Asp Pro Arg Ala Glu Leu
1               5                   10                  15

Val Glu Arg Val Ala Ala Ile Asp Val Thr His Leu Glu Glu Ala Asp
            20                  25                  30

Gly Gly Pro Glu Pro Thr Arg Asn Gly Val Asp Pro Pro Arg Ala
        35                  40                  45

Arg Ala Ala Ser Val Ile Pro Gly Ser Thr Ser Arg Leu Leu Pro Ala

```
            50                  55                  60
Arg Pro Ser Leu Ser Ala Arg Lys Leu Ser Leu Gln Glu Arg Pro Ala
65                  70                  75                  80

Gly Ser Tyr Leu Glu Ala Gln Ala Gly Pro Tyr Ala Thr Gly Pro Ala
                85                  90                  95

Ser His Ile Ser Pro Arg Ala Trp Arg Pro Thr Ile Glu Ser His
            100                 105                 110

His Val Ala Ile Ser Asp Ala Glu Asp Cys Val Gln Leu Asn Gln Tyr
            115                 120                 125

Lys Leu Gln Ser Glu Ile Gly Lys Gly Ala Tyr Gly Val Val Arg Leu
130                 135                 140

Ala Tyr Asn Glu Ser Glu Asp Arg His Tyr Ala Met Lys Val Leu Ser
145                 150                 155                 160

Lys Lys Lys Leu Leu Lys Gln Tyr Gly Phe Pro Arg Arg Pro Pro Pro
                165                 170                 175

Arg Gly Ser Gln Ala Ala Gln Gly Gly Pro Ala Lys Gln Leu Leu Pro
            180                 185                 190

Leu Glu Arg Val Tyr Gln Glu Ile Ala Ile Leu Lys Lys Leu Asp His
            195                 200                 205

Val Asn Val Val Lys Leu Ile Glu Val Leu Asp Asp Pro Ala Glu Asp
210                 215                 220

Asn Leu Tyr Leu Val Phe Asp Leu Leu Arg Lys Gly Pro Val Met Glu
225                 230                 235                 240

Val Pro Cys Asp Lys Pro Phe Ser Glu Glu Gln Ala Arg Leu Tyr Leu
                245                 250                 255

Arg Asp Val Ile Leu Gly Leu Glu Tyr Leu His Cys Gln Lys Ile Val
            260                 265                 270

His Arg Asp Ile Lys Pro Ser Asn Leu Leu Leu Gly Asp Asp Gly His
            275                 280                 285

Val Lys Ile Ala Asp Phe Gly Val Ser Asn Gln Phe Glu Gly Asn Asp
290                 295                 300

Ala Gln Leu Ser Ser Thr Ala Gly Thr Pro Ala Phe Met Ala Pro Glu
305                 310                 315                 320

Ala Ile Ser Asp Ser Gly Gln Ser Phe Ser Gly Lys Ala Leu Asp Val
                325                 330                 335

Trp Ala Thr Gly Val Thr Leu Tyr Cys Phe Val Tyr Gly Lys Cys Pro
            340                 345                 350

Phe Ile Asp Asp Phe Ile Leu Ala Leu His Arg Lys Ile Lys Asn Glu
            355                 360                 365

Pro Val Val Phe Pro Glu Glu Pro Glu Ile Ser Glu Glu Leu Lys Asp
370                 375                 380

Leu Ile Leu Lys Met Leu Asp Lys Asn Pro Glu Thr Arg Ile Gly Val
385                 390                 395                 400

Pro Asp Ile Lys Leu His Pro Trp Val Thr Lys Asn Gly Glu Glu Pro
                405                 410                 415

Leu Pro Ser Glu Glu Glu His Cys Ser Val Val Glu Val Thr Glu Glu
            420                 425                 430

Glu Val Lys Asn Ser Val Arg Leu Ile Pro Ser Trp Thr Thr Val Ile
            435                 440                 445

Leu Val Lys Ser Met Leu Arg Lys Arg Ser Phe Gly Asn Pro Phe Glu
            450                 455                 460

Pro Gln Ala Arg Arg Glu Glu Arg Ser Met Ser Ala Pro Gly Asn Leu
465                 470                 475                 480
```

Leu Val Lys Glu Gly Phe Gly Glu Gly Gly Lys Ser Pro Glu Leu Pro
            485                 490                 495
Gly Val Gln Glu Asp Glu Ala Ala Ser
            500                 505

<210> SEQ ID NO 19
<211> LENGTH: 2535
<212> TYPE: DNA
<213> ORGANISM: Artificial Sequence
<220> FEATURE:
<223> OTHER INFORMATION: Synthetic

<400> SEQUENCE: 19

| | | | | | |
|---|---|---|---|---|---|
| ctgggcccca | gcgaggcggt | ggggcgggc | ggggcgggc | ggggcgcgca | gcaggagcga | 60 |
| gtggggccgc | cgccgggcc | gcggacactg | tcgcccggcg | cccaggttcc | caacaaggct | 120 |
| acgcagaaga | accccttga | ctgaagcaat | ggaggggggt | ccagctgtct | gctgccagga | 180 |
| tcctcgggca | gagctggtag | aacgggtggc | agccatcgat | gtgactcact | ggaggaggc | 240 |
| agatggtggc | ccagagccta | ctagaaacgg | tgtggacccc | ccaccacggg | ccagagctgc | 300 |
| ctctgtgatc | cctggcagta | cttcaagact | gctcccagcc | cggcctagcc | tctcagccag | 360 |
| gaagctttcc | ctacaggagc | ggccagcagg | aagctatctg | gaggcgcagg | ctgggcctta | 420 |
| tgccacgggg | cctgccagcc | acatctcccc | ccgggcctgg | cggaggccca | ccatcgagtc | 480 |
| ccaccacgtg | gccatctcag | atgcagagga | ctgcgtgcag | ctgaaccagt | acaagctgca | 540 |
| gagtgagatt | ggcaagggtg | cctacggtgt | ggtgaggctg | gcctacaacg | aaagtgaaga | 600 |
| cagacactat | gcaatgaaag | tcctttccaa | aaagaagtta | ctgaagcagt | atggcttttcc | 660 |
| acgtcgccct | ccccgagag | ggtcccaggc | tgcccaggga | ggaccagcca | agcagctgct | 720 |
| gccctggag | cgggtgtacc | aggagattgc | catcctgaag | aagctggacc | acgtgaatgt | 780 |
| ggtcaaactg | atcgaggtcc | tggatgaccc | agctgaggac | aacctctatt | tggccctgca | 840 |
| gaaccaggcc | cagaatatcc | agttagattc | aacaaatatc | gccaagcccc | actccctgct | 900 |
| tccctctgag | cagcaagaca | gtggatccac | gtgggctgcg | cgctcagtgt | ttgacctcct | 960 |
| gagaaagggg | cccgtcatgg | aagtgccctg | tgacaagccc | ttctcggagg | agcaagctcg | 1020 |
| cctctacctg | cgggacgtca | tcctgggcct | cgagtacttg | cactgccaga | gatcgtcca | 1080 |
| cagggacatc | aagccatcca | acctgctcct | gggggatgat | gggcacgtga | gatcgccga | 1140 |
| ctttggcgtc | agcaaccagt | ttgagggaa | cgacgctcag | ctgtccagca | cggcgggaac | 1200 |
| cccagcattc | atgccccccg | aggccatttc | tgattccggc | cagagcttca | gtgggaaggc | 1260 |
| cttggatgta | tgggccactg | gcgtcacgtt | gtactgcttt | gtctatggga | agtgcccatt | 1320 |
| catcgacgat | ttcatcctgg | ccctccacag | gaagatcaag | aatgagcccg | tggtgtttcc | 1380 |
| tgaggagcca | gaaatcagcg | aggagctcaa | ggacctgatc | ctgaagatgt | tagacaagaa | 1440 |
| tcccgagacg | agaattgggg | tgccagacat | caagttgcac | ccttgggtga | ccaagaacgg | 1500 |
| ggaggagccc | cttccttcgg | aggaggagca | ctgcagcgtg | gtggaggtga | cagaggagga | 1560 |
| ggttaagaac | tcagtcaggc | tcatccccag | ctgaccacg | gtgatcctgg | tgaagtccat | 1620 |
| gctgaggaag | cgttcctttg | gaacccgtt | tgagccccaa | gcacggaggg | aagagcgatc | 1680 |
| catgtctgct | ccaggaaacc | tactggtgta | agtactggtg | ggccagggac | tgccgggcac | 1740 |
| tccctggagt | tgggtgggga | ggtctgaggc | ccatcctccc | actctcactg | tcgttgggcc | 1800 |
| aaggccagag | cctgggggact | tggccaggtc | tcggtgttgg | ccccatttgc | atctctgtcc | 1860 |

```
ccaaggttag tcggggctag aagggacctt ttgggcccag ctcttgcttc attcctgggg      1920
ccagcatccc tcacacacac acttccaggg atgaggagct cacgcagccc ctccatggga      1980
caggaagacc cttcttccat gcagcttgat gtcactctct cactgggtcc agcccctctg      2040
gggcttcaaa tctgtggccc cctcagccct tggcagcctg cagaggttt gcagacaggc       2100 tgatgttggc ttcctgtagg aggctggcgg gctgtagagg aggggtgctg gcccctctgc     2160
ctggccctgg ggactgttgg ctgctctccc aagtgggcca ggctgcctgc agccattgct     2220
ggggctctgt gcccagtcag cactttgtga gtgcttgttc agtgagtaag cagggacagg     2280
ctggccggtg gaccacggga gaggaacccg cattggccga gggctcccta tggtgagcca     2340
cgcctgtggg ttcaccacct cctaggaggg tccagaaaag cagctcccca agcctgtgcg     2400
cctcgtcctc agcagatcca ccttcttcac tataataaaa gccagtctgg gatgctaaaa     2460
aaaaaaaaaa aaaaaaaaaa aaaaaaaaaa aaaaaaaaaa aaaaaaaaaa aaaaaaaaaa     2520
aaaaaaaaaa aaaaa                                                      2535

<210> SEQ ID NO 20
<211> LENGTH: 520
<212> TYPE: PRT
<213> ORGANISM: Artificial Sequence
<220> FEATURE:
<223> OTHER INFORMATION: Synthetic

<400> SEQUENCE: 20

Met Glu Gly Gly Pro Ala Val Cys Cys Gln Asp Pro Arg Ala Glu Leu
1               5                   10                  15

Val Glu Arg Val Ala Ala Ile Asp Val Thr His Leu Glu Glu Ala Asp
            20                  25                  30

Gly Gly Pro Glu Pro Thr Arg Asn Gly Val Asp Pro Pro Arg Ala
        35                  40                  45

Arg Ala Ala Ser Val Ile Pro Gly Ser Thr Ser Arg Leu Leu Pro Ala
    50                  55                  60

Arg Pro Ser Leu Ser Ala Arg Lys Leu Ser Leu Gln Glu Arg Pro Ala
65                  70                  75                  80

Gly Ser Tyr Leu Glu Ala Gln Ala Gly Pro Tyr Ala Thr Gly Pro Ala
                85                  90                  95

Ser His Ile Ser Pro Arg Ala Trp Arg Arg Pro Thr Ile Glu Ser His
            100                 105                 110

His Val Ala Ile Ser Asp Ala Glu Asp Cys Val Gln Leu Asn Gln Tyr
        115                 120                 125

Lys Leu Gln Ser Glu Ile Gly Lys Gly Ala Tyr Gly Val Val Arg Leu
    130                 135                 140

Ala Tyr Asn Glu Ser Glu Asp Arg His Tyr Ala Met Lys Val Leu Ser
145                 150                 155                 160

Lys Lys Lys Leu Leu Lys Gln Tyr Gly Phe Pro Arg Arg Pro Pro Pro
                165                 170                 175

Arg Gly Ser Gln Ala Ala Gln Gly Gly Pro Ala Lys Gln Leu Leu Pro
            180                 185                 190

Leu Glu Arg Val Tyr Gln Glu Ile Ala Ile Leu Lys Lys Leu Asp His
        195                 200                 205

Val Asn Val Val Lys Leu Ile Glu Val Leu Asp Asp Pro Ala Glu Asp
    210                 215                 220

Asn Leu Tyr Leu Ala Leu Gln Asn Gln Ala Gln Asn Ile Gln Leu Asp
225                 230                 235                 240
```

```
Ser Thr Asn Ile Ala Lys Pro His Ser Leu Leu Pro Ser Glu Gln Gln
                245                 250                 255

Asp Ser Gly Ser Thr Trp Ala Ala Arg Ser Val Phe Asp Leu Leu Arg
            260                 265                 270

Lys Gly Pro Val Met Glu Val Pro Cys Asp Lys Pro Phe Ser Glu Glu
        275                 280                 285

Gln Ala Arg Leu Tyr Leu Arg Asp Val Ile Leu Gly Leu Glu Tyr Leu
    290                 295                 300

His Cys Gln Lys Ile Val His Arg Asp Ile Lys Pro Ser Asn Leu Leu
305                 310                 315                 320

Leu Gly Asp Asp Gly His Val Lys Ile Ala Asp Phe Gly Val Ser Asn
                325                 330                 335

Gln Phe Glu Gly Asn Asp Ala Gln Leu Ser Ser Thr Ala Gly Thr Pro
            340                 345                 350

Ala Phe Met Ala Pro Glu Ala Ile Ser Asp Ser Gly Gln Ser Phe Ser
        355                 360                 365

Gly Lys Ala Leu Asp Val Trp Ala Thr Gly Val Thr Leu Tyr Cys Phe
    370                 375                 380

Val Tyr Gly Lys Cys Pro Phe Ile Asp Asp Phe Ile Leu Ala Leu His
385                 390                 395                 400

Arg Lys Ile Lys Asn Glu Pro Val Val Phe Pro Glu Glu Pro Glu Ile
                405                 410                 415

Ser Glu Glu Leu Lys Asp Leu Ile Leu Lys Met Leu Asp Lys Asn Pro
            420                 425                 430

Glu Thr Arg Ile Gly Val Pro Asp Ile Lys Leu His Pro Trp Val Thr
        435                 440                 445

Lys Asn Gly Glu Glu Pro Leu Pro Ser Glu Glu His Cys Ser Val
    450                 455                 460

Val Glu Val Thr Glu Glu Val Lys Asn Ser Val Arg Leu Ile Pro
465                 470                 475                 480

Ser Trp Thr Thr Val Ile Leu Val Lys Ser Met Leu Arg Lys Arg Ser
                485                 490                 495

Phe Gly Asn Pro Phe Glu Pro Gln Ala Arg Arg Glu Glu Arg Ser Met
            500                 505                 510

Ser Ala Pro Gly Asn Leu Leu Val
        515                 520

<210> SEQ ID NO 21
<211> LENGTH: 5085
<212> TYPE: DNA
<213> ORGANISM: Artificial Sequence
<220> FEATURE:
<223> OTHER INFORMATION: Synthetic

<400> SEQUENCE: 21
agcgccatgc gcagactcag ttcctggaga aagatggcga cagccgagaa gcagaaacac      60
gacgggcggg tgaagatcgg ccactacatt ctgggtgaca cgctgggggt cggcaccttc     120
ggcaaagtga aggttggcaa acatgaattg actgggcata agtagctgt gaagatactc      180 aatcgacaga agattcggag ccttgatgtg gtaggaaaaa tccgcagaga aattcagaac     240
ctcaagcttt tcaggcatcc tcatataatt aaactgtacc aggtcatcag tacaccatct     300
gatattttca tggtgatgga atatgtctca ggaggagagc tatttgatta tatctgtaag     360
aatggaaggc tggatgaaaa agaaagtcgg cgtctgttcc aacagatcct ttctggtgtg     420
gattattgtc acaggcatat ggtggtccat agagatttga aacctgaaaa tgtcctgctt     480
```

```
gatgcacaca tgaatgcaaa gatagctgat tttggtctttt caaacatgat gtcagatggt      540
gaatttttaa gaacaagttg tggctcaccc aactatgctg caccagaagt aatttcagga      600
agattgtatg caggcccaga ggtagatata tggagcagtg gggttattct ctatgcttta      660
ttatgtggaa cccttccatt tgatgatgac catgtgccaa ctctttttaa gaagatatgt      720
gatgggatct tctataccc tcaatattta aatccttctg tgattagcct tttgaaacat       780
atgctgcagg tggatcccat gaagagggcc acaatcaaag atatcaggga acatgaatgg      840
tttaaacagg accttccaaa atatctcttt cctgaggatc catcatatag ttcaaccatg      900
attgatgatg aagccttaaa agaagtatgt gaaaagtttg agtgctcaga agaggaagtt      960
ctcagctgtc tttacaacag aaatcaccag gatcctttgg cagttgccta ccatctcata     1020
atagataaca ggagaataat gaatgaagcc aaagatttct atttggcgac aagcccacct     1080
gattcttttc ttgatgatca tcacctgact cggccccatc ctgaaagagt accattcttg     1140
gttgctgaaa caccaagggc acgccatacc cttgatgaat aaatccaca gaaatccaaa      1200 caccaaggtg taaggaaagc aaaatggcat ttaggaatta gaagtcaaag tcgaccaaat     1260
gatattatgg cagaagtatg tagagcaatc aaacaattgg attatgaatg gaaggttgta     1320
aacccatatt atttgcgtgt acgaaggaag aatcctgtga caagcactta ctccaaaatg     1380
agtctacagt tataccaagt ggatagtaga acttatctac tggatttccg tagtattgat     1440
gatgaaatta cagaagccaa atcagggact gctactccac agagatcggg atcagttagc     1500
aactatcgat cttgccaaag gagtgattca gatgctgagg ctcaaggaaa atcctcagaa     1560
gtttctctta cctcatctgt gacctcactt gactcttctc ctgttgacct aactccaaga     1620
cctggaagtc acacaataga attttttgag atgtgtgcaa atctaattaa aattcttgca     1680
caataaacag aaaactttgc ttatttcttt tgcagcaata agcatgcata taagtcaca      1740 gccaaatgct tccatttgta atcaagttat acataattat aaccgagggc tggcgttttg     1800
gaatgcaatt tgcacaggga ttggaacatg atttatagtt aaaagcctaa tatgcagaaa     1860
tgaattaaga tcattttgtt gttcattgtg cagtatgtat atagcataat atacacagtg     1920
aattataggt ctcaggctta cttgattttt ggctatttta tatttagtgt acacagggct     1980
ttgaaatatt aatttacata aaggccttca tatattatta cgtgttatat attacgtgtt     2040
ataaatttat tcaataaata tttgcctaga attcccaaga cctttatagg tgattttgtt     2100
ttctgggctc cttaacttca taaatagcta gtatcttcca gcagtagtaa cagtctggat     2160
aacttcttcc atatccctcc ctctttgttt ttttgagaca gtgtcacttt gtcacccagg     2220
ctggagtgca atggtgtggt ctcggctcac tgcaacctcc acctcccggg ttcaagtgat     2280
tctcccgcct cagcttcctg agtagctgga actacaggcg tgtgccacca cacccggcta     2340 attttttcgta tttttagtgt agacggggtt tcactatgtt gcccaggctg gtctcgaact     2400
cctgaccgcg tgatccacca cctcagcttc ccaaagtggt gggattacag gcgtgagcca     2460
ccgcacccgg cctccatatc ccccttttaa aattctgtag tgtatggtaa gtcatatcag     2520
atatcagacc taatttaaat ttcattttag ctttacaagt ccaaaaacac agaatttata     2580
tattcagata ctctagcact aatttttagtc ttaaatatt cccacgatat tctgtacaca     2640
aaatgttctt tttgttacaa gagctgagtt gcatatactg tagataaatc atattatttt     2700
tgccaatttc acaaattcct ctggcccatc atgtcagtca ttattgagta tatgcacaca     2760
ttgctactta tttgattatg tatcttttaa attgattcag tgcatagaaa actatctctt     2820
```

```
acaaacttta agtgctctga tatgacttcc cccccaaatt ttattatgaa cattttttaaa    2880
aacagaaaaa ttgaaaaact gtttggtaag cacatgtata tctaccattt agattcagca    2940
gttgttaatg ttttgtcatt tgttttctct atacctatat atgtatagat acagctagtt    3000
atgcatatat atgcatatat gtgtttgttt gtgtatgtat atatgctttt ttcccctga     3060
accatttgga tgttacagac atacttatca ccgtgaaaat acttcaagta tctcctacag    3120
ataatgacat tctcctaaaa atccgtaata ccattgtaaa agtaataatt ccccaatatc    3180
atctaatcaa gccatatttta aatttctgaa gttaactcca aatttcttta tagctgatta   3240
tttcaaacta ggatccaatt aaagtttaca tatgacactt ggttataact ctttagttgg    3300
atataacatt attattattt tgataaaata tggaacaaat caattctatt aataagtggt    3360
cacatttgtt ttgggcttaa attacttttt aaagatactg gattttccta agatttctga    3420
tttacactga tattttttttt tgtcattctt aattgcatca cacaatagat gtaaatgaag   3480
atgtagtcac ctcagataaa attggtatcg tgtatgataa tattgtatca tttatatttg    3540
ccttatgtta actttaagaa attgattttt ttgtattaat cattttccca ttgcaacaga    3600
gctatatttt ttctatttta agaatcatat tttaggatta ttttttggcaa atacagtgag   3660
cacttatgta accagatgat aatgaactca atgtcatga tagcttgcat aaatggtgac     3720
tctagtagat ttgactcaag cacttctaga atcatgcact gaattcaaaa gaaaaatctt    3780
gctgcttttt gtccagggct tgttctattc aacttctaat ttgaaagctg tacaaagtaa    3840
tagaagttcc atttaaatat gagttcaaaa ctgtatttac tttttatgtg gccctctctt    3900
taggggattc taatttttact tagggtctct aagtgcagca taatgttcct gatgttaaca   3960
gaagactgta ttttttaaagt tacaaatttg tatatggaat taagtaatgg cgctatatac   4020
gctgttgtgg ggaggggga agaaaaggag gaaccaatta aataggacct tttaaaaatt    4080
gttaatttttg taaactttgc ttctcttata agttattgtg attcatttta gttactgtgt   4140
tttattttga aaaatatttaa atattgcact tctataaata gtatgataaa tgcacagaca   4200
attgcagtaa attctttttt aagctaggat atttgaaatg acaacctttg gttaagtgtg    4260
tcaaggttgc aacagaattt tcacaatttt tttgttgttt gcaaattgtt actaatattg    4320
aagaggtaag ggaggcaatg caaatgattt ttaatctttt tttattatct tttcagcagt    4380
ttatattttt tgtgacttta tgcaaccata ttttttacttt gtcttgacaa ctgaaagatg   4440
tataaggttt tttgccagaa atgtactgta tacatagttt taagtataac agatttttact  4500
gatatgtaaa aattttgcca ttaaaataaa tgatttctca ctgagaggaa cttttctacc    4560
aggttgggc atatgggagc ttaatatatc atatctaatt taaaataatt tcactgaaat     4620
aaactccatt gcttttacct aatttttttc ttgagatgct tttgtagttt ttcagagttt    4680
tagatgattt tatacaaaat cctctgccta gcactgctct ttttgatgtt gtagtgacac    4740
catttacatt gaattaatgc ttggtagcct ggggctagat gtggaactcc atggatctgt    4800
gttctgactg gcacctttgg aatgaaagaa aagtgtgtgc tgtccaaatt ttttcccctt    4860
aattctttcc ctcatcttct cacccataat agaaatttta tttccattgt gagttctgac    4920
aagaatgaaa ttccacatac aacataactg taaattgttg gtaggtagaa gttaatattt    4980
gtggttcatg tatattttga ccagagtata tttaagtata taatttcagc ttccttgatt    5040
tagaaatatg atataataaa gaaaaactcc atttatcatc tgtta                    5085
```

<210> SEQ ID NO 22
<211> LENGTH: 559

```
<212> TYPE: PRT
<213> ORGANISM: Artificial Sequence
<220> FEATURE:
<223> OTHER INFORMATION: Synthetic

<400> SEQUENCE: 22

Met Arg Arg Leu Ser Ser Trp Arg Lys Met Ala Thr Ala Glu Lys Gln
1               5                   10                  15

Lys His Asp Gly Arg Val Lys Ile Gly His Tyr Ile Leu Gly Asp Thr
            20                  25                  30

Leu Gly Val Gly Thr Phe Gly Lys Val Lys Val Gly Lys His Glu Leu
        35                  40                  45

Thr Gly His Lys Val Ala Val Lys Ile Leu Asn Arg Gln Lys Ile Arg
    50                  55                  60

Ser Leu Asp Val Val Gly Lys Ile Arg Arg Glu Ile Gln Asn Leu Lys
65                  70                  75                  80

Leu Phe Arg His Pro His Ile Ile Lys Leu Tyr Gln Val Ile Ser Thr
                85                  90                  95

Pro Ser Asp Ile Phe Met Val Met Glu Tyr Val Ser Gly Gly Glu Leu
            100                 105                 110

Phe Asp Tyr Ile Cys Lys Asn Gly Arg Leu Asp Glu Lys Glu Ser Arg
        115                 120                 125

Arg Leu Phe Gln Gln Ile Leu Ser Gly Val Asp Tyr Cys His Arg His
    130                 135                 140

Met Val Val His Arg Asp Leu Lys Pro Glu Asn Val Leu Leu Asp Ala
145                 150                 155                 160

His Met Asn Ala Lys Ile Ala Asp Phe Gly Leu Ser Asn Met Met Ser
                165                 170                 175

Asp Gly Glu Phe Leu Arg Thr Ser Cys Gly Ser Pro Asn Tyr Ala Ala
            180                 185                 190

Pro Glu Val Ile Ser Gly Arg Leu Tyr Ala Gly Pro Glu Val Asp Ile
        195                 200                 205

Trp Ser Ser Gly Val Ile Leu Tyr Ala Leu Leu Cys Gly Thr Leu Pro
    210                 215                 220

Phe Asp Asp Asp His Val Pro Thr Leu Phe Lys Lys Ile Cys Asp Gly
225                 230                 235                 240

Ile Phe Tyr Thr Pro Gln Tyr Leu Asn Pro Ser Val Ile Ser Leu Leu
                245                 250                 255

Lys His Met Leu Gln Val Asp Pro Met Lys Arg Ala Thr Ile Lys Asp
            260                 265                 270

Ile Arg Glu His Glu Trp Phe Lys Gln Asp Leu Pro Lys Tyr Leu Phe
        275                 280                 285

Pro Glu Asp Pro Ser Tyr Ser Ser Thr Met Ile Asp Asp Glu Ala Leu
    290                 295                 300

Lys Glu Val Cys Glu Lys Phe Glu Cys Ser Glu Glu Val Leu Ser
305                 310                 315                 320

Cys Leu Tyr Asn Arg Asn His Gln Asp Pro Leu Ala Val Ala Tyr His
                325                 330                 335

Leu Ile Ile Asp Asn Arg Arg Ile Met Asn Glu Ala Lys Asp Phe Tyr
            340                 345                 350

Leu Ala Thr Ser Pro Pro Asp Ser Phe Leu Asp Asp His His Leu Thr
        355                 360                 365

Arg Pro His Pro Glu Arg Val Pro Phe Leu Val Ala Glu Thr Pro Arg
    370                 375                 380
```

```
Ala Arg His Thr Leu Asp Glu Leu Asn Pro Gln Lys Ser Lys His Gln
385                 390                 395                 400

Gly Val Arg Lys Ala Lys Trp His Leu Gly Ile Arg Ser Gln Ser Arg
            405                 410                 415

Pro Asn Asp Ile Met Ala Glu Val Cys Arg Ala Ile Lys Gln Leu Asp
        420                 425                 430

Tyr Glu Trp Lys Val Val Asn Pro Tyr Tyr Leu Arg Val Arg Arg Lys
    435                 440                 445

Asn Pro Val Thr Ser Thr Tyr Ser Lys Met Ser Leu Gln Leu Tyr Gln
    450                 455                 460

Val Asp Ser Arg Thr Tyr Leu Leu Asp Phe Arg Ser Ile Asp Asp Glu
465                 470                 475                 480

Ile Thr Glu Ala Lys Ser Gly Thr Ala Thr Pro Gln Arg Ser Gly Ser
                485                 490                 495

Val Ser Asn Tyr Arg Ser Cys Gln Arg Ser Asp Ser Asp Ala Glu Ala
                500                 505                 510

Gln Gly Lys Ser Ser Glu Val Ser Leu Thr Ser Ser Val Thr Ser Leu
            515                 520                 525

Asp Ser Ser Pro Val Asp Leu Thr Pro Arg Pro Gly Ser His Thr Ile
530                 535                 540

Glu Phe Phe Glu Met Cys Ala Asn Leu Ile Lys Ile Leu Ala Gln
545                 550                 555

<210> SEQ ID NO 23
<211> LENGTH: 5130
<212> TYPE: DNA
<213> ORGANISM: Artificial Sequence
<220> FEATURE:
<223> OTHER INFORMATION: Synthetic

<400> SEQUENCE: 23
agcgccatgc gcagactcag ttcctggaga aagatggcga cagccgagaa gcagaaacac     60
gacgggcggg tgaagatcgg ccactacatt ctgggtgaca cgctgggggt cggcaccttc    120
ggcaaagtga aggttggcaa acatgaattg actgggcata agtagctgt gaagatactc     180 aatcgacaga gattcggag ccttgatgtg gtaggaaaaa tccgcagaga aattcagaac     240
ctcaagcttt tcaggcatcc tcatataatt aaactgtacc aggtcatcag tacaccatct    300
gatattttca tggtgatgga atatgtctca ggaggagagc tatttgatta tatctgtaag    360
aatggaagga atctgatgt acctggagta gtaaaaacag ctccacgaa ggagctggat      420 gaaaagaaa gtcggcgtct gttccaacag atcctttctg gtgtggatta ttgtcacagg    480
catatggtgg tccatagaga tttgaaacct gaaaatgtcc tgcttgatgc acacatgaat    540
gcaaagatag ctgattttgg tctttcaaac atgatgtcag atggtgaatt tttaagaaca    600
agttgtggct cacccaacta tgctgcacca gaagtaattt caggaagatt gtatgcaggc    660
ccagaggtag atatatggag cagtggggtt attctctatg ctttattatg tggaaccctt    720
ccatttgatg atgaccatgt gccaactctt tttaagaaga tatgtgatgg gatcttctat    780
acccctcaat atttaaatcc ttctgtgatt agccttttga acatatgct gcaggtggat    840 cccatgaaga gggccacaat caaagatatc agggaacatg aatggtttaa acaggacctt    900
ccaaaatatc tctttcctga ggatccatca tatagttcaa ccatgattga tgatgaagcc    960 ttaaagaag tatgtgaaaa gtttgagtgc tcagaagagg aagttctcag ctgtctttac   1020
aacagaaatc accaggatcc tttggcagtt gcctaccatc tcataataga taacaggaga   1080
```

```
ataatgaatg aagccaaaga tttctatttg gcgacaagcc cacctgattc tttttcttgat    1140 gatcatcacc tgactcggcc ccatcctgaa agagtaccat tcttggttgc tgaaacacca    1200
agggcacgcc ataccettga tgaattaaat ccacagaaat ccaaacacca aggtgtaagg    1260
aaagcaaaat ggcatttagg aattagaagt caaagtcgac caaatgatat tatggcagaa    1320
gtatgtagag caatcaaaca attggattat gaatggaagg ttgtaaaccc atattatttg    1380
cgtgtacgaa ggaagaatcc tgtgacaagc acttactcca aaatgagtct acagttatac    1440
caagtggata gtagaactta tctactggat ttccgtagta ttgatgatga aattacagaa    1500
gccaaatcag ggactgctac tccacagaga tcgggatcag ttagcaacta tcgatcttgc    1560
caaaggagtg attcagatgc tgaggctcaa ggaaaatcct cagaagtttc tcttacctca    1620
tctgtgacct cacttgactc ttctcctgtt gacctaactc caagacctgg aagtcacaca    1680
atagaatttt ttgagatgtg tgcaaatcta attaaaattc ttgcacaata aacagaaaac    1740
tttgcttatt tcttttgcag caataagcat gcataataag tcacagccaa atgcttccat    1800
ttgtaatcaa gttatacata attataaccg agggctggcg ttttggaatg caatttgcac    1860
agggattgga acatgattta tagttaaaag cctaatatgc agaaatgaat taagatcatt    1920
ttgttgttca ttgtgcagta tgtatatagc ataatataca cagtgaatta taggtctcag    1980
gcttacttga tttttggcta ttttatattt agtgtacaca gggctttgaa atattaattt    2040
acataaaggc cttcatatat tattacgtgt tatatattac gtgttataaa tttattcaat    2100
aaatatttgc ctagaattcc caagaccttt ataggtgatt tgttttctg  ggctccttaa    2160 cttcataaat agctagtatc ttccagcagt agtaacagtc tggataactt cttccatatc    2220
cctccctctt tgttttttg  agacagtgtc actttgtcac ccaggctgga gtgcaatggt    2280
gtggtctcgg ctcactgcaa cctccacctc ccgggttcaa gtgattctcc cgcctcagct    2340
tcctgagtag ctggaactac aggcgtgtgc caccacaccc ggctaatttt tcgtattttt    2400
agtgtagacg gggtttcact atgttgccca ggctggtctc gaactcctga ccgcgtgatc    2460
caccacctca gcttcccaaa gtggtgggat tacaggcgtg agccaccgca cccggcctcc    2520
atatccccct tttaaaattc tgtagtgtat ggtaagtcat atcagatatc agacctaatt    2580
taaatttcat tttagcttta caagtccaaa acacagaat  ttatatattc agatactcta    2640
gcactaattt tagtcttaaa atattcccac gatattctgt acacaaaatg ttcttttgt    2700 tacaagagct gagttgcata tactgtagat aaatcatatt attttttgcca atttcacaaa    2760 ttcctctggc ccatcatgtc agtcattatt gagtatatgc acacattgct acttatttga    2820
ttatgtatct tttaaattga ttcagtgcat agaaaactat ctcttacaaa ctttaagtgc    2880
tctgatatga cttcccccc  aaattttatt atgaacattt ttaaaaacag aaaaattgaa    2940
aaactgtttg gtaagcacat gtatatctac catttagatt cagcagttgt taatgttttg    3000
tcatttgttt tctctatacc tatatatgta tagatacagc tagttatgca tatatatgca    3060
tatatgtgtt tgtttgtgta tgtatatatg ctttttccc  cctgaaccat ttggatgtta    3120
cagacatact tatcaccgtg aaaatacttc aagtatctcc tacagataat gacattctcc    3180
taaaaatccg taataccatt gtaaaagtaa taattcccca atatcatcta atcaagccat    3240
atttaaattt ctgaagttaa ctccaaattt ctttatagct gattatttca aactaggatc    3300
caattaaagt ttacatatga cacttggtta taactcttta gttggatata acattattat    3360
tattttgata aaatatggaa caaatcaatt ctattaataa gtggtcacat ttgttttggg    3420
cttaaattac tttttaaaga tactggattt tcctaagatt tctgatttac actgatattt    3480
```

```
tttttttgtca ttcttaattg catcacacaa tagatgtaaa tgaagatgta gtcacctcag   3540
ataaaattgg tatcgtgtat gataatattg tatcatttat atttgcctta tgttaacttt   3600
aagaaattga ttttttttgta ttaatcattt tcccattgca acagagctat attttttcta   3660
ttttaagaat catattttag gattattttt ggcaaataca gtgagcactt atgtaaccag   3720
atgataatga actcaaatgt catgatagct tgcataaatg gtgactctag tagatttgac   3780
tcaagcactt ctagaatcat gcactgaatt caaaagaaaa atcttgctgc ttttttgtcca   3840 gggcttgttc tattcaactt ctaatttgaa agctgtacaa agtaatagaa gttccattta   3900
aatatgagtt caaaactgta tttacttttt atgtggccct ctctttaggg gattctaatt   3960
ttacttaggg tctctaagtg cagcataatg ttcctgatgt taacagaaga ctgtattttt   4020
aaagttacaa atttgtatat ggaattaagt aatggcgcta tacgctgt tgtggggagg      4080 ggggaagaaa aggaggaacc aattaaatag gaccttttaa aaattgttaa ttttgtaaac   4140
tttgcttctc ttataagtta ttgtgattca ttttagttac tgtgtttat tttgaaaata     4200 tttaaatatt gcacttctat aaatagtatg ataaatgcac agacaattgc agtaaattct   4260
tttttaagct aggatattttg aaatgacaac ctttggttaa gtgtgtcaag gttgcaacag  4320
aattttcaca atttttttgt tgtttgcaaa ttgttactaa tattgaagag gtaagggagg   4380
caatgcaaat gatttttaat cttttttttat tatctttttca gcagtttata ttttttgtga  4440
ctttatgcaa ccatattttt actttgtctt gacaactgaa agatgtataa ggttttttgc   4500
cagaaatgta ctgtatacat agttttaagt ataacagatt ttactgatat gtaaaaattt   4560
tgccattaaa ataaatgatt tctcactgag aggaactttt ctaccaggtt ggggcatatg   4620
ggagcttaat atatcatatc taatttaaaa taatttcact gaaataaact ccattgcttt   4680
tacctaattt ttttcttgag atgcttttgt agttttcag agttttagat gatttttatac   4740 aaaatcctct gcctagcact gctctttttg atgttgtagt gacaccattt acattgaatt   4800
aatgcttggt agcctggggc tagatgtgga actccatgga tctgtgttct gactggcacc   4860
tttggaatga aagaaaagtg tgtgctgtcc aaatttttcc ccttaattc tttccctcat     4920 cttctcaccc ataatagaaa ttttatttcc attgtgagtt ctgacaagaa tgaaattcca   4980
catacaacat aactgtaaat tgttggtagg tagaagttaa tatttgtggt tcatgtatat   5040
tttgaccaga gtatatttaa gtatataatt tcagcttcct tgatttagaa atatgatata  5100
ataaagaaaa actccatttta tcatctgtta                                   5130
```

<210> SEQ ID NO 24
<211> LENGTH: 574
<212> TYPE: PRT
<213> ORGANISM: Artificial Sequence
<220> FEATURE:
<223> OTHER INFORMATION: Synthetic

<400> SEQUENCE: 24

Met Arg Arg Leu Ser Ser Trp Arg Lys Met Ala Thr Ala Glu Lys Gln
1               5                   10                  15

Lys His Asp Gly Arg Val Lys Ile Gly His Tyr Ile Leu Gly Asp Thr
            20                  25                  30

Leu Gly Val Gly Thr Phe Gly Lys Val Lys Val Gly Lys His Glu Leu
        35                  40                  45

Thr Gly His Lys Val Ala Val Lys Ile Leu Asn Arg Gln Lys Ile Arg
    50                  55                  60

-continued

```
Ser Leu Asp Val Val Gly Lys Ile Arg Arg Glu Ile Gln Asn Leu Lys
 65                  70                  75                  80

Leu Phe Arg His Pro His Ile Ile Lys Leu Tyr Gln Val Ile Ser Thr
                 85                  90                  95

Pro Ser Asp Ile Phe Met Val Met Glu Tyr Val Ser Gly Gly Glu Leu
            100                 105                 110

Phe Asp Tyr Ile Cys Lys Asn Gly Arg Lys Ser Asp Val Pro Gly Val
        115                 120                 125

Val Lys Thr Gly Ser Thr Lys Glu Leu Asp Glu Lys Gly Ser Arg Arg
    130                 135                 140

Leu Phe Gln Gln Ile Leu Ser Gly Val Asp Tyr Cys His Arg His Met
145                 150                 155                 160

Val Val His Arg Asp Leu Lys Pro Glu Asn Val Leu Leu Asp Ala His
                165                 170                 175

Met Asn Ala Lys Ile Ala Asp Phe Gly Leu Ser Asn Met Met Ser Asp
            180                 185                 190

Gly Glu Phe Leu Arg Thr Ser Cys Gly Ser Pro Asn Tyr Ala Ala Pro
        195                 200                 205

Glu Val Ile Ser Gly Arg Leu Tyr Ala Gly Pro Glu Val Asp Ile Trp
    210                 215                 220

Ser Ser Gly Val Ile Leu Tyr Ala Leu Leu Cys Gly Thr Leu Pro Phe
225                 230                 235                 240

Asp Asp Asp His Val Pro Thr Leu Phe Lys Lys Ile Cys Asp Gly Ile
                245                 250                 255

Phe Tyr Thr Pro Gln Tyr Leu Asn Pro Ser Val Ile Ser Leu Leu Lys
            260                 265                 270

His Met Leu Gln Val Asp Pro Met Lys Arg Ala Thr Ile Lys Asp Ile
        275                 280                 285

Arg Glu His Glu Trp Phe Lys Gln Asp Leu Pro Lys Tyr Leu Phe Pro
    290                 295                 300

Glu Asp Pro Ser Tyr Ser Ser Thr Met Ile Asp Asp Glu Ala Leu Lys
305                 310                 315                 320

Glu Val Cys Glu Lys Phe Glu Cys Ser Glu Glu Glu Val Leu Ser Cys
                325                 330                 335

Leu Tyr Asn Arg Asn His Gln Asp Pro Leu Ala Val Ala Tyr His Leu
            340                 345                 350

Ile Ile Asp Asn Arg Arg Ile Met Asn Glu Ala Lys Asp Phe Tyr Leu
        355                 360                 365

Ala Thr Ser Pro Pro Asp Ser Phe Leu Asp Asp His His Leu Thr Arg
    370                 375                 380

Pro His Pro Glu Arg Val Pro Phe Leu Val Ala Glu Thr Pro Arg Ala
385                 390                 395                 400

Arg His Thr Leu Asp Glu Leu Asn Pro Gln Lys Ser Lys His Gln Gly
                405                 410                 415

Val Arg Lys Ala Lys Trp His Leu Gly Ile Arg Ser Gln Ser Arg Pro
            420                 425                 430

Asn Asp Ile Met Ala Glu Val Cys Arg Ala Ile Lys Gln Leu Asp Tyr
        435                 440                 445

Glu Trp Lys Val Val Asn Pro Tyr Tyr Leu Arg Val Arg Arg Lys Asn
    450                 455                 460

Pro Val Thr Ser Thr Tyr Ser Lys Met Ser Leu Gln Leu Tyr Gln Val
465                 470                 475                 480

Asp Ser Arg Thr Tyr Leu Leu Asp Phe Arg Ser Ile Asp Asp Glu Ile
```

|     |     |     | 485 |     |     |     | 490 |     |     |     | 495 |     |
| --- | --- | --- | --- | --- | --- | --- | --- | --- | --- | --- | --- | --- |
| Thr | Glu | Ala | Lys | Ser | Gly | Thr | Ala | Thr | Pro | Gln | Arg | Ser | Gly | Ser | Val |
|     |     |     | 500 |     |     |     | 505 |     |     |     | 510 |     |

Ser Asn Tyr Arg Ser Cys Gln Arg Ser Asp Ser Asp Ala Glu Ala Gln
            515                 520                 525

Gly Lys Ser Ser Glu Val Ser Leu Thr Ser Ser Val Thr Ser Leu Asp
        530                 535                 540

Ser Ser Pro Val Asp Leu Thr Pro Arg Pro Gly Ser His Thr Ile Glu
545             550                 555                 560

Phe Phe Glu Met Cys Ala Asn Leu Ile Lys Ile Leu Ala Gln
                565                 570

<210> SEQ ID NO 25
<211> LENGTH: 1501
<212> TYPE: DNA
<213> ORGANISM: Artificial Sequence
<220> FEATURE:
<223> OTHER INFORMATION: Synthetic

<400> SEQUENCE: 25

```
ggagagagcc gccgagccga gccgagcccc agctccagca agagcgcggg cgggtggccc     60
aggcacgcag cggtgaggac gcggccaca gctcggcgcc aaccaccgcg ggcctcccag    120
ccagccccgc ggcggggcag ccgcaggagc cctggctgtg gtcggggggc agtgggccat    180
gctgggggca gtggaaggcc caggtggaa gcaggcggag gacattagag acatctacga    240
cttccgagat gttctgggca cggggggcctt ctcggaggtg atcctggcag aagataagag    300
gacgcagaag ctggtggcca tcaaatgcat tgccaaggag gccctggagg caaggaagg    360
cagcatggag aatgagattg ctgtcctgca caagatcaag cacccccaaca ttgtagccct    420
ggatgacatc tatgagagtg ggggccacct ctacctcatc atgcagctgg tgtcgggtgg    480
ggagctcttt gaccgtattg tggaaaaagg cttctacacg gagcgggacg ccagccgcct    540
catcttccag gtgctggatg ctgtgaaata cctgcatgac ctgggcattg taccacggga    600
tctcaagcca gagaatctgc tgtactacag cctggatgaa gactccaaaa tcatgatctc    660
cgactttggc ctctccaaga tggaggaccc gggcagtgtg ctctccaccg cctgtggaac    720
tccgggatac gtggcccctg aagtcctggc ccagaagccc tacagcaagg ctgtggattg    780
ctggtccata ggtgtcatcg cctacatctt gctctgcggt taccctccct tctatgacga    840
gaatgatgcc aaactctttg aacagatttt gaaggccgag tacgagtttg actctcctta    900
ctgggacgac atctctgact ctgccaaaga tttcatccgg cacttgatgg agaaggaccc    960
agagaaaaga ttcacctgtg agcaggcctt gcagcaccca tggattgcag agatacagc   1020
tctagataag aatatccacc agtcggtgag tgagcagatc aagaagaact ttgccaagag   1080
caagtggaag caagccttca atgccacggc tgtggtgcgg cacatgagga aactgcagct   1140
gggcaccagc caggagggc aggggcagac ggcgagccat gggagctgc tgacaccagt   1200
ggctgggggg ccggcagctg ctgttgctg tcgagactgc tgcgtggagc cgggcacaga   1260
actgtcccc acactgcccc accagctcta gggccctgga cctcgggtca tgatcctctg   1320
cgtgggaggg cttgggggca gcctgctccc cttccctccc tgaaccggga gtttctctgc   1380
cctgtcccct cctcacctgc ttccctacca ctcctcactg cattttccat acaaatgttt   1440
ctattttatt gttccttctt gtaataaagg gaagataaaa ccaaaaaaaa aaaaaaaaa   1500
a                                                                 1501
```

<210> SEQ ID NO 26
<211> LENGTH: 370
<212> TYPE: PRT
<213> ORGANISM: Artificial Sequence
<220> FEATURE:
<223> OTHER INFORMATION: Synthetic

<400> SEQUENCE: 26

```
Met Leu Gly Ala Val Glu Gly Pro Arg Trp Lys Gln Ala Glu Asp Ile
1               5                   10                  15

Arg Asp Ile Tyr Asp Phe Arg Asp Val Leu Gly Thr Gly Ala Phe Ser
            20                  25                  30

Glu Val Ile Leu Ala Glu Asp Lys Arg Thr Gln Lys Leu Val Ala Ile
        35                  40                  45

Lys Cys Ile Ala Lys Glu Ala Leu Glu Gly Lys Glu Gly Ser Met Glu
    50                  55                  60

Asn Glu Ile Ala Val Leu His Lys Ile Lys His Pro Asn Ile Val Ala
65                  70                  75                  80

Leu Asp Asp Ile Tyr Glu Ser Gly Gly His Leu Tyr Leu Ile Met Gln
                85                  90                  95

Leu Val Ser Gly Gly Glu Leu Phe Asp Arg Ile Val Glu Lys Gly Phe
            100                 105                 110

Tyr Thr Glu Arg Asp Ala Ser Arg Leu Ile Phe Gln Val Leu Asp Ala
        115                 120                 125

Val Lys Tyr Leu His Asp Leu Gly Ile Val His Arg Asp Leu Lys Pro
    130                 135                 140

Glu Asn Leu Leu Tyr Tyr Ser Leu Asp Glu Asp Ser Lys Ile Met Ile
145                 150                 155                 160

Ser Asp Phe Gly Leu Ser Lys Met Glu Asp Pro Gly Ser Val Leu Ser
                165                 170                 175

Thr Ala Cys Gly Thr Pro Gly Tyr Val Ala Pro Glu Val Leu Ala Gln
            180                 185                 190

Lys Pro Tyr Ser Lys Ala Val Asp Cys Trp Ser Ile Gly Val Ile Ala
        195                 200                 205

Tyr Ile Leu Leu Cys Gly Tyr Pro Pro Phe Tyr Asp Glu Asn Asp Ala
    210                 215                 220

Lys Leu Phe Glu Gln Ile Leu Lys Ala Glu Tyr Glu Phe Asp Ser Pro
225                 230                 235                 240

Tyr Trp Asp Asp Ile Ser Asp Ser Ala Lys Asp Phe Ile Arg His Leu
                245                 250                 255

Met Glu Lys Asp Pro Glu Lys Arg Phe Thr Cys Glu Gln Ala Leu Gln
            260                 265                 270

His Pro Trp Ile Ala Gly Asp Thr Ala Leu Asp Lys Asn Ile His Gln
        275                 280                 285

Ser Val Ser Glu Gln Ile Lys Lys Asn Phe Ala Lys Ser Lys Trp Lys
    290                 295                 300

Gln Ala Phe Asn Ala Thr Ala Val Val Arg His Met Arg Lys Leu Gln
305                 310                 315                 320

Leu Gly Thr Ser Gln Glu Gly Gln Gly Gln Thr Ala Ser His Gly Glu
                325                 330                 335

Leu Leu Thr Pro Val Ala Gly Gly Pro Ala Ala Gly Cys Cys Cys Arg
            340                 345                 350

Asp Cys Cys Val Glu Pro Gly Thr Glu Leu Ser Pro Thr Leu Pro His
        355                 360                 365
```

Gln Leu
  370

<210> SEQ ID NO 27
<211> LENGTH: 1888
<212> TYPE: DNA
<213> ORGANISM: Artificial Sequence
<220> FEATURE:
<223> OTHER INFORMATION: Synthetic

<400> SEQUENCE: 27

| | | | | | |
|---|---|---|---|---|---:|
| gacttggatt | gacatagaga | gctgcaggag | ggtgacatga | tctcaataaa | aggaatgctc | 60 |
| tggctgctgg | gtagagaaga | aagcgagggt | gagggattaa | tggtggagcc | agagggagcc | 120 |
| cagtgagtgc | cgggagccca | gggtggcaga | gctgtggtgc | agggttgcag | ggtcctggag | 180 |
| ctaggcatgg | aggctgcttt | cgggcaagtg | gccgggtcag | cctgtcctcg | gagaggcggt | 240 |
| gaaggcagag | actggaaggc | agagagcctt | gccgacctgt | ggccgaagag | ctctccggga | 300 |
| gacagccacc | ggtggtgcaa | aggccctggg | gccggcccag | ccgggccgca | gctccgggag | 360 |
| gcggcgcgag | cgagcagtgg | gctgggcggt | ggcggccggc | acccgagccg | gatcccggcg | 420 |
| attgccttac | aagacatgct | gctgctgaag | aaacacacgg | aggacatcag | cagcgtctac | 480 |
| gagatccgcg | agaggctcgg | ctcgggtgcc | ttctccgagg | tggtgctggc | ccaggagcgg | 540 |
| ggctccgcac | acctcgtggc | cctcaagtgc | atccccaaga | aggccctccg | gggcaaggag | 600 |
| gccctggtgg | agaacgagat | cgcagtgctc | cgtaggatca | gtcaccccaa | catcgtcgct | 660 |
| ctggaggatg | tccacgagag | cccttcccac | ctctacctgg | ccatggaact | ggtgacgggt | 720 |
| ggcgagctgt | ttgaccgcat | catggagcgc | ggctcctaca | cagagaagga | tgccagccat | 780 |
| ctggtgggtc | aggtccttgg | cgccgtctcc | tacctgcaca | gcctggggat | cgtgcaccgg | 840 |
| gacctcaagc | ccgaaaacct | cctgtatgcc | acgccctttg | aggactcgaa | gatcatggtc | 900 |
| tctgactttg | gactctccaa | aatccaggct | gggaacatgc | taggcaccgc | tgtgggacc | 960 |
| cctggatatg | tgccccaga | gctcttggag | cagaaaccct | acgggaaggc | cgtagatgtg | 1020 |
| tgggccctgg | gcgtcatctc | ctacatcctg | ctgtgtgggt | accccccctt | ctacgacgag | 1080 |
| agcgaccctg | agctcttcag | ccagatcctg | agggccagct | atgagtttga | ctctcctttc | 1140 |
| tgggatgaca | tctcagaatc | agccaaagac | ttcatccggc | accttctgga | gcgagacccc | 1200 |
| cagaagaggt | tcacctgcca | acaggccttg | cggcaccttt | ggatctctgg | ggacacagcc | 1260 |
| ttcgacaggg | acatcttagg | ctctgtcagt | gagcagatcc | ggaagaactt | gctcggaca | 1320 |
| cactggaagc | gagccttcaa | tgccacctcg | ttcctgcgcc | acatccggaa | gctggggcag | 1380 |
| atcccagagg | gcgaggggc | ctctgagcag | ggcatggccc | gccacagcca | ctcaggcctc | 1440 |
| cgtgctggcc | agccccccaa | gtggtgatgc | ccaggcagat | gccgaggcca | agtggactga | 1500 |
| cccccagatt | tccttcccctt | ggatgctttc | ggtcccctcc | cccaacccct | cccctgggg | 1560 |
| ctggcctctg | ctggattttg | agatttgagg | gtgtggcgca | tggcgctggg | gttggaatgg | 1620 |
| ggcaccccca | agtctgtccc | caggctctgc | cctgcctggg | ggcagtggct | cccctcccct | 1680 |
| gttgcctctc | ccgcccctgc | ccccccgcc | ccgccaaaag | ccgaggggggt | gctggcaggc | 1740 |
| gggcctcagg | ggctgtctttt | cctgcacggc | tgttgtgtgc | ttcgctgagt | gtgggtggtc | 1800 |
| ctgcttgtgt | catggtcatg | gccttccagc | cccctccagt | tttccccaaa | ccaataaaga | 1860 |
| aagatacagc | aaaaaaaaaa | aaaaaaaa | | | | 1888 |

<210> SEQ ID NO 28

<211> LENGTH: 426
<212> TYPE: PRT
<213> ORGANISM: Artificial Sequence
<220> FEATURE:
<223> OTHER INFORMATION: Synthetic

<400> SEQUENCE: 28

```
Met Glu Ala Ala Phe Gly Gln Val Ala Gly Ser Ala Cys Pro Arg Arg
1               5                   10                  15

Gly Gly Glu Gly Arg Asp Trp Lys Ala Glu Ser Leu Ala Asp Leu Trp
            20                  25                  30

Pro Lys Ser Ser Pro Gly Asp Ser His Arg Trp Cys Lys Gly Pro Gly
        35                  40                  45

Ala Gly Pro Ala Gly Pro Gln Leu Arg Glu Ala Ala Arg Ala Ser Ser
    50                  55                  60

Gly Leu Gly Gly Gly Arg His Pro Ser Arg Ile Pro Ala Ile Ala
65                  70                  75                  80

Leu Gln Asp Met Leu Leu Lys Lys His Thr Glu Asp Ile Ser Ser
                85                  90                  95

Val Tyr Glu Ile Arg Glu Arg Leu Gly Ser Gly Ala Phe Ser Glu Val
                100                 105                 110

Val Leu Ala Gln Glu Arg Gly Ser Ala His Leu Val Ala Leu Lys Cys
            115                 120                 125

Ile Pro Lys Lys Ala Leu Arg Gly Lys Glu Ala Leu Val Glu Asn Glu
        130                 135                 140

Ile Ala Val Leu Arg Arg Ile Ser His Pro Asn Ile Val Ala Leu Glu
145                 150                 155                 160

Asp Val His Glu Ser Pro Ser His Leu Tyr Leu Ala Met Glu Leu Val
                165                 170                 175

Thr Gly Gly Glu Leu Phe Asp Arg Ile Met Glu Arg Gly Ser Tyr Thr
                180                 185                 190

Glu Lys Asp Ala Ser His Leu Val Gly Gln Val Leu Gly Ala Val Ser
            195                 200                 205

Tyr Leu His Ser Leu Gly Ile Val His Arg Asp Leu Lys Pro Glu Asn
        210                 215                 220

Leu Leu Tyr Ala Thr Pro Phe Glu Asp Ser Lys Ile Met Val Ser Asp
225                 230                 235                 240

Phe Gly Leu Ser Lys Ile Gln Ala Gly Asn Met Leu Gly Thr Ala Cys
                245                 250                 255

Gly Thr Pro Gly Tyr Val Ala Pro Glu Leu Leu Glu Gln Lys Pro Tyr
                260                 265                 270

Gly Lys Ala Val Asp Val Trp Ala Leu Gly Val Ile Ser Tyr Ile Leu
            275                 280                 285

Leu Cys Gly Tyr Pro Pro Phe Tyr Asp Glu Ser Asp Pro Glu Leu Phe
        290                 295                 300

Ser Gln Ile Leu Arg Ala Ser Tyr Glu Phe Asp Ser Pro Phe Trp Asp
305                 310                 315                 320

Asp Ile Ser Glu Ser Ala Lys Asp Phe Ile Arg His Leu Leu Glu Arg
                325                 330                 335

Asp Pro Gln Lys Arg Phe Thr Cys Gln Gln Ala Leu Arg His Leu Trp
            340                 345                 350

Ile Ser Gly Asp Thr Ala Phe Asp Arg Asp Ile Leu Gly Ser Val Ser
        355                 360                 365

Glu Gln Ile Arg Lys Asn Phe Ala Arg Thr His Trp Lys Arg Ala Phe
        370                 375                 380
```

```
Asn Ala Thr Ser Phe Leu Arg His Ile Arg Lys Leu Gly Gln Ile Pro
385                 390                 395                 400

Glu Gly Glu Gly Ala Ser Glu Gln Gly Met Ala Arg His Ser His Ser
                405                 410                 415

Gly Leu Arg Ala Gly Gln Pro Pro Lys Trp
            420                 425

<210> SEQ ID NO 29
<211> LENGTH: 1727
<212> TYPE: DNA
<213> ORGANISM: Artificial Sequence
<220> FEATURE:
<223> OTHER INFORMATION: Synthetic

<400> SEQUENCE: 29
agccggcgcg cggcggcggc aggaagtctg tgcccgagaa cagcagaaat aagagccagg      60
gagggaccgc ggccgcggcg gcggcggcga gagcgaaaga ggaaactgca gaggaggaag     120
ctgcgccgca gcccgagccg cccggcatcc ccgccgcctc tgcgcccgcg ccgcgccccc     180 ggcgcccccct ccccagcgcg ccccccggcc ctcctccgcg ccgcgctcgt cggccatggc     240
ccgggagaac ggcgagagca gctcctcctg gaaaaagcaa gctgaagaca tcaagaagat     300
cttcgagttc aaagagaccc tcggaaccgg ggccttttcc gaagtggttt tagctgaaga     360
gaaggcaact ggcaagctct ttgctgtgaa gtgtatccct aagaaggcgc tgaagggcaa     420
ggaaagcagc atagagaatg agatagccgt cctgagaaag attaagcatg aaaatattgt     480
tgccctggaa gacattttatg aaagcccaaa tcacctgtac ttggtcatgc agctggtgtc     540
cggtggagag ctgtttgacc ggatagtgga agggggttt tatacagaga aggatgccag     600
cactctgatc cgccaagtct tggacgccgt gtactatctc cacagaatgg gcatcgtcca     660
cagagacctc aagcccgaaa atctcttgta ctacagtcaa gatgaggagt ccaaaataat     720
gatcagtgac tttggattgt caaaaatgga gggcaaagga gatgtgatgt ccactgcctg     780
tggaactcca ggctatgtcg ctcctgaagt cctcgcccag aaaccttaca gcaaagccgt     840
tgactgctgg tccatcggag tgattgccta catcttgctc tgcggctacc ctccttttta     900
tgatgaaaat gactccaagc tctttgagca gatcctcaag gcggaatatg agtttgactc     960 tcccctactgg gatgacatct ccgactctgc aaaagacttc attcggaacc tgatggagaa    1020
ggacccgaat aaaagataca cgtgtgagca ggcagctcgg cacccatgga tcgctggtga    1080
cacagccctc aacaaaaaca tccacgagtc cgtcagcgcc cagatccgga aaaactttgc    1140
caagagcaaa tggagacaag catttaatgc cacggccgtc gtcagacata tgagaaaact    1200
acacctcggc agcagcctgg acagttcaaa tgcaagtgtt tcgagcagcc tcagtttggc    1260
cagccaaaaa gactgtgcgt atgtagcaaa accagaatcc ctcagctgac actgaagacg    1320
agcctggggt ggagaggagg gagccggcat ctgccgagca cctcctgttt gccaggcgct    1380
ttctatactt aatcccatgt catgcgaccc taggactttt tttaacatgt aatcactggg    1440
ctgggtgcag tggctcacgc ctgtaatccc aacactttgg gaggctgagg caggaggact    1500
gtttgagttc aggagtttta agaccagcct gaccaacatg gtgaaacccc atctctacta    1560
aaatataaaa attagccggg tgtggtggcg agcacctgta atgtcagcta cttgggaggc    1620
tgaggcagga gaatcacttg aacccaggaa gcggaggttg caatgagctg agatcacacc    1680
actgcactcc agcctgggtg acagattgag actccctctc aaaaaaa                   1727
```

```
<210> SEQ ID NO 30
<211> LENGTH: 357
<212> TYPE: PRT
<213> ORGANISM: Artificial Sequence
<220> FEATURE:
<223> OTHER INFORMATION: Synthetic

<400> SEQUENCE: 30

Met Ala Arg Glu Asn Gly Glu Ser Ser Ser Trp Lys Lys Gln Ala
1               5                   10                  15

Glu Asp Ile Lys Lys Ile Phe Glu Phe Lys Glu Thr Leu Gly Thr Gly
                20                  25                  30

Ala Phe Ser Glu Val Val Leu Ala Glu Glu Lys Ala Thr Gly Lys Leu
            35                  40                  45

Phe Ala Val Lys Cys Ile Pro Lys Lys Ala Leu Lys Gly Lys Glu Ser
        50                  55                  60

Ser Ile Glu Asn Glu Ile Ala Val Leu Arg Lys Ile Lys His Glu Asn
65                  70                  75                  80

Ile Val Ala Leu Glu Asp Ile Tyr Glu Ser Pro Asn His Leu Tyr Leu
                85                  90                  95

Val Met Gln Leu Val Ser Gly Gly Glu Leu Phe Asp Arg Ile Val Glu
            100                 105                 110

Lys Gly Phe Tyr Thr Glu Lys Asp Ala Ser Thr Leu Ile Arg Gln Val
        115                 120                 125

Leu Asp Ala Val Tyr Tyr Leu His Arg Met Gly Ile Val His Arg Asp
130                 135                 140

Leu Lys Pro Glu Asn Leu Leu Tyr Tyr Ser Gln Asp Glu Glu Ser Lys
145                 150                 155                 160

Ile Met Ile Ser Asp Phe Gly Leu Ser Lys Met Glu Gly Lys Gly Asp
                165                 170                 175

Val Met Ser Thr Ala Cys Gly Thr Pro Gly Tyr Val Ala Pro Glu Val
            180                 185                 190

Leu Ala Gln Lys Pro Tyr Ser Lys Ala Val Asp Cys Trp Ser Ile Gly
        195                 200                 205

Val Ile Ala Tyr Ile Leu Leu Cys Gly Tyr Pro Pro Phe Tyr Asp Glu
210                 215                 220

Asn Asp Ser Lys Leu Phe Glu Gln Ile Leu Lys Ala Glu Tyr Glu Phe
225                 230                 235                 240

Asp Ser Pro Tyr Trp Asp Asp Ile Ser Asp Ser Ala Lys Asp Phe Ile
                245                 250                 255

Arg Asn Leu Met Glu Lys Asp Pro Asn Lys Arg Tyr Thr Cys Glu Gln
            260                 265                 270

Ala Ala Arg His Pro Trp Ile Ala Gly Asp Thr Ala Leu Asn Lys Asn
        275                 280                 285

Ile His Glu Ser Val Ser Ala Gln Ile Arg Lys Asn Phe Ala Lys Ser
290                 295                 300

Lys Trp Arg Gln Ala Phe Asn Ala Thr Ala Val Val Arg His Met Arg
305                 310                 315                 320

Lys Leu His Leu Gly Ser Ser Leu Asp Ser Ser Asn Ala Ser Val Ser
                325                 330                 335

Ser Ser Leu Ser Leu Ala Ser Gln Lys Asp Cys Ala Tyr Val Ala Lys
            340                 345                 350

Pro Glu Ser Leu Ser
        355
```

<210> SEQ ID NO 31
<211> LENGTH: 2507
<212> TYPE: DNA
<213> ORGANISM: Artificial Sequence
<220> FEATURE:
<223> OTHER INFORMATION: Synthetic

<400> SEQUENCE: 31

```
tggagcagct aatcctcaca gacctgtagg agctggagtg ggagctcaag caggattctt    60
cccgagtccc tggcatcctc agaagcttca actctggagg caatgggtcg aaaggaagaa   120
gatgactgca gttcctggaa gaaacagacc accaacatcc ggaaaacctt cattttatg    180
gaagtgctgg gatcaggagc tttctcagaa gttttcctgg tgaagcaaag actgactggg   240
aagctctttg ctctgaagtg catcaagaag tcacctgcct tccgggacag cagcctggag   300
aatgagattc tgtgttgaa aaagatcaag catgaaaaca ttgtgaccct ggaggacatc   360
tatgagagca ccacccacta ctacctggtc atgcagcttg tttctggtgg ggagctcttt   420
gaccggatcc tggagcgggg tgtctacaca gagaaggatg ccagtctggt gatccagcag   480
gtcttgtcgg cagtgaaata cctacatgag aatggcatcg tccacagaga cttaaagccc   540
gaaaacctgc tttaccttac ccctgaagag aactctaaga tcatgatcac tgactttggt   600
ctgtccaaga tggaacagaa tggcatcatg tccactgcct gtgggacccc aggctacgtg   660
gctccagaag tgctggccca gaaacccta agcaaggctg tggattgctg gtccatcggc   720
gtcatcacct acatattgct ctgtggatac cccccattct atgaagaaac ggagtctaag   780
cttttcgaga gatcaagga gggctactat gagtttgagt ctccattctg ggatgacatt   840
tctgagtcag ccaaggactt tatttgccac ttgcttgaga aggatccgaa cgagcggtac   900
acctgtgaga aggccttgag tcatccctgg attgacggaa acacagccct ccaccgggac   960
atctacccat cagtcagcct ccagatccag aagaactttg ctaagagcaa gtggaggcaa  1020
gccttcaacg cagcagctgt ggtgcaccac atgaggaagc tacacatgaa cctgcacagc  1080
ccgggcgtcc gcccagaggt ggagaacagg ccgcctgaaa ctcaagcctc agaaacctct  1140
agacccagct cccctgagat caccatcacc gaggcacctg tcctggacca cagtgtagca  1200
ctccctgccc tgacccaatt accctgccag catgccgcc ggcccactgc ccctggtggc  1260
aggtccctca actgcctggt caatggctcc ctccacatca gcagcagcct ggtgcccatg  1320
catcaggggt ccctggccgc cgggcccctgt ggctgctgct ccagctgcct gaacattggg  1380
agcaaaggaa agtcctccta ctgctctgag cccacactcc tcaaaaaggc aacaaaaaaa  1440
cagaacttca gtcggaggt catggtacca gttaaagcca gtggcagctc ccactgccgg  1500
gcagggcaga ctggagtctg tctcattatg tgattcctgg agcctgtgcc tatgtcactg  1560
caattttcag gagacatatt caactcctct gctcttccaa acctggtgtc tatccggcag  1620
agggaggaag gcagagcaag tggagcaggg cttagcagga gcagtttctg gccagaagca  1680
ccagcctgct gccagcgggg cagcccctca taggaggccc aggagggagc cccaaggcgt  1740
agaagccttg ttgaagctgt gagcaggaga agcggtgccc accagcttcc aggtctccct  1800
gacctgcctg ctctatgccc cacacccac gtgccgtggc tctgtgcagt gtacgtagat  1860
agctctcgcc tgggtctgtg ctgtttgtcg tgaaaagctt aatgggctgg ccaggctgtg  1920
tcaccttctc caagcaaagc catatggagc atctacccag actcccactc tgcacacact  1980
cactcccacc tctcaagcct caacctctt ggccagattg gctcattaa tgtcgttgcc  2040
tgcccatctg catgaatgac aggcagctcc ccatggtggt ctgcctgtga gctcttcaag  2100
```

```
ttctaatcct taactccagg attagctccc aagtgcgctg agacccagcc agcacacttc    2160
tggcccttct ccctgcctca atctaaaagc agtgccacac cctccaaagt ggaatagaaa    2220
gaagttcatg agtaagggct gcaaggaatt cttatcctgg ccacatgtcc tccgtgcaca    2280
cacccaatgg agttaacctt ggaagttgac tattttaatg tctgccagga gttctaatcc    2340
tgcctctgtt ccctttctc tccttgaaag tccagcacac cattcttgtc cttccccagt     2400
ttcctcgccc tccacccctc cagcttcatg ctcagtgttg tgcttaataa aatggacata    2460
tttttctcta aaaaaaaaa aaaaaaaaa aaaaaaaaa aaaaaa                      2507

<210> SEQ ID NO 32
<211> LENGTH: 476
<212> TYPE: PRT
<213> ORGANISM: Artificial Sequence
<220> FEATURE:
<223> OTHER INFORMATION: Synthetic

<400> SEQUENCE: 32

Met Gly Arg Lys Glu Glu Asp Asp Cys Ser Ser Trp Lys Lys Gln Thr
1               5                   10                  15

Thr Asn Ile Arg Lys Thr Phe Ile Phe Met Glu Val Leu Gly Ser Gly
            20                  25                  30

Ala Phe Ser Glu Val Phe Leu Val Lys Gln Arg Leu Thr Gly Lys Leu
        35                  40                  45

Phe Ala Leu Lys Cys Ile Lys Lys Ser Pro Ala Phe Arg Asp Ser Ser
    50                  55                  60

Leu Glu Asn Glu Ile Ala Val Leu Lys Lys Ile Lys His Glu Asn Ile
65                  70                  75                  80

Val Thr Leu Glu Asp Ile Tyr Glu Ser Thr Thr His Tyr Tyr Leu Val
                85                  90                  95

Met Gln Leu Val Ser Gly Gly Glu Leu Phe Asp Arg Ile Leu Glu Arg
            100                 105                 110

Gly Val Tyr Thr Glu Lys Asp Ala Ser Leu Val Ile Gln Gln Val Leu
        115                 120                 125

Ser Ala Val Lys Tyr Leu His Glu Asn Gly Ile Val His Arg Asp Leu
    130                 135                 140

Lys Pro Glu Asn Leu Leu Tyr Leu Thr Pro Glu Glu Asn Ser Lys Ile
145                 150                 155                 160

Met Ile Thr Asp Phe Gly Leu Ser Lys Met Glu Gln Asn Gly Ile Met
                165                 170                 175

Ser Thr Ala Cys Gly Thr Pro Gly Tyr Val Ala Pro Glu Val Leu Ala
            180                 185                 190

Gln Lys Pro Tyr Ser Lys Ala Val Asp Cys Trp Ser Ile Gly Val Ile
        195                 200                 205

Thr Tyr Ile Leu Leu Cys Gly Tyr Pro Pro Phe Tyr Glu Glu Thr Glu
    210                 215                 220

Ser Lys Leu Phe Glu Lys Ile Lys Glu Gly Tyr Tyr Glu Phe Glu Ser
225                 230                 235                 240

Pro Phe Trp Asp Asp Ile Ser Glu Ser Ala Lys Asp Phe Ile Cys His
                245                 250                 255

Leu Leu Glu Lys Asp Pro Asn Glu Arg Tyr Thr Cys Glu Lys Ala Leu
            260                 265                 270

Ser His Pro Trp Ile Asp Gly Asn Thr Ala Leu His Arg Asp Ile Tyr
        275                 280                 285

Pro Ser Val Ser Leu Gln Ile Gln Lys Asn Phe Ala Lys Ser Lys Trp
```

```
                    290                 295                 300
Arg Gln Ala Phe Asn Ala Ala Val His His Met Arg Lys Leu
305                 310                 315                 320

His Met Asn Leu His Ser Pro Gly Val Arg Pro Glu Val Glu Asn Arg
                325                 330                 335

Pro Pro Glu Thr Gln Ala Ser Glu Thr Ser Arg Pro Ser Ser Pro Glu
            340                 345                 350

Ile Thr Ile Thr Glu Ala Pro Val Leu Asp His Ser Val Ala Leu Pro
        355                 360                 365

Ala Leu Thr Gln Leu Pro Cys Gln His Gly Arg Arg Pro Thr Ala Pro
    370                 375                 380

Gly Gly Arg Ser Leu Asn Cys Leu Val Asn Gly Ser Leu His Ile Ser
385                 390                 395                 400

Ser Ser Leu Val Pro Met His Gln Gly Ser Leu Ala Ala Gly Pro Cys
                405                 410                 415

Gly Cys Cys Ser Ser Cys Leu Asn Ile Gly Ser Lys Gly Lys Ser Ser
            420                 425                 430

Tyr Cys Ser Glu Pro Thr Leu Leu Lys Lys Ala Asn Lys Lys Gln Asn
        435                 440                 445

Phe Lys Ser Glu Val Met Val Pro Val Lys Ala Ser Gly Ser Ser His
    450                 455                 460

Cys Arg Ala Gly Gln Thr Gly Val Cys Leu Ile Met
465                 470                 475

<210> SEQ ID NO 33
<211> LENGTH: 4918
<212> TYPE: DNA
<213> ORGANISM: Artificial Sequence
<220> FEATURE:
<223> OTHER INFORMATION: Synthetic

<400> SEQUENCE: 33
ggttgccatg gggacctgga tgctgacgaa ggctcgcgag gctgtgagca gccacagtgc      60
cctgctcaga agccccgggc tcgtcagtca aaccggttct ctgtttgcac tcggcagcac     120
gggcaggcaa gtggtcccta ggttcgggag cagagcagca gcgcctcagt cctggtcccc     180
cagtcccaag cctcacctgc ctgcccagcg ccaggatggc caccatcacc tgcacccgct     240
tcacggaaga gtaccagctc ttcgaggaat gggcaagggg agccttctcg gtggtgcgaa     300
ggtgtgtgaa ggtgctggct ggccaggagt atgctgccaa gatcatcaac acaaagaagc     360
tgtcagccag agaccatcag aagctggagc gtgaagcccg catctgccgc tgctgaagc      420 accccaacat cgtccgacta catgacagca tctcagagga gggacaccac tacctgatct     480
tcgacctggt cactggtggg gaactgtttg aagatatcgt ggcccgggag tattacagtg     540
aggcggatgc cagtcactgt atccagcaga tcctggaggc tgtgctgcac tgccaccaga     600
tgggggtggt gcaccgggac ctgaagcctg agaatctgtt gctggcctcc aagctcaagg     660
gtgccgcagt gaagctggca gactttggcc tggccataga ggtggagggg gagcagcagg     720
catggtttgg gtttgcaggg actcctggat atctctcccc agaagtgctg cggaaggacc     780
cgtacgggaa gcctgtggac ctgtgggctt gtgggtcat cctgtacatc ctgctggttg      840 ggtaccccc gttctgggat gaggaccagc accgcctgta ccagcagatc aaagccggcg     900
cctatgattt cccatcgccg gaatgggaca ctgtcacccc ggaagccaag gatctgatca     960
ataagatgct gaccattaac ccatccaaac gcatcacagc tgccgaagcc cttaagcacc    1020
```

```
cctggatctc gcaccgctcc accgtggcat cctgcatgca cagacaggag accgtggact    1080
gcctgaagaa gttcaatgcc aggaggaaac tgaagggagc cattctcacc acgatgctgg    1140
ccaccaggaa cttctccgga gggaagagtg ggggaaacaa gaagagcgat ggtgtgaaga    1200
aaagaaagtc cagttccagc gttcagttaa tggaatcctc agagagcacc aacaccacca    1260
tcgaggatga agacaccaaa gtgcggaaac aggaaattat aaaagtgaca gagcagctga    1320
ttgaagccat aagcaatgga gattttgagt cctacacgaa gatgtgcgac cctggcatga    1380
cagccttcga acctgaggcc ctggggaacc tggttgaggg cctggacttc catcgattct    1440
attttgaaaa cctgtggtcc cggaacagca agcccgtgca caccaccatc ctgaatcccc    1500
acatccacct gatgggcgac gagtcagcct gcatcgccta catccgcatc acgcagtacc    1560
tggacgctgg cggcatccca cgcaccgccc agtcggagga gacccgtgtc tggcaccgcc    1620
gggatggcaa atggcagatc gtccacttcc acagatctgg ggcgccctcc gtcctgcccc    1680
actgagggac caggctgggg tcgctgcgtt gctgtgccgc agagatccac tctgtccgtg    1740
gagtggagct gctggttctc ccaggtggat tttgctggaa ttctcccatg tcatcacccc    1800
accaccgtca cttctgtacc tgcatcaaga aaacctgctt gttcacaaaa gtcatcgcaa    1860
cttcagagcg aacggccaca tctccccacc tctcacccccc accctctccc ctgccaggct    1920
ggggcttcct caggcatggg tgtccacagc actggccccc tctccccagc ctcagctgct    1980
gtccgcctga tctgtcttgg gctgtaggct agaatgcccg ggctggtgcc caccaggggc    2040
tggggagaag gaggggtggc atgatgagga aggcagcatc cgtccgtccc tctcccagac    2100
ctctcctctt ccagtgtccc cggggaaggg cagatgacac tcccttcccc ctaagccaac    2160
cgcactgaag gagtggggag aagagcatac gccaggagcc tcctgcctca aagtgctccc    2220
ctaagtcttc ttcctcctgt gctgacctca gggtggtctg acccttccct cggtgtgggg    2280
gatgtggccc tctcaggtgc ccctacttgc tttctgcttc cttctggtga agtccacctc    2340
caacattaac ctgcccaccc cacccccgtc atccctggag aattccagct ttgtcgtatc    2400
tcagagaggg aatctaattg ttttttggggg gcaaaagaaa gcaacgttta ggtatcactt    2460
ctacttggac cgcatgcctt tttatagcca aatttctgtg tatttcgtaa atggatttcg    2520
cgttaatgga tatttatgta ataactagac ttctcagatt attgtgagaa gggtcaggtt    2580
ggaaggggtg taggaagagg ggtgaggggt agttttttttc tgttctagtt ttttttttttt    2640 tttttgtcat ctctgaggtg gaccttgtca cctgtggtta ttggggccaa ggtggactca    2700
gctccgggga aagggcctc tctgccattt cggtcccaag gtgagctgac acaggcgttc    2760
cttttgggac tgtggaagca tcagatgcca gcactgactc aggaacagca agtcagggca    2820
gagaggagga gggaggctgt caggatggaa atacctggac ttttctttgc ttccctcgca    2880
aactggggtc ttctctaccg aacttcccag gatttcatct caccatatct gtgtgccgcc    2940
cccagcaccc cccacccacc tctgggggc ccgtgagcgt gtgtcttcat gcctctctc     3000 cccttggcgt ctgatgacca cagcaaagca ctgggaattt ctactcttca tgcctcatcc    3060
tgcagcctcg ggttcgcatt ctctcttttct tttcctcttt ccctcttttcc ctgggattga    3120 ctctgagtgg aataccttgg cacatccact aggatctact gtctgcactg ttttctttgc    3180
atgactttat acgcagtaag tatgttgaaa acaaacaaaa agaagaaaac actcaacaaa    3240
accaatctac atgttttgga ctaaaaaaaa aaatagaggt tgtattctca gtgtccgact    3300
cggaattatg ttgctgcctc tctgtgcttt tggcctctgt gtggccgtgt tttgccagca    3360
tgagatactg tcccctctgg aggattttag gggaggaaga gccacgtccc cagggattgg    3420
```

-continued

```
aggaggctcc ggtaccctcg accctcctgg gtgttggttg gagcagaact ggtgaggatg    3480
tttgatccga gattttctga gctctcccca atcaccagct gtctgctggg ttcttttctc    3540
aagtcctgct gcccaggccc aggtgagaca ggcaacgcca ggtctgcagg ccaggagaga    3600
tgctgcccag gctcctggt ttccaagctg gtccatcact ggcctctgtc cttggcagag     3660
accttgctgc caggcccag gggcaggctc ttggcctgcc ccaggcccag agggcttccc     3720
agtaaggccc agtgatccca ttatcccagg ggcaaaacca cctgtcccct tttgagctgc    3780
cagttcccta cagccatccc cagtcaaggg tgagggtgtg gccttcacca ggggctgctg    3840
taattaccga gcaaggtctg agctcttctt cagcctcagt tccctcattg gttaaaggg     3900
ttctttgttc ccatccagcc gatgaaggag caaacgtctg gctatgtgaa gcctaattta    3960
cctgcaggaa ctgcaggga tagtcactgg ctggactcct gtttacttct agacctggtc     4020
aggctccatc ccctccccca cctgccctg attccctcg tcggtgcctg tcaactgctt      4080
ttcagcagtg gactgcaggg gaaagagcag tgatttgggg tgagtaggct tcaattccca    4140
gctctgacca gacttgctgt gtgaccttgg gcaagttcct ttccctcttt ggagcttggt    4200
ttccctgcca gaggaaactg agctggagga gcctgaggtc ctgcctttca ttggctgaca    4260
cacctcctgt ccactgtgtc actctccaag tgccagagaa gtggaggcag atcgctaccc    4320
caggctgaga tggcccccac tgtgaaggcc acgcctgtgg gtgggcagcc acctggtgcc    4380
accacagggc accagggatg atcctgatgt ggcaggcagg ggagactcac agaaaaatct    4440
gcccagagcc taccctcacc agacaaactc tgtgctcctc caaaacatcc tttagatgca    4500
aaataataat aataataata ataaataaat aaataaaaat ccaaacccaa gtcaaaacct    4560
tggctccagc atgaaaacac gtttacagga aagtgttctc ctgggtttgt gcccaccatg    4620
gtgcgaatcc tgacccaagg cctcctgtct cccttcaaag ggagacccctt ttgggggatg   4680
agtttgccag actccccgtg ctggtttctt tgttactatt tgtttggggt tttgttttag    4740
ttctttttttt ttttctttc tttttaaaa atatgtggct gtgaacttga atgaacactg     4800
ctcaaacttt ctgctattgg gggggcggg tgggatggga agaaggggcg tttgttttat     4860
tcttggtgtt ttcagtgcaa taaatagcta caaacttctg tgcaaaaaaa aaaaaaaa     4918
```

<210> SEQ ID NO 34
<211> LENGTH: 489
<212> TYPE: PRT
<213> ORGANISM: Artificial Sequence
<220> FEATURE:
<223> OTHER INFORMATION: Synthetic

<400> SEQUENCE: 34

```
Met Ala Thr Ile Thr Cys Thr Arg Phe Thr Glu Glu Tyr Gln Leu Phe
1               5                   10                  15

Glu Glu Leu Gly Lys Gly Ala Phe Ser Val Val Arg Arg Cys Val Lys
            20                  25                  30

Val Leu Ala Gly Gln Glu Tyr Ala Ala Lys Ile Ile Asn Thr Lys Lys
        35                  40                  45

Leu Ser Ala Arg Asp His Gln Lys Leu Glu Arg Glu Ala Arg Ile Cys
    50                  55                  60

Arg Leu Leu Lys His Pro Asn Ile Val Arg Leu His Asp Ser Ile Ser
65                  70                  75                  80

Glu Glu Gly His His Tyr Leu Ile Phe Asp Leu Val Thr Gly Gly Glu
                85                  90                  95
```

-continued

```
Leu Phe Glu Asp Ile Val Ala Arg Glu Tyr Tyr Ser Glu Ala Asp Ala
            100                 105                 110

Ser His Cys Ile Gln Gln Ile Leu Glu Ala Val Leu His Cys His Gln
        115                 120                 125

Met Gly Val Val His Arg Asp Leu Lys Pro Glu Asn Leu Leu Leu Ala
    130                 135                 140

Ser Lys Leu Lys Gly Ala Ala Val Lys Leu Ala Asp Phe Gly Leu Ala
145                 150                 155                 160

Ile Glu Val Glu Gly Glu Gln Gln Ala Trp Phe Gly Phe Ala Gly Thr
                165                 170                 175

Pro Gly Tyr Leu Ser Pro Glu Val Leu Arg Lys Asp Pro Tyr Gly Lys
            180                 185                 190

Pro Val Asp Leu Trp Ala Cys Gly Val Ile Leu Tyr Ile Leu Leu Val
        195                 200                 205

Gly Tyr Pro Pro Phe Trp Asp Glu Asp Gln His Arg Leu Tyr Gln Gln
    210                 215                 220

Ile Lys Ala Gly Ala Tyr Asp Phe Pro Ser Pro Glu Trp Asp Thr Val
225                 230                 235                 240

Thr Pro Glu Ala Lys Asp Leu Ile Asn Lys Met Leu Thr Ile Asn Pro
                245                 250                 255

Ser Lys Arg Ile Thr Ala Ala Glu Ala Leu Lys His Pro Trp Ile Ser
            260                 265                 270

His Arg Ser Thr Val Ala Ser Cys Met His Arg Gln Glu Thr Val Asp
        275                 280                 285

Cys Leu Lys Lys Phe Asn Ala Arg Arg Lys Leu Lys Gly Ala Ile Leu
    290                 295                 300

Thr Thr Met Leu Ala Thr Arg Asn Phe Ser Gly Gly Lys Ser Gly Gly
305                 310                 315                 320

Asn Lys Lys Ser Asp Gly Val Lys Lys Arg Lys Ser Ser Ser Ser Val
                325                 330                 335

Gln Leu Met Glu Ser Ser Glu Ser Thr Asn Thr Thr Ile Glu Asp Glu
            340                 345                 350

Asp Thr Lys Val Arg Lys Gln Glu Ile Ile Lys Val Thr Glu Gln Leu
        355                 360                 365

Ile Glu Ala Ile Ser Asn Gly Asp Phe Glu Ser Tyr Thr Lys Met Cys
    370                 375                 380

Asp Pro Gly Met Thr Ala Phe Glu Pro Glu Ala Leu Gly Asn Leu Val
385                 390                 395                 400

Glu Gly Leu Asp Phe His Arg Phe Tyr Phe Glu Asn Leu Trp Ser Arg
                405                 410                 415

Asn Ser Lys Pro Val His Thr Thr Ile Leu Asn Pro His Ile His Leu
            420                 425                 430

Met Gly Asp Glu Ser Ala Cys Ile Ala Tyr Ile Arg Ile Thr Gln Tyr
        435                 440                 445

Leu Asp Ala Gly Gly Ile Pro Arg Thr Ala Gln Ser Glu Glu Thr Arg
    450                 455                 460

Val Trp His Arg Arg Asp Gly Lys Trp Gln Ile Val His Phe His Arg
465                 470                 475                 480

Ser Gly Ala Pro Ser Val Leu Pro His
                485

<210> SEQ ID NO 35
<211> LENGTH: 4586
<212> TYPE: DNA
```

<213> ORGANISM: Artificial Sequence
<220> FEATURE:
<223> OTHER INFORMATION: Synthetic

<400> SEQUENCE: 35

| | | | | | |
|---|---|---|---|---|---|
| aggtgtgcgg | cgcgctcctg | gcgaggacgg | agcgagcaga | tctcgcgtgc | gctcgccgcc | 60
| cggcgcagcc | cagcccggcc | cccgcctggc | gccgcgagcc | gaggtgtctc | ccgcgcccgc | 120
| gcccgtgtcg | ccgccgtgcc | cgcgagcggg | agcggagtc  | gccgccgccc | gagcgcagcc | 180
| gagcgcacgc | cgagcccgtc | cgccgccgcc | atggccacca | cggtgacctg | caccccgcttc | 240
| accgacgagt | accagctcta | cgaggatatt | ggcaagggg  | cttctctgt  | ggtccgacgc | 300
| tgtgtcaagc | tctgcaccgg | ccatgagtat | gcagccaaga | tcatcaacac | caagaagctg | 360
| tcagccagag | atcaccagaa | gctggagaga | gaggctcgga | tctgccgcct | tctgaagcat | 420
| tccaacatcg | tgcgtctcca | cgacagcatc | tccgaggagg | gcttccacta | cctggtcttc | 480
| gatctggtca | ctggtgggga | gctctttgaa | gacattgtgg | cgagagagta | ctacagcgag | 540
| gctgatgcca | gtcactgtat | ccagcagatc | ctggaggccg | ttctccattg | tcaccaaatg | 600
| ggggtcgtcc | acagagacct | caagccggag | aacctgcttc | tggccagcaa | gtgcaaaggg | 660
| gctgcagtga | agctggcaga | cttcggccta | gctatcgagg | tgcagggga  | ccagcaggca | 720
| tggtttggtt | tcgctggcac | accaggctac | ctgtcccctg | aggtccttcg | caaagaggcg | 780
| tatggcaagc | ctgtggacat | ctgggcatgt | ggggtgatcc | tgtacatcct | gctcgtgggc | 840
| tacccaccct | tctgggacga | ggaccagcac | aagctgtacc | agcagatcaa | ggctggtgcc | 900
| tatgacttcc | cgtcccctga | gtgggacacc | gtcactcctg | aagccaaaaa | cctcatcaac | 960
| cagatgctga | ccatcaaccc | tgccaagcgc | atcacagccc | atgaggccct | gaagcacccg | 1020
| tgggtctgcc | aacgctccac | ggtagcatcc | atgatgcaca | gacaggagac | tgtggagtgt | 1080
| ctgaaaaagt | tcaatgccag | agaaaagctc | aagggagcca | tcctcaccac | catgctggcc | 1140
| acacggaatt | tctcagtggg | cagacagacc | accgctccgg | ccacaatgtc | caccgcggcc | 1200
| tccggcacca | ccatggggct | ggtggaacaa | gccaagagtt | tactcaacaa | gaaagcagat | 1260
| ggagtcaagc | cccagacgaa | tagcaccaaa | aacagtgcag | ccgccaccag | ccccaaaggg | 1320
| acgcttcctc | ctgccgccct | ggagcctcaa | accaccgtca | tccataaccc | agtggacggg | 1380
| attaaggagt | cttctgacag | tgccaatacc | accatagagg | atgaagacgc | taaagccccc | 1440
| agggtccccg | acatcctgag | ctcagtgagg | aggggctcgg | gagcccagga | agccgagggg | 1500
| cccctgccct | gccatctcc  | ggctccctttt | agcccctgc  | cagccccatc | ccccaggatc | 1560
| tctgacatcc | tgaactctgt | gagaaggggt | tcaggaaccc | cagaagccga | gggccccctc | 1620
| tcagcgggc  | cccgccctg  | cctgtctccg | gctctcctag | gccccctgtc | ctccccgtcc | 1680
| cccaggatct | ctgacatcct | gaactctgtg | aggaggggct | cagggacccc | agaagccgag | 1740
| ggccctcgc  | cagtggggcc | cccgccctgc | ccatctccga | ctatccctgg | cccctgccc  | 1800
| accccatccc | ggaagcagga | gatcattaag | accacgagc  | agctcatcga | ggccgtcaac | 1860
| aacggtgact | ttgaggccta | cgcgaaaatc | tgtgacccag | gctgacctc  | gtttgagcct | 1920
| gaagcactgg | gcaacctggt | tgaagggatg | gacttccaca | gattctactt | cgagaacctg | 1980
| ctggccaaga | acagcaagcc | gatccacacg | accatcctga | acccacacgt | gcacgtcatt | 2040
| ggagaggatg | ccgcctgcat | cgcttacatc | cggctcacgc | agtacattga | cgggcagggc | 2100
| cggccccgca | ccagccagtc | tgaggagacc | cgcgtgtggc | accgccgcga | cggcaagtgg | 2160
| cagaacgtgc | acttccactg | ctcgggcgcg | cctgtggccc | cgctgcagtg | aagagctgcg | 2220

```
ccctggtttc gccggacaga gttggtgttt ggagcccgac tgccctcggg cacacggcct    2280
gcctgtcgca tgtttgtgtc tgcctcgttc cctcccctgg tgcctgtgtc tgcagaaaaa    2340
caagaccaga tgtgatttgt taaaaaaaaa caaaaaaaaa aaaaaaaaaa acaagatgac    2400
gacgacaacc acaaaaaaaa ttgacatcag atgaaatgaa aaaaaaaaaa aacaaaaaaa    2460
actaaaggaa ggaaaaagct gtaaaaatca ctggcattcg tggggccact ccccacccaa    2520
gctccacgtg tgtccgtctg tgctcctggc tctgggggga ccagctggga catgaacttg    2580
tctgccaggc ccccgtcgcg tgctgaacgg tgttagtttg taggtaacgc acacacccca    2640
cacctaaggt gtctgcatcc tcctgccaac gcatgggctc cacgtggtgt gctcgctggc    2700
tgtcgtgact gtcagctgtc tcttgggagg ggctgtgggg gcccgctggg ctgcctcctt    2760
tcccgctagt tgtgcctgag agttgctgtt gttcctgctt tcccttccct tcctttcatc    2820
ccctgaaggg ctaggtgtgg gttttccgtg cccggtatcc ccacacaccc agcacggaca    2880
acccttcggc agagcccagg ccggcccctc accccctgga gtattgaaac tggagtcccg    2940
tccccaaggc cttcagagat gcccctacac acccagggct ccagctctgg tccttctggg    3000
ggagtaaagt gcaaagaggg gcacagctta gttttgggcc tctcgccgag caagagacag    3060
cactgctggc tacagctcca acacagccag ctgtggcaag aggactctgc ctgggctggc    3120 cccctcctg tgtgaggtgt ctgtcccttc tctgctggcc agcagcagat gcactggcag    3180
ctcccaaccc tgtttccgcc cctcggccct ccccagcct gttcggcttc tctgcagccc    3240
gcaaggggga gcagactttt gacaaaggac tgcgggcctc gctcaagtcc ctgagccccc    3300
agctgaagct gggaggggag gccaggcttt gtgtctgggc atattcgtct gctgatgggg    3360
tttggggaag cctggggctt ggggtttggt cgggtggtgc agctagtggc agagcgggat    3420
cagaggtggt ggctgcccag cttctgggct gagacaaggg tctgtgcagg ggtttactga    3480
agtgggagtg cctttggaat ctgggccggg agcagaaggg agcaaaagct acagtgggag    3540
ccagcctagg gcacatggga ggcgtgaggg cagtgctgcc cgtgcagtgt caggtgtgcc    3600
agtgccttgg cgggctgcag tgcgtgtgag ggcaccttct aggtgggcca gggatgcagc    3660
tatggagata aggcgggctg gggacagaaa caggtgggca cagggcccag gacaccagcg    3720
gatggagggc agggtctagc cctgtgctcc tgagcgtcgg ctgcctgggt tcgaggcggt    3780
gggtccccgg cccccttgtga tggtgtgtac catgggggag ctcggggaca gggcaagccc    3840
gagcatggtg gggctgcagg gtgggtctga agccaggttg ggtgggggtg gtcacaagcc    3900
ctgactgcag agggtcaggg gctcctgccc cagtgcctgc ccactttcaa ttcacattgt    3960
tttcaacaag gattttcttt atcttcccct acaaatcaag ccaagggagg ggcacagaat    4020
ggggaacagg acacaggatc ctaaactcca aggggactgt ccaccgatga acactcagag    4080
tggacaccat cttccgtcca cgctgtgccc aggacagctg tccccatcca tgaacacagg    4140
gtaaacatct gccgggctcc gcaccagtgg ctccctgggc catgggacag cggcagggct    4200
caccacggac agcacgtggc ccagcagccg gccaccctgg cgtcctgggg cctcctcccc    4260
tcctctccct ctcaccttgt cacctccacg gagctgcctg tctgggataa tttggggatt    4320
ttttttctgg gggataattc ttttgcatga ccccctaaaga gcaagccaca ccggtctgct    4380
agctaggtgt ccgcggtgtg gtggtggcgg ccgctggcca gcgctgcaag gggtcggctg    4440 cccacggtgtc tggctggcct cccctcctct ctcttttttgc tgagtttcat tgtcttttct    4500
ttctgagcct tgtaagtgta caaaaattat tcttattttg ttctgtctcg ggaaactgca    4560
```
aataaaagaa aaacaggaca aactgc                                              4586

<210> SEQ ID NO 36
<211> LENGTH: 666
<212> TYPE: PRT
<213> ORGANISM: Artificial Sequence
<220> FEATURE:
<223> OTHER INFORMATION: Synthetic

<400> SEQUENCE: 36

```
Met Ala Thr Thr Val Thr Cys Thr Arg Phe Thr Asp Glu Tyr Gln Leu
1               5                   10                  15

Tyr Glu Asp Ile Gly Lys Gly Ala Phe Ser Val Val Arg Arg Cys Val
            20                  25                  30

Lys Leu Cys Thr Gly His Glu Tyr Ala Ala Lys Ile Ile Asn Thr Lys
        35                  40                  45

Lys Leu Ser Ala Arg Asp His Gln Lys Leu Glu Arg Glu Ala Arg Ile
    50                  55                  60

Cys Arg Leu Leu Lys His Ser Asn Ile Val Arg Leu His Asp Ser Ile
65                  70                  75                  80

Ser Glu Glu Gly Phe His Tyr Leu Val Phe Asp Leu Val Thr Gly Gly
                85                  90                  95

Glu Leu Phe Glu Asp Ile Val Ala Arg Glu Tyr Tyr Ser Glu Ala Asp
            100                 105                 110

Ala Ser His Cys Ile Gln Gln Ile Leu Glu Ala Val Leu His Cys His
        115                 120                 125

Gln Met Gly Val Val His Arg Asp Leu Lys Pro Glu Asn Leu Leu Leu
    130                 135                 140

Ala Ser Lys Cys Lys Gly Ala Ala Val Lys Leu Ala Asp Phe Gly Leu
145                 150                 155                 160

Ala Ile Glu Val Gln Gly Asp Gln Gln Ala Trp Phe Gly Phe Ala Gly
                165                 170                 175

Thr Pro Gly Tyr Leu Ser Pro Glu Val Leu Arg Lys Glu Ala Tyr Gly
            180                 185                 190

Lys Pro Val Asp Ile Trp Ala Cys Gly Val Ile Leu Tyr Ile Leu Leu
        195                 200                 205

Val Gly Tyr Pro Pro Phe Trp Asp Glu Asp Gln His Lys Leu Tyr Gln
    210                 215                 220

Gln Ile Lys Ala Gly Ala Tyr Asp Phe Pro Ser Pro Glu Trp Asp Thr
225                 230                 235                 240

Val Thr Pro Glu Ala Lys Asn Leu Ile Asn Gln Met Leu Thr Ile Asn
                245                 250                 255

Pro Ala Lys Arg Ile Thr Ala His Glu Ala Leu Lys His Pro Trp Val
            260                 265                 270

Cys Gln Arg Ser Thr Val Ala Ser Met Met His Arg Gln Glu Thr Val
        275                 280                 285

Glu Cys Leu Lys Lys Phe Asn Ala Arg Arg Lys Leu Lys Gly Ala Ile
    290                 295                 300

Leu Thr Thr Met Leu Ala Thr Arg Asn Phe Ser Val Gly Arg Gln Thr
305                 310                 315                 320

Thr Ala Pro Ala Thr Met Ser Thr Ala Ala Ser Gly Thr Thr Met Gly
                325                 330                 335

Leu Val Glu Gln Ala Lys Ser Leu Leu Asn Lys Lys Ala Asp Gly Val
            340                 345                 350

Lys Pro Gln Thr Asn Ser Thr Lys Asn Ser Ala Ala Ala Thr Ser Pro
```

```
            355                 360                 365
Lys Gly Thr Leu Pro Pro Ala Ala Leu Glu Pro Gln Thr Thr Val Ile
    370                 375                 380

His Asn Pro Val Asp Gly Ile Lys Glu Ser Ser Asp Ser Ala Asn Thr
385                 390                 395                 400

Thr Ile Glu Asp Glu Asp Ala Lys Ala Pro Arg Val Pro Asp Ile Leu
                405                 410                 415

Ser Ser Val Arg Arg Gly Ser Gly Ala Pro Glu Ala Glu Gly Pro Leu
            420                 425                 430

Pro Cys Pro Ser Pro Ala Pro Phe Ser Pro Leu Pro Ala Pro Ser Pro
        435                 440                 445

Arg Ile Ser Asp Ile Leu Asn Ser Val Arg Arg Gly Ser Gly Thr Pro
    450                 455                 460

Glu Ala Glu Gly Pro Leu Ser Ala Gly Pro Pro Cys Leu Ser Pro
465                 470                 475                 480

Ala Leu Leu Gly Pro Leu Ser Ser Pro Ser Pro Arg Ile Ser Asp Ile
                485                 490                 495

Leu Asn Ser Val Arg Arg Gly Ser Gly Thr Pro Glu Ala Glu Gly Pro
            500                 505                 510

Ser Pro Val Gly Pro Pro Cys Pro Ser Pro Thr Ile Pro Gly Pro
        515                 520                 525

Leu Pro Thr Pro Ser Arg Lys Gln Glu Ile Ile Lys Thr Thr Glu Gln
    530                 535                 540

Leu Ile Glu Ala Val Asn Asn Gly Asp Phe Glu Ala Tyr Ala Lys Ile
545                 550                 555                 560

Cys Asp Pro Gly Leu Thr Ser Phe Glu Pro Glu Ala Leu Gly Asn Leu
                565                 570                 575

Val Glu Gly Met Asp Phe His Arg Phe Tyr Phe Glu Asn Leu Leu Ala
            580                 585                 590

Lys Asn Ser Lys Pro Ile His Thr Thr Ile Leu Asn Pro His Val His
        595                 600                 605

Val Ile Gly Glu Asp Ala Ala Cys Ile Ala Tyr Ile Arg Leu Thr Gln
    610                 615                 620

Tyr Ile Asp Gly Gln Gly Arg Pro Arg Thr Ser Gln Ser Glu Glu Thr
625                 630                 635                 640

Arg Val Trp His Arg Arg Asp Gly Lys Trp Gln Asn Val His Phe His
                645                 650                 655

Cys Ser Gly Ala Pro Val Ala Pro Leu Gln
            660                 665

<210> SEQ ID NO 37
<211> LENGTH: 5820
<212> TYPE: DNA
<213> ORGANISM: Artificial Sequence
<220> FEATURE:
<223> OTHER INFORMATION: Synthetic

<400> SEQUENCE: 37
aaaggaggga gtgcgagaga tccacgaagg acaggcttg gagtcgctag agggaggtgt      60
gggaccagcg aggaggggc ttcgccaggg aggggtgct ggcaggcgga gggagcggcg     120
ggaggaggcg ccggaggagg agacggaggc ctggggacgg cagaagaggc ttcgcctgag    180
ccgagcgctc tttctctcgc cgcgccgtct tgaagccgcg cgggctcgtg agcagcgcga    240
ggccgccaag gtgcctcgct tcgccggagc cgctgccgcc cgccgagggg aagccggcct    300
```

```
cgggcgcgca cgctcgtcgg agccccggcg cgccccgcgc ctgagcctgc tgacagcggc    360
cgctgggctc aggctgtccg ctctgggctc cgcggcctcg gccccgctgc actccacctc    420 cgcccctcg gactccctcc cctctgcttc tactcctcct gctccagtgc ggatcgtttc    480
gcaactgctt gccactcgtc ccgtgcctgg ctgttttcc atttcccggc cccctcttct    540
tgagtacttt accccctgca tttggggaca gggactggaa aaggggcggg tggagcgtcc    600
agtggagaag aaggaagcga ggcccgcagg aggaggagga tcggcggact gtggggagga    660
gaccccacgc caccctttct ggtcatctcc cctcccgccc cgcccctgcg cacactccct    720
cgcgggcgag ctactttcgg accaggaaag taagagcggc cctgggtgac agcgccgcgg    780
ggccagtccc ggggttagcc gcgcgtctgc tcgcttctgg tccgtcgcgc tcccagccag    840
ggcacagccc ggaccgagga tggcttcgac cacaacctgc accaggttca cggacgagta    900
tcagcttttc gaggagcttg aaagggggc attctcagtg gtgagaagat gtatgaaaat    960
tcctactgga caagaatatg ctgccaaaat tatcaacacc aaaaagcttt ctgctaggga   1020
tcatcagaaa ctagaaagag aagctagaat ctgccgtctt ttgaagcacc ctaatattgt   1080
gcgacttcat gatagcatat cagaagaggg cttttcactac ttggtgtttg atttagttac   1140
tggaggtgaa ctgtttgaag acatagtggc aagagaatac tacagtgaag ctgatgccag   1200
tcattgtata cagcagattc tagaaagtgt taatcattgt cacctaaatg catagttca    1260 cagggacctg aagcctgaga atttgctttt agctagcaaa tccaagggag cagctgtgaa   1320
attggcagac tttggcttag ccatagaagt tcaaggggac cagcaggcgt ggtttggttt   1380
tgctggcaca cctggatatc tttctccaga agttttacgt aaagatcctt atggaaagcc   1440
agtggatatg tgggcatgtg gtgtcattct ctatattcta cttgtggggt atccacccctt   1500 ctgggatgaa gaccaacaca gactctatca gcagatcaag gctggagctt atgattttcc   1560
atcaccagaa tgggacacgg tgactcctga agccaaagac ctcatcaata aaatgcttac   1620
tatcaaccct gccaaacgca tcacagcctc agaggcactg aagcacccat ggatctgtca   1680
acgttctact gttgcttcca tgatgcacag acaggagact gtagactgct tgaagaaatt   1740
taatgctaga agaaaactaa agggtgccat cttgacaact atgctggcta caaggaattt   1800
ctcagcagcc aagagtttgt tgaagaaacc agatggagta aaggagtcaa ctgagagttc   1860
aaatacaaca attgaggatg aagatgtgaa agcacgaaag caagagatta tcaaagtcac   1920
tgaacaactg atcgaagcta tcaacaatgg ggactttgaa gcctacacaa aaatctgtga   1980
cccaggcctt actgcttttg aacctgaagc tttgggtaat ttagtggaag ggatggattt   2040
tcaccgattc tactttgaaa atgctttgtc caaaagcaat aaaccaatcc acactattat   2100
tctaaaccct catgtacatc tggtagggga tgatgccgcc tgcatagcat atattaggct   2160
cacacagtac atggatggca gtggaatgcc aaagacaatg cagtcagaag agactcgtgt   2220
gtggcaccgc cgggatggaa agtggcagaa tgttcatttt catcgctcgg ggtcaccaac   2280
agtacccatc aagtaaatat ttccaggctg tcagcttctt tgttaataca cccatgctaa   2340
atttcaacag tgccacttct gcattctctg ttctcaaggc acctggatgg tgaccctggg   2400
ccgtcctctc ctcctcttca tgcatgtttc tgagtgcatg aagttgtgaa ggtcctacat   2460
gtaatgcata tgtgatgcat catcttatca tatattcctt cctatacatt gtttacactt   2520
caactacggg gatgttccac acaaacttaa attactgttg gcaaaacaat agggggagat   2580
tagacaaaaa aaaaaatcca caatattcca agtacaactc ttcatcaagt ttctctgtta   2640
atgccaagat ttaacagact taagaactat tgttctctga atgacagttg taagagaaat   2700
```

```
gtaaattttt tagaactctt tgctgttaat ctgttttggt ttgtttggtt tttttttttt    2760 ttttttaaggt aaaaaaaaaa tacaccttca gtttcctggt gtgatcctgg ttaaaatgga    2820 tgattttttca ttgaaagttt tgctgattaa caattaaagt gggatgatat gtgggcaaaa   2880
tcacttatga aagtagaagc aagaatcagt tggtttgcta ccacataaag ccatgctgtt    2940
tttggtcaaa ctgtgtaaac tggaaaaatt cacatcattt ctgagtttaa tcactttagg    3000
atatattcac attgttttgg tgaatttgct gaattgaatt ttttttcttt ctcaaatctg    3060
tgatctcttt tctttatcct gtttctttgt tcctttcgtt tgctttctta ttttttcttt   3120
gttccattct tttcttactt ttttcccttt tcctttttttg gggaggctgg ctagtagtgt   3180
gtgagaaaag aatagaagtg aaatttgcat aatgaatgta aagggaaat aaaagtcttt     3240 tgaaggtagc tatactagca cttttgatca tcttcagggc ccacaaaaat gttgtcaaga    3300
ttttaaaggt ttataattct gcttaagctc tagtttggac ttaggtatcc taactatgtt   3360
ggaggtattt gcattgttta aagttaggat aaaagcaagt tcctcctgtg actgcaacgt    3420
cttactgatt gggacagttg ccaggaggat accaacttga tagcagaggg ggttttatgc    3480
aaacgcactc acctccgcct tggggaatga aagggtcact tctgcatcat cactagctag    3540
ttttctagtg ttagagaggc ttacaaatgt ttgccattct cataagtgtt ttgaacttga    3600
tctttgtgac ttgtgctttt ttagcttctc tcttgaatca gagtatcatt gtcttcctcc    3660
aaggagttag aatttcccag tttaaaacaa aagggaaat gtcctaggtt ttctttgtgc     3720
ttctcatttt tccttgtttg attcaattcc tgtgattttt gttctcttcc ctgaagtgct    3780
ttacagtgca tggaatctcc atcattgtta ttttaacgat agtaattcac agtcctcaga    3840
agcctatttt taaagcagaa gcaaaaaaga aaacaaaat aacaaaaaca acccttcctc     3900
ttttctctca tctcacctct ctgtgttgat tactaatcat cttagatatt attgctagtg    3960
gatgtatggt agatgggttg aagcttttct gataattatt acacaattta aaacaacata    4020
tatatttaaa ataaatatat acagtaaata tattgagcca tgttaacctg ccaatgagat    4080
ctgtgaaaaa ataatggcct cattttttctc ttttttaattt cttttacccct tttgtgaagc   4140 agctatacgt ggcatacatg tatttaaaga aaaaaaaata gatgtagagt gttttttttta   4200 cacttttaac ttagcatgtg gtgttgaagt attactgtag atcaagtttg tcttccgcac    4260
taagatgtga ggaaattgtg atttgttctc tccaccacaa atgaattaca catttattat    4320
cttctatcat tttgaaacac tgcagtttac catgggacac tgtatatatt tcttgccata    4380
atggtaaagg actgattgat atatttaaga gttaataaat ttgtgatttc tgctgacagt    4440
gcgtccatct ttatttcttc agaagaggta ctgtatgtat gcctgcatag tgctggccag    4500
tgtcaagggc agtgtgtcct actctggtct catttagtac ataacaattt gcacttggtg    4560
agaatggcaa gttaattgtt ctctgtgagc aaaacaatgg tctcttctgg gaaaatgttg    4620
ctgagaacaa tatagttaac aactaagact cctaaaagct tctctaaact gtaccctcca    4680
atccagcctt cacatggctg cttttttttt ttttttttaa tacgaacctg tccttgtaac    4740
actttgatgt tatcatttct gggatacagg caagcacccc agctcctgct actcccagc    4800 ttgaacttga gcatacatgg atgctcagct tcttttgatt tgctaaaaac atcacacttg    4860
ctcacatgcc tgtttatgct gttcatgttg tttatgtttc ttacctagaa taaatagtct    4920 cttccccctac ttctttttccc gacttcttac ttttttcctaa gattcagtgt acagcatcat  4980
gctccacagc aaaccttcct aggccctatt ctgggcttgc cttccctctc aaaacctaca    5040
```

```
taatagattg tatttacctc tcctgtcaac cacattgttt tgaaaatata tttctatttg    5100
tgtctcctct actgcagtat aatgtctcca tgggcaagaa ctgtgtattc atcattgcat    5160
tcctaaaccc aaaccaaggc caggaatgga gatatcattg ataaatagtt gttgaattga    5220
ggccaagccc ttttgataac agaagcctca aggggtaccc agatagtcct tgttttaatg    5280
atgggttctc tcaccactgt cttgatgctc tgagcaagtt acctcttccc tctgaccctc    5340
agtttccata tttgtaaaat gagaataaac ataccaactt aataaagata ttgtgaggat    5400
taatgggtac agagtgacta gaatgatatt tgatagaaat taaatggtag cagtataact    5460
attctgatca ctgacattaa tattcctatt gttattattc tttgctcacg agggtataca    5520
actcttgttt tgctgttggg ctgccctctt tatgtaggtt tactgttaat gctgaggata    5580
tactcggact caaatgtctc agcagaaggc tgagagacac caaatgaagt ggtcatctag    5640
ctgaatgtag gaaaaatgaa atgtagtagc aaatcagtat attctaagga aattttcaag    5700
gaatattaat cttcacccaa attttgaatt tttatgtaaa aaattataat ttaagggtaa    5760
acatagatga cacagctttc gagtgatttc attgaataaa attctactga cttctatgaa    5820
```

<210> SEQ ID NO 38
<211> LENGTH: 478
<212> TYPE: PRT
<213> ORGANISM: Artificial Sequence
<220> FEATURE:
<223> OTHER INFORMATION: Synthetic

<400> SEQUENCE: 38

Met Ala Ser Thr Thr Thr Cys Thr Arg Phe Thr Asp Glu Tyr Gln Leu
1               5                   10                  15

Phe Glu Glu Leu Gly Lys Gly Ala Phe Ser Val Val Arg Arg Cys Met
                20                  25                  30

Lys Ile Pro Thr Gly Gln Glu Tyr Ala Ala Lys Ile Ile Asn Thr Lys
            35                  40                  45

Lys Leu Ser Ala Arg Asp His Gln Lys Leu Glu Arg Glu Ala Arg Ile
        50                  55                  60

Cys Arg Leu Leu Lys His Pro Asn Ile Val Arg Leu His Asp Ser Ile
65                  70                  75                  80

Ser Glu Glu Gly Phe His Tyr Leu Val Phe Asp Leu Val Thr Gly Gly
                85                  90                  95

Glu Leu Phe Glu Asp Ile Val Ala Arg Glu Tyr Tyr Ser Glu Ala Asp
                100                 105                 110

Ala Ser His Cys Ile Gln Gln Ile Leu Glu Ser Val Asn His Cys His
            115                 120                 125

Leu Asn Gly Ile Val His Arg Asp Leu Lys Pro Glu Asn Leu Leu Leu
        130                 135                 140

Ala Ser Lys Ser Lys Gly Ala Ala Val Lys Leu Ala Asp Phe Gly Leu
145                 150                 155                 160

Ala Ile Glu Val Gln Gly Asp Gln Gln Ala Trp Phe Gly Phe Ala Gly
                165                 170                 175

Thr Pro Gly Tyr Leu Ser Pro Glu Val Leu Arg Lys Asp Pro Tyr Gly
                180                 185                 190

Lys Pro Val Asp Met Trp Ala Cys Gly Val Ile Leu Tyr Ile Leu Leu
            195                 200                 205

Val Gly Tyr Pro Pro Phe Trp Asp Glu Asp Gln His Arg Leu Tyr Gln
        210                 215                 220

Gln Ile Lys Ala Gly Ala Tyr Asp Phe Pro Ser Pro Glu Trp Asp Thr

```
                225                 230                 235                 240
Val Thr Pro Glu Ala Lys Asp Leu Ile Asn Lys Met Leu Thr Ile Asn
                    245                 250                 255
Pro Ala Lys Arg Ile Thr Ala Ser Glu Ala Leu Lys His Pro Trp Ile
                    260                 265                 270
Cys Gln Arg Ser Thr Val Ala Ser Met Met His Arg Gln Glu Thr Val
                    275                 280                 285
Asp Cys Leu Lys Lys Phe Asn Ala Arg Arg Lys Leu Lys Gly Ala Ile
                    290                 295                 300
Leu Thr Thr Met Leu Ala Thr Arg Asn Phe Ser Ala Ala Lys Ser Leu
305                 310                 315                 320
Leu Lys Lys Pro Asp Gly Val Lys Glu Ser Thr Glu Ser Ser Asn Thr
                    325                 330                 335
Thr Ile Glu Asp Glu Asp Val Lys Ala Arg Lys Gln Glu Ile Ile Lys
                    340                 345                 350
Val Thr Glu Gln Leu Ile Glu Ala Ile Asn Asn Gly Asp Phe Glu Ala
                    355                 360                 365
Tyr Thr Lys Ile Cys Asp Pro Gly Leu Thr Ala Phe Glu Pro Glu Ala
                    370                 375                 380
Leu Gly Asn Leu Val Glu Gly Met Asp Phe His Arg Phe Tyr Phe Glu
385                 390                 395                 400
Asn Ala Leu Ser Lys Ser Asn Lys Pro Ile His Thr Ile Ile Leu Asn
                    405                 410                 415
Pro His Val His Leu Val Gly Asp Asp Ala Ala Cys Ile Ala Tyr Ile
                    420                 425                 430
Arg Leu Thr Gln Tyr Met Asp Gly Ser Gly Met Pro Lys Thr Met Gln
                    435                 440                 445
Ser Glu Glu Thr Arg Val Trp His Arg Arg Asp Gly Lys Trp Gln Asn
                    450                 455                 460
Val His Phe His Arg Ser Gly Ser Pro Thr Val Pro Ile Lys
465                 470                 475
```

<210> SEQ ID NO 39
<211> LENGTH: 3821
<212> TYPE: DNA
<213> ORGANISM: Artificial Sequence
<220> FEATURE:
<223> OTHER INFORMATION: Synthetic

<400> SEQUENCE: 39

| | | | | | |
|---|---|---|---|---|---|
| agtctcgcgg | tgctgccggg | ctcagcccg | tctcctcctc | ttgctccctc | ggccgggcgg | 60 |
| cggtgactgt | gcaccgacgt | cggcgcgggc | tgcaccgccg | cgtccgcccg | cccgccagca | 120 |
| tggccaccac | cgccacctgc | acccgtttca | ccgacgacta | ccagctcttc | gaggagcttg | 180 |
| gcaagggtgc | tttctctgtg | gtccgcaggt | gtgtgaagaa | aacctccacg | caggagtacg | 240 |
| cagcaaaaat | catcaatacc | aagaagttgt | ctgcccggga | tcaccagaaa | ctagaacgtg | 300 |
| aggctcggat | atgtcgactt | ctgaaacatc | aaacatcgt | gcgcctccat | gacagtattt | 360 |
| ctgaagaagg | gtttcactac | ctcgtgtttg | accttgttac | cggcggggag | ctgtttgaag | 420 |
| acattgtggc | cagagagtac | tacagtgaag | cagatgccag | ccactgtata | catcagattc | 480 |
| tggagagtgt | taaccacatc | accagcatg | acatcgtcca | cagggacctg | aagcctgaga | 540 |
| acctgctgct | ggcgagtaaa | tgcaagggtg | ccgccgtcaa | gctggctgat | tttggcctag | 600 |
| ccatcgaagt | acagggagag | cagcaggctt | ggtttggttt | tgctggcacc | ccaggttact | 660 |

```
tgtccnctga ggtcttgagg aaagatccct atggaaaacc tgtggatatc tgggcctgcg    720
gggtcatcct gtatatcctc ctggtgggct atcctcnctt ctgggatgag gatcagcaca    780
agctgtatca gcagatcaag gctggagcct atgatttccc atcaccagaa tgggacacgg    840
taactcctga agccaagaac ttgatcaacc agatgctgac cataaaccca gcaaagcgca    900
tcacggctga ccaggctctc aagcacccgt gggtctgtca acgatccacg gtggcatcca    960
tgatgcatcg tcaggagact gtggagtgtt tgcgcaagtt caatgcccgg agaaaactga   1020
agggtgccat cctcacgacc atgcttgtct ccaggaactt ctcagctgcc aaaagcctat   1080
tgaacaagaa gtcggatggc ggtgtcaagc cacagagcaa caacaaaaac agtctcgtaa   1140
gcccagccca agagcccgcg cccttgcaga cggccatgga gccacaaacc actgtggtac   1200
acaacgctac agatgggatc aagggctcca cagagagctg caacaccacc acagaagatg   1260
aggacctcaa agctgcnccg ctccgcactg ggaatggcag ctcggtgcct gaaggacgga   1320
gctcccggga cagaacagcc ccctctgcag gcatgcagcc ccagccttct ctctgctcct   1380
cagccatgcg aaaacaggag atcattaaga ttacagaaca gctgattgaa gccatcaaca   1440
atggggactt tgaggcctac acgaagattt gtgatccagg cctcacttcc tttgagcctg   1500
aggcccttgg taacctcgtg gagggatgg atttccataa gttttacttt gagaatctcc   1560
tgtccaagaa cagcaagcct atccatacca ccatcctaaa cccacacgtc acgtgattg   1620 gggaggacgc agcgtgcatc gcctacatcc gcctcaccca gtacatcgac gggcagggtc   1680
ggcctcgcac cagccagtca gaagagaccc gggtctggca ccgtcgggat ggcaagtggc   1740
tcaatgtcca ctatcactgc tcaggggccc ctgccgcacc gctgcagtga gctcagccac   1800
aggggcttta ggagattcca gccggaggtc caaccttcgc agccagtggc tctggagggc   1860
ctgagtgaca gcggcagtcc tgtttgtttg aggtttaaaa caattcaatt acaaaagcgg   1920
cagcagccaa tgcacgcccc tgcatgcagc cctcccgccc gcccttcgtg tctgtctctg   1980
ctgtaccgag gtgttttta catttaagaa aaaaaaaaa gaaaaaaga ttgtttaaaa   2040 aaaaaaggaa tccataccat gatgcgtttt aaaaccaccg acagcccttg ggttggcaag   2100
aaggcaggag tatgtatgag gtccatcctg gcatgagcag tggctcaccc accggccttg   2160
aagaggtgag cttggcctct ctggtcccca tggacttagg gggaccaggc aagaactctg   2220
acagagcttt gggggccgtg atgtgattgc agctcctgag gtggcctgct taccccaggt   2280
ctaggaatga acttctttgg aacttgcata ggcgcctaga atggggctga tgagaacatc   2340
gtgaccatca gacctacttg ggagagaacg cagagctccc agcctgctgt ggaggcagct   2400
gagaagtggt ggcctcagga ctgagagccc ggacgttgct gtactgtctt gtttagtgta   2460
gaagggaaga gaattggtgc tgcagaagtg tacccgccat gaagccgatg agaaacctcg   2520
tgttagtctg acatgcactc actcatccat ttctatagga tgcacaatgc atgtgggccc   2580
taatattgag gccttatccc tgcagctagg agggggaggg gttgttgctg ctttgcttcg   2640
tgttttcttc taacctggca aggagagagc caggccctgg tcagggctcc cgtgccgcct   2700
ttggcggttc tgtttctgtg ctgatctgga ccatctttgt cttgcctttt cacggtagtg   2760
gtccccatgc tgaccctcat ctgggcctgg gccctctgcc aagtgcccct gtgggatggg   2820
aggagtgagg cagtgggaga agaggtggtg gtcgtttcta tgcattcagg ctgcctttgg   2880
ggctgcctcc cttcttattc ttccttgctg cacgtccatc tcttttcctg tctttgagat   2940
tgacctgact gctctggcaa gaagaagagg tgtccttaca gaggcctctt tactgaccaa   3000
ctgaagtata gacttactgc tggacaatct gcatgggcat caccctccc cgcatgtaac   3060
```

```
ccaaaagagg tgtccagagc caaggcttct accttcattg tccctctctg tgctcaagga    3120
gttccattcc aggaggaaga gatctatacc ctaagcagat agcaaagaag ataatggagg    3180
agcaattggt catggccttg gtttccctca aaacaacgct gcagatttat ctgcacaaac    3240
atctccactt ttgggggaaa ggtgggtaga ttccagttcc ctggactacc ttcaggaggc    3300
acgagagctg ggagaagagg caaagctaca ggtttacttg ggagccagct gagaagagag    3360
cagactcaca ggtgctggtg cttggattta gccaggctcc tccgagcacc tcatgcatgt    3420
cccagcccct gggccctagc cctttcctgc cctgcagtct gcagtgccag cacgcaaatc    3480
ccttcaccac agggtttcgt tttgctggct tgaagacaaa tggtcttaga attcattgag    3540
acccatagct tcatatggct gctccagccc cacttcttag cattcttact cctcttctgg    3600
ggctaatgtc agcatctata gacaatagac tattaaaaaa tcacctttta aacaagaaac    3660
ggaaggcatt tgatgcagaa ttttgcatg acaacataga aataatttaa aaatagtgtt     3720
tgttctgaat gttggtagac ccttcatagc tttgttacaa tgaaaccttg aactgaaaat    3780
atttaataaa ataacctta aacagtcaaa aaaaaaaaa a                         3821
```

<210> SEQ ID NO 40
<211> LENGTH: 556
<212> TYPE: PRT
<213> ORGANISM: Artificial Sequence
<220> FEATURE:
<223> OTHER INFORMATION: Synthetic

<400> SEQUENCE: 40

```
Met Ala Thr Thr Ala Thr Cys Thr Arg Phe Thr Asp Asp Tyr Gln Leu
1               5                   10                  15

Phe Glu Glu Leu Gly Lys Gly Ala Phe Ser Val Val Arg Arg Cys Val
            20                  25                  30

Lys Lys Thr Ser Thr Gln Glu Tyr Ala Ala Lys Ile Ile Asn Thr Lys
        35                  40                  45

Lys Leu Ser Ala Arg Asp His Gln Lys Leu Glu Arg Glu Ala Arg Ile
    50                  55                  60

Cys Arg Leu Leu Lys His Pro Asn Ile Val Arg Leu His Asp Ser Ile
65                  70                  75                  80

Ser Glu Glu Gly Phe His Tyr Leu Val Phe Asp Leu Val Thr Gly Gly
                85                  90                  95

Glu Leu Phe Glu Asp Ile Val Ala Arg Glu Tyr Tyr Ser Glu Ala Asp
            100                 105                 110

Ala Ser His Cys Ile His Gln Ile Leu Glu Ser Val Asn His Ile His
        115                 120                 125

Gln His Asp Ile Val His Arg Asp Leu Lys Pro Glu Asn Leu Leu Leu
    130                 135                 140

Ala Ser Lys Cys Lys Gly Ala Ala Val Lys Leu Ala Asp Phe Gly Leu
145                 150                 155                 160

Ala Ile Glu Val Gln Gly Glu Gln Gln Ala Trp Phe Gly Phe Ala Gly
                165                 170                 175

Thr Pro Gly Tyr Leu Ser Pro Glu Val Leu Arg Lys Asp Pro Tyr Gly
            180                 185                 190

Lys Pro Val Asp Ile Trp Ala Cys Gly Val Ile Leu Tyr Ile Leu Leu
        195                 200                 205

Val Gly Tyr Pro Pro Phe Trp Asp Glu Asp Gln His Lys Leu Tyr Gln
    210                 215                 220
```

Gln Ile Lys Ala Gly Ala Tyr Asp Phe Pro Ser Pro Glu Trp Asp Thr
225                 230                 235                 240

Val Thr Pro Glu Ala Lys Asn Leu Ile Asn Gln Met Leu Thr Ile Asn
            245                 250                 255

Pro Ala Lys Arg Ile Thr Ala Asp Gln Ala Leu Lys His Pro Trp Val
        260                 265                 270

Cys Gln Arg Ser Thr Val Ala Ser Met Met His Arg Gln Glu Thr Val
    275                 280                 285

Glu Cys Leu Arg Lys Phe Asn Ala Arg Arg Lys Leu Lys Gly Ala Ile
290                 295                 300

Leu Thr Thr Met Leu Val Ser Arg Asn Phe Ser Ala Ala Lys Ser Leu
305                 310                 315                 320

Leu Asn Lys Lys Ser Asp Gly Val Lys Pro Gln Ser Asn Ser Asn Lys
            325                 330                 335

Asn Ser Leu Val Ser Pro Ala Gln Glu Pro Ala Pro Leu Gln Thr Ala
        340                 345                 350

Met Glu Pro Gln Thr Thr Val Val His Asn Ala Thr Asp Gly Ile Lys
    355                 360                 365

Gly Ser Thr Glu Ser Cys Asn Thr Thr Thr Glu Asp Glu Asp Leu Lys
370                 375                 380

Ala Ala Pro Leu Arg Thr Gly Asn Gly Ser Ser Val Pro Glu Gly Arg
385                 390                 395                 400

Ser Ser Arg Asp Arg Thr Ala Pro Ser Ala Gly Met Gln Pro Gln Pro
            405                 410                 415

Ser Leu Cys Ser Ser Ala Met Arg Lys Gln Glu Ile Ile Lys Ile Thr
        420                 425                 430

Glu Gln Leu Ile Glu Ala Ile Asn Asn Gly Asp Phe Glu Ala Tyr Thr
    435                 440                 445

Lys Ile Cys Asp Pro Gly Leu Thr Ser Phe Glu Pro Glu Ala Leu Gly
450                 455                 460

Asn Leu Val Glu Gly Met Asp Phe His Lys Phe Tyr Phe Glu Asn Leu
465                 470                 475                 480

Leu Ser Lys Asn Ser Lys Pro Ile His Thr Thr Ile Leu Asn Pro His
            485                 490                 495

Val His Val Ile Gly Glu Asp Ala Ala Cys Ile Ala Tyr Ile Arg Leu
        500                 505                 510

Thr Gln Tyr Ile Asp Gly Gln Gly Arg Pro Arg Thr Ser Gln Ser Glu
    515                 520                 525

Glu Thr Arg Val Trp His Arg Arg Asp Gly Lys Trp Leu Asn Val His
530                 535                 540

Tyr His Cys Ser Gly Ala Pro Ala Ala Pro Leu Gln
545                 550                 555

<210> SEQ ID NO 41
<211> LENGTH: 2168
<212> TYPE: DNA
<213> ORGANISM: Artificial Sequence
<220> FEATURE:
<223> OTHER INFORMATION: Synthetic

<400> SEQUENCE: 41
ctctctcgct cctgcgttcg caggcggcgg ctggcggccg gcttctcgct cgggcagcgg     60
cggcggcggc ggcggcggct tccggagtcc cgctgcgaag atgctcaaag tcacggtgcc    120
ctcctgctcc gcctcgtcct gctcttcggt caccgccagt gcggcccctgg ggaccgcgag    180

| | |
|---|---|
| cctcgtcccg gattactgga tcgacggctc aacagggat gcgctgagcg atttcttcga | 240 |
| ggtggagtcg gagctggac ggggtgctac atccattgtg tacagatgca acagaaggg | 300 |
| gacccagaag ccttatgctc tcaaagtgtt aaagaaaaca gtggacaaaa aaatcgtaag | 360 |
| aactgagata ggagttcttc ttcgcctctc acatccaaac attataaaac ttaaagagat | 420 |
| atttgaaacc cctacagaaa tcagtctggt cctagaactc gtcacaggag gagaactgtt | 480 |
| tgataggatt gtggaaaagg gatattacag tgagcgagat gctgcagatg ccgttaaaca | 540 |
| aatcctggag gcagttgctt atctacatga aaatgggatt gtccatcgtg atctcaaacc | 600 |
| agagaatctt ctttatgcaa ctccagcccc agatgcacca ctcaaaatcg ctgattttgg | 660 |
| actctctaaa attgtggaac atcaagtgct catgaagaca gtatgtggaa ccccagggta | 720 |
| ctgcgcacct gaaattctta gaggttgtgc ctatggacct gaggtggaca tgtggtctgt | 780 |
| aggaataatc acctacatct tactttgtgg attttgaacca ttctatgatg aaagaggcga | 840 |
| tcagttcatg ttcaggagaa ttctgaattg tgaatattac tttatctccc cctggtggga | 900 |
| tgaagtatct ctaaatgcca aggacttggt cagaaaatta attgttttgg atccaaagaa | 960 |
| acggctgact acatttcaag ctctccagca tccgtgggtc acaggtaaag cagccaattt | 1020 |
| tgtacacatg gataccgctc aaaagaagct ccaagaattc aatgcccggc gtaagcttaa | 1080 |
| ggcagcggtg aaggctgtgg tggcctcttc gcgcctggga agtgccagca gcagccatgg | 1140 |
| cagcatccag gagagccaca aggctagccg agacccttct ccaatccaag atggcaacga | 1200 |
| ggacatgaaa gctattccag aaggagagaa aattcaaggc gatggggccc aagccgcagt | 1260 |
| taaggggca caggctgagc tgatgaaggt gcaagcctta gagaaagtta aggtgcaga | 1320 |
| tataaatgct gaagaggccc ccaaaatggt gcccaaggca gtggaggatg ggataaaggt | 1380 |
| ggctgacctg gaactagagg agggcctagc agaggagaag ctgaagactg tggaggaggc | 1440 |
| agcagctccc agagaagggc aaggaagctc tgctgtgggt tttgaagttc cacagcaaga | 1500 |
| tgtgatcctg ccagagtact aaacagcttc cttcagatct ggaagccaaa caccggcatt | 1560 |
| ttatgtactt tgtccttcag caagaaaggt gtggaagcat gatatgtact atagtgattc | 1620 |
| tgttttttgag gtgcaaaaaa catacatata taccagttgg taattctaac ttcaatgcat | 1680 |
| gtgactgctt tatgaaaata atagtgtctt ctatggcatg taatggatac ctaataccga | 1740 |
| tgagttaaat cttgcaagtt aacacaacgt aacacttaaa agcatacatt ttcagcaacc | 1800 |
| agtggcacat atttgaagtg aatagtagca aattgttttt gctttgaaaa tctagccatc | 1860 |
| ctacatcctt tggatttctt cacaaggcag taattccttt gaactactgc ttagctaata | 1920 |
| ctaggtagtg ctaaaagaca tgttcccata acttttacaa cattttactt tttatcattg | 1980 |
| atgtgttcaa actgtttaca aggagatgct tatagatgat agttgtacat atgtgcaaaa | 2040 |
| aaaaatccac ttgcaatggt aagaaattga agtatcctta aaggccatga agccatatgt | 2100 |
| ccctaaaaaa aaaaaaaaaa aaaaaaaaaa aaaaaaaaaa aaaaaaaaaa aaaaaaaaaa | 2160 |
| aaaaaaaa | 2168 |

<210> SEQ ID NO 42
<211> LENGTH: 473
<212> TYPE: PRT
<213> ORGANISM: Artificial Sequence
<220> FEATURE:
<223> OTHER INFORMATION: Synthetic

<400> SEQUENCE: 42

Met Leu Lys Val Thr Val Pro Ser Cys Ser Ala Ser Ser Cys Ser Ser

-continued

```
1               5                   10                  15
Val Thr Ala Ser Ala Ala Pro Gly Thr Ala Ser Leu Val Pro Asp Tyr
            20                  25                  30

Trp Ile Asp Gly Ser Asn Arg Asp Ala Leu Ser Asp Phe Phe Glu Val
            35                  40                  45

Glu Ser Glu Leu Gly Arg Gly Ala Thr Ser Ile Val Tyr Arg Cys Lys
50                      55                  60

Gln Lys Gly Thr Gln Lys Pro Tyr Ala Leu Lys Val Leu Lys Lys Thr
65                  70                  75                  80

Val Asp Lys Lys Ile Val Arg Thr Glu Ile Gly Val Leu Leu Arg Leu
                85                  90                  95

Ser His Pro Asn Ile Ile Lys Leu Lys Glu Ile Phe Glu Thr Pro Thr
                100                 105                 110

Glu Ile Ser Leu Val Leu Glu Leu Val Thr Gly Gly Glu Leu Phe Asp
                115                 120                 125

Arg Ile Val Glu Lys Gly Tyr Tyr Ser Glu Arg Asp Ala Ala Asp Ala
        130                 135                 140

Val Lys Gln Ile Leu Glu Ala Val Ala Tyr Leu His Glu Asn Gly Ile
145                 150                 155                 160

Val His Arg Asp Leu Lys Pro Glu Asn Leu Leu Tyr Ala Thr Pro Ala
                165                 170                 175

Pro Asp Ala Pro Leu Lys Ile Ala Asp Phe Gly Leu Ser Lys Ile Val
                180                 185                 190

Glu His Gln Val Leu Met Lys Thr Val Cys Gly Thr Pro Gly Tyr Cys
                195                 200                 205

Ala Pro Glu Ile Leu Arg Gly Cys Ala Tyr Gly Pro Glu Val Asp Met
        210                 215                 220

Trp Ser Val Gly Ile Ile Thr Tyr Ile Leu Leu Cys Gly Phe Glu Pro
225                 230                 235                 240

Phe Tyr Asp Glu Arg Gly Asp Gln Phe Met Phe Arg Arg Ile Leu Asn
                245                 250                 255

Cys Glu Tyr Tyr Phe Ile Ser Pro Trp Trp Asp Glu Val Ser Leu Asn
                260                 265                 270

Ala Lys Asp Leu Val Arg Lys Leu Ile Val Leu Asp Pro Lys Lys Arg
                275                 280                 285

Leu Thr Thr Phe Gln Ala Leu Gln His Pro Trp Val Thr Gly Lys Ala
        290                 295                 300

Ala Asn Phe Val His Met Asp Thr Ala Gln Lys Lys Leu Gln Glu Phe
305                 310                 315                 320

Asn Ala Arg Arg Lys Leu Lys Ala Ala Val Lys Ala Val Val Ala Ser
                325                 330                 335

Ser Arg Leu Gly Ser Ala Ser Ser Ser His Gly Ser Ile Gln Glu Ser
                340                 345                 350

His Lys Ala Ser Arg Asp Pro Ser Pro Ile Gln Asp Gly Asn Glu Asp
                355                 360                 365

Met Lys Ala Ile Pro Glu Gly Glu Lys Ile Gln Gly Asp Gly Ala Gln
        370                 375                 380

Ala Ala Val Lys Gly Ala Gln Ala Glu Leu Met Lys Val Gln Ala Leu
385                 390                 395                 400

Glu Lys Val Lys Gly Ala Asp Ile Asn Ala Glu Glu Ala Pro Lys Met
                405                 410                 415

Val Pro Lys Ala Val Glu Asp Gly Ile Lys Val Ala Asp Leu Glu Leu
                420                 425                 430
```

Glu Gly Leu Ala Glu Glu Lys Leu Lys Thr Val Glu Glu Ala Ala
            435                 440                 445

Ala Pro Arg Glu Gly Gln Gly Ser Ser Ala Val Gly Phe Glu Val Pro
    450                 455                 460

Gln Gln Asp Val Ile Leu Pro Glu Tyr
465                 470

<210> SEQ ID NO 43
<211> LENGTH: 1522
<212> TYPE: DNA
<213> ORGANISM: Artificial Sequence
<220> FEATURE:
<223> OTHER INFORMATION: Synthetic

<400> SEQUENCE: 43
agcagctgta ggcctgggat gtggaggcgt gtatgcggtg gcctcgctgg gaggcgtccg      60
tctggggaca tgctgctgct gaagaaacac acggaggaca tcagcagcgt ctacgagatc     120
cgcgagaggc tcggctcggg tgccttctcc gaggtggtgc tggcccagga gcggggctcc     180
gcacacctcg tggccctcaa gtgcatcccc aagaaggccc tccggggcaa ggaggccctg     240
gtggagaacg agatcgcagt gctccgtagg atcagtcacc ccaacatcgt cgctctggag     300
gatgtccacg agagcccttc ccacctctac ctggccatgg aactggtgac gggtggcgag     360
ctgtttgacc gcatcatgga gcgcggctcc tacacagaga aggatgccag ccatctggtg     420
ggtcaggtcc ttggcgccgt ctcctacctg cacagcctgg ggatcgtgca ccgggacctc     480
aagcccgaaa acctcctgta tgccacgccc tttgaggact cgaagatcat ggtctctgac     540
tttggactct ccaaaatcca ggctgggaac atgctaggca ccgcctgtgg accccctgga     600
tatgtggccc cagagctctt ggagcagaaa ccctacggga aggccgtaga tgtgtgggcc     660
ctgggcgtca tctcctacat cctgctgtgt gggtaccccc ccttctacga cgagagcgac     720
cctgagctct tcagccagat cctgagggcc agctatgagt ttgactctcc tttctgggat     780
gacatctcag aatcagccaa agacttcatc cggcaccttc tggagcgaga ccccagaag     840 aggttcacct gccaacaggc cttgcggcac ctttggatct ctggggacac agccttcgac     900
agggacatct aggctctgt cagtgagcag atccggaaga actttgctcg acacactgg      960 aagcgagcct tcaatgccac ctcgttcctg cgccacatcc ggaagctggg gcagatccca    1020
gagggcgagg gggcctctga gcagggcatg gcccgccaca gccactcagg cctccgtgct    1080
ggccagcccc ccaagtggtg atgcccaggc agatgcgag gccaagtgga ctgaccccca     1140
gatttccttc ccttggatgc tttcggtccc ctcccccaac ccctcccct ggggctggcc     1200 tctgctggat tttgagattt gagggtgtgg cgcatggcgc tggggttgga atggggcacc    1260
cccaagtctg tccccaggct ctgccctgcc tgggggcagt ggctcccctc ccctgttgcc    1320
tctcccgccc ctgccccccc cgccccgcca aaagccgagg gggtgctggc aggcgggcct    1380
caggggctgt ctttcctgca cggctgttgt gtgcttcgct gagtgtgggt ggtcctgctt    1440
gtgtcatggt catggccttc cagccccctc cagttttccc caaaccaata agaaagata    1500 cagcaaaaaa aaaaaaaaaa aa                                              1522

<210> SEQ ID NO 44
<211> LENGTH: 360
<212> TYPE: PRT
<213> ORGANISM: Artificial Sequence
<220> FEATURE:
<223> OTHER INFORMATION: Synthetic

<400> SEQUENCE: 44

```
Met Trp Arg Arg Val Cys Gly Gly Leu Ala Gly Arg Pro Ser Gly
1               5                   10                  15

Asp Met Leu Leu Leu Lys Lys His Thr Glu Asp Ile Ser Ser Val Tyr
                20                  25                  30

Glu Ile Arg Glu Arg Leu Gly Ser Gly Ala Phe Ser Glu Val Val Leu
            35                  40                  45

Ala Gln Glu Arg Gly Ser Ala His Leu Val Ala Leu Lys Cys Ile Pro
    50                  55                  60

Lys Lys Ala Leu Arg Gly Lys Glu Ala Leu Val Glu Asn Glu Ile Ala
65                  70                  75                  80

Val Leu Arg Arg Ile Ser His Pro Asn Ile Val Ala Leu Glu Asp Val
                85                  90                  95

His Glu Ser Pro Ser His Leu Tyr Leu Ala Met Glu Leu Val Thr Gly
            100                 105                 110

Gly Glu Leu Phe Asp Arg Ile Met Glu Arg Gly Ser Tyr Thr Glu Lys
        115                 120                 125

Asp Ala Ser His Leu Val Gly Gln Val Leu Gly Ala Val Ser Tyr Leu
130                 135                 140

His Ser Leu Gly Ile Val His Arg Asp Leu Lys Pro Glu Asn Leu Leu
145                 150                 155                 160

Tyr Ala Thr Pro Phe Glu Asp Ser Lys Ile Met Val Ser Asp Phe Gly
                165                 170                 175

Leu Ser Lys Ile Gln Ala Gly Asn Met Leu Gly Thr Ala Cys Gly Thr
            180                 185                 190

Pro Gly Tyr Val Ala Pro Glu Leu Leu Glu Gln Lys Pro Tyr Gly Lys
        195                 200                 205

Ala Val Asp Val Trp Ala Leu Gly Val Ile Ser Tyr Ile Leu Leu Cys
210                 215                 220

Gly Tyr Pro Pro Phe Tyr Asp Glu Ser Asp Pro Glu Leu Phe Ser Gln
225                 230                 235                 240

Ile Leu Arg Ala Ser Tyr Glu Phe Asp Ser Pro Phe Trp Asp Asp Ile
                245                 250                 255

Ser Glu Ser Ala Lys Asp Phe Ile Arg His Leu Leu Glu Arg Asp Pro
            260                 265                 270

Gln Lys Arg Phe Thr Cys Gln Gln Ala Leu Arg His Leu Trp Ile Ser
        275                 280                 285

Gly Asp Thr Ala Phe Asp Arg Asp Ile Leu Gly Ser Val Ser Glu Gln
    290                 295                 300

Ile Arg Lys Asn Phe Ala Arg Thr His Trp Lys Arg Ala Phe Asn Ala
305                 310                 315                 320

Thr Ser Phe Leu Arg His Ile Arg Lys Leu Gly Gln Ile Pro Glu Gly
                325                 330                 335

Glu Gly Ala Ser Glu Gln Gly Met Ala Arg His Ser His Ser Gly Leu
            340                 345                 350

Arg Ala Gly Gln Pro Pro Lys Trp
        355                 360
```

<210> SEQ ID NO 45
<211> LENGTH: 2242
<212> TYPE: DNA
<213> ORGANISM: Artificial Sequence
<220> FEATURE:
<223> OTHER INFORMATION: Synthetic

```
<400> SEQUENCE: 45
agccggcgcg cggcggcggc aggaagtctg tgcccgagaa cagcagaaat aagagccagg      60
gagggaccgc ggccgcggcg gcggcggcga gagcgaaaga ggaaactgca gaggaggaag     120
ctgcgccgca gcccgagccg cccggcatcc ccgccgcctc tgcgcccgcg ccgcgccccc     180
ggcgccccct ccccagcgcg ccccggccg ctcctccgcg ccgcgctcgt cggccatggc     240
ccgggagaac ggcgagagca gctcctcctg gaaaaagcaa gctgaagaca tcaagaagat     300
cttcgagttc aaagagaccc tcggaaccgg ggccttttcc gaagtggttt tagctgaaga     360
gaaggcaact ggcaagctct ttgctgtgaa gtgtatccct aagaaggcgc tgaagggcaa     420
ggaaagcagc atagagaatg agatagccgt cctgagaaag attaagcatg aaaatattgt     480
tgccctggaa gacatttatg aaagcccaaa tcacctgtac ttggtcatgc agctggtgtc     540
cggtggagag ctgtttgacc ggatagtgga aaggggtttt tatacagaga aggatgccag     600
cactctgatc cgccaagtct ggacgccgt gtactatctc cacagaatgg gcatcgtcca     660
cagagacctc aagcccgaaa atctcttgta ctacagtcaa gatgaggagt ccaaaataat     720
gatcagtgac tttggattgt caaaaatgga gggcaaagga gatgtgatgt ccactgcctg     780
tggaactcca ggctatgtcg ctcctgaagt cctcgcccag aaaccttaca gcaaagccgt     840
tgactgctgg tccatcggag tgattgccta catcttgctc tgcggctacc ctccttttta     900
tgatgaaaat gactccaagc tctttgagca gatcctcaag gcggaatatg agtttgactc     960
tccctactgg gatgacatct ccgactctgc aaaagacttc attcggaacc tgatggagaa    1020
ggacccgaat aaaagataca cgtgtgagca ggcagctcgg cacccatgga tcgctggtga    1080
cacagccctc aacaaaaaca tccacgagtc cgtcagcgcc cagatccgga aaaactttgc    1140
caagagcaaa tggagacaag catttaatgc cacggccgtc gtcagacata tgagaaaact    1200
acacctcggc agcagcctgg acagttcaaa tgcaagtgtt tcgagcagcc tcagtttggc    1260
cagccaaaaa gactgtctgg caccttccac gctctgtagt ttcatttctt cttcgtcggg    1320
ggtctcagga gttggagccg agcggagacc caggcccacc actgtgacgg cagtgcactc    1380
tggaagcaag tgactggccc tggaggtggg gcccggggtc ggggctgggg aaggggagcc    1440
ccagggtcgc cagagccgcg agccactcca gcgagacccc accttgcatg gtgcccttc    1500
ctgcatagga ctgaagacc gaagttttt tatggccata ttttctactg caattctgaa    1560
gtgttcattt ctcacaaact gtactgactc gaggggcgct gatttcatag gatctggtgc    1620
tgtatatacg aatcttgcaa agctctaact gaacggacct tcttattcct ctccctaac    1680
accatcgttt ccactcttct cagtgtaggt aaccgtctat ggtgtgtttt ttcattaatg    1740
acaaaaaaaa aaaggtttca actggattat ttaaatattg gtaaatattg tgcattaggg    1800
tttgttttc cttttaagaa gtatgtcctt tgtatctcta agttacatga cctatatctt    1860
ttcctcttta atagtagttt tatgttaacc tttaagagat ttgttttcc tcaaaggaga    1920
atttaaaggt attttttaaa attctaataa gaggatcagc cgggtgcaat gactcatgcc    1980
tgtaatccca gcacgttggg aggccaagtc gggcggatca caaggtcagg agatcaaggc    2040
catcctggcc aacatggtga aaccccacgt ctactaaaaa tacaaaaaat tagccgggcg    2100
tggtggcaca cacctgtagt cccggctact cgggaggctg aggcaggaga attgcttgaa    2160
cccgggagac ggaggttgca gtgagctgag atcgtgccac tgcactccag cctgggtgac    2220
agagcaagac tctgtctcaa aa                                             2242
```

```
<210> SEQ ID NO 46
<211> LENGTH: 385
<212> TYPE: PRT
<213> ORGANISM: Artificial Sequence
<220> FEATURE:
<223> OTHER INFORMATION: Synthetic

<400> SEQUENCE: 46

Met Ala Arg Glu Asn Gly Glu Ser Ser Ser Trp Lys Lys Gln Ala
1               5                  10                  15

Glu Asp Ile Lys Lys Ile Phe Glu Phe Lys Glu Thr Leu Gly Thr Gly
                20                  25                  30

Ala Phe Ser Glu Val Val Leu Ala Glu Glu Lys Ala Thr Gly Lys Leu
            35                  40                  45

Phe Ala Val Lys Cys Ile Pro Lys Lys Ala Leu Lys Gly Lys Glu Ser
        50                  55                  60

Ser Ile Glu Asn Glu Ile Ala Val Leu Arg Lys Ile Lys His Glu Asn
65                  70                  75                  80

Ile Val Ala Leu Glu Asp Ile Tyr Glu Ser Pro Asn His Leu Tyr Leu
                85                  90                  95

Val Met Gln Leu Val Ser Gly Gly Glu Leu Phe Asp Arg Ile Val Glu
            100                 105                 110

Lys Gly Phe Tyr Thr Glu Lys Asp Ala Ser Thr Leu Ile Arg Gln Val
        115                 120                 125

Leu Asp Ala Val Tyr Tyr Leu His Arg Met Gly Ile Val His Arg Asp
130                 135                 140

Leu Lys Pro Glu Asn Leu Leu Tyr Tyr Ser Gln Asp Glu Glu Ser Lys
145                 150                 155                 160

Ile Met Ile Ser Asp Phe Gly Leu Ser Lys Met Glu Gly Lys Gly Asp
                165                 170                 175

Val Met Ser Thr Ala Cys Gly Thr Pro Gly Tyr Val Ala Pro Glu Val
            180                 185                 190

Leu Ala Gln Lys Pro Tyr Ser Lys Ala Val Asp Cys Trp Ser Ile Gly
        195                 200                 205

Val Ile Ala Tyr Ile Leu Leu Cys Gly Tyr Pro Pro Phe Tyr Asp Glu
210                 215                 220

Asn Asp Ser Lys Leu Phe Glu Gln Ile Leu Lys Ala Glu Tyr Glu Phe
225                 230                 235                 240

Asp Ser Pro Tyr Trp Asp Asp Ile Ser Asp Ser Ala Lys Asp Phe Ile
                245                 250                 255

Arg Asn Leu Met Glu Lys Asp Pro Asn Lys Arg Tyr Thr Cys Glu Gln
            260                 265                 270

Ala Ala Arg His Pro Trp Ile Ala Gly Asp Thr Ala Leu Asn Lys Asn
        275                 280                 285

Ile His Glu Ser Val Ser Ala Gln Ile Arg Lys Asn Phe Ala Lys Ser
290                 295                 300

Lys Trp Arg Gln Ala Phe Asn Ala Thr Ala Val Val Arg His Met Arg
305                 310                 315                 320

Lys Leu His Leu Gly Ser Ser Leu Asp Ser Ser Asn Ala Ser Val Ser
                325                 330                 335

Ser Ser Leu Ser Leu Ala Ser Gln Lys Asp Cys Leu Ala Pro Ser Thr
            340                 345                 350

Leu Cys Ser Phe Ile Ser Ser Ser Gly Val Ser Gly Val Gly Ala
        355                 360                 365
```

Glu Arg Arg Pro Arg Pro Thr Thr Val Thr Ala Val His Ser Gly Ser
370                 375                 380

Lys
385

<210> SEQ ID NO 47
<211> LENGTH: 2349
<212> TYPE: DNA
<213> ORGANISM: Artificial Sequence
<220> FEATURE:
<223> OTHER INFORMATION: Synthetic

<400> SEQUENCE: 47

| | | | | | |
|---|---|---|---|---|---|
| agggaggtgg | ctgagcatca | aataaatggt | acagtccttg | ctttaagaca | tcagagagag | 60 |
| gagcgggcag | ggagggcctg | gctcacagca | tttcaggaaa | ctatcaggaa | aagcaactct | 120 |
| tgagctaggg | tttggatttg | tagggcact | tcccaacctt | tcttacttaa | ttggctttta | 180 |
| agtttacaca | gctgtgtgta | tatctaagtt | tctgcctgtg | tgagctacag | tgttctaata | 240 |
| aaacacaggc | aatttagtaa | catgatgtaa | acatacagaa | ttgtttaaca | agtaccagga | 300 |
| aaagacatcc | agtaacagga | aaggacaccc | aaatctattt | tggttacctt | agtaaagcag | 360 |
| ggttgccaaa | ctatttattg | cccataagct | aaatctgtca | tgccacctgt | tttttatggc | 420 |
| ctgctaagaa | tggttttttac | gttttttcttt | tttcttttttg | tcaagatggg | tcttgccatg | 480 |
| ttgtccaggc | tggtctcaaa | cttctaggct | caagtgatcc | tgcccctcg | gcctcccaga | 540 |
| gtgctaagat | tgtaatcacg | cgtgtaggtg | taagccacca | cacctggcct | ttcacattt | 600 |
| tcaatggtta | aataaaaacc | aaaacagtaa | tattttgtga | cttatgaaaa | tcatatgaaa | 660 |
| ttcagttttc | agtgtctgta | aataaagttt | tattggaaca | ctgccgcatg | cattcattta | 720 |
| ctatttcctg | tggctgctag | gatggcaggg | ttgagtagct | gcattacaga | gcctatggct | 780 |
| tgcaaagcct | aaaatattta | ctatctggcc | ctttacaaag | tttgctgacc | ctgccttaaa | 840 |
| gtgccccaga | taatctccac | caggcctgat | acatattttt | ttggggggg | ggggggaaa | 900 |
| tatgagaata | tagaaaaata | cgggactatg | catcccccat | tcagaattga | ctattgctaa | 960 |
| cagtttgcca | tttgcctcac | agccatttat | aagtactaaa | aggaataaaa | ctttacaaca | 1020 |
| ttccttatgc | tccctgtccc | gttctgtgct | ttttccttc | tttgtggcac | actgtcatga | 1080 |
| atttaatgta | tattcttctc | tttgacttta | aaaatcttgt | atgtaagcat | gtgtccatga | 1140 |
| acagtatcta | ctgcatggga | ttttaaggta | cacacaaatt | gtacatcatg | ttgtattctg | 1200 |
| caacttgctg | ttttactcaa | cattatgttt | ttgggatttc | cttatgtcag | tacagatcca | 1260 |
| gtgcacccct | tttatctatt | agatggtatt | ccatcaaaca | actataatga | gtttcattta | 1320 |
| tccattcctt | tgatgaacat | ataggaagtt | gttcccaggt | ggttttttt | ttgtgttttt | 1380 |
| gttttgtttt | gttttgtttt | tgagatggag | tcttgctctg | tcacccaggc | tggagtgcag | 1440 |
| tggcatgatc | tcggctcact | gcaacctctg | cctcccgggt | ttcaagcgat | tctcctgcct | 1500 |
| cagcctcctg | agtagttggg | attacaggcg | cgcgccacca | tgcctggcta | atttttgcat | 1560 |
| ttttttttta | agtagagacg | gggtttcacc | atgctggtca | ggctggactt | gaactcctga | 1620 |
| cttcgtgatc | tgcccacctt | ggcctcccaa | agtgctggga | ttacaggcgt | gagccactgt | 1680 |
| gcccagactt | ttttttttt | ttttgaaaca | gtcttggtct | gtcgtccagg | ctggagggta | 1740 |
| gtggtgcgat | ctctctgcct | cccggttcaa | gtggttctcg | tgcttcagcc | tcctgagtag | 1800 |
| ctgggattac | gggcaccgcc | accacaccgg | gctaatttttt | gtatttttga | tagagatggg | 1860 |
| gtttcaccat | gctggccagg | ctagtctcga | acttctggcc | tcaagtgatc | tctccgcccg | 1920 |

```
ggcctcccaa agtgctggga tcataggcgt gagccaccat gcccggcctc aggttttgc    1980 catttccagc aaatgcatgc acgttgagta acatcagaag aggtggatgg ccgagcatgt   2040
tggctcatgc ctataatccc agcactttgg gaggcagagg caggaggatc acttgagccc   2100
aggagtttga ccagcctg ggcaacatag ggagaactct gtctctacaa aaatagaaa    2160 aaattagcca ggtgtggtgg tgtgtgcctg tagtcccagc tactcaggag gctgaggctg   2220
gaggatcacc tgagcctggg gaggtcgagg gtgcagcgag ccgtgatcgt gctactgcac   2280
tccagcctgg gcaacacaga gagaccctgt ctcaaaacaa acaaacaaac aaacaaacaa   2340
acaaacaaa                                                            2349
```

<210> SEQ ID NO 48
<211> LENGTH: 21
<212> TYPE: DNA
<213> ORGANISM: Artificial Sequence
<220> FEATURE:
<223> OTHER INFORMATION: Synthetic

<400> SEQUENCE: 48

```
ggacatgttg ctggccaata a                                              21
```

<210> SEQ ID NO 49
<211> LENGTH: 18
<212> TYPE: DNA
<213> ORGANISM: Artificial Sequence
<220> FEATURE:
<223> OTHER INFORMATION: Synthetic

<400> SEQUENCE: 49

```
gggcccgaga ccagtgtt                                                  18
```

<210> SEQ ID NO 50
<211> LENGTH: 20
<212> TYPE: DNA
<213> ORGANISM: Artificial Sequence
<220> FEATURE:
<223> OTHER INFORMATION: Synthetic

<400> SEQUENCE: 50

```
tccagaccag cccgacatag                                                20
```

<210> SEQ ID NO 51
<211> LENGTH: 20
<212> TYPE: DNA
<213> ORGANISM: Artificial Sequence
<220> FEATURE:
<223> OTHER INFORMATION: Synthetic

<400> SEQUENCE: 51

```
cagggtgca gcttgatttc                                                 20
```

<210> SEQ ID NO 52
<211> LENGTH: 21
<212> TYPE: DNA
<213> ORGANISM: Artificial Sequence
<220> FEATURE:
<223> OTHER INFORMATION: Synthetic

<400> SEQUENCE: 52

```
tggccttatc ctgcctggta t                                              21
```

<210> SEQ ID NO 53

```
<211> LENGTH: 21
<212> TYPE: DNA
<213> ORGANISM: Artificial Sequence
<220> FEATURE:
<223> OTHER INFORMATION: Synthetic

<400> SEQUENCE: 53
aggagtcgat gctgatccca a                                              21

<210> SEQ ID NO 54
<211> LENGTH: 20
<212> TYPE: DNA
<213> ORGANISM: Artificial Sequence
<220> FEATURE:
<223> OTHER INFORMATION: Synthetic

<400> SEQUENCE: 54
ccatggcacc ttcagacttt                                                20

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
actgggccat atgaggatca                                                20

<210> SEQ ID NO 56
<211> LENGTH: 22
<212> TYPE: DNA
<213> ORGANISM: Artificial Sequence
<220> FEATURE:
<223> OTHER INFORMATION: Synthetic

<400> SEQUENCE: 56
ctcagttcct ggagaaagat gg                                             22

<210> SEQ ID NO 57
<211> LENGTH: 21
<212> TYPE: DNA
<213> ORGANISM: Artificial Sequence
<220> FEATURE:
<223> OTHER INFORMATION: Synthetic

<400> SEQUENCE: 57
cccagtcaat tcatgtttgc c                                              21

<210> SEQ ID NO 58
<211> LENGTH: 22
<212> TYPE: DNA
<213> ORGANISM: Artificial Sequence
<220> FEATURE:
<223> OTHER INFORMATION: Synthetic

<400> SEQUENCE: 58
atggaatatg tgtctggagg tg                                             22

<210> SEQ ID NO 59
<211> LENGTH: 21
<212> TYPE: DNA
<213> ORGANISM: Artificial Sequence
<220> FEATURE:
<223> OTHER INFORMATION: Synthetic

<400> SEQUENCE: 59
```
tggtttcagg tctcgatgaa c                                              21

<210> SEQ ID NO 60
<211> LENGTH: 20
<212> TYPE: DNA
<213> ORGANISM: Artificial Sequence
<220> FEATURE:
<223> OTHER INFORMATION: Synthetic

<400> SEQUENCE: 60
gcacagtttg cacacctgaa                                                20

<210> SEQ ID NO 61
<211> LENGTH: 20
<212> TYPE: DNA
<213> ORGANISM: Artificial Sequence
<220> FEATURE:
<223> OTHER INFORMATION: Synthetic

<400> SEQUENCE: 61
gctttggatt taggccctgt                                                20

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
aacaggaaag gacacccaaa                                                20

<210> SEQ ID NO 63
<211> LENGTH: 21
<212> TYPE: DNA
<213> ORGANISM: Artificial Sequence
<220> FEATURE:
<223> OTHER INFORMATION: Synthetic

<400> SEQUENCE: 63
aaaccattct tagcaggcca t                                              21

<210> SEQ ID NO 64
<211> LENGTH: 31
<212> TYPE: DNA
<213> ORGANISM: Artificial Sequence
<220> FEATURE:
<223> OTHER INFORMATION: Synthetic

<400> SEQUENCE: 64
cgctagcagg gaggtggctg agcatcaaat a                                   31

<210> SEQ ID NO 65
<211> LENGTH: 32
<212> TYPE: DNA
<213> ORGANISM: Artificial Sequence
<220> FEATURE:
<223> OTHER INFORMATION: Synthetic

<400> SEQUENCE: 65
caaagctttg agacagggtc tctctgtgtt gc                                  32

<210> SEQ ID NO 66
<211> LENGTH: 31
<212> TYPE: DNA

```
<213> ORGANISM: Artificial Sequence
<220> FEATURE:
<223> OTHER INFORMATION: Synthetic

<400> SEQUENCE: 66
cgctagcgaa ttgcaactgt gagaccaggc a                                31

<210> SEQ ID NO 67
<211> LENGTH: 32
<212> TYPE: DNA
<213> ORGANISM: Artificial Sequence
<220> FEATURE:
<223> OTHER INFORMATION: Synthetic

<400> SEQUENCE: 67
caaagcttgt ggccttgggc aaatgacttg at                               32

<210> SEQ ID NO 68
<211> LENGTH: 31
<212> TYPE: DNA
<213> ORGANISM: Artificial Sequence
<220> FEATURE:
<223> OTHER INFORMATION: Synthetic

<400> SEQUENCE: 68
cgctagcatc aagtcatttg cccaaggcca c                                31

<210> SEQ ID NO 69
<211> LENGTH: 32
<212> TYPE: DNA
<213> ORGANISM: Artificial Sequence
<220> FEATURE:
<223> OTHER INFORMATION: Synthetic

<400> SEQUENCE: 69
caaagcttaa cactgtagct cacacaggca ga                               32

<210> SEQ ID NO 70
<211> LENGTH: 31
<212> TYPE: DNA
<213> ORGANISM: Artificial Sequence
<220> FEATURE:
<223> OTHER INFORMATION: Synthetic

<400> SEQUENCE: 70
cgctagcatc aagtcatttg cccaaggcca c                                31

<210> SEQ ID NO 71
<211> LENGTH: 32
<212> TYPE: DNA
<213> ORGANISM: Artificial Sequence
<220> FEATURE:
<223> OTHER INFORMATION: Synthetic

<400> SEQUENCE: 71
caaagcttta tttgatgctc agccacctcc ct                               32

<210> SEQ ID NO 72
<211> LENGTH: 31
<212> TYPE: DNA
<213> ORGANISM: Artificial Sequence
<220> FEATURE:
<223> OTHER INFORMATION: Synthetic

<400> SEQUENCE: 72
cgctagcagg gaggtggctg agcatcaaat a                                31
```

<210> SEQ ID NO 73
<211> LENGTH: 32
<212> TYPE: DNA
<213> ORGANISM: Artificial Sequence
<220> FEATURE:
<223> OTHER INFORMATION: Synthetic

<400> SEQUENCE: 73
caaagcttaa atgtgaaagg ccaggtgtgg tg                                32

<210> SEQ ID NO 74
<211> LENGTH: 31
<212> TYPE: DNA
<213> ORGANISM: Artificial Sequence
<220> FEATURE:
<223> OTHER INFORMATION: Synthetic

<400> SEQUENCE: 74
cgctagctgc ctgtgtgagc tacagtgttc t                                 31

<210> SEQ ID NO 75
<211> LENGTH: 32
<212> TYPE: DNA
<213> ORGANISM: Artificial Sequence
<220> FEATURE:
<223> OTHER INFORMATION: Synthetic

<400> SEQUENCE: 75
caaagcttaa atgtgaaagg ccaggtgtgg tg                                32

<210> SEQ ID NO 76
<211> LENGTH: 31
<212> TYPE: DNA
<213> ORGANISM: Artificial Sequence
<220> FEATURE:
<223> OTHER INFORMATION: Synthetic

<400> SEQUENCE: 76
cgctagcagg gaggtggctg agcatcaaat a                                 31

<210> SEQ ID NO 77
<211> LENGTH: 32
<212> TYPE: DNA
<213> ORGANISM: Artificial Sequence
<220> FEATURE:
<223> OTHER INFORMATION: Synthetic

<400> SEQUENCE: 77
caaagcttaa cactgtagct cacacaggca ga                                32

<210> SEQ ID NO 78
<211> LENGTH: 31
<212> TYPE: DNA
<213> ORGANISM: Artificial Sequence
<220> FEATURE:
<223> OTHER INFORMATION: Synthetic

<400> SEQUENCE: 78
cgctagccac cacacctggc ctttcacatt t                                 31

<210> SEQ ID NO 79
<211> LENGTH: 32
<212> TYPE: DNA
<213> ORGANISM: Artificial Sequence
<220> FEATURE:

<223> OTHER INFORMATION: Synthetic

<400> SEQUENCE: 79
caaagcttgc actttaaggc agggtcagca aa                                     32

<210> SEQ ID NO 80
<211> LENGTH: 31
<212> TYPE: DNA
<213> ORGANISM: Artificial Sequence
<220> FEATURE:
<223> OTHER INFORMATION: Synthetic

<400> SEQUENCE: 80
cgctagcgtt tcaagcgatt ctcctgcctc a                                      31

<210> SEQ ID NO 81
<211> LENGTH: 32
<212> TYPE: DNA
<213> ORGANISM: Artificial Sequence
<220> FEATURE:
<223> OTHER INFORMATION: Synthetic

<400> SEQUENCE: 81
caaagctttc acgcctgtaa tcccagcact tt                                     32

<210> SEQ ID NO 82
<211> LENGTH: 31
<212> TYPE: DNA
<213> ORGANISM: Artificial Sequence
<220> FEATURE:
<223> OTHER INFORMATION: Synthetic

<400> SEQUENCE: 82
cgctagcagg gaggtggctg agcatcaaat a                                      31

<210> SEQ ID NO 83
<211> LENGTH: 32
<212> TYPE: DNA
<213> ORGANISM: Artificial Sequence
<220> FEATURE:
<223> OTHER INFORMATION: Synthetic

<400> SEQUENCE: 83
caaagcttta cacgggtgat tacaatctta gc                                     32

<210> SEQ ID NO 84
<211> LENGTH: 31
<212> TYPE: DNA
<213> ORGANISM: Artificial Sequence
<220> FEATURE:
<223> OTHER INFORMATION: Synthetic

<400> SEQUENCE: 84
cgctagcagg gaggtggctg agcatcaaat a                                      31

<210> SEQ ID NO 85
<211> LENGTH: 32
<212> TYPE: DNA
<213> ORGANISM: Artificial Sequence
<220> FEATURE:
<223> OTHER INFORMATION: Synthetic

<400> SEQUENCE: 85
caaagctttg gacaacatgg caagacccat ct                                     32

```
<210> SEQ ID NO 86
<211> LENGTH: 31
<212> TYPE: DNA
<213> ORGANISM: Artificial Sequence
<220> FEATURE:
<223> OTHER INFORMATION: Synthetic

<400> SEQUENCE: 86
cgctagcagg gaggtggctg agcatcaaat a                              31

<210> SEQ ID NO 87
<211> LENGTH: 32
<212> TYPE: DNA
<213> ORGANISM: Artificial Sequence
<220> FEATURE:
<223> OTHER INFORMATION: Synthetic

<400> SEQUENCE: 87
caaagcttct ggatctcttt tcctggtact tg                             32

<210> SEQ ID NO 88
<211> LENGTH: 31
<212> TYPE: DNA
<213> ORGANISM: Artificial Sequence
<220> FEATURE:
<223> OTHER INFORMATION: Synthetic

<400> SEQUENCE: 88
cgctagcagg gaggtggctg agcatcaaat a                              31

<210> SEQ ID NO 89
<211> LENGTH: 32
<212> TYPE: DNA
<213> ORGANISM: Artificial Sequence
<220> FEATURE:
<223> OTHER INFORMATION: Synthetic

<400> SEQUENCE: 89
caaagcttac actgtagctc acacaggcag aa                             32

<210> SEQ ID NO 90
<211> LENGTH: 31
<212> TYPE: DNA
<213> ORGANISM: Artificial Sequence
<220> FEATURE:
<223> OTHER INFORMATION: Synthetic

<400> SEQUENCE: 90
cgctagcagg gaggtggctg agcatcaaat a                              31

<210> SEQ ID NO 91
<211> LENGTH: 32
<212> TYPE: DNA
<213> ORGANISM: Artificial Sequence
<220> FEATURE:
<223> OTHER INFORMATION: Synthetic

<400> SEQUENCE: 91
caaagcttta caaatccaaa ccctagctca ag                             32

<210> SEQ ID NO 92
<211> LENGTH: 31
<212> TYPE: DNA
<213> ORGANISM: Artificial Sequence
<220> FEATURE:
<223> OTHER INFORMATION: Synthetic
```

<400> SEQUENCE: 92
cgctagcagg gaggtggctg agcatcaaat a        31

<210> SEQ ID NO 93
<211> LENGTH: 32
<212> TYPE: DNA
<213> ORGANISM: Artificial Sequence
<220> FEATURE:
<223> OTHER INFORMATION: Synthetic

<400> SEQUENCE: 93
caaagctttg ctgtgagcca ggccctccct gc        32

<210> SEQ ID NO 94
<211> LENGTH: 31
<212> TYPE: DNA
<213> ORGANISM: Artificial Sequence
<220> FEATURE:
<223> OTHER INFORMATION: Synthetic

<400> SEQUENCE: 94
cgctagcagg gaggtggctg agcatcaaat a        31

<210> SEQ ID NO 95
<211> LENGTH: 32
<212> TYPE: DNA
<213> ORGANISM: Artificial Sequence
<220> FEATURE:
<223> OTHER INFORMATION: Synthetic

<400> SEQUENCE: 95
caaagcttct gcccgctcct ctctctgatg tc        32

<210> SEQ ID NO 96
<211> LENGTH: 25
<212> TYPE: DNA
<213> ORGANISM: Artificial Sequence
<220> FEATURE:
<223> OTHER INFORMATION: Synthetic

<400> SEQUENCE: 96
catacagaat tgtttaacaa gtacc        25

<210> SEQ ID NO 97
<211> LENGTH: 29
<212> TYPE: DNA
<213> ORGANISM: Artificial Sequence
<220> FEATURE:
<223> OTHER INFORMATION: Synthetic

<400> SEQUENCE: 97
taaattgcct gtgttttatt agaacactg        29

<210> SEQ ID NO 98
<211> LENGTH: 24
<212> TYPE: DNA
<213> ORGANISM: Artificial Sequence
<220> FEATURE:
<223> OTHER INFORMATION: Synthetic

<400> SEQUENCE: 98
acctgtaatc ccagcacttt cgga        24

<210> SEQ ID NO 99
<211> LENGTH: 24

```
<212> TYPE: DNA
<213> ORGANISM: Artificial Sequence
<220> FEATURE:
<223> OTHER INFORMATION: Synthetic

<400> SEQUENCE: 99
cgatctcgga tcactgcaac ctct                                            24

<210> SEQ ID NO 100
<211> LENGTH: 22
<212> TYPE: DNA
<213> ORGANISM: Artificial Sequence
<220> FEATURE:
<223> OTHER INFORMATION: Synthetic

<400> SEQUENCE: 100
tgagccgagc cgagccgagc tg                                              22

<210> SEQ ID NO 101
<211> LENGTH: 23
<212> TYPE: DNA
<213> ORGANISM: Artificial Sequence
<220> FEATURE:
<223> OTHER INFORMATION: Synthetic

<400> SEQUENCE: 101
tcacagggct tctggctttc gct                                             23

<210> SEQ ID NO 102
<211> LENGTH: 24
<212> TYPE: DNA
<213> ORGANISM: Artificial Sequence
<220> FEATURE:
<223> OTHER INFORMATION: Synthetic

<400> SEQUENCE: 102
agctgaggac ttgaaggacc tgat                                            24

<210> SEQ ID NO 103
<211> LENGTH: 23
<212> TYPE: DNA
<213> ORGANISM: Artificial Sequence
<220> FEATURE:
<223> OTHER INFORMATION: Synthetic

<400> SEQUENCE: 103
aggttgtctt cgctgccttg ctt                                             23

<210> SEQ ID NO 104
<211> LENGTH: 24
<212> TYPE: DNA
<213> ORGANISM: Artificial Sequence
<220> FEATURE:
<223> OTHER INFORMATION: Synthetic

<400> SEQUENCE: 104
acctgggctg gctatgtgta tgaa                                            24

<210> SEQ ID NO 105
<211> LENGTH: 25
<212> TYPE: RNA
<213> ORGANISM: Artificial Sequence
<220> FEATURE:
<223> OTHER INFORMATION: Synthetic

<400> SEQUENCE: 105
```
ggaccaucug uacauggugu ucgaa                                               25

<210> SEQ ID NO 106
<211> LENGTH: 25
<212> TYPE: RNA
<213> ORGANISM: Artificial Sequence
<220> FEATURE:
<223> OTHER INFORMATION: Synthetic

<400> SEQUENCE: 106
gcugacuuug gugugagcaa ugaau                                               25

<210> SEQ ID NO 107
<211> LENGTH: 25
<212> TYPE: RNA
<213> ORGANISM: Artificial Sequence
<220> FEATURE:
<223> OTHER INFORMATION: Synthetic

<400> SEQUENCE: 107
caccugggca uggaguccuu cauug                                               25

<210> SEQ ID NO 108
<211> LENGTH: 25
<212> TYPE: RNA
<213> ORGANISM: Artificial Sequence
<220> FEATURE:
<223> OTHER INFORMATION: Synthetic

<400> SEQUENCE: 108
cagaugucuu cugccuguua uaacu                                               25

<210> SEQ ID NO 109
<211> LENGTH: 25
<212> TYPE: RNA
<213> ORGANISM: Artificial Sequence
<220> FEATURE:
<223> OTHER INFORMATION: Synthetic

<400> SEQUENCE: 109
cccauccuga aagaguacca uucuu                                               25

<210> SEQ ID NO 110
<211> LENGTH: 25
<212> TYPE: RNA
<213> ORGANISM: Artificial Sequence
<220> FEATURE:
<223> OTHER INFORMATION: Synthetic

<400> SEQUENCE: 110
cccucaauau uuaaauccuu cugug                                               25

<210> SEQ ID NO 111
<211> LENGTH: 25
<212> TYPE: RNA
<213> ORGANISM: Artificial Sequence
<220> FEATURE:
<223> OTHER INFORMATION: Synthetic

<400> SEQUENCE: 111
accaugauug augaugaagc cuuaa                                               25

<210> SEQ ID NO 112
<211> LENGTH: 25
<212> TYPE: RNA
<213> ORGANISM: Artificial Sequence
<220> FEATURE:
<223> OTHER INFORMATION: Synthetic

<400> SEQUENCE: 112
gauggugaau uucugagaac uaguu        25

<210> SEQ ID NO 113
<211> LENGTH: 25
<212> TYPE: RNA
<213> ORGANISM: Artificial Sequence
<220> FEATURE:
<223> OTHER INFORMATION: Synthetic

<400> SEQUENCE: 113
ccguaugaca uuauggcuga aguuu        25

<210> SEQ ID NO 114
<211> LENGTH: 25
<212> TYPE: DNA
<213> ORGANISM: Artificial Sequence
<220> FEATURE:
<223> OTHER INFORMATION: Synthetic

<400> SEQUENCE: 114
ggagatacag ctctagataa gaata        25

<210> SEQ ID NO 115
<211> LENGTH: 25
<212> TYPE: DNA
<213> ORGANISM: Artificial Sequence
<220> FEATURE:
<223> OTHER INFORMATION: Synthetic

<400> SEQUENCE: 115
ccataggtgt catcgcctac atctt        25

<210> SEQ ID NO 116
<211> LENGTH: 15
<212> TYPE: DNA
<213> ORGANISM: Artificial Sequence
<220> FEATURE:
<223> OTHER INFORMATION: Synthetic

<400> SEQUENCE: 116
gtaacatgat gtaaa        15

<210> SEQ ID NO 117
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(9)
<223> OTHER INFORMATION: n is a, c, g, or t

<400> SEQUENCE: 117
agaacannnt gttct        15

<210> SEQ ID NO 118
<211> LENGTH: 19
<212> TYPE: PRT
<213> ORGANISM: Artificial Sequence
<220> FEATURE:
<223> OTHER INFORMATION: Synthetic

```
<400> SEQUENCE: 118

Lys Lys Lys Lys Glu His Gln Val Leu Met Lys Thr Val Cys Gly Thr
1               5                   10                  15

Pro Gly Tyr

<210> SEQ ID NO 119
<211> LENGTH: 23
<212> TYPE: PRT
<213> ORGANISM: Artificial Sequence
<220> FEATURE:
<223> OTHER INFORMATION: Synthetic

<400> SEQUENCE: 119

Ala Lys Pro Lys Gly Asn Lys Asp Tyr His Leu Gln Thr Cys Cys Gly
1               5                   10                  15

Ser Leu Ala Tyr Arg Arg Arg
                20
```

CAMKK-β AS A TARGET FOR TREATING CANCER

CROSS-REFERENCE TO RELATED APPLICATIONS

This application is a continuation of U.S. patent application Ser. No. 13/817,382, filed May 10, 2013, which is a national stage filing under 35 U.S.C 371 of International Application No. PCT/US2011/047846 which is related to and claims the benefit of priority to U.S. Provisional Patent application Ser. No. 61/374,106, filed Aug. 16, 2010, and U.S. Provisional Patent application Ser. No. 61/379,226, filed Sep. 1, 2010. The content of both applications are incorporated herein by reference.

STATEMENT REGARDING FEDERALLY SPONSORED RESEARCH

This work was supported in part by grants R01 CA139818 (U.S. National Institutes of Health, National Cancer Institute); 1K01 DK084205 (U.S. National Institutes of Health, National Institute of Diabetes and Digestive and Kidney Diseases), and R01 GM033976 (U.S. National Institutes of Health, National Institute of General Medical Sciences). The United States government has certain rights in this invention.

FIELD

The disclosure relates to cancer, including diagnostic markers of cancer, methods for the diagnosis of cancer, methods and compounds for the treatment of cancer, methods for identifying cancer stage in a subject, methods for identifying a cancer that is responsive to particular therapies, and methods for evaluating efficacy of cancer therapy.

SEQUENCE LISTING

An electronic version of the sequence listing ("028193_9098_SeqList.txt") which is 233,472 bytes in size and created on Aug. 16, 2011, is submitted herewith and is herein incorporated by reference.

BACKGROUND

Prostate cancer is the most common malignancy in men and is second only to lung cancer in terms of cancer mortalities [Cancer Facts and Figures: American Cancer Society; 2007.]. Early diagnosis of prostate cancer usually allows for successful surgical treatment of localized tumors and thus, good patient outcomes. However, as with many cancers, the treatment of the advanced disease state requires a systemic approach to inhibit the growth and spread of secondary metastases. Prostate cancers express the androgen receptor (AR) and rely on androgens for growth and survival [Isaacs J T, Isaacs W B., Nat Med 2004; 10:26-7.]. Consequently, androgen ablation therapies are the standard of care for late-stage disease. While 80% of patients with prostate cancer respond favorably to initial androgen ablation therapy, most patients experience a relapse of the disease within 1-2 years [Isaacs J T, Isaacs W B., Nat Med 2004; 10:26-7.]. Despite the unresponsiveness of the hormone-refractory disease to androgen-deprivation therapy, AR-regulated signaling pathways remain active and are necessary for cancer progression [Chen C. D., et al., Nature Med 2004; 10:33-9.].

Several approaches are currently used to target the AR signaling axis in prostate cancer. Existing therapies focus on decreasing the levels of circulating androgens and/or competitively blocking the AR transcriptional complex. Specifically, gonadotropin-releasing hormone (GnRH) agonists are used to suppress the testicular production of testosterone whereas antiandrogens, such as bicalutamide, function by competitively inhibiting the interaction of androgens with AR. The initial response to either form of androgen deprivation is very high. Nevertheless, the rapid onset of resistance to these interventions highlights the need for other strategies that target the hormone-independent activities of AR.

Most of the studies on the role of androgens in prostate cancer have focused on defining the mechanisms underlying the mitotic actions of this class of hormone [Balk S. P., Nucl Recept Signal 2008; 6:e001]. However, there is a growing body of evidence that AR signaling also influences tumor cell migration and invasion. For example, different clinical trials of goserelin (a GnRH analog) in prostate cancer patients demonstrate reduced incidences of distant metastases [Lawton C. A., et al. Int J Radiation Oncology Biol Phys 2001; 49:937-46; Bolla M., et al. The Lancet 2002; 360: 103-8.]. Furthermore, it has recently been reported that MDV3100, a second generation AR-antagonist, decreases the number of circulating tumor cells in approximately half of the treated patients having a castration-resistant type cancer [Scher H. I., et al. The Lancet; 375:1437-46].

Compounds of Formula I are known and have been used as dye molecules. See, for example, U.S. Pat. No. 2,820,037 which describes:

Formula I

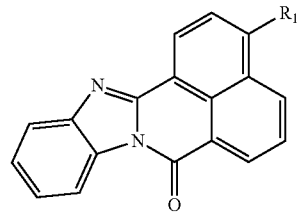

wherein $R_1$ is selected from CN, COOH, or COCl. The dye industry has generated a number of compounds that are structurally related to those of Formula I. See, e.g., U.S. Pat. Nos. 2,835,674; 2,965,644; 2,949,467; 3,953,452; 3,960, 867; 4,239,868; and 4,336,383.

Japanese Patent Application No. 2003-012516 (Sumitomo Pharmaceutical Co.) identifies compounds as $Ca^{2+}$/calmodulin dependent kinase kinase (CaMKK) inhibitors. The compounds are described as Formula II:

Formula II

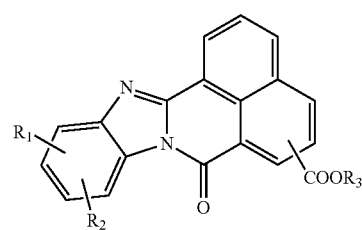

wherein $R_1$ and $R_2$ are independently selected from H, halo, alkyl, or haloalkyl; and $R_3$ is H, alkyl, or substituted alkyl, or three $COOR_3$ groups can be substituted at any location on the naphthalene ring.

U.S. Patent Application Publication No: 2010/0105716 discloses methods of treating obesity, insulin resistance, and hyperglycemia by administering a CaMKK inhibitor compound of Formula III:

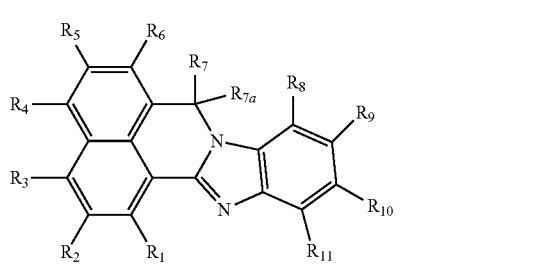

Formula III wherein $R_1$, $R_2$, $R_3$, $R_4$, $R_5$, $R_6$, $R_7$, $R_{7a}$, $R_8$, $R_9$, $R_{10}$, and $R_{11}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy; or a pharmaceutically acceptable salt or prodrug thereof.

None of these documents disclose or suggest that any of the compounds of Formula I-III would be useful in methods relating to cancer, or that CaMKKβ represents a therapeutic target in the treatment of cancers.

SUMMARY OF THE INVENTION

In an aspect, the disclosure provides a method of diagnosing prostate cancer in a subject comprising: determining an amount of at least one of CaMKKβ, CaMKKβ splice variant 2, CaMKKβ splice variant 7, phosphorylated AMPK, phosphorylated AMPKα1 subunit, and phosphorylated AMPKα2 subunit in a sample from the subject; and comparing the amount to a control sample comprising an amount of CaMKKβ, CaMKKβ splice variant 2, CaMKKβ splice variant 7, phosphorylated AMPK, phosphorylated AMPKα1 subunit, and phosphorylated AMPKα2 subunit in a control sample; wherein the subject is diagnosed as having prostate cancer when the amount of at least one of CaMKKβ, CaMKKβ splice variant 2, CaMKKβ splice variant 7, phosphorylated AMPK, phosphorylated AMPKα1 subunit, and phosphorylated AMPKα2 subunit in the sample from the subject is greater than the amount in the control sample.

In an aspect the disclosure relates to a method for determining disease stage in a subject having prostate cancer, the method comprising: determining an amount of at least one of CaMKKβ, CaMKKβ splice variant 2, CaMKKβ splice variant 7, phosphorylated AMPK, phosphorylated AMPKα1 subunit, and phosphorylated AMPKα2 subunit in a sample from the subject; and comparing the amount to a control sample comprising an amount of at least one of CaMKKβ, CaMKKβ splice variant 2, CaMKKβ splice variant 7, phosphorylated AMPK, phosphorylated AMPKα1 subunit, and phosphorylated AMPKα2 subunit in the sample from the subject and the amount in the control sample.

Aspects also relate to a method for predicting the likelihood of success of hormone-based therapeutic treatment of a subject having prostate cancer, the method comprising determining an amount of at least one of CaMKKβ, CaMKKβ splice variant 2, CaMKKβ splice variant 7, phosphorylated AMPK, phosphorylated AMPKα1 subunit, and phosphorylated AMPKα2 subunit in a sample from the subject; and comparing the amount to a control sample comprising an amount of the CaMKKβ, CaMKKβ splice variant 2, CaMKKβ splice variant 7, phosphorylated AMPK, phosphorylated AMPKα1 subunit, and phosphorylated AMPKα2 subunit. Embodiments provide for a likely successful response to hormone-based therapeutic treatment when the amount of at least one of CaMKKβ, CaMKKβ splice variant 2, CaMKKβ splice variant 7, phosphorylated AMPK, phosphorylated AMPKα1 subunit, and phosphorylated AMPKα2 subunit in the sample from the subject is greater than the amount in the control sample.

In an aspect the disclosure relates to a method for early detection of prostate cancer in a subject comprising obtaining a sample from the subject; determining an amount of at least one of CaMKKβ, CaMKKβ splice variant 2, CaMKKβ splice variant 7, phosphorylated AMPK, phosphorylated AMPKα1 subunit, and phosphorylated AMPKα2 subunit in the sample from the subject; and comparing the amount of at least one of CaMKKβ, CaMKKβ splice variant 2, CaMKKβ splice variant 7, phosphorylated AMPK, phosphorylated AMPKα1 subunit, and phosphorylated AMPKα2 subunit from the sample from the subject to an amount of the CaMKKβ, CaMKKβ splice variant 2, CaMKKβ splice variant 7, AMPK, and AMPKα1 subunit in a control sample; wherein early detection of prostate cancer is made when the amount of at least one of CaMKKβ, CaMKKβ splice variant 2, CaMKKβ splice variant 7, phosphorylated AMPK, phosphorylated AMPKα1 subunit, and phosphorylated AMPKα2 subunit in the sample from the subject is greater than the amount in the control sample.

In another aspect the disclosure provides a method for identifying a selective inhibitor of CaMKKβ where the method includes contacting CaMKKβ and a substrate therefor, in the presence and in the absence of the test compound, under conditions such that CaMKKβ-dependent phosphorylation of the substrate can be effected, and determining the level of phosphorylation of the substrate resulting from the contacting, and comparing the amount of phosphorylated substrate with a level of phosphorylation of the substrate in the absence of the test compound, wherein an decrease in phosphorylation of the substrate in the presence of the test compound indicates that the test compound is a selective inhibitor of CaMKKβ.

In an aspect the disclosure provides a method of screening a test compound for anti-cancer activity comprising: contacting CaMKKβ and a substrate therefor in the presence of the test compound, under conditions that allow for CaMKKβ-dependent phosphorylation of the substrate; determining the level of phosphorylation of the substrate resulting from the contacting; and comparing that level with a level of phosphorylation of the substrate obtained in the absence of the test compound, wherein a reduction in the level of phosphorylation of the substrate in the presence of the test compound indicates that the test compound has anti-cancer activity.

In an aspect the disclosure provides a method of treating cancer in a subject, comprising administering to the subject an effective amount of a compound that inhibits activity of a CaMK biological cascade in the subject.

In an aspect the disclosure provides a method of treating cancer in a subject, comprising administering to the subject an effective amount of a compound that inhibits activity of at least one of CaMKK or AMPK.

In an aspect the disclosure provides a method of treating cancer in a subject, comprising administering to the subject an effective amount of a compound that inhibits activity of at least one of CaMKKβ, CaMKKβ splice variant 2, or CaMKKβ splice variant 7.

In a further aspect the disclosure provides a method of treating prostate cancer in a subject, comprising administering to the subject an effective amount of a compound that inhibits activity of a CaMK biological cascade in the subject.

In a further aspect the disclosure provides a method of treating prostate cancer in a subject, comprising administering to the subject an effective amount of a compound that inhibits activity of at least one of CaMKK or AMPK.

In a further aspect the disclosure provides a method of treating prostate cancer in a subject, comprising administering to the subject an effective amount of a compound that inhibits activity of at least one of CaMKKβ, CaMKKβ splice variant 2, or CaMKKβ splice variant 7.

In yet another aspect, the disclosure relates to a method of treating prostate cancer in a subject, the method comprising administering to the subject an effective amount of an inhibitor of phosphorylated AMPK, phosphorylated AMPKα1 subunit, or phosphorylated AMPKα2 subunit.

In another aspect, the disclosure provides a method of determining the efficacy of therapy in a patient being treated for prostate cancer, the method comprising: determining an amount of at least one of CaMKKβ, CaMKKβ splice variant 2, CaMKKβ splice variant 7, phosphorylated AMPK, phosphorylated AMPKα1 subunit, and phosphorylated AMPKα2 subunit in a series of samples from the subject, where the samples are taken from the subject at different time points during the therapy; and comparing the determined amount over the course of the time points; wherein when the amount of at least one of CaMKKβ, CaMKKβ splice variant 2, CaMKKβ splice variant 7, phosphorylated AMPK, phosphorylated AMPKα1 subunit, and phosphorylated AMPKα2 in the series of samples is about the same or increases over the course of the time points, the therapy is not effective.

In an aspect the disclosure provides a method of inhibiting androgen-mediated migration of a prostate cancer cell in a subject comprising administering to the subject an effective amount of a compound that inhibits activity of a CaMK biological cascade in the subject.

In an aspect the disclosure provides a method of inhibiting androgen-mediated migration of a prostate cancer cell in a subject comprising administering to the subject an effective amount of a compound that inhibits activity of at least one of CaMKK or AMPK.

In another aspect the disclosure provides a method of inhibiting androgen-mediated migration of a prostate cancer cell in a subject comprising administering to the subject an effective amount of an inhibitor of at least one of CaMKKβ, CaMKKβ splice variant 7, or CaMKKβ splice variant 2 or any combination thereof.

In an aspect the disclosure provides a method of inhibiting androgen-mediated invasion of a prostate cancer cell in a subject comprising administering to the subject an effective amount of a compound that inhibits activity of a CaMK biological cascade in the subject.

In an aspect the disclosure provides a method of inhibiting androgen-mediated invasion of a prostate cancer cell in a subject comprising administering to the subject an effective amount of a compound that inhibits activity of at least one of CaMKK or AMPK.

In an aspect the disclosure provides a method of inhibiting androgen-mediated invasion of a prostate cancer cell in a subject comprising administering to the subject an effective amount of an inhibitor of at least one of CaMKKβ, CaMKKβ splice variant 7, or CaMKKβ splice variant 2 or any combination thereof.

In an aspect the disclosure provides a method of inhibiting metastasis of prostate cancer in a subject comprising administering to the subject an effective amount of a compound that inhibits activity of a CaMK biological cascade in the subject.

In an aspect the disclosure provides a method of inhibiting metastasis of prostate cancer in a subject comprising administering to the subject an effective amount of a compound that inhibits activity of at least one of CaMKK or AMPK.

In an aspect the disclosure provides a method of inhibiting metastasis of prostate cancer in a subject comprising administering to the subject an effective amount of an inhibitor of at least one of CaMKKβ, CaMKKβ splice variant 7, or CaMKKβ splice variant 2 or any combination thereof.

Aspects also relate to a nucleic acid molecule comprising a sequence that binds under stringent conditions to a region that is about 2.3 kb upstream (5') relative to a CaMKKβ transcriptional start site.

Further aspects relate to an antibody that specifically binds to a C-terminal portion of a CaMKKb.

Aspects also relate to polynucleotides (e.g., siRNA) that comprise a sequence that is complementary to CaMKKβ, CaMKKα, or AMPK and having kinase-inhibitory activity.

The disclosure provides for and encompasses additional aspects and embodiments, which will be apparent to those of skill in the art in light of the following description.

DETAILED DESCRIPTION

Figure 1:
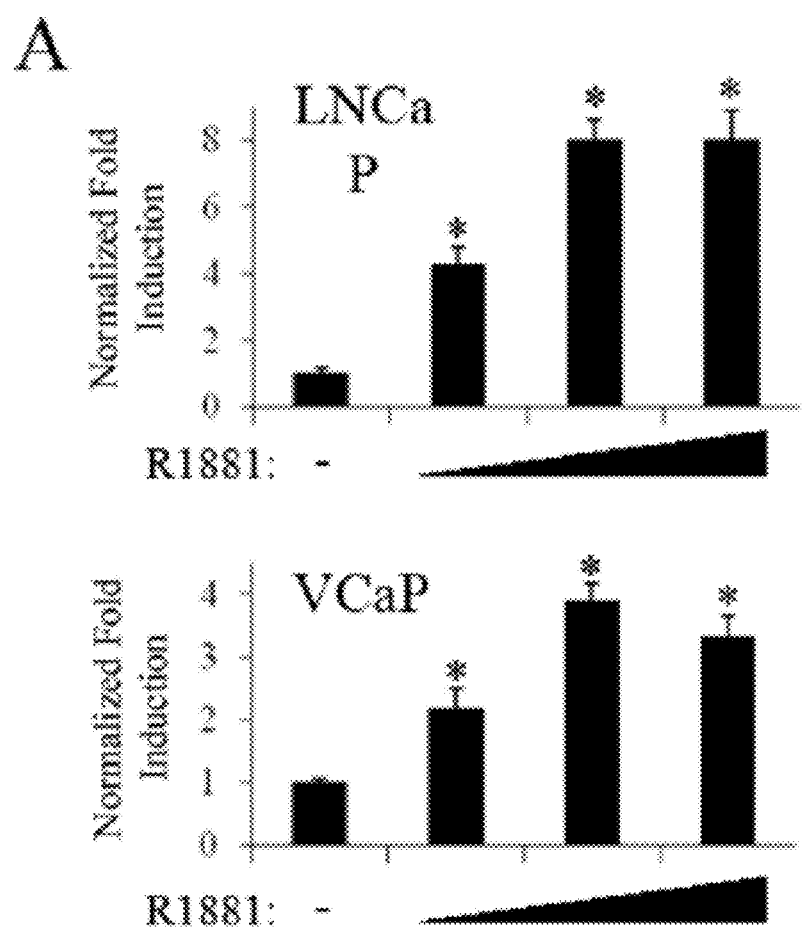
FIG. 1. Androgens increase CaMKKβ levels in an AR-dependent manner. LNCaP or VCaP cells were treated for 24 h with vehicle or increasing concentrations of the synthetic androgen R1881 (A—0.1, 1, and 10 nM; B—0.01, 0.1, 1, and 10 nM). A, after treatment, cells were lysed, and RNA was isolated and reversed transcribed. The expression of CaMKKβ was assessed using qPCR. B, after treatment, cells were subjected to western blot analysis and subsequent densitometry (top). CaMKKβ protein levels were normalized to GAPDH loading control. A and B, results are expressed as fold induction over vehicle-treated cells+SE (n=3). *, significant changes from vehicle-treated cells. C, LNCaP cells were transiently transfected with mock or Stealth siRNAs targeting a negative control (siLacZ) or CaMKKβ (#1-3). Two days later, cells were treated for 24 h+/−10 nM R1881. Whole-cell extracts were subjected to western blot analysis and densitometry (top) as described in B. *, significant changes from mock-transfected cells. D, LNCaP cells were transfected as described in C with mock or Stealth siRNAs targeting LacZ or AR and treated for 24 h. The expression of CaMKKβ was assessed as in A using qPCR.
Figure 1:
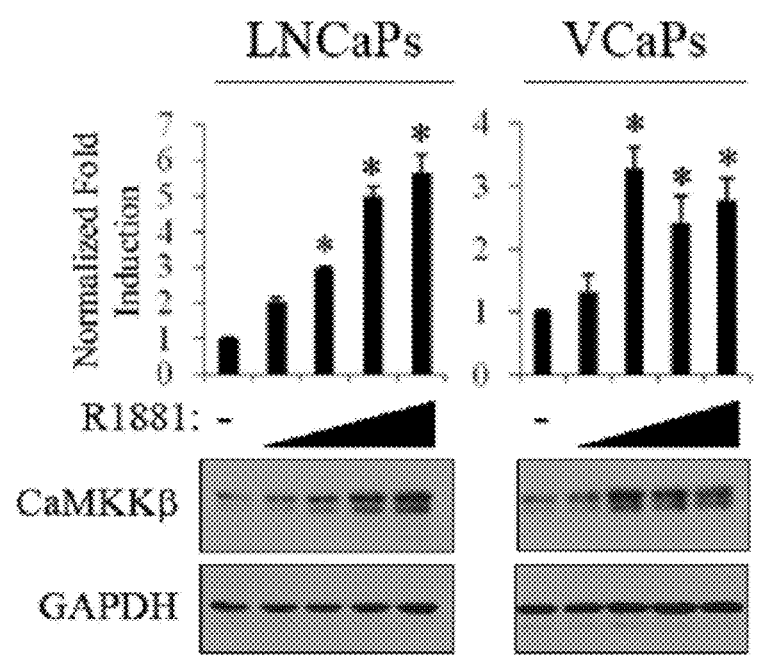
Figure 1:
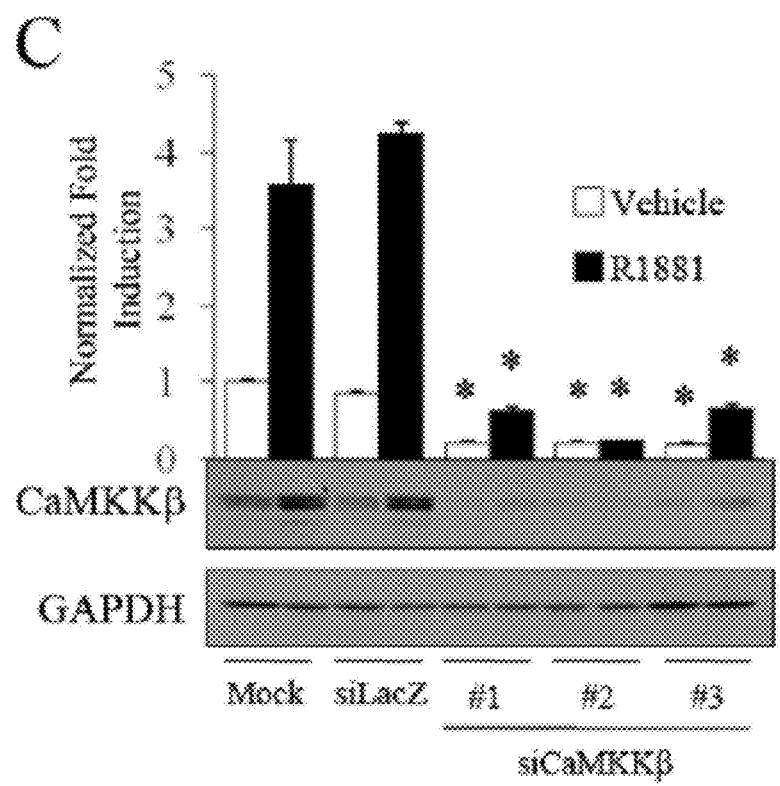
Figure 1:
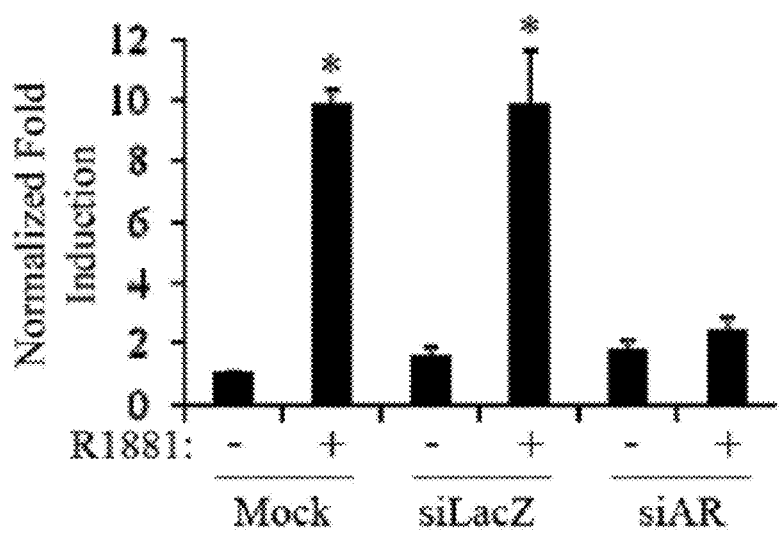

The inventors have identified $Ca^{2+}$/calmodulin-dependent protein kinase kinases (CaMKKs), such as CaMKKβ, as viable targets for therapeutic intervention in various cancers such as, for example, prostate cancer, glioblastoma, and myeloid leukemia as well as other cancer types described herein. In a general sense, the disclosure provides an array of compounds and compositions that are active inhibitors of CaMKK and use of such compounds in methods relating to detection, determination of disease stage/progression, prognostic evaluation of hormone therapy, treatment of disease, identification of active agents against various cancers, as well as identification of CaMKK inhibitors, including inhibitors that are selective for a particular CaMKK. For purposes of illustration some particular aspects and embodiments are explicitly described herein, relating to $Ca^{2+}$/calmodulin-dependent protein kinase kinase β (CaMKKβ) which is shown (a) to be expressed in the prostate, (b) to be regulated by AR, (c) to correspond to prostate cancer progression/disease stage and, accordingly, provides a therapeutic target for prostate cancer.

As used herein, the term "$Ca^{2+}$/calmodulin-dependent protein kinase kinase" and/or "CaMKK" are used interchangeably herein and refer to a serine/threonine protein kinase that can phosphorylate and activate members of the $Ca^{2+}$/calmodulin-dependent protein kinase (CaMK) family of enzymes as well as other protein substrates such as AMPK (e.g., SEQ ID NOs: 21-24). The terms encompass all of the various isoforms, orthologs, and splice variants of CaMKK proteins such as, for example, $Ca^{2+}$/calmodulin-dependent protein kinase kinase β (CaMKKβ, or CaMKK2) $Ca^{2+}$/calmodulin-dependent protein kinase kinase α (CaMKKα, or CaMKK1), splice variants such as, for example, CaMKKβ splice variants 1-7, CaMKKα splice variants 1-3, and the like (e.g., SEQ ID NOs: 1-20 and 25-46). Some embodiments relate to CaMKKβ that comprises the amino acid sequence of SEQ ID NO:2, or a fragment thereof. The CaMKK amino acid sequences, such as CaMKKβ, can be encoded by any appropriate polynucleotide molecule as determined by the genetic code and codon usage in any particular organism. In embodiments, CaMKKβ is encoded by a polynucleotide comprising SEQ ID NO:1, or a fragment thereof. Some embodiments relate to CaMKKα that comprises the amino acid sequence of SEQ ID NO:16, or a fragment thereof. In some embodiments, CaMKKα like CaMKKβ above, is encoded by any polynucleotide that can be envisioned by one of skill in the art and, in some embodiments, comprises SEQ ID NO:15, or a fragment thereof.

In some embodiments the disclosure relates to a CaMKK splice variant. Non-limiting examples of CaMKK splice variants include nucleotide sequences of SEQ ID NOs: 3, 5, 7, 9, 11, 13, 17, and 19. Some embodiments relate to "CaMKKβ splice variant 2" and comprise a nucleotide sequence of SEQ ID NO:3, or a fragment thereof. Some embodiments relate to "CaMKKβ splice variant 7" and comprise a nucleotide sequence of SEQ ID NO: 13. In these embodiments, the splice variant proteins encoded by SEQ ID NO:3 and SEQ ID NO:13 are identical in sequence. Thus, embodiments of disclosure provide for a polynucleotide that encodes a CaMKKβ splice variant protein comprising SEQ ID NO:4, or a fragment thereof. Similarly, the disclosure relates to polynucleotide sequences that encodes an amino acid sequence of any CaMKK or CaMK protein such as, for example those of SEQ ID NOs: 2, 4, 6, 8, 10, 12, 14, 16, 18, or 20. As noted above, CaMKKβ splice variant 2 and splice variant 7 encode for the same amino acid sequence; thus, in embodiments relating to a CaMKKβ amino acid sequence encoded by splice variant 2 or splice variant 7, reference to an amino acid sequence encoded by either splice variant will also encompass the other (i.e., each term is interchangeable with and inclusive of the other when it relates to the encoded amino acid sequence).

Any sample can be used in the methods described herein. Embodiments provide for the use of a biological sample (e.g., tissue biopsy, cerebrospinal fluid, blood, sera, sputum, urine and/or tumor biopsies) from a subject with and/or without a cancer (which can be determined using standard clinical tests).

Embodiments of the disclosure relate to compounds that are inhibitors of a CaMK biochemical cascade. A CaMK biochemical cascade refers to a biochemical activation pathway that typically involves the phosphorylation of a first $Ca^{2+}$/calmodulin-dependent protein kinase (CaMK) by a second $Ca^{2+}$/calmodulin-dependent protein kinase (thus, a $Ca^{2+}$/calmodulin-dependent protein kinase kinase (CaMKK)). The phosphorylated CaMK can subsequently phosphorylate a substrate. CaMK cascades are described in the literature. See, Corcoran, E. E., and Means, A. R., *J Biol Chem*, (Feb. 2, 2001); 276(5):2975-2978, incorporated herein by reference.

Methods of Treatment

In an aspect, the disclosure provides a method for treating cancer in a subject in need thereof comprising administering to the subject an effective amount of a $Ca^{2+}$/calmodulin-dependent protein kinase kinase (CaMKK) inhibitor. In embodiments, the method comprises administering an effective amount of a CaMKK inhibitor that is a selective inhibitor of CaMKKα and/or CaMKKβ. In some embodiments the CaMKK inhibitor is a selective inhibitor of CaMKKα. In some embodiments the CaMKK inhibitor is a selective inhibitor of CaMKKβ. The term "selective inhibitor," including "selective inhibitor of CaMKKβ/α" or "CaMKKβ/α selective inhibitor" relates to a compound (e.g., a small molecule or biological molecule) that has increased inhibitory activity for a target, for example, CaMKKβ or CaMKKα, relative to the inhibitory activity for other CaMKs. For purposes of illustration, when describing embodiments comprising a selective inhibitor of CaMKKβ, examples of "other" CaMKs include natural/physiological substrates of CaMKKβ such as, for example, $Ca^{2+}$/calmodulin-dependent protein kinases (e.g., CaMKI and CaMKIV), CaMKs that are not substrates of CaMKKβ (e.g., CaMKII and CaMKIII), AMP-activated protein kinase (e.g., AMPKα1 subunit and AMPKα2 subunit) as well as other kinases that can phosphorylate such substrates (CaMKKα). Embodiments also relate to polypeptide fragments comprising a sequence that contains a portion of a CaMKKβ substrate. In such embodiments, the fragment comprises an amino acid that can be phosphorylated. In some embodiments a selective inhibitor comprises a ratio of $IC_{50}$ concentrations (concentration inhibiting 50% of activity) wherein the ratio of the $IC_{50}$ concentration for one or more other CaMKs to the $IC_{50}$ concentration for CaMKKβ is greater than 1. The ratio of $IC_{50}$ values can be readily determined from data obtained from one or more assay(s) (performed separately, in parallel or series) that is effective to measure activity or abundance of a CaMK or CaMKK (e.g., phosphorylation, mRNA transcription, protein expression, etc.), and can comprise any methods known in the art such as, for example those disclosed in U.S. Pat. No. 7,105,312, which is incorporated herein by reference. The inhibitory activity can be assessed and demonstrated either in vivo and/or in vitro optionally in cell-based or cell-free assay systems.

In general, the CaMKK inhibitor, including a CaMKK selective inhibitor, can be any type of chemical or biological molecule that exhibits inhibitory activity against one or more CaMKK. Effective CaMKK inhibitors for use in the methods described herein can inhibit the kinase activity of a CaMKK or they can regulate the amount of a CaMKK in a cell. Accordingly, the CaMKK inhibitors can inhibit phosphorylation associated with a CaMK cascade, and/or regulate expression of a CaMKK (e.g., by inhibiting a CaMKK gene promoter, inhibiting CaMKK gene transcription, inhibiting CaMKK mRNA translation, and/or affect CaMKK mRNA stability).

In some embodiments of this aspect, the method includes at least one selective inhibitor of CaMKKβ that comprises a compound of Formula III:

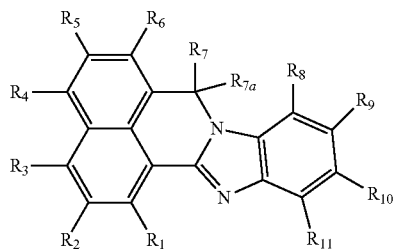

Formula III wherein $R_1, R_2, R_3, R_4, R_5, R_6, R_7, R_{7a}, R_8, R_9, R_{10},$ and $R_{11}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, aminoacyloxy, and, for the groups $R_7$ and $R_{7a}$, can optionally be taken together to form oxo; or a pharmaceutically acceptable salt or prodrug thereof. Such compounds are disclosed in U.S. patent application publication US 2010/0105716, incorporated herein by reference.

In further embodiments $R_7$ and $R_{7a}$ together form oxo (C=O).

In some embodiments, $R_7$ and $R_{7a}$ do not form oxo (C=O).

In some embodiments, $R_3$ is —COOH, —CH$_2$COOH, —CH$_2$CH$_2$COOH, or an ester thereof.

In some embodiments, $R_1, R_2, R_4, R_5, R_6, R_7, R_{7a}, R_8, R_9, R_{10}, R_{11}$ are all H.

In some embodiments, at least one, two, or three of $R_1, R_2, R_4, R_5, R_6, R_7, R_{7a}, R_8, R_9, R_{10},$ and $R_{11}$ is not H. Thus, in some embodiments, $R_1$ is not H; in some embodiments $R_2$ is not H; in some embodiments $R_3$ is not H; in some embodiments $R_4$ is not H; in some embodiments $R_5$ is not H; in some embodiments $R_6$ is not H; in some embodiments $R_7$ is not H; in some embodiments $R_9$ is not H; in some embodiments $R_{10}$ is not H; and/or in some embodiments $R_{11}$ is not H.

Compounds of Formula III, including further definitions of substituent terms and various formulations thereof are disclosed in U.S. Patent Application Publication No: 2010/0105716 as useful in methods of treating metabolic diseases/disorders including obesity, insulin resistance, hyperglycemia, diabetes, and the like. Synthetic routes and strategies for the compounds of Formula III are known in the art. The disclosure of US 2010/0105716 is incorporated herein by reference.

Embodiments of this aspect relate to a method comprising a selective inhibitor of CaMKKβ of Formula I:

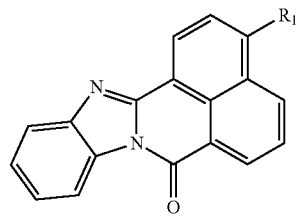

Formula I wherein $R_1$ is selected from CN, COOH, or COCl. Compounds of Formula I are described in U.S. Pat. No. 2,820,037 for use as dye molecules, and is incorporated herein by reference.

Other embodiments of this aspect relate to a method comprising a selective inhibitor of CaMKKβ of Formula II:

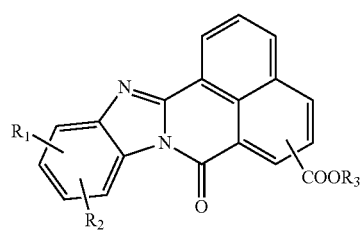

Formula II wherein $R_1$ and $R_2$ are independently selected from H, halo, alkyl, or haloalkyl; and $R_3$ is H, alkyl, or substituted alkyl, or three COOR$_3$ groups can be substituted at any location on the naphthalene ring. Compounds of Formula II are disclosed in Japanese Patent Application No. 2003-012516 as Ca$^{2+}$/calmodulin dependent kinase kinase (CaMKK) inhibitors; however the reference fails to disclose the use of these compounds as effective in methods relating to cancer. The disclosure of Japanese Patent Application No. 2003-012516 is incorporated herein by reference.

The compounds of Formulas I-III can be synthesized by any method known in the art such as, for example, the methods described Japanese Patent Application No. 2003-012516; U.S. Pat. No. 2,820,037; U.S. Pat. No. 2,835,674; U.S. Pat. No. 2,965,644; U.S. Pat. No. 2,949,467; U.S. Pat. No. 3,953,452; U.S. Pat. No. 3,960,867; U.S. Pat. No. 4,239,868; and U.S. Pat. No. 4,336,383, each of which is incorporated herein by reference.

In other embodiments, the CaMKK inhibitor is a biological molecule, such as a polynucleotide having RNAi activity against a CaMKK or a substrate thereof, or an antibody that can specifically bind to a CaMKK or a substrate thereof.

Nucleic Acids/RNAi

Embodiments of the disclosure relate to methods that include CaMKK inhibitors, wherein the inhibitors comprise nucleic acid molecules having inhibitory activity against one or more biological molecules involved in a CaMK cascade including CaMK enzymes such as, for example, CaMKI and/or CaMKIV as well as kinases for such molecules (CaMKKα, CaMKKβ, etc.), other biological substrates of CaMKKs (e.g., AMPK), as well as other CaMKs (e.g., CaMKII and CaMKIII). In embodiments, the nucleic acid molecules can include decoy RNAs, dsRNAs, siRNAs, nucleic acid aptamers, antisense nucleic acid molecules, and enzymatic nucleic acid molecules that comprise a sequence that is sufficient allow for binding to a CaMK, AMPK, or CaMKK encoding nucleic acid sequence and inhibit activity thereof (i.e., are complementary to such encoding nucleic acid sequences).

In embodiments, the inhibitory nucleic acid molecule can bind to a target CaMK, AMPK, or CaMKK nucleic acid sequence under stringent binding conditions. The terms "stringent conditions" "stringent binding conditions" or "stringent hybridization conditions" refers to conditions under which a polynucleotide will hybridize to a target sequence, to a detectably greater degree than other sequences (e.g., at least 2-fold over background). An example of stringent conditions include those in which hybridization in 50% formamide, 1 M NaCl, 1% SDS at 37° C., and a wash in 0.1×SSC at 60° C. to 65° C. is performed. Amino acid and polynucleotide identity, homology and/or similarity can be determined using the ClustalW algorithm, MEGALIGN™ (Lasergene, Wis.).

Given a target polynucleotide sequence of a CaMK, CaMKK, or biological substrate thereof, an inhibitory nucleic acid molecule can be designed using motifs and targeted to a region that is anticipated to be effective for inhibitory activity, such as is known in the art.

Antibodies

Embodiments of the disclosure relate to methods that include CaMKK inhibitors, wherein the inhibitors comprise antibodies having specific binding activity against one or more biological molecules involved in a CaMK cascade including CaMK enzymes such as, for example, CaMKI and/or CaMKIV as well as kinases for such molecules (CaMKKα, CaMKKβ, etc.), biological substrates of CaMKKs (e.g., AMPK), and CaMKs that are not substrates of CaMKKs (e.g., CaMKII and CaMKIII).

Preparation of Antibodies

The antibodies described herein can be produced by any method known in the art, such as by immunization with a full-length CaMK or CaMKK, or fragments thereof. The antibodies can be polyclonal or monoclonal, and/or may be recombinant antibodies. In embodiments, antibodies that are human antibodies can be prepared, for example, by immunization of transgenic animals capable of producing a human antibody (see, for example, International Patent Application, Publication WO 93/12227).

Monoclonal antibodies (mAbs) can be produced by a variety of techniques, including conventional monoclonal antibody methodology, e.g., the standard somatic cell hybridization technique of Kohler and Milstein [*Nature* (1975); 256:495], and other techniques, e.g., viral or oncogenic transformation of B-lymphocytes.

Animal systems for preparing hybridomas include mouse. Hybridoma production in the mouse is very well established, and immunization protocols and techniques for isolation of immunized splenocytes for fusion are well known in the art. Fusion partners (e.g., murine myeloma cells) and fusion procedures are also known.

In embodiments, human monoclonal antibodies directed against a CaMK or CaMKK can be generated using transgenic mice carrying parts of the human immune system rather than the mouse system. These transgenic mice, referred to herein as "HuMab" mice, contain a human immunoglobulin gene minilocus that encodes unrearranged human heavy (μ and γ) and κ light chain immunoglobulin sequences, together with targeted mutations that inactivate the endogenous μ and κ chain loci [Lonberg et al., Nature (1994); 368:856-859]. The preparation of HuMab mice is described in detail in Taylor et al., Nucleic Acids Res. (1992); 20:6287-6295; Chen et al., International Immunology (1993); 5:647-656; Tuaillon et al., J. Immunol. (1994); 152:2912-2920; Lonberg et al., Nature (1994); 368:856-859; Lonberg, Handbook of Exp. Pharmacology (1994); 113:49-101; Taylor et al., International Immunology (1994); 6:579-591; Lonberg & Huszar, Intern. Rev. Immunol. (1995); 13:65-93; Harding & Lonberg, Ann. N.Y. Acad. Sci (1995); 764:536-546; Fishwild et al., Nature Biotechnology (1996); 14:845-851, the contents of all of which are hereby incorporated by reference in their entirety. See further U.S. Pat. Nos. 5,545,806; 5,569,825; 5,625,126; 5,633,425; 5,789,650; 5,877,397; 5,661,016; 5,814,318; 5,874,299; and 5,770,429; all to Lonberg and Kay, as well as U.S. Pat. No. 5,545,807 to Surani et al.; International Patent Application Publication Nos. WO 93/1227, published Jun. 24, 1993; WO 92/22646, published Dec. 23, 1992; and WO 92/03918, published Mar. 19, 1992, the disclosures of all of which are hereby incorporated by reference in their entirety.

Embodiments provide human monoclonal antibodies that are specific for and neutralize biological activity of human CaMK and/or CaMKK polypeptides. Such antibodies can comprise heavy and light chain amino acid sequences, the light and heavy chain variable regions, and any combination (including all) hypervariable CDR regions, which are specific for and neutralize CaMK and/or CaMKK polypeptides when they bind. Such antibodies can provide an effective immunotherapy for CaMK and CaMKK associated diseases including various cancers, such prostate cancer, glioma, glioblastoma, and myeloid leukemia. Such antibodies also provide a useful reagent for the detection of a CaMK or a CaMKK in a biological sample.

In an embodiment, the antibodies target an epitope in a region of CaMK and/or CaMKK located in the C-terminal portion. In some embodiments, the antibody recognizes and binds specifically to an epitope in the C-terminal region of CaMKKβ splice variants 2 and/or 7.

In some embodiments, the antibodies are of the IgG1, IgG2, IgG3, or IgG4 isotype. In other embodiments, the antibodies of the invention are of the IgM, IgA, IgE, or IgD isotype. In certain embodiments, the antibodies are cloned for expression in mammalian cells. In embodiments, the antibodies can be a fragment of an antibody that retains specific binding activity for a CaMK or CaMKK polypeptide and is effective to inhibit biological activity. Such fragments are known in the art and include, for example, single-chain antibodies (scFV), Fab, Fab', Fab$_2$, and the like.

Any of the CaMKK inhibitors disclosed herein and which are useful in the methods described herein can be provided as salts such as, for example, basic or acidic addition salts. The selection and formation of such salts are within the ability of one skilled in the art. See, e.g., *Remington: The Science and Practice of Pharmacy*, 21$^{st}$ ed., Lippincott Williams & Wilkins, A Wolters Kluwer Company, Philadelphia, Pa. (2005).

Further, embodiments of the disclosure provide for compositions or formulations comprising any of the CaMKK inhibitors disclosed herein that can are suitable for pharmaceutical use. Further, such formulations can be provided in suitable dosage forms. Such compositions, formulations, and dosage forms are known to those of skill in the art. For example, compounds of Formulas I-III can be provided as a composition or formulation and prepared in a dosage form as described U.S. patent application publication number US 2010/0105716, which is incorporated by reference herein. See, also, *Remington: The Science and Practice of Pharmacy*, 21$^{st}$ ed., Lippincott Williams & Wilkins, A Wolters Kluwer Company, Philadelphia, Pa. (2005).

In an aspect, the disclosure provides a method for screening or identifying a compound having agonist or antagonist activity for CaMKK (including CaMKKβ and/or CaMKKα) that includes contacting CaMKK and a substrate therefor, in the presence and absence of a test compound, under conditions that allow for CaMKK-dependent phosphorylation of the substrate; and determining, directly or indirectly, the level of phosphorylation of the substrate, wherein a reduction in phosphorylation of the substrate in the presence of the test compound is indicative of a CaMKK antagonist (for example, an anticancer agent) and an increase in phosphorylation of the substrate in the presence of the test compound is indicative of a CaMKK agonist. In embodiments, the CaMKK is CaMKKβ.

In some embodiments of this aspect, the method identifies a compound that is selective for a specific CaMK relative to at least one other CaMK. In further embodiments, the method identifies a compound that is selective for CaMKKβ relative to at least one other CaMK such as, for example, CaMKI, CaMKII, CaMKIII, CaMKIV, or CaMKKα. Yet further embodiments of the method provide identification of a compound that is selective for CaMKKβ splice variant 2 or CaMKKβ splice variant 7, relative to at least one other CaMKKβ isoform, and relative to at least one other CaMK such as, for example, CaMKI, CaMKII, CaMKIII, CaMKIV, or CaMKKα.

Embodiments of these methods provide compounds having selective antagonist activity for a CaMK wherein the CaMK-dependent phosphorylation of the substrate is reduced by about 4-fold or more in the presence of the compound compared to phosphorylation in the absence of the compound (e.g., about 4-fold to about 100-fold or more).

Merely for purposes of illustration of an embodiment of this aspect, an assay system can comprise calmodulin (CaM), calcium, CaMKKβ, and a substrate (such as a synthetic peptide that can be phosphorylated by CaMKKβ such as from either AMPK or CaMKIV). The assay can further comprise evaluation of the test compound(s) that involves AMPK as the enzyme and a peptide from acetyl-CoA-carboxylase (ACC) as the substrate. In particular, assay conditions that allow for phosphorylation are provided (e.g., any appropriate buffer system) and further includes one or the other of CaMKKα and CaMKKβ (i.e., run in parallel), a calcium salt (e.g., $CaCl_2$), a phosphate source (e.g., ATP, optionally comprising radiolabelled $^{32}P$), calmodulin (CaM, e.g., from bovine), and two substrates (one that can be phosphorylated by both CaMKKα and CaMKKβ, while the other can only be phosphorylated by one or the other of CaMKKα or CaMKKβ). A non-limiting example of a substrate that can be phosphorylated by both CaMKKα and CaMKKβ includes CaMIV, or a peptide fragment thereof (for example, Lys-Lys-Lys-Lys-Glu-His-Gln-Val-Leu-Met-Lys-Thr-Val-Cys-Gly-Thr-Pro-Gly-Tyr). A non-limiting example of a substrate that can be phosphorylated by CaMKKβ and not CaMKKα includes AMPK, or a peptide fragment thereof (for example, Ala-Lys-Pro-Lys-Gly-Asn-Lys-Asp-Tyr-His-Leu-Gln-Thr-Cys-Cys-Gly-Ser-Leu-Ala-Tyr-Arg-Arg-Arg). Any substrate, including fragments thereof can be used in these methods, as long as the substrate can be phosphorylated. Differences between the amount of phosphorylation of the substrates can be used to evaluate the substrate specificity and selectivity of a candidate test compound. Concentrations of the various assay components can vary widely, but are usually in the range of 1 nM to 500 μM (for active reagents including proteins and substrates, phosphate source(s) and test compounds) and in the mM range for other assay components (calcium and magnesium salts/cofactors, reducing agents, buffer systems, etc.). Incubation time and temperature can also be varied depending on the particular activity and sensitivity of the assay components. In embodiments, the temperature can range from about 4° C. to about 30° C., and the incubation time can be on the order of minutes (e.g., 10 minutes) to hours (e.g., 1 hrs, 1.5 hrs, 2 hrs, 2.5 hrs, 3 hrs, 3.5 hrs, etc.). In embodiments, a selective inhibitor will inhibit CaMKKβ activity to a greater extent than it will inhibit CaMKKα activity. In some embodiments the selective inhibitor will inhibit CaMKKβ activity about anywhere from about 3-100 fold or more, relative to CaMKKα activity (e.g., about 10-20 fold, about 20-30 fold, about 40-50 fold, about 50-60 fold, about 60-70 fold, about 70-80 fold, about 80-90 fold, about 90-100 fold, or over 100 fold).

Embodiments of the disclosure provide for detection of CaMKK, such as CaMKKβ and/or CaMKKα in circulating tumor cells (CTCs). CTCs are known in the art and comprise cells that have detached from a primary tumor and circulate in the bloodstream. It is thought that CTCs may indicate potential for metastasis and spread of a primary tumor to different tissues. Thus, circulating tumor cells can be a factor indicating the metastatic spread of cancers, such as carcinomas, and can be used in methods for the detection of, and prognosticate the likelihood of, metastatic disease. See, e.g., Fidler I. J., *Nat Rev Cancer* (2003); 3:453-8; Sleijfer S., et al., *Eur J Cancer* (2007); 43:2645-50; Hayes D. F., and Smerage J., *Clin Cancer Res* (2008); 14:3646-50; Pantel K, et al., *Nat Rev Clin Oncol* (2009); 6:339-51; Pantel K., and Riethdorf S., *Nat Rev Clin Oncol.* (2009); 6:190-1; and Panteleakou Z., et al., *Mol Med* (2009); 15:101-14, all incorporated by reference. Methods for expanding and enriching the number of CTCs in a biological sample are known in the art and allow for measurable amounts of a biochemical marker (a genetic or biochemical signature, such as CaMKKβ) of disease (e.g., an androgen-driven cancer). Accordingly, methods for detecting the presence of a CaMK, such as CaMKKβ/α or phosphorylated AMPK allow for identification of therapies that can be useful in treatment of disease. In embodiments, such methods provide for a method of monitoring the course of a therapeutic treatment, such as administering an inhibitor of CaMKKβ, in a patient undergoing therapy, based on a detectable increase or decrease in the amount of the biochemical marker(s) in a sample comprising CTCs. Such analytic methods include Kaplan Meier Analysis which has been used to correlate overall survival before starting a new line of therapy for patients with metastatic breast, colorectal and prostate cancer. Patients can be divided into those with Favorable and Unfavorable CTC (Unfavorable: >5 CTC/7.5 mL for breast and prostate, >3 CTC/7.5 mL for colon). See, Miller, M. C., et al., *J of Oncology.* 2010. doi:10.1155/2010/617421. incorporated by reference. Methods known in the art, such as the CellSearch system ("Veridex CellSearch Website". March 2010. http://veridex.com/CellSearch/CellSearchHCP.aspx. Retrieved Mar. 14, 2010), as well as other methods, have been demonstrated as a strong prognostic factor for overall survival in patients with metastatic breast, colorectal or prostate cancer. See, e.g., Paterlini-Brechot P, and Benali N. L., *Cancer Lett.* (2007); 253:180-204; "Veridex LLC. CellSearch circulating tumor cell kit premarket notification—expanded indications for use—metastatic prostate cancer". March 2010. http://www.fda.gov/cdrh/pdf7/K073338.pdf. Retrieved Mar. 14, 2010; Cristofanilli M., et al., *NEJM* (2004); 351:781-91; Budd G., et al., *Clin Can Res* (2006); 12:6404-09; Cohen, S. J., et al., *JCO* (2008); 26:3213-21; DeBono, J. S., et al., *Clin Can Res* (2008); 14:6302-9; Allard, W. J., et al., *Clin Can Res* (2004);

10:6897-6904; and Riethdorf et al., *Clin Cancer Res* (2007); 13:920-8, all incorporated by reference.

In an aspect, the disclosure also provides a method for treating conditions or diseases associated with abnormal AMP-activated protein kinase (AMPK) activity, which includes increased phosphorylation of AMPK, by administering an effective amount of at least one compound that inhibits CaMKKβ to a subject having such a condition or disease. Diseases characterized by abnormal AMPK activity include, but are not limited to, various cancers including prostate cancer.

As used herein, the term "subject" is intended to include human and non-human animals. Exemplary human subjects include a human patient having a disorder, e.g., a disorder described herein, such as cancer, or a normal subject. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, etc.), and rodents (such as mice, rats, hamsters, guinea pigs, etc.).

"Treatment" or "treat" refers to both therapeutic treatment and prophylactic or preventative measures. Those subjects in need of treatment include those already with the disorder as well as those prone to have the disorder or those in which the disorder is to be prevented.

The terms "treating" and "treatment" refer to both therapeutic treatment and prophylactic or preventative measures. Those subjects in need of treatment include those already with the disorder as well as those prone to have the disorder or those in which the disorder is to be prevented. When used with reference to a disease or a subject in need of treatment the terms accordingly include, but are not limited to, halting or slowing of disease progression, remission of disease, prophylaxis of symptoms, reduction in disease and/or symptom severity, or reduction in disease length as compared to an untreated subject. In embodiments, the methods of treatment can abate one or more clinical indications of the particular disease being treated. Certain embodiments relating to methods of treating a disease or condition associated with activation of a substrate in a CaMK cascade (CaMKI, CaMKIV, AMPK) and comprise administration of therapeutically effective amounts of a compound that inhibits CaMKKβ, as well as pharmaceutical compositions thereof. In embodiments, the method of treating can relate to any method that prevents further progression of the disease and/or symptoms, slows or reduces the further progression of the disease and/or symptoms, or reverses the disease and/or clinical symptoms associated with expression of CaMKKβ or kinase activity thereof.

In embodiments, the methods are used to treat cancer in a subject, wherein the subject is a mammal. Yet further embodiments relate to methods wherein the mammal is a human.

Aspects of the disclosure provide a method of inhibiting CaMKKβ in a cell, including a cell within a subject, comprising contacting the cell with a compound in an amount effective to inhibit CaMKKβ activity. In embodiments, the method provides for inhibiting CaMKKβ activity in a cell in a subject, wherein the method includes administering to the subject a compound, or a pharmaceutically acceptable salt thereof, according to Formula I in an amount effective to inhibit CaMKKβ activity in the cell in the subject. Both the activity of CaMKKβ and AMPK can be monitored by any method familiar to those of skill in the art. In some embodiments CaMKKβ and/or AMPK activity can be monitored by clinical evaluation of the symptoms or stage of a disease associated with abnormal CaMKKβ and/or AMPK activity. In embodiments, the disease is cancer. In further embodiments, the cancer is glioma, glioblastoma, carcinoma, or leukemia. In some embodiments, the cancer is prostate cancer, cancer of the blood or bone marrow, or cancer of the brain/CNS.

In these embodiments, "inhibiting" or "inhibition" of CaMKKβ means that there is a measurable decrease in the activity of CaMKKβ in the presence of a compound (e.g., through contacting/administration), relative to the activity of CaMKKβ in the absence of the compound. As described above, the decrease in CaMKKβ activity can arise from direct inhibition of kinase activity by, for example, binding of a small molecule inhibitor of Formulas I-III to the active site of CaMKKβ. A decrease in CaMKKβ activity can also arise from inhibition of expression of a CaMKKβ gene via antisense inhibition, gene silencing, disruption or degradation of CaMKKβ mRNA via RNAi (e.g., siRNA). CaMKKβ expression can also be modulated indirectly by manipulating the activity or expression of a regulator of CaMKKβ, such as androgen receptor (AR) or proteins involved in CaMKKβ splicing activity such as Fox2/RTA-1, using any agent having such activity. In embodiments, CaMKKβ can be inhibited by about 10% to about 100% or more (e.g., about 10%, 20%, 30%, 40%, 50%, 60%, 70%, 80%, 90%, 100%, 200%, 300%, 500%, etc.) relative to a control. In some embodiments compounds can inhibit CaMKKβ (e.g., $IC_{50}$) at concentrations from about 0.1 nM to about 500 μM, (e.g., about 0.1 nM to about 250 μM, about 0.5 nM to about 200 μM, about 1.0 nM to about 100 μM, about 10 nM to about 50 μM, or about 100 nM to about 10 μM, and the like).

In some embodiments the therapeutically effective amount is an amount sufficient to stop or slow the progression of the cancer. In further embodiments, the therapeutically effective amount is an amount sufficient to reduce the number of cancer cells in the subject (i.e., killing of cancer cells). Methods for monitoring the proliferation of cancer cells and progress of cancer in a subject (e.g., tumor size, cell counts, biochemical markers, secondary indications, etc.) are known in the art.

In various embodiments of the method, the cancer is associated with the activity of CaMKKβ. Non-limiting examples of cancer that are associated with CaMKKβ activity include carcinoma, melanoma, leukemia, myeloid leukemia, glioma, and glioblastoma. In embodiments, the cancer is leukemia, cancer of the prostate or cancer of the brain/central nervous system. In further embodiments, the cancer is prostate cancer.

In some embodiments, the method of treatment is used as a co-therapy such as, for example, administration in conjunction with radiation, surgery, or other chemotherapeutics. In some embodiments, the method includes administration of a therapeutically effective amount of a compound that inhibits CaMKKβ in combination with an additional anti-cancer agent. A wide variety of anti-cancer (i.e., anti-neoplastic) agents are known in the art and include, for example alkylating agents, antimetabolites, natural antineoplastic agents, hormonal antineoplastic agents, angiogenesis inhibitors, differentiating reagents, RNA inhibitors, antibodies or immunotherapeutic agents, gene therapy agents, small molecule enzymatic inhibitors, biological response modifiers, and anti-metastatic agents.

In embodiments, the method comprises treating prostate cancer in a subject who is in need of treatment, where the method includes administering to the subject an effective amount of a CaMKK inhibitor in combination with a second treatment. In such embodiments, the second treatment can include such non-limiting examples as surgery, radiation, and chemotherapy. In further embodiments, the method comprises co-administration of an effective amount of a CaMKK inhibitor and a second agent effective against prostate cancer such as, for example, anti-androgens, Selective Androgen Receptor Modulators (SARMs), Selective Androgen Receptor Degraders (SARDs), CYP17 inhibitors, suphatase inhibitors, Src inhibitors, anti-estrogens, estrogens, Selective Estrogen Receptor Modulators (SERMs), Selective Estrogen Receptor Degraders (SERDs), ERb antagonists, aromatase inhibitors, vaccine-based therapeutics such as sipuleucel-T (Provenge®), and the like. In further embodiments the method comprises administration an effective amount of a CaMKK inhibitor and an active agent selected from MDV3100 (an androgen receptor antagonist from Medivation Inc., San Francisco, Calif.); ARN-509 (an androgen receptor antagonist from Aragon Pharmaceuticals, San Diego, Calif.); bicalutamide (Casodex® a non-steroidal anti-androgen from AstraZeneca); or flutamide (Eulexin® a non-steroidal anti-androgen from Schering-Plough).

In some embodiments, the method of treatment can be used an adjuvant therapy (i.e., additional treatment) such as, for example, when compounds of any of Formulas I-III, or pharmaceutical compositions thereof, are administered after surgery or other treatments (e.g., radiation, hormone therapy, or chemotherapy). Accordingly, in such embodiments, the method of adjuvant therapy encompasses administering the compounds of Formula I-III to a subject following a primary or initial treatment, and can be administered either alone or in combination with one or more other adjuvant treatments, including, for example surgery, radiation therapy, or systemic therapy (e.g., chemotherapy, immunotherapy, hormone therapy, or biological response modifiers). Those of skill in the art will be able to use statistical evidence to assess the risk of disease relapse before deciding on the specific adjuvant therapy. The aim of adjuvant treatment is to improve disease-specific and overall survival. Because the treatment is essentially for a risk, rather than for provable disease, it is accepted that a proportion of patients who receive adjuvant therapy will already have been effectively treated or cured by their primary surgery. Adjuvant therapy is often given following surgery for many types of cancer including, for example, colon cancer, lung cancer, pancreatic cancer, breast cancer, prostate cancer, and some gynecological cancers.

Some embodiments of the method relate to neoadjuvant therapy, which is administered prior to a primary treatment. Effective neoadjuvant therapy is commonly characterized by a reduction in the number of cancer cells (e.g., size of the tumor) so as to facilitate more effective primary treatment such as, for example, surgery.

The term "cancer" refers to or describes the physiological condition in mammals that is typically characterized by unregulated cell growth. Some non-limiting examples of cancer include carcinoma, melanoma, lymphoma, blastoma, sarcoma, germ cell tumors, and leukemia or lymphoid malignancies. Non-limiting examples of cancers that fall within these broad categories include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, melanoma, multiple myeloma and B-cell lymphoma, brain, as well as head and neck cancer, and associated metastases.

The term "cancer" also encompasses cell proliferative disorders which are associated with some degree of abnormal cell proliferation, and includes tumors. "Tumor" as used herein, refers to any neoplasm or neoplastic cell growth and proliferation, whether malignant or benign, and all pre-cancerous and cancerous cells and tissues. In embodiments disclosed above, the cancer can be prostate cancer, cancer of the brain/CNS (glioma, glioblastoma, etc.), or leukemia (myeloid leukemia).

Administration of an effective amount of an inhibitor of CaMKK such as, for example a compound of Formula I-III, such as STO-609 for example, to a subject may be carried out by any means known in the art including, but not limited to intraperitoneal, intravenous, intramuscular, subcutaneous, or transcutaneous injection or oral, nasopharyngeal or transmucosal absorption. Such administration encompasses the administration of a CaMKK inhibitor formulated as a pharmaceutical composition. Delivery (administration route) also includes targeted delivery wherein the CaMKK inhibitor is only active in a targeted region of the body (for example, in the prostate and/or cancerous tissues), as well as sustained release formulations in which the CaMKK inhibitor compound is released over a period of time in a controlled manner. Sustained release formulations and methods for targeted delivery are known in the art and include, for example, use of liposomes, drug loaded biodegradable microspheres, drug-polymer conjugates, drug-specific binding agent conjugates and the like. Pharmaceutically acceptable carriers are well known to those of skill in the art. Determination of particular pharmaceutical formulations and therapeutically effective amounts and dosing regimen for a given treatment is within the ability of one of skill in the art taking into consideration, for example, patient age, weight, sex, ethnicity, organ (e.g., liver and kidney) function, the extent of desired treatment, the stage and severity of the disease and associated symptoms, and the tolerance of the patient for the treatment.

Kits

In an aspect, the disclosure relates to kits. Such kits can be used in methods of identifying a cancer that can be responsive to a method of treatment comprising administration of a CaMKK inhibitor, methods of identifying a compound as an inhibitor of CaMKK, methods of evaluating efficacy of a therapeutic regimen comprising administration of a CaMKK inhibitor, and the like. Kits can also include appropriate buffer systems and reagents, such as substrates of one or more CaMKKs, phosphate-donating groups (optionally radiolabelled phosphate-donating groups such as $^{32}$P-ATP), a calmodulin and a calcium source, typically a calcium salt, and molecules that can detect the presence of a CaMK or CaMKK (e.g., antibodies). Kits also include instructions for use.

It will be understood that any numerical value recited herein includes all values from the lower value to the upper value. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between the lowest value and the highest value enumerated are to be considered to be expressly stated in this application.

Also, it is to be understood that the phraseology and terminology used herein is for the purpose of description and should not be regarded as limiting. The use herein of terms such as "comprising," "including," "having," and variations thereof is meant to encompass the items listed thereafter and equivalents thereof as well as additional items. "Comprising" encompasses the terms "consisting of" and "consisting essentially of." The use of "consisting essentially of" means that the composition or method may include additional ingredients and/or steps, but only if the additional ingredients and/or steps do not materially alter the basic and novel characteristics of the claimed composition or method.

All patents publications and references cited herein are hereby fully incorporated by reference.

While the following examples provide further detailed description of certain embodiments of the invention, they should be considered merely illustrative and not in any way limiting the invention, as defined by the claims.

EXAMPLES

Materials and Methods.

Cell culture and RNA. The LNCaP and VCaP human prostate carcinoma cell lines were obtained from ATCC and maintained as recommended. All experiments were performed with cells of passage less than 25. These cells were authenticated by morphological inspection and mycoplasma testing by the ATCC. Furthermore, their response to androgens was authenticated using growth and reporter gene assays. RNA from placenta, skeletal muscle, cerebellum, whole brain and normal prostate was from Clontech (Mountain View, Calif.). RNA from glioblastoma cell lines was a generous gift from Valerie Curtis (Duke University, Durham, N.C.).

RNA isolation, cDNA preparation, and quantitative and standard reverse transcription (RT)-PCR. RNA isolation, cDNA preparation and quantitative RT-PCR (qPCR) were performed as previously described using 36B4 as a control (12). Standard RT-PCR was performed using the Advantage GC 2 Polymerase Mix and PCR Kit (Clontech). All qPCR and RT-PCR primers used in this study are listed in Table 1.

Western blot analysis. Western blots were performed as previously described (12) with the exception that a modified radioimmunoprecipitation assay (RIPA) buffer [50 mM Tris (pH 8.0), 200 mM NaCl, 1.5 mM $MgCl_2$, 1% Triton X-100, 1 mM EGTA, 10% glycerol, 50 mM NaF, 2 mM $Na_3VO_4$ and protease inhibitors] was used. Results shown are representative blots. For each sample, protein levels were determined by densitometry using the ImageJ software (NIH) and normalizing to indicated controls.

Small interfering RNA (siRNA) transfection of human prostate cells. Stealth siRNA (Invitrogen) transfections were performed as previously described (5). The sequences of all siRNAs used in this study are listed in Table 1.

Chromatin immunoprecipitation (ChIP). ChIP was performed as previously described (4). All primers used for ChIP qPCR analysis are listed in Table 1.

Transient transfections and reporter gene assays. Transient transfections and reporter gene assays were performed as previously described (4).

Cell proliferation assay. Proliferation assays were performed as previously described (12) by measuring the cellular DNA content using the FluoReporter Blue Fluorometric double-stranded DNA Quantitation Kit (Invitrogen) as per the manufacturer's protocol.

Migration and invasion assays. Boyden dual chamber migration assays were performed as previously described (4). Invasion assays were performed the same as migration assays except that inserts were layered with 100 ml of Matrigel extracellular matrix (BD Biosciences) prior to reseeding of cells.

Statistical analysis. Data were analyzed using one-way ANOVA and post hoc Dunnett's test with GraphPad Prism, Version 4 (GraphPad Software, Inc.). Unless otherwise noted, significance was determined at the P<0.05 level.

Chemicals. Methyltrienolone (R1881) was purchased from PerkinElmer (Waltham, Mass.) and dissolved in ethanol. Bicalutamide (Casodex) was provided as a gift from P. Turnbull (GlaxoSmithKline, Research Triangle Park, N.C.) and resuspended in a 1:1 mixture of ethanol and dimethylsulfoxide (DMSO). Cycloheximide was obtained from Sigma (St Louis, Mo.) and dissolved in DMSO. Compound C (in DMSO) was from Calbiochem (San Diego, Calif.). STO-609 was purchased from Tocris (Ellisville, Mo.) and resuspended in 100 mM NaOH. 5-aminoimidazole-4-carboxamide 1-b-D-ribo-furanoside (AICAR) was from Enzo Life Sciences (Plymouth Meeting, Pa.) and dissolved in water.

Antibodies. The CaMKK antibody used, unless otherwise specified, was from BD Biosciences (Palo Alto, Calif.). The CaMKKβ (clone 1A11) antibody was from Abnova (Walnut, Calif.). The v5 antibody was purchased from Invitrogen (Carlsbad, Calif.). The GAPDH and AR antibodies have previously been described (1). Phospho-CaMKI (T177), CaMKI and Lamin A antibodies were from Santa Cruz Biotechnology, Inc. (Santa Cruz, Calif.). Phospho-AMPKa (T172), AMPKa, phospho-acetyl-CoA carboxylase (S79), and acetyl-CoA carboxylase antibodies were from Cell Signaling Technology (Danvers, Mass.).

Plasmids. The CMV-βgal and PSA-Luc plasmids were previously described (2). The pGL4.14 (lacks both basal promoter and enhancers) and pGL4.26 (lacks enhancer, but contains basal promoter) vectors were obtained from Promega (Madison, Wis.). MSCV-GWb-GAL4(DNA-binding domain (DBD))-IRES-EGFP, MSCV-GWb-CaMKKβ-IRES-EGFP, MSCV-GWb-v5-ARwt-IRES-EGFP and MSCV-GWb-v5-AR(C562S)-IRES-EGFP were created using the Invitrogen Gateway recombinase subcloning system according to the manufacturer's instructions. To do this, GAL4(DBD), CaMKKβ, v5-ARwt or v5-AR(C562S) were shuttled from pENTR-GAL4(DBD), pENTR-v5-ARwt, pENTR-v5-AR(C562) or pOTB7-CaMKKβ □□prostate splice variant□ (American Type Culture Collection (ATCC), Manassas, Va.) to MSCV-IRES-EGFP that was converted to a Gateway destination vector. The pGL4.14-CaMKKβ promoter construct was created by PCR amplifying a 2.1 kb genomic sequence that encompassed the CaMKKβ transcriptional start site through the potential AR binding site identified using ChIP on Chip (previously described (3)). This fragment was then cloned into the pGL4.14 vector using NheI and HindIII restriction sites. Subsequent deletion constructs were created by PCR amplifying smaller fragments that were cloned into pGL4.26 using NheI and HindIII restriction sites. Finally, the pGL4.14-CaMKKβ promoter-ARE deletion construct was created from the original pGL4.14-CaMKKβ promoter construct using the ExSite PCR-Based Site-Directed Mutagenesis Kit (Stratagene, La Jolla, Calif.). All primers used for the creation of constructs are listed in Supplementary Table 1. All sequences were confirmed using restriction digests and sequencing.

Creation of stable cell lines. To create LNCaP-GAL4, LNCaP-CAMKKβ□□LNCaP-v5-ARwt and LNCaP-v5-AR(C562S) cells, parental cells were infected with retrovirus expressing MSCV-GWb-GAL4(DBD)-IRES-EGFP (negative control), MSCV-GWb-CAMKKβ-IRES-EGFP, MSCV-GWb-v5-ARwt-IRES-EGFP or MSCV-GWb-v5-AR(C562S)-IRES-EGFP. EGFP positive cells were then selected through two rounds of cells sorting using flow cytometry and expression levels were confirmed by western blot and/or qPCR.

TABLE 1

Primers and siRNA sequences used in these studies

| Primer/siRNA | Sequence (SEQ ID NO) |
|---|---|
| qPCR primers | |
| 36B4 | Forward: 5'-GGACATGTTGCTGGCCAATAA-3' (SEQ ID NO: 48)<br>Reverse: 5'-GGGCCCGAGACCAGTGTT-3' (SEQ ID NO: 49) |
| CaMKKβ | Forward: 5'-TCCAGACCAGCCCGACATAG-3' (SEQ ID NO: 50)<br>Reverse: 5'-CAGGGGTGCAGCTTGATTTC-3' (SEQ ID NO: 51) |
| CXCR4 | Forward: 5'-TGGCCTTATCCTGCCTGGTAT-3' (SEQ ID NO: 52)<br>Reverse: 5'-AGGAGTCGATGCTGATCCCAA-3' (SEQ ID NO: 53) |
| AR 3'UTR | Forward: 5'-CCATGGCACCTTCAGACTTT-3' (SEQ ID NO: 54)<br>Reverse: 5'-ACTGGGCCATATGAGGATCA-3' (SEQ ID NO: 55) |
| AMPKα1 | Forward: 5'-CTCAGTTCCTGGAGAAAGATGG-3' (SEQ ID NO: 56)<br>Reverse: 5'-CCCAGTCAATTCATGTTTGCC-3' (SEQ ID NO: 57) |
| AMPKα2 | Forward: 5'-ATGGAATATGTGTCTGGAGGTG-3' (SEQ ID NO: 58)<br>Reverse: 5'-TGGTTTCAGGTCTCGATGAAC-3' (SEQ ID NO: 59) |
| CaMKKβ enhancer ChIP primers | |
| distal upstream control | Forward: 5'-GCACAGTTTGCACACCTGAA-3' (SEQ ID NO: 60)<br>Reverse: 5'-GCTTTGGATTTAGGCCCTGT-3' (SEQ ID NO: 61) |
| CaMKKβ enhancer | Forward: 5'-AACAGGAAAGGACACCCAAA-3' (SEQ ID NO: 62)<br>Reverse: 5'-AAACCATTCTTAGCAGGCCAT-3' (SEQ ID NO: 63) |
| CaMKKβ enhancer and promoter reporter gene primers | |
| promoter | Fwd: 5'-CGCTAGCAGGGAGGTGGCTGAGCATCAAATA-3' (SEQ ID NO: 64)<br>Rv: 5'-CAAAGCTTTGAGACAGGGTCTCTCTGTGTTGC-3' (SEQ ID NO: 65) |
| fragment A enhancer | Fwd: 5'-CGCTAGCGAATTGCAACTGTGAGACCAGGCA-3' (SEQ ID NO: 66)<br>Rv: 5'-CAAAGCTTGTGGCCTTGGGCAAATGACTTGAT-3' (SEQ ID NO: 67) |
| fragment B enhancer | Fwd: 5'-CGCTAGCATCAAGTCATTTGCCCAAGGCCAC-3' (SEQ ID NO: 68)<br>Rv: 5'-CAAAGCTTAACACTGTAGCTCACACAGGCAGA-3' (SEQ ID NO: 69) |
| fmgment C enhancer | Fwd: 5'-CGCTAGCATCAAGTCATTTGCCCAAGGCCAC-3' (SEQ ID NO: 70)<br>Rv: 5'-CAAAGCTTTATTTGATGCTCAGCCACCTCCCT-3' (SEQ ID NO: 71) |
| fragment D/598 bp enhancer | Fwd: 5'-CGCTAGCAGGGAGGTGGCTGAGCATCAAATA-3' (SEQ ID NO: 72)<br>Rv: 5'-CAAAGCTTAAATGTGAAAGGCCAGGTGTGGTG-3' (SEQ ID NO: 73) |
| fragment E enhancer | Fwd: 5'-CGCTAGCTGCCTGTGTGAGCTACAGTGTTCT-3' (SEQ ID NO: 74)<br>Rv: 5'-CAAAGCTTAAATGTGAAAGGCCAGGTGTGGTG-3' (SEQ ID NO: 75) |
| fragment F enhancer | Fwd: 5'-CGCTAGCAGGGAGGTGGCTGAGCATCAAATA-3' (SEQ ID NO: 76)<br>Rv: 5'-CAAAGCTTAACACTGTAGCTCACACAGGCAGA-3' (SEQ ID NO: 77) |
| fragment G enhancer | Fwd: 5'-CGCTAGCCACCACACCTGGCCTTTCACATTT-3' (SEQ ID NO: 78)<br>Rv: 5'-CAAAGCTTGCACTTTAAGGCAGGGTCAGCAAA-3' (SEQ ID NO: 79) |
| fragment H enhancer | Fwd: 5'-CGCTAGCGTTTCAAGCGATTCTCCTGCCTCA-3' (SEQ ID NO: 80)<br>Rv: 5'-CAAAGCTTTCACGCCTGTAATCCCAGCACTTT-3' (SEQ ID NO: 81) |
| 566 bp enhancer | Fwd: 5'-CGCTAGCAGGGAGGTGGCTGAGCATCAAATA-3' (SEQ ID NO: 82)<br>Rv: 5'-CAAAGCTTTACACGGGTGATTACAATCTTAGC-3' (SEQ ID NO: 83) |
| 487 bp enhancer | Fwd: 5'-CGCTAGCAGGGAGGTGGCTGAGCATCAAATA-3' (SEQ ID NO: 84)<br>Rv: 5'-CAAAGCTTTGGACAACATGGCAAGACCCATCT-3' (SEQ ID NO: 85) |
| 312 bp enhancer | Fwd: 5'-CGCTAGCAGGGAGGTGGCTGAGCATCAAATA-3' (SEQ ID NO: 86)<br>Rv: 5'-CAAAGCTTCTGGATCTCTTTTCCTGGTACTTG-3' (SEQ ID NO: 87) |

TABLE 1-continued

Primers and siRNA sequences used in these studies

| Primer/siRNA | Sequence (SEQ ID NO) |
|---|---|
| 233 bp enhancer | Fwd: 5'-CGCTAGCAGGGAGGTGGCTGAGCATCAAATA-3' (SEQ ID NO: 88)<br>Rv: 5'-CAAAGCTTACACTGTAGCTCACACAGGCAGAA-3' (SEQ ID NO: 89) |
| 152 bp enhancer | Fwd: 5'-CGCTAGCAGGGAGGTGGCTGAGCATCAAATA-3' (SEQ ID NO: 90)<br>Rv: 5'-CAAAGCTTTACAAATCCAAACCCTAGCTCAAG-3' (SEQ ID NO: 91) |
| 90 bp enhancer | Fwd: 5'-CGCTAGCAGGGAGGTGGCTGAGCATCAAATA-3' (SEQ ID NO: 92)<br>Rv: 5'-CAAAGCTTTGCTGTGAGCCAGGCCCTCCCTGC-3' (SEQ ID NO: 93) |
| 69 bp enhancer | Fwd: 5'-CGCTAGCAGGGAGGTGGCTGAGCATCAAATA-3' (SEQ ID NO: 94)<br>Rv: 5'-CAAAGCTTCTGCCCGCTCCTCTCTCTGATGTC-3' (SEQ ID NO: 95) |
| promoter-ARE deletion | Forward: 5'-CATACAGAATTGTTTAACAAGTACC-3' (SEQ ID NO: 96)<br>Rv: 5'-TAAATTGCCTGTGTTTTATTAGAACACTG-3' (SEQ ID NO: 97) |
| CaMKKβ RT-PCR primers | |
| F(1-6) | 5'-ACCTGTAATCCCAGCACTTTCGGA-3' (SEQ ID NO: 98) |
| R(1-6) | 5'-CGATCTCGGATCACTGCAACCTCT-3' (SEQ ID NO: 99) |
| F(7) | 5'-TGAGCCGAGCCGAGCCGAGCTG-3' (SEQ ID NO: 100) |
| R(1-7) | 5'-TCACAGGGCTTCTGGCTTTCGCT-3' (SEQ ID NO: 101) |
| F1 | 5'-AGCTGAGGACTTGAAGGACCTGAT-3' (SEQ ID NO: 102) |
| R1 | 5'-AGGTTGTCTTCGCTGCCTTGCTT-3' (SEQ ID NO: 103) |
| R2 | 5'-ACCTGGGCTGGCTATGTGTATGAA-3' (SEQ ID NO: 104) |
| siRNA sequences | |
| CaMKKβ #1 | 5'-GGACCAUCUGUACAUGGUGUUCGAA-3' (SEQ ID NO: 105) |
| CaMKKβ #2 | 5'-GCUGACUUUGGUGUGAGCAAUGAAU-3' (SEQ ID NO: 106) |
| CaMKKβ #3 | 5'-CACCUGGGCAUGGAGUCCUUCAUUG-3' (SEQ ID NO: 107) |
| AR 3'UTR | 5'-CAGAUGUCUUCUGCCUGUUAUAACU-3' (SEQ ID NO: 108) |
| AMPKα1 #1 | 5'-CCCAUCCUGAAAGAGUACCAUUCUU-3' (SEQ ID NO: 109) |

TABLE 1-continued

Primers and siRNA sequences used in these studies

| Primer/siRNA | Sequence (SEQ ID NO) |
|---|---|
| AMPKα1 #2 | 5'-CCCUCAAUAUUUAAAUCCUUCUGUG-3' (SEQ ID NO: 110) |
| AMPKα1 #3 | 5'-ACCAUGAUUGAUGAUGAAGCCUUAA-3' (SEQ ID NO: 111) |
| AMPKα2 #1 | 5'-GAUGGUGAAUUUCUGAGAACUAGUU-3' (SEQ ID NO: 112) |
| AMPKα2 #2 | 5'-CCGUAUGACAUUAUGGCUGAAGUUU-3' (SEQ ID NO: 113) |
| CaMKI #1 | 5'-GGAGATACAGCTCTAGATAAGAATA-3' (SEQ ID NO: 114) |
| CaMKI #2 | 5'-CCATAGGTGTCATCGCCTACATCTT-3' (SEQ ID NO: 115) |

Figure 2:
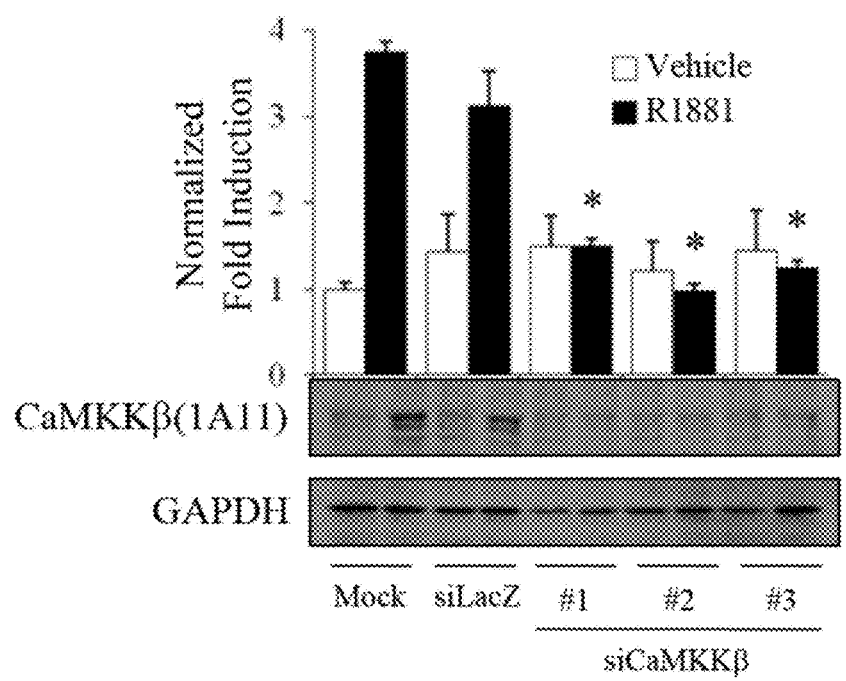
FIG. 2. Validation of CaMKKβ protein bands. For CaMKKβ western blot analysis, a different monoclonal CaMKKβ antibody (clone 1A11) was used than in FIG. 1. CaMKKβ protein levels were normalized to GAPDH loading control. Results are expressed as fold induction over vehicle-treated cells+SE (n=2). *, P<0.05 indicates significant changes from mock-transfected cells.

Example 1: Androgens Increase CaMKKβ mRNA and Protein Levels in an AR-Dependent Manner In an effort to identify novel prostate cancer therapeutics, we have focused on defining key regulators downstream of AR action that contribute to prostate pathobiology and that may be amenable to pharmacological exploitation. As a first step in this process, we analyzed the expression level of mRNAs encoding targetable signaling molecules using microarray data derived from androgen-treated LNCaP prostate cancer cells (13). These studies suggested that one such candidate, CaMKKβ, was upregulated by androgens. To confirm the significance of this observation, CaMKKβ mRNA levels were analyzed by qPCR following treatment with the synthetic androgen R1881. In both LNCaP and VCaP prostate cancer cell lines, CaMKKβ mRNA levels increased in a dose-dependent manner (FIG. 1A). Further, western immunoblot analysis revealed a corresponding dose-dependent increase in CaMKKβ protein levels in both cell lines (FIG. 1B). The specificity of the antibodies used in this study was verified using three siRNAs targeting CaMKKβ mRNA (FIG. 1C). In addition, analogous immunoblot results were obtained using a second antibody (clone 1A11) directed against CaMKKβ (FIG. 2). Finally, androgen-mediated induction, but not the basal expression, of CaMKKβ mRNA was abrogated in cells in which AR expression was inhibited using a validated siRNA (4) directed against the AR mRNA (FIG. 1D). Taken together, these data demonstrate that androgens, acting through AR, increase both CaMKKβ mRNA and protein levels in multiple cellular models of prostate cancer.

Figure 3:
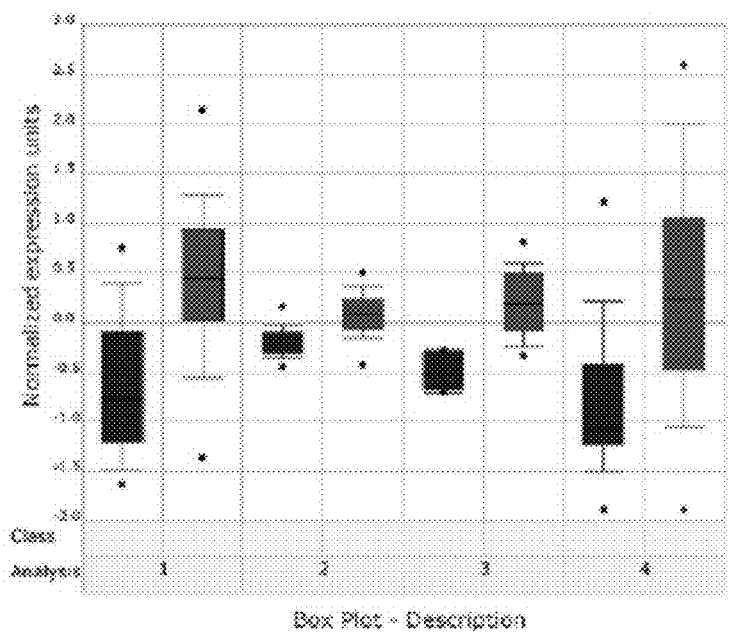
FIG. 3. CaMKKβ levels are increased in prostate cancer samples. Independent microarrays were analyzed using the Oncomine resource. A, four separate studies determined that CaMKKβ levels were elevated in prostate cancer samples (red) compared to normal prostate controls (blue). B, CaMKKβ levels correlated with disease progression. C, CaMKKβ levels are significantly higher in prostate cancer samples compared to other cancers (a—bladder, b—kidney, c—colon, d—breast, e—esophageal, f—liver, g—lung, h—ovarian, i—pancreatic, j—squamous cell lung). All changes in expression were at the P<0.001 level.
Figure 3:
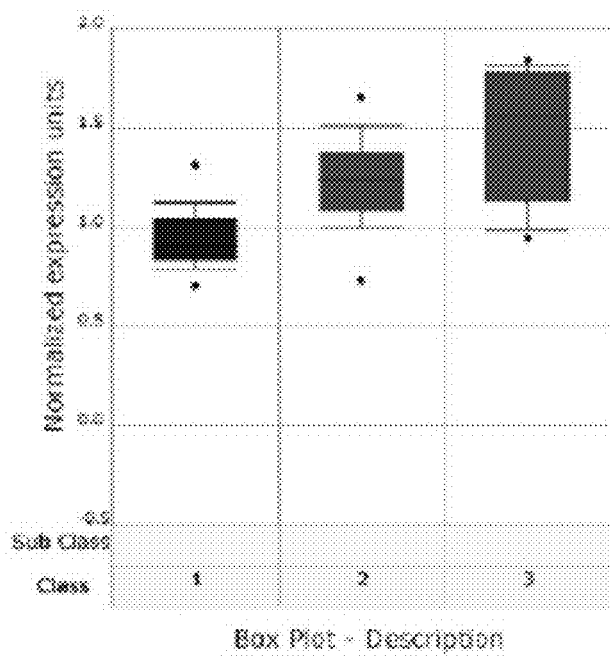
Figure 3:
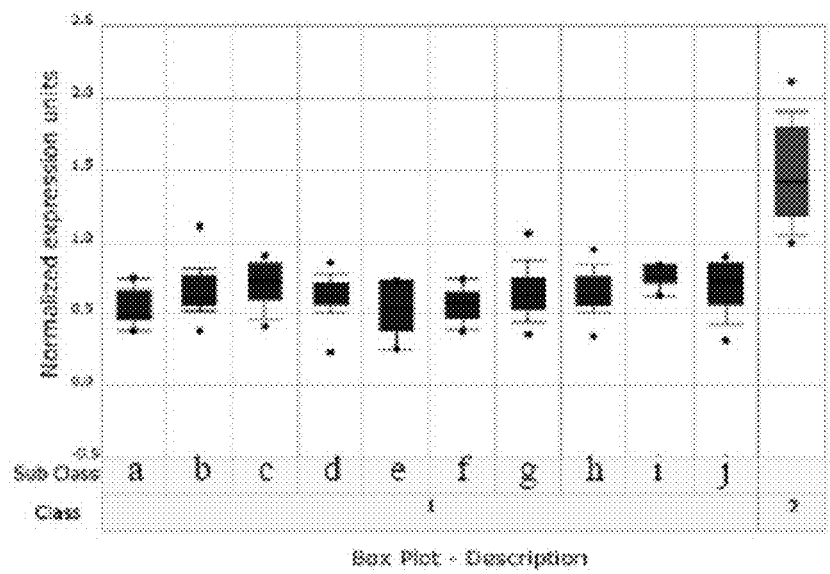

Example 2: Functionally Active Splice Variants of CaMKKβ are Expressed in Response to Androgens in the Prostate Given that AR increases CaMKKβ levels in multiple cellular models of prostate cancer, we next determined if its expression correlated with the development of prostate cancer in human samples. Analysis of the clinically annotated prostate cancer data sets accessible through Oncomine revealed that CaMKKβ expression increases with grade (14-17) (FIG. 3A and FIG. 3B). Interestingly, this analysis also revealed that CaMKKβ was consistently overexpressed in prostate tumors, but not other malignancies (FIG. 3C) (18).

Figure 4:
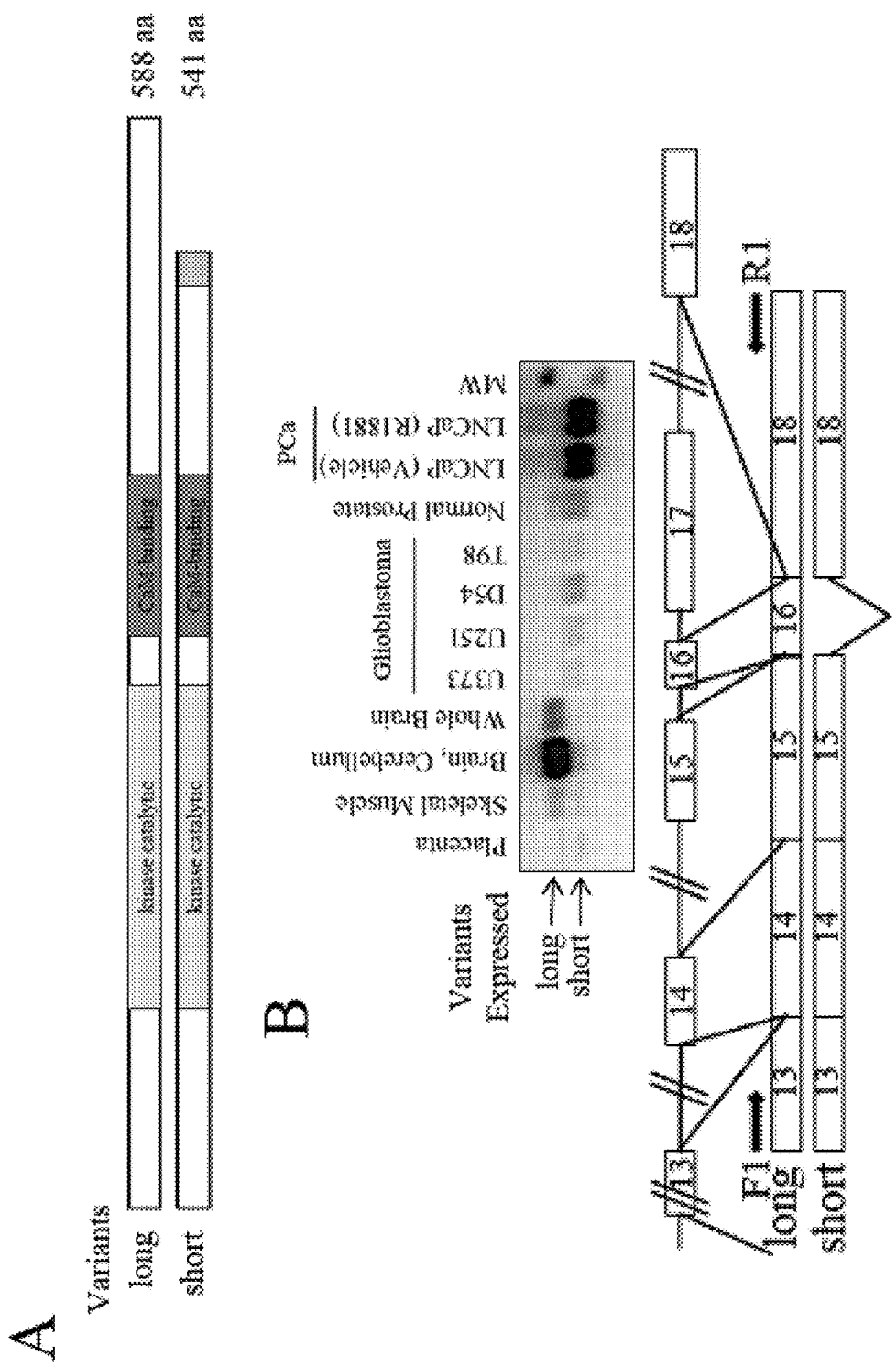
FIG. 4. The prostate expresses a different functional splice variant of CaMKKβ□ compared to brain. A, schematic of CaMKKβ splice variants. B, RT-PCR using primers spanning specific exons (indicated in right schematic) was performed on cDNA generated from various tissues and cell lines. C, LNCaP or VCaP cells were treated for 24 h+/−10 nM R1881. Cell lysates were then subjected to western blot analysis and subsequent densitometry (right). Phospho-CaMKI (p-CaMKI) protein levels were normalized to total CaMKI. Results are expressed as fold CaMKI phosphorylation over vehicle-treated cells+SE (n=3). *, significant changes from vehicle-treated cells.
Figure 4:
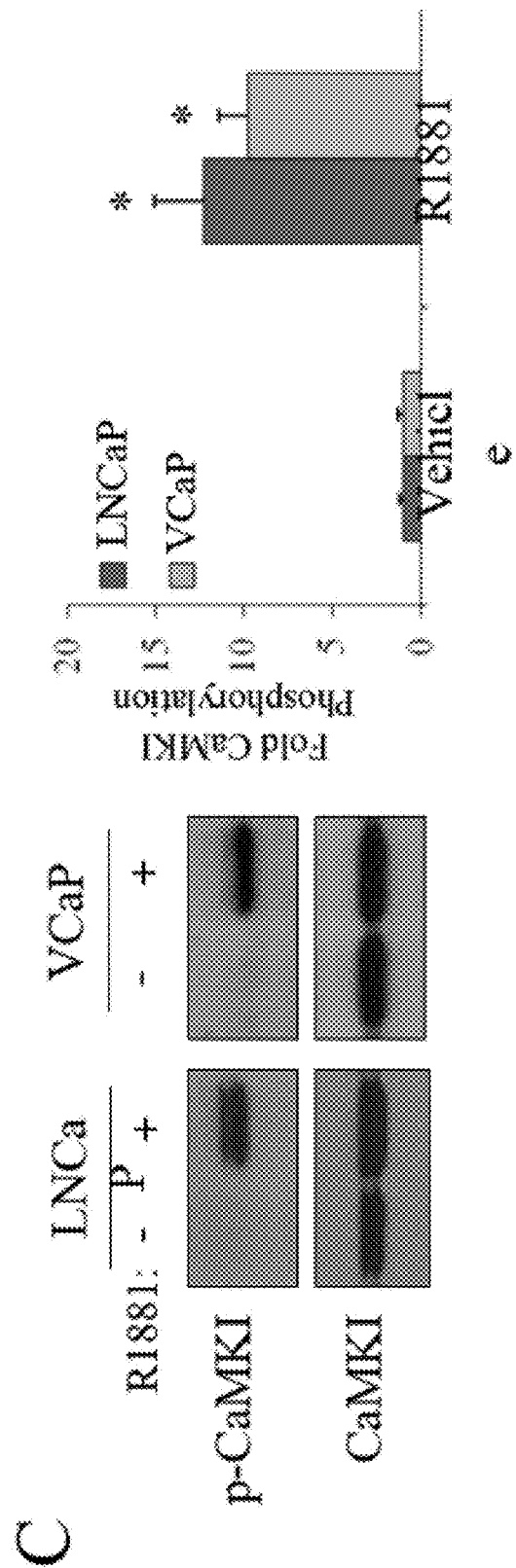
Figure 5:
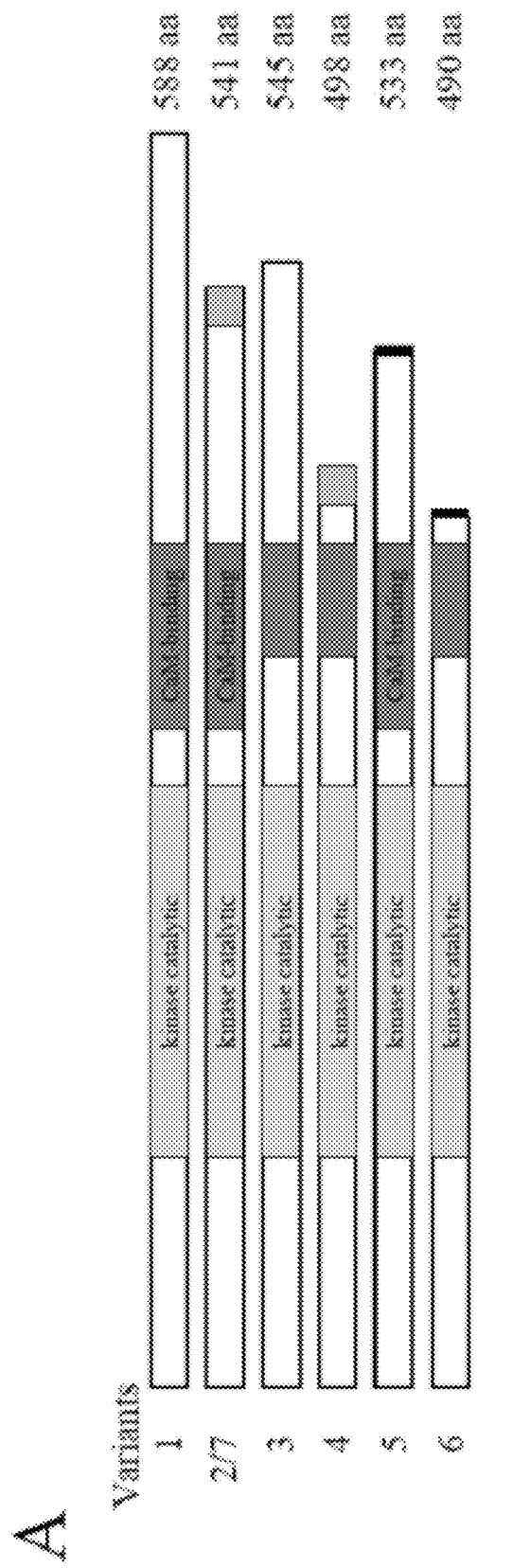
FIG. 5. The prostate expresses different splice variants of CaMKKβ □compared □to □brain (expanded FIG. 4A and FIG. 4B). A, schematic of CaMKKβ splice variants. B, RT-PCR using primers spanning specific exon-exon boundaries (indicated in right schematic) was performed on cDNA generated from various tissues and cell lines.
Figure 5:
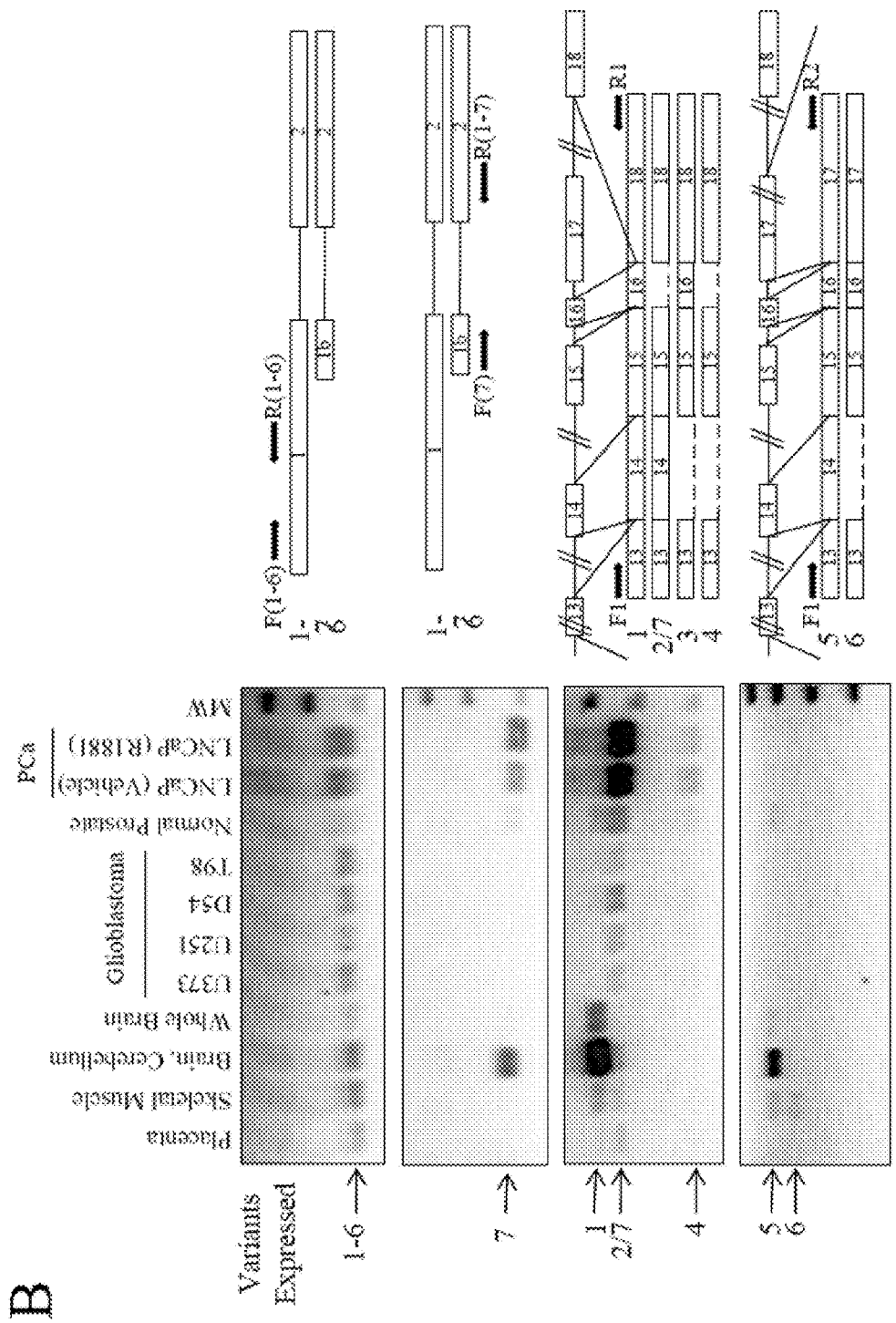

The full-length CaMKKβ protein is encoded by an mRNA composed of 18 exons. Interestingly, the majority of commercially available CaMKKβ antibodies target the C-terminus of the protein that is absent in some functionally active splice variants (19). Thus, given that the expression of CaMKKβ in the prostate has not been reported previously, we hypothesized that the prostate, and prostate cancers, may express a functionally important splice variant(s) of CaMKKβ that was not recognized by the most commonly used antibodies. To test this hypothesis, we performed RT-PCR analysis using primers spanning various exon boundaries to examine the splice variant repertoire in the normal prostate and in prostate cancer cells. In this manner, it was demonstrated that unlike in brain, which expresses a longer variant, both normal prostate and prostate cancer cells predominantly express shorter variants of CaMKKβ (FIG. 4A, FIG. 4B, and FIG. 5). The variants found are equivalent to the previously described CaMKKβ splice variants 2 and 7 that lack exon 16 (of note, splice variants 2 and 7 make identical protein products) (19). Interestingly, these shorter variants were also found in brain tumors (FIG. 4B). A complete analysis of the additional variants expressed in the prostate/prostate cancer is described in FIG. 5. Phosphorylation of the classical CaMKKβ target CaMKI was observed in both androgen-treated LNCaP and VCaP cells (FIG. 4C), indicating that the CaMKKβ variant expressed in prostate cancer cells is functionally active.

Figure 6:
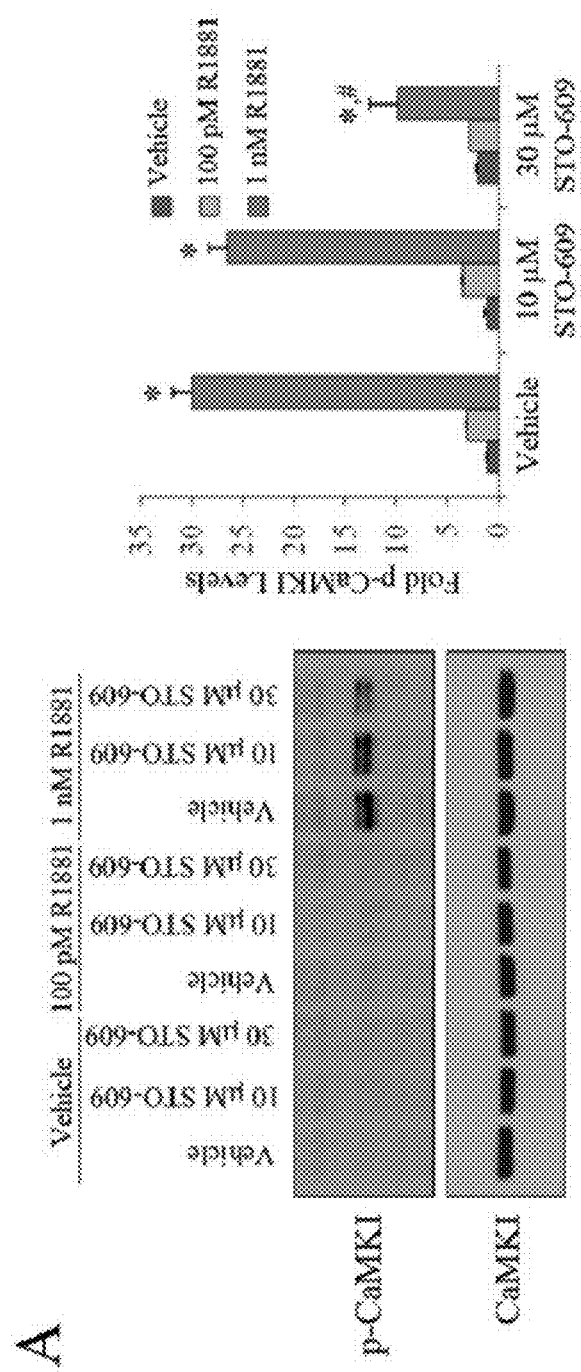
FIG. 6. CaMKKβ activity in androgen-mediated cell migration in prostate cancer cells. A, LNCaP cells were pretreated for 1 h with vehicle, 10 or 30 mM STO-609 prior to overnight treatment with vehicle, 100 pM or 10 nM R1881. Cell lysates were then subjected to western blot analysis and subsequent densitometry (right). Phospho-CaMKI (p-CaMKI) levels were normalized to total CaMKI. Results are expressed as fold induction/phosphorylation over double vehicle-treated cells+SE (n=2). *, P<0.05 indicates significant changes from vehicle-treated cells. #, P<0.05 indicates significant changes from vehicle (no STO-609)-treated cells. B, VCaP cells were plated in 96-well plates and grown for 3 d. Cells were treated+/−1 nM R1881 and +/−30 mM STO-609 on d 3, d 5, and d 7. On d 10, cells were lysed and the relative number of cells was measured with the fluorescent DNA binding dye FluoReporter Blue. Each sample was performed in triplicate, and results from a representative experiment are shown. Results are expressed as relative cell number±SE (n=2). *, P<0.05 indicates significant changes from vehicle (no R1881)-treated cells. C, VCaP cells were pretreated for 1 h+/−30 mM STO-609 prior to overnight treatment+/−10 nM R1881. Cells were then dissociated and reseeded into the top chamber for a Boyden dual chamber migration assay. Fresh medium with the corresponding treatments was added to the top and bottom chambers while either no chemoattractant or 5% FBS (serum) was added to the bottom chamber. After 16 h, migrated cells were fixed, stained with crystal violet and counted in three different microscopic fields and added together. The results are expressed as mean±SE (n=2). *, P<0.05 indicates significant changes from vehicle (no R1881)-treated cells. D and E, densitometry results for western blots in FIG. 7C and FIG. 7D respectively. *, P<0.05 indicates significant changes from vehicle-treated (D) or GAL4 control (E) cells. #, P<0.05 indicates significant changes from control (siLacZ)-transfected cells (D).
Figure 6:
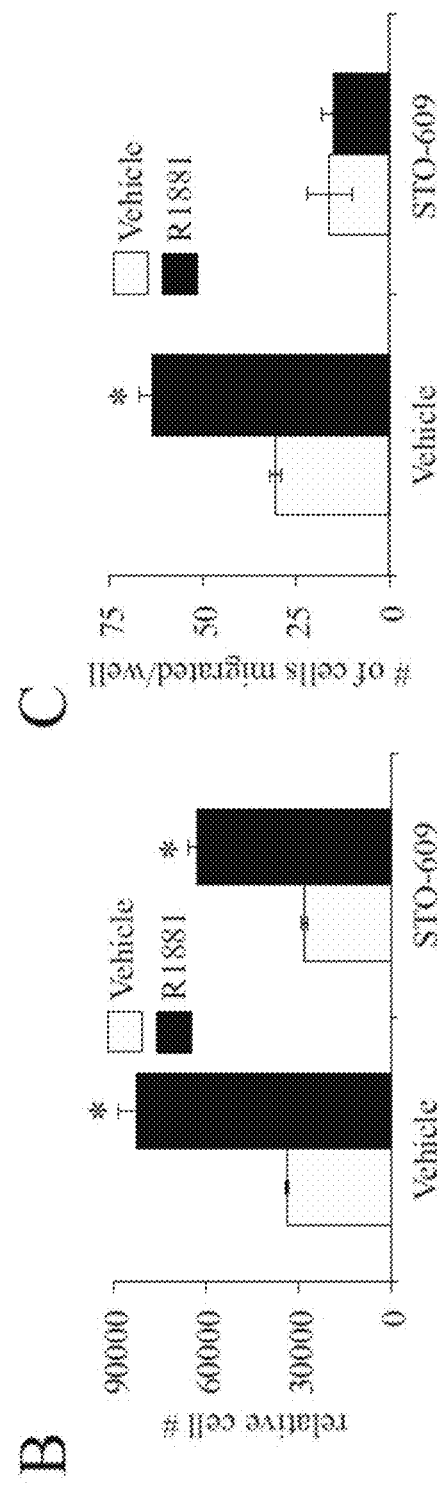
Figure 6:
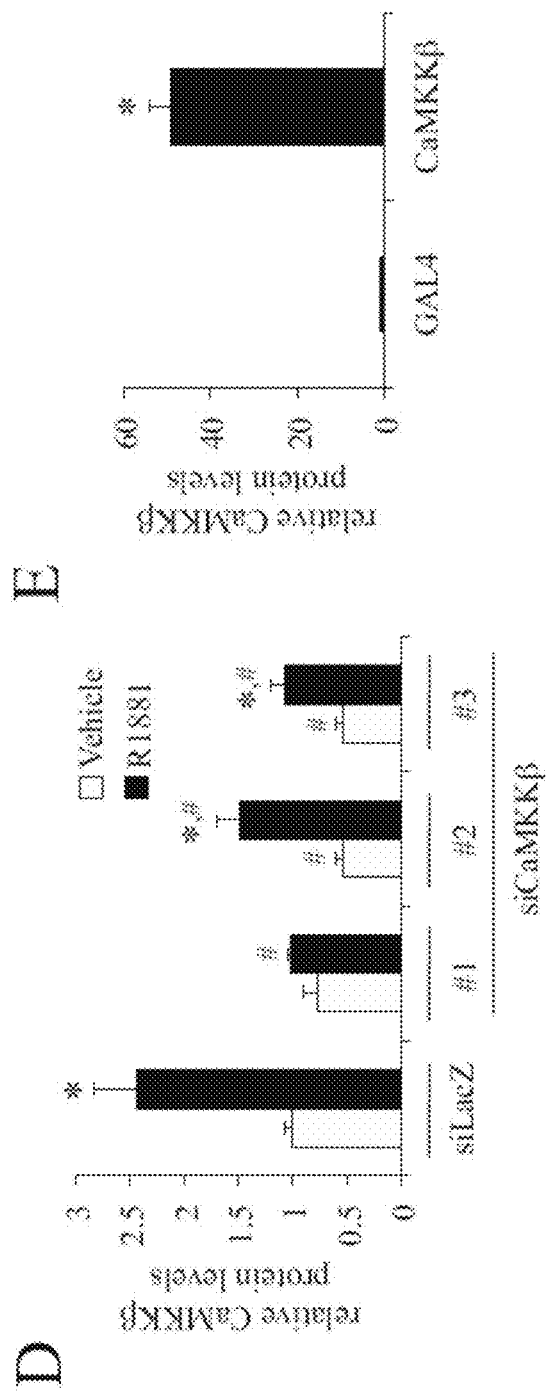
Figure 7:
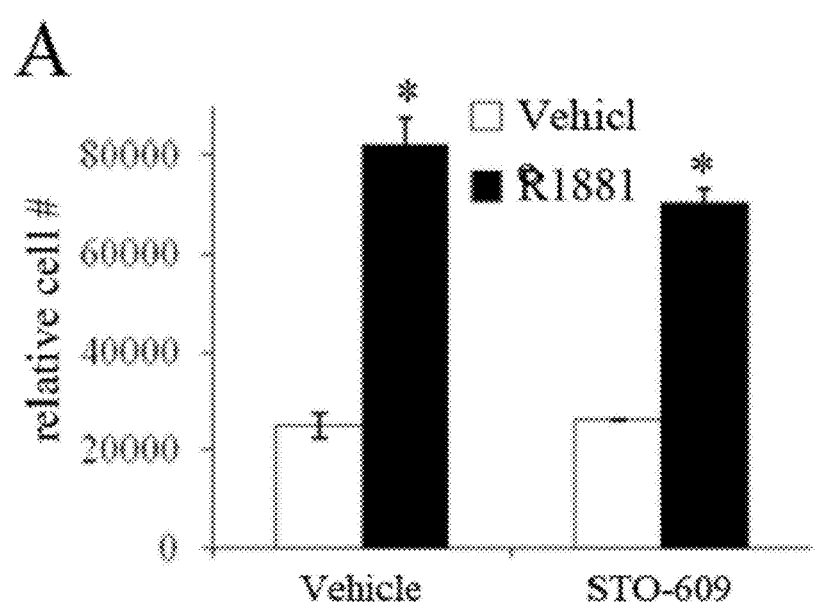
FIG. 7. CaMKKβ activity in the androgen-mediated migration and invasion of prostate cancer cells. A, LNCaP cells were plated in 96-well plates and grown for 3 d. Cells were treated+/−1 nM R1881 and +/−30 mM STO-609 on d 3, d 5, and d 7. On d 10, cells were lysed and the relative number of cells was measured with the fluorescent DNA binding dye FluoReporter Blue. Each sample was performed in triplicate, and results from a representative experiment are shown. Results are expressed as relative cell number±SE (n=2). *, significant changes from vehicle (no R1881)-treated cells. B, LNCaP cells were pretreated for 1 h+/−30 mM STO-609 prior to overnight treatment+/−10 nM R1881. Cells were then dissociated and reseeded into the top chamber for a Boyden migration or Matrigel extracellular matrix invasion assay. Fresh medium with the corresponding treatments was added to the top and bottom chambers while either no chemoattractant or 5% FBS (serum) was added to the bottom chamber. After 16 h, migrated cells were fixed, stained and counted in three different microscopic fields and added together. The results are expressed as mean±SE (n=3). *, significant changes from vehicle (no R1881)-treated cells. #, significant changes from vehicle (no STO-609)-treated cells. C top, LNCaP cells were transfected with indicated siRNAs. Two days after transfection, cells were treated+/−10 nM R1881 and subjected to a Boyden migration assay as described in B. *, significant changes from vehicle-treated cells. #, significant changes from control (siLacZ)-transfected cells. C bottom, western blot to demonstrate CaMKKβ□ knockdown. Quantification of these blots is presented in FIG. 6D. D right, LNCaP cells stably expressing either GAL4 (control) or CaMKKβ were subjected to a migration assay as described in B using +/−5% FBS as chemoattractant. The results are expressed as mean+SE (n=3). *, significant changes from LNCaP-GAL4 cells. D left, western blot confirming CaMKKβ □expression. Quantification of these blots is presented in FIG. 6E.
Figure 7:
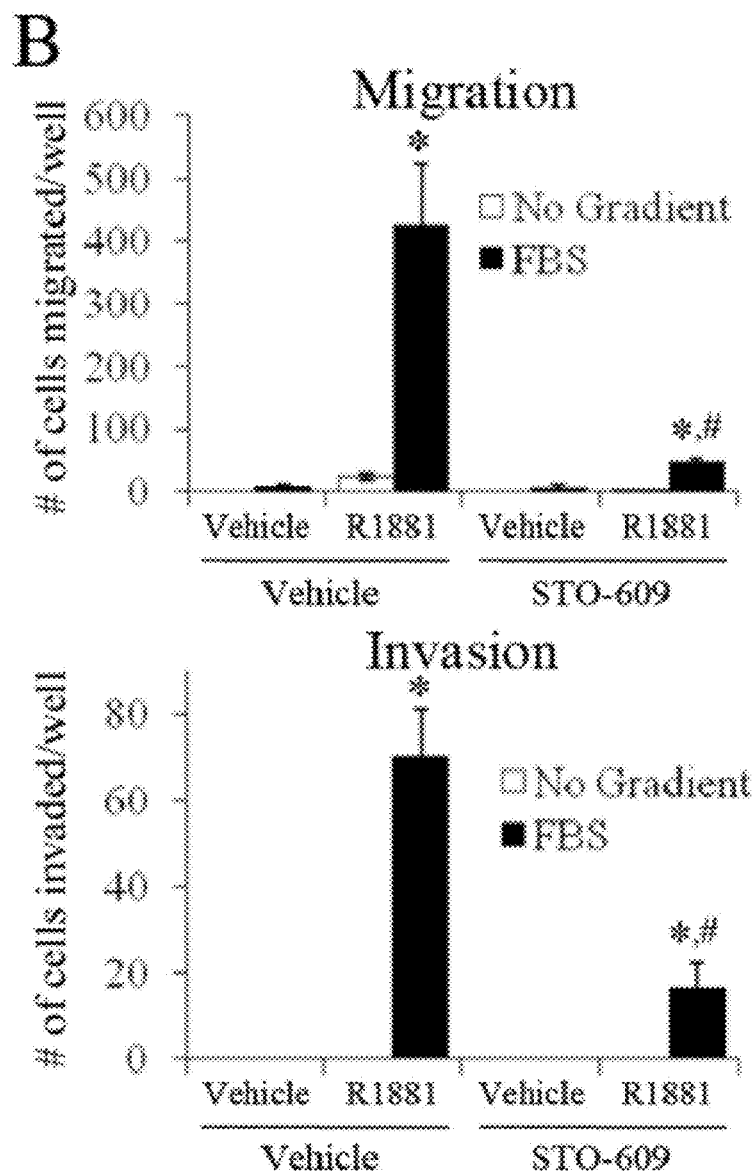
Figure 7:
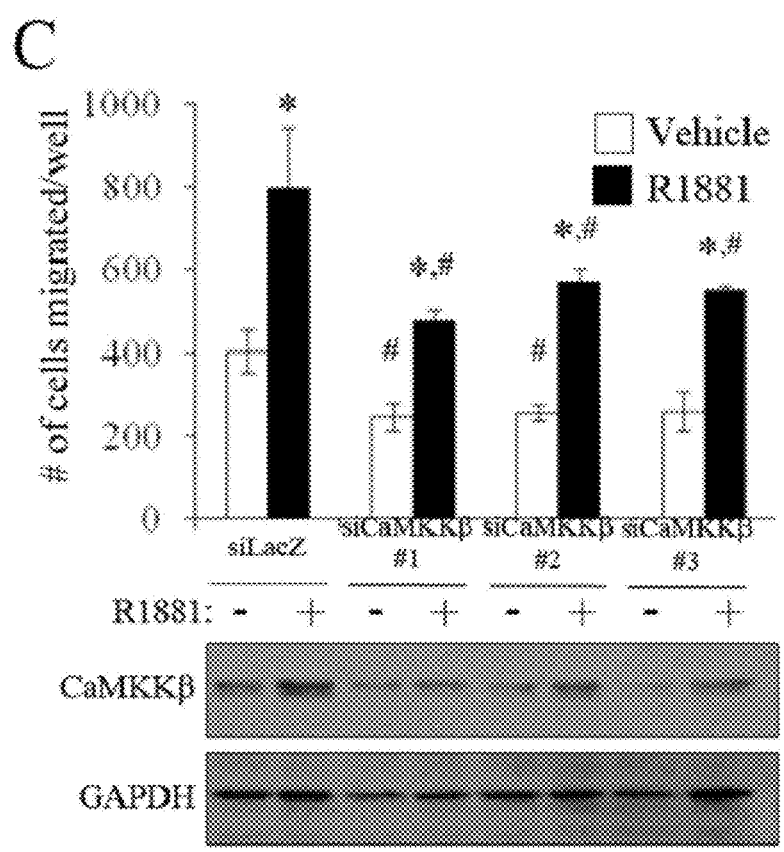
Figure 7:
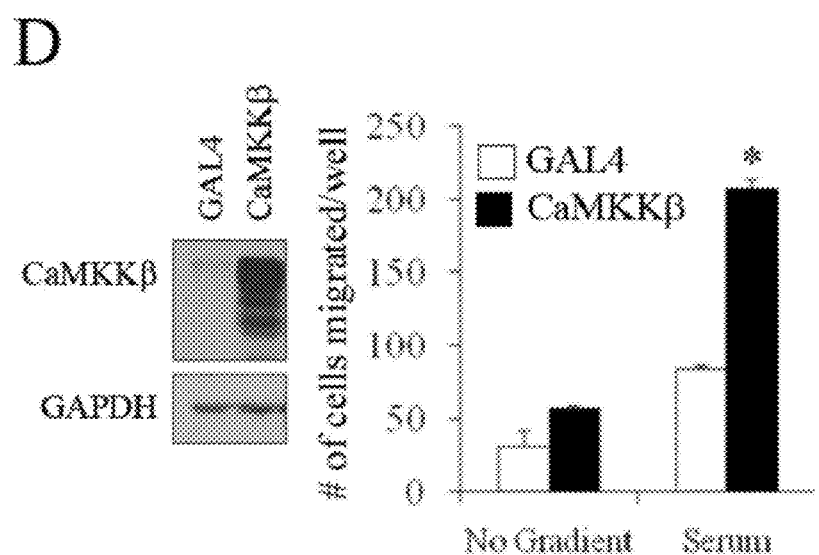

Example 3: CaMKKβ is Necessary and Sufficient for AR-Mediated Prostate Cancer Cell Migration and Invasion Given that the expression of CaMKKβ is upregulated by androgens and is elevated in prostate cancer, we next wanted to assess its potential role(s) in processes of pathological importance in this disease. As a first step, we evaluated the ability of the CaMKK antagonist STO-609 to inhibit the androgen-mediated cellular growth of prostate cancer cells. However, at a concentration that suppressed CaMKKβ activity (FIG. 6A), this drug had no significant effect on LNCaP and VCaP cell number over the seven-day period of this assay (FIG. 7A and FIG. 6B).

In addition to proliferation, androgens increase the migration of prostate cancer cells (4, 20). Since CaMKKβ has recently been implicated in cell migration during neuronal development (21, 22), we next asked whether CaMKKβ is involved with AR-meditated prostate cancer cell migration and/or invasion. Using Boyden dual chamber migration assays, treatment with the CaMKK antagonist STO-609 blocked the androgen-mediated migration of both LNCaP (FIG. 7B, top) and VCaP prostate cancer cells (FIG. 6C). STO-609 also inhibited androgen-mediated invasion of LNCaP cells through a Matrigel extracellular matrix (FIG. 7B, bottom). Furthermore, knockdown of CaMKKβ suppressed, while its overexpression increased, both basal and androgen-stimulated cell migration (FIG. 7C, FIG. 7D, FIG. 6D, and FIG. 6E). These findings highlight a heretofore-unrecognized role for CaMKKβ in prostate cancer cell migration and invasion.

Figure 8:
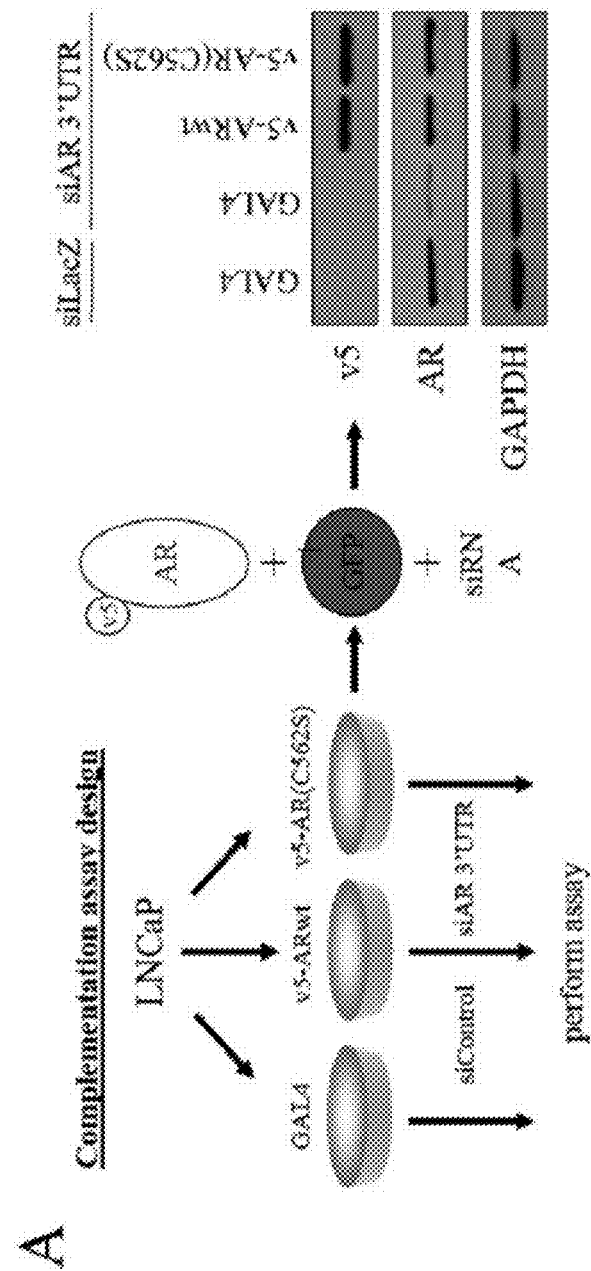
FIG. 8. Androgen mediated prostate cancer cell migration and functional AR-mediated transcription. A and B, an example of the AR replacement strategy is shown. This method has the advantage of using cells with endogenous androgen signaling as opposed to the common reintroducing of AR into AR-negative cells, which often has artificial biological consequences. Here, cells that express endogenous AR, in this case LNCaPs, were retrovirally infected to create stable cell lines expressing a control (GAL4) or a v5-tagged version of AR (wild type or a DNA-binding domain mutant (C562S)) linked to an IRES-EGFP. Cells were then selected using 2 rounds of flow cytometry. Subsequently, EGFP-positive cells were transfected with chemical siRNAs targeting either a control sequence (siLacZ) or the 3'-UTR of AR (eliminates endogenous receptor). A, a western blot characterization of the resultant cell lines is shown at the right using antibodies for v5 (recognizes only exogenous AR), AR (recognizes both exogenous and endogenous AR) or GAPDH (loading control). B, LNCaP cells used in the AR replacement experiments were also subjected to qPCR analysis using primers targeting the AR 3'UTR (monitors endogenous AR levels). The expression of AR was normalized to 36B4 levels and results are expressed as relative mRNA levels of AR compared to mock-transfected cells+SE (n=2). *, P<0.05 indicates significant changes from mock-transfected cells. C, cells were then subjected to a migration assay as described in FIG. 9. *, P<0.05 indicates significant changes from vehicle-treated cells.
Figure 8:
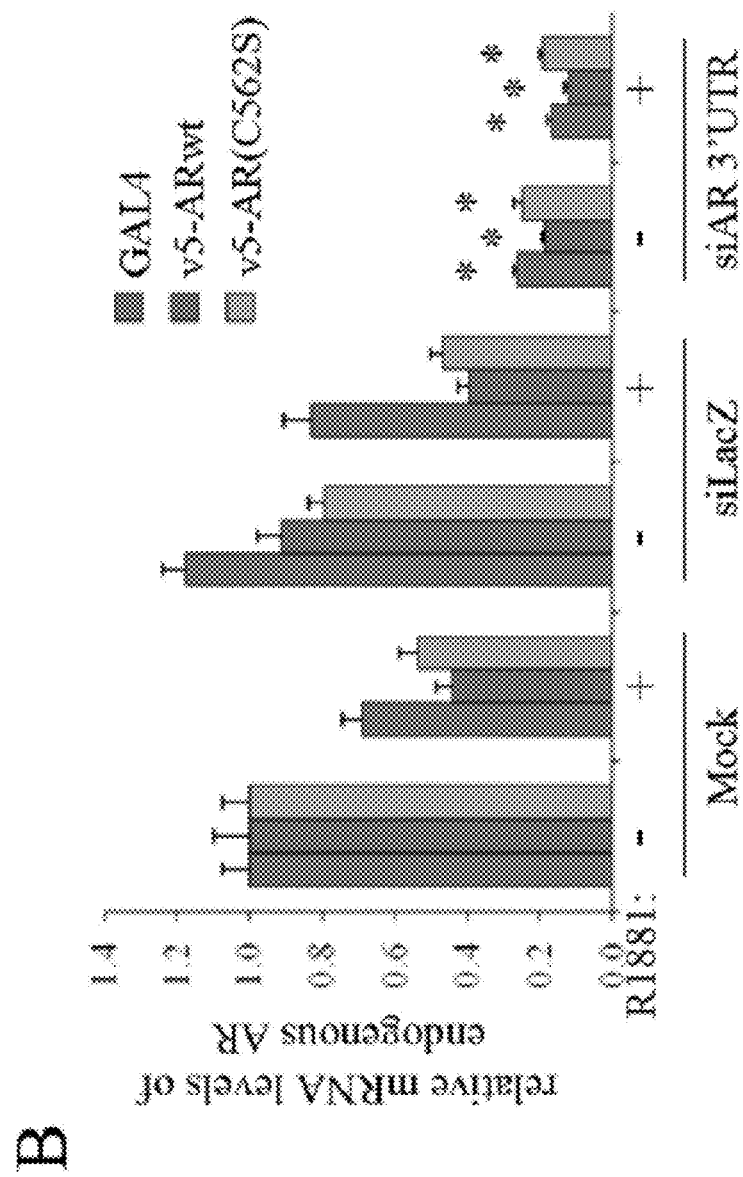
Figure 8:
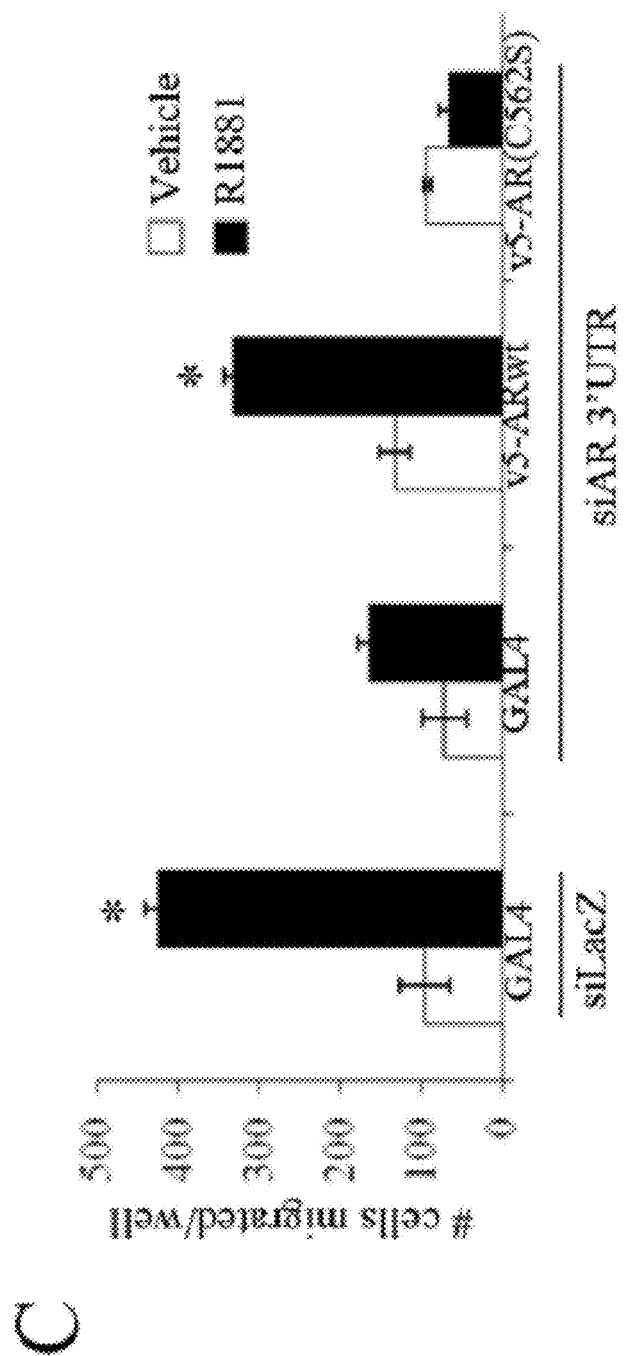
Figure 9:
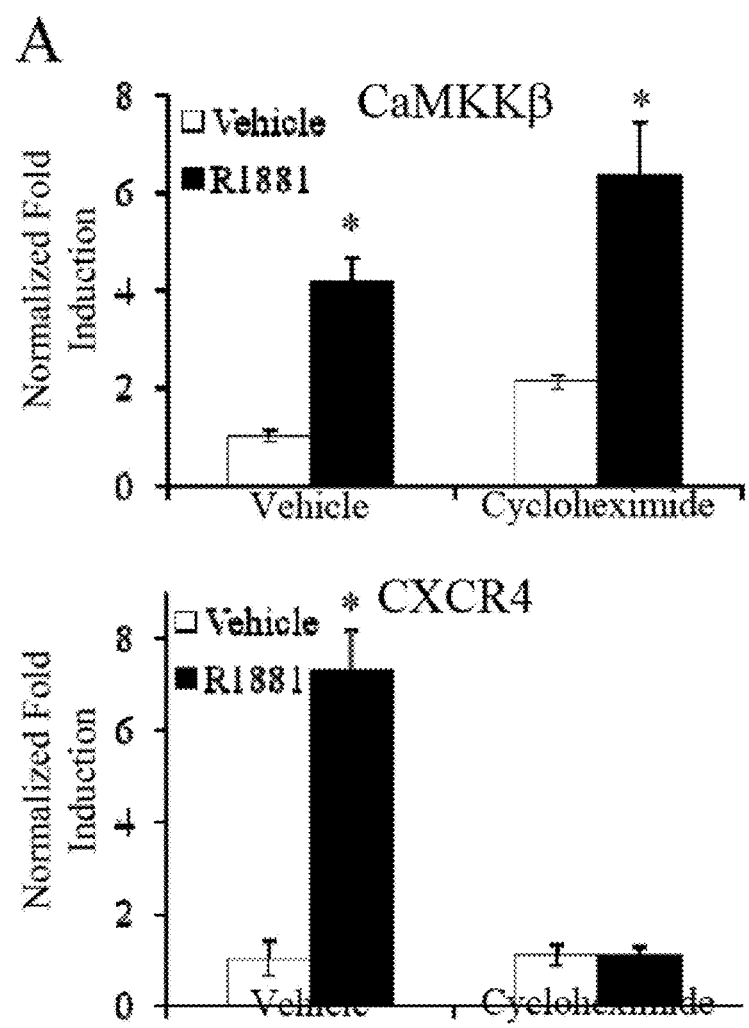
FIG. 9. Identification of the ARE that regulates CaMKKβ expression. A, LNCaP cells were pretreated for 1 h with vehicle or 1 mg/mL cycloheximide followed by vehicle or 10 nM R1881 for 24 h. CaMKKβ or CXCR4 mRNA levels were quantified using qPCR. Results are expressed as fold induction over vehicle (no R1881)-treated cells±SE (n=3). *, significant changes from vehicle-treated cells. B, LNCaP cells were treated with vehicle (V) or 10 nM R1881 for 1 or 4 h. Cross-linked chromatin was immunoprecipitated with indicated antibodies. The precipitated DNA was amplified using primers spanning a region identified using ChIP on Chip data as a potential AR-binding site (indicated in top schematic) or a distal upstream region (negative control). The results are presented as percent input±SE (n=3). *, significant changes from IgG controls. C, various enhancer luciferase reporter constructs (depicted in top model) were transfected into LNCaP cells and treated overnight+/−10 nM R1881. After treatment, cells were harvested and assayed for luciferase activity. Luciferase values were normalized to β-galactosidase control. Data are the mean relative light units (RLUs)+SEM for one representative experiment performed in triplicate (n=3). *, significant changes from vehicle-treated cells. D, CaMKKβ promoter constructs (depicted in top model) were transfected into LNCaP cells and then treated overnight with vehicle or 10 nM R1881. After treatment, cells were harvested and assayed for luciferase activity as in C. Emp Vec, empty vector.
Figure 9:
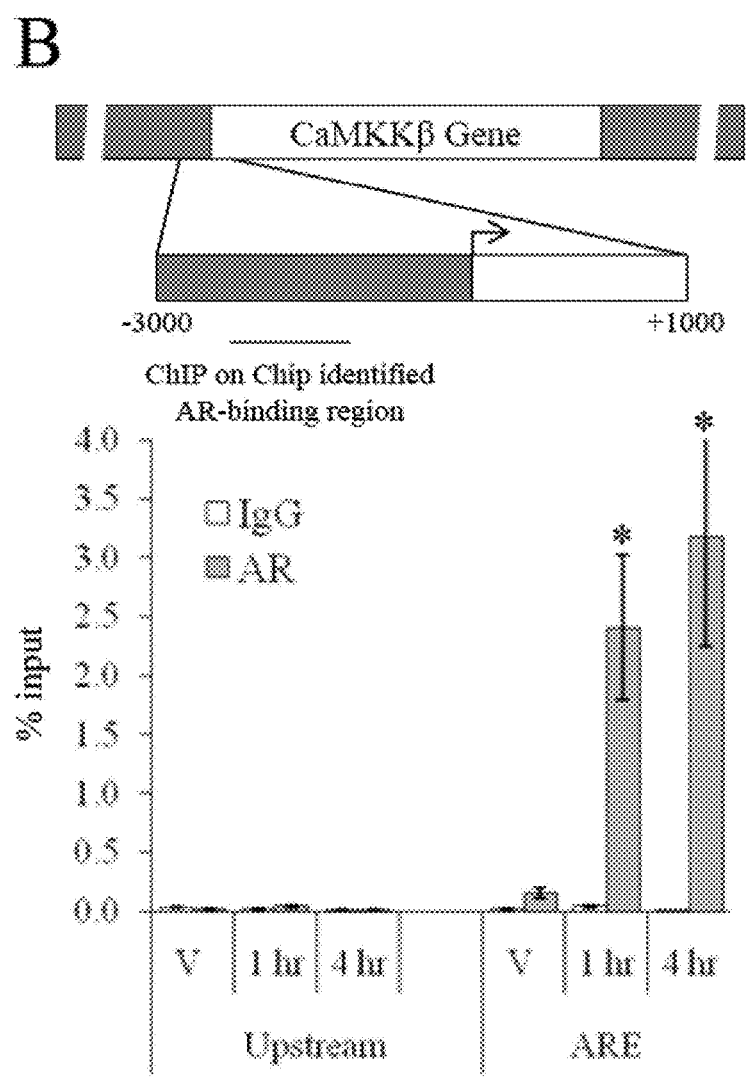
Figure 9:
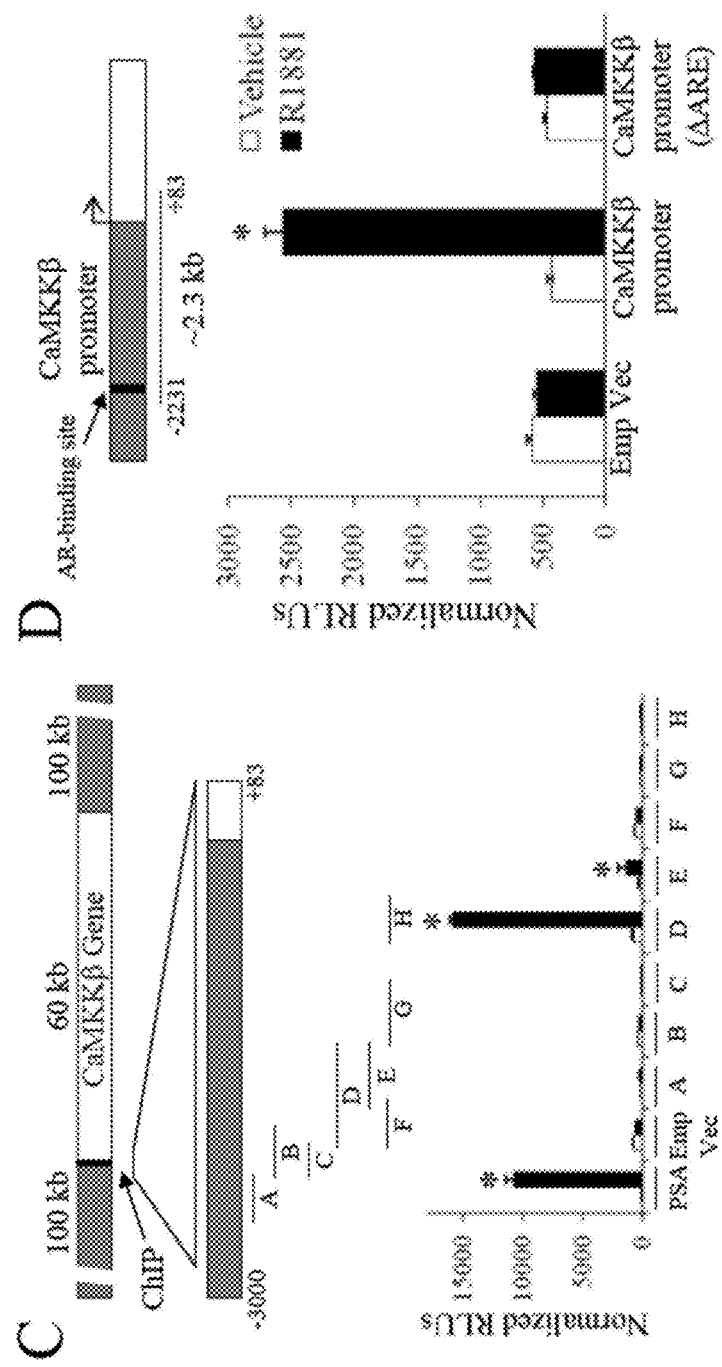

Example 4: Definition of the Molecular Mechanism for AR-Mediated CaMKKβ mRNA Expression Using a knockdown/replacement strategy, it was demonstrated that expression of wild-type AR, but not a transcriptionally inactive DNA binding mutant (C562S), was able to complement the knockdown of endogenously expressed AR in an LNCaP cell migration assay (FIG. 8). Further, at a concentration that inhibits the expression of secondary androgen target genes (ex. CXCR4 (4)), cycloheximide treatment did not block the R1881-mediated increase in CaMKKβ mRNA levels (FIG. 9A). Together, these data indicate that CaMKKβ is a primary AR target gene.

Figure 10:
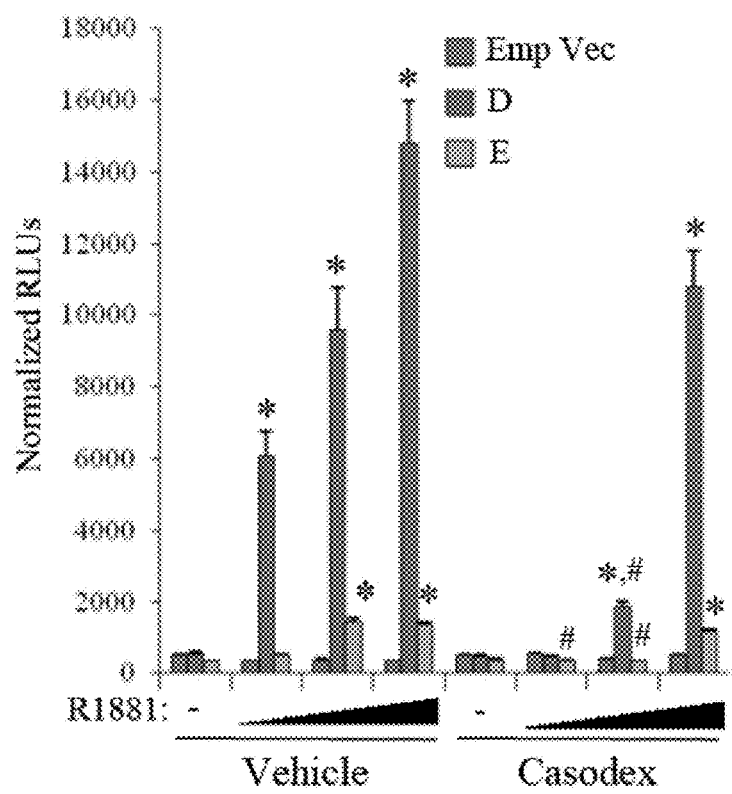
FIG. 10. Identification of the ARE that regulates CaMKKβ expression. A, two CaMKKβ enhancer (fragments D and E from FIG. 9C) luciferase reporter constructs were transfected into LNCaP cells and then pretreated for 30 minutes with vehicle or 10 mM Casodex followed by treatment overnight with vehicle or various concentrations of R1881 (0, 0.1, 1 and 10 nM). After treatment, cells were harvested and assayed for luciferase activity. Luciferase values were normalized to β-galactosidase control. Data are the mean relative light units (RLUs)+SEM for one representative experiment performed in triplicate (n=3). *, P<0.05 indicates significant changes from vehicle (no R1881)-treated cells. #P<0.05 indicates significant changes from vehicle (no Casodex)-treated cells. B, VCaP cells were transfected, treated and assayed for luciferase activity as in A using the PSA enhancer and CaMKKβ enhancer fragments D and E. C, CaMKKβ enhancer deletion constructs were transfected into LNCaP cells and then treated and assayed for luciferase activity as in A (n=2). Emp Vec, empty vector.
Figure 10:
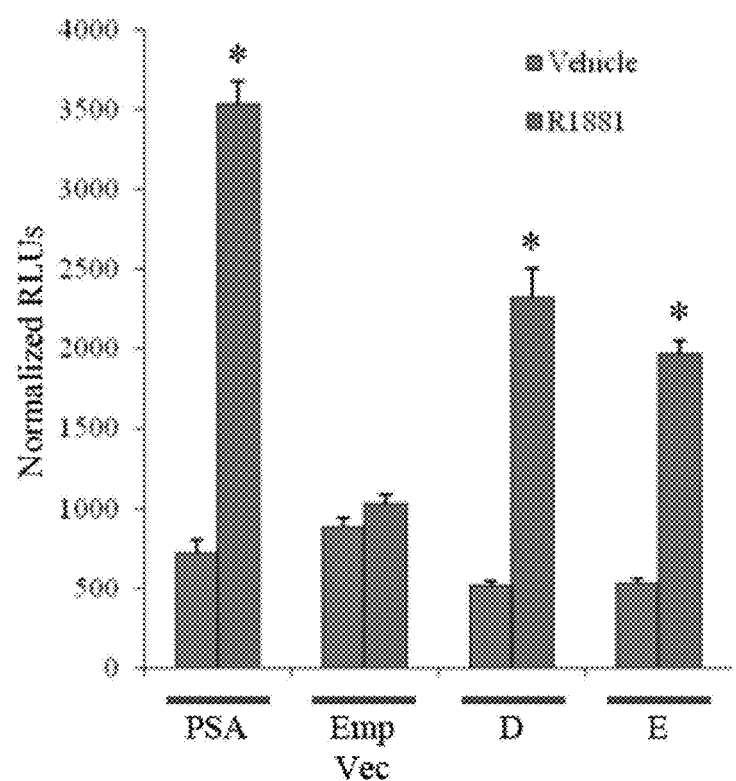
Figure 10:
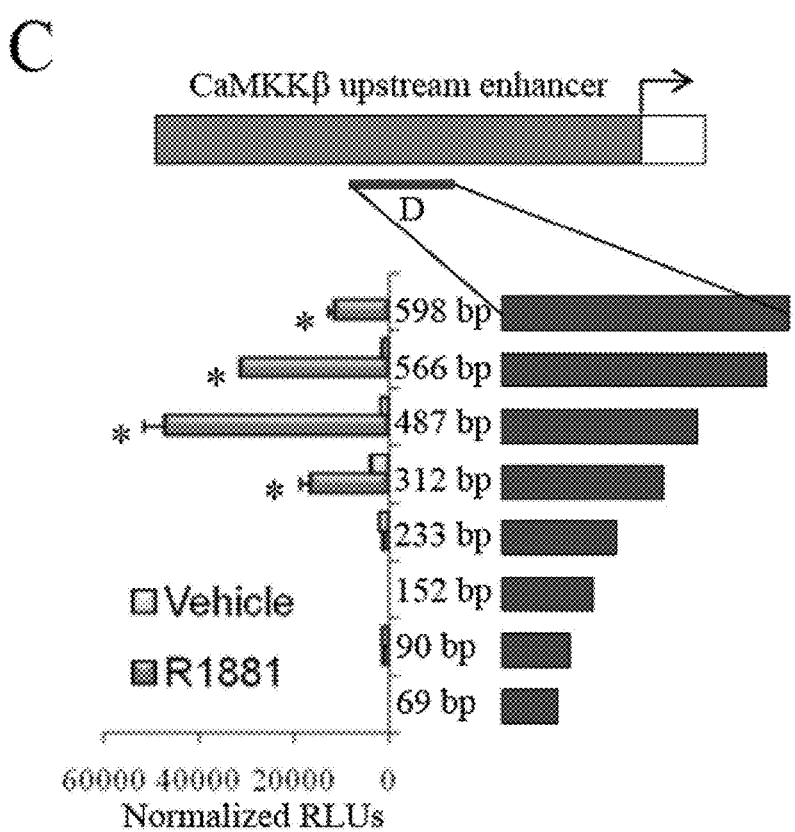

By mining our previously published ChIP on Chip data (23), we identified a putative AR binding region located ~2.3 kb upstream of the CaMKKβ transcriptional start site (FIG. 9B, top). No other AR binding was detected within the CaMKKβ gene or within 100 kb in either direction of the gene. The validity of this AR-binding site was confirmed using ChIP assays, which showed that AR was recruited to this region of the promoter within one hour following R1881 treatment (FIG. 9B, bottom). Given these data, we focused on characterizing the functionality of the putative ARE identified. To this end, we cloned overlapping regions of CaMKKβ's 5' upstream region and tested their ability to confer androgen responsiveness to an enhancerless luciferase reporter gene. In this manner, we determined that a construct incorporating a fragment, −2231 to −1632 (D), and an overlapping fragment, −2019 to −1632 (E), contained an AR-dependent enhancer (FIG. 9C). Both fragments D and E demonstrated androgen responsiveness in a dose-dependent manner that was suppressed by the antiandrogen Casodex (FIG. 10A). Similar results were obtained in VCaP cells (FIG. 10B). Deletion analysis further narrowed down the androgen-responsive region to a 79 bp stretch of DNA that included a sequence, GTAACAtgaTGTAAA, that resembled the consensus androgen response element (ARE) AGAA-CAnnnTGTTCT (FIG. 10C). Deletion of the 15 bp ARE in the full-length CaMKKβ promoter construct (−2231 to +83) completely abolished the androgen responsiveness (FIG. 9D). Thus, in the context of prostate cancer cells, CaMKKβ is a direct target of AR.

Figure 11:
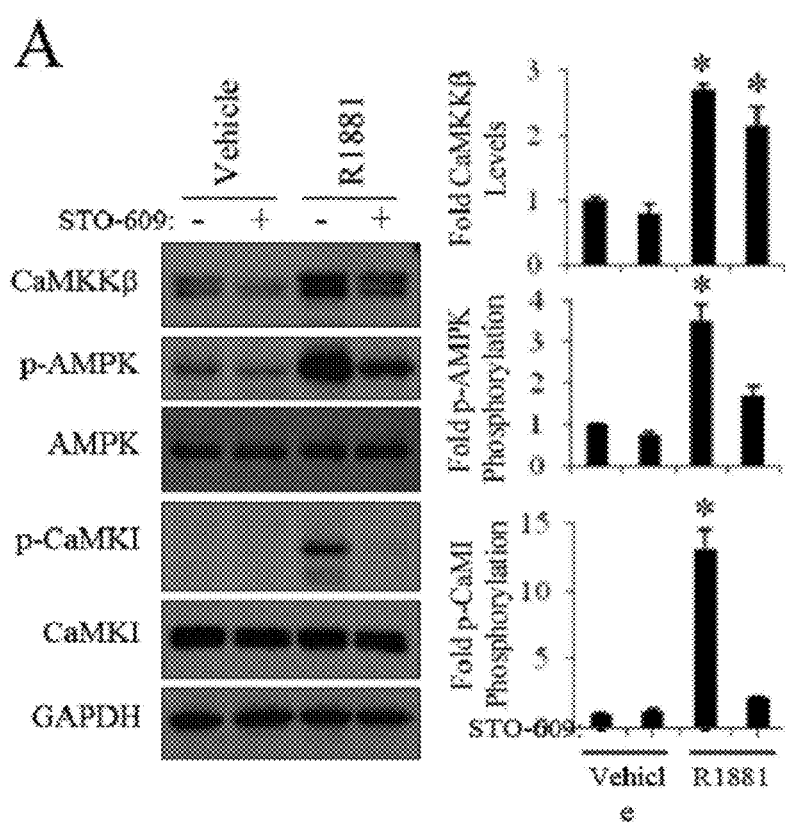
FIG. 11. Androgen-mediated migration occurs through a CaMKKβ-AMPK-dependent pathway. A, LNCaP cells were pretreated for 1 h+/−30 mM STO-609 prior to overnight treatment+/−10 nM R1881. Cell lysates were then subjected to western blot analysis and subsequent densitometry (right). CaMKKβ levels were normalized to GAPDH. Phospho-CaMKI (p-CaMKI) levels were normalized to total CaMKI. Phospho-AMPK (p-AMPK) levels were normalized to total AMPK. Results are expressed as fold induction/phosphorylation over double vehicle-treated cells+SE (n=3). *, significant changes from vehicle-treated cells. B, LNCaP cells stably expressing either GAL4 or CaMKKβ □were treated overnight+/−10 nM R1881. Cell lysates were then subjected as in A to western blot analysis and densitometry (right). Results are expressed as fold induction/phosphorylation over LNCaP-GAL4 vehicle-treated cells+SE (n=3). *, significant changes from LNCaP-GAL4 vehicle-treated cells. C and D, LNCaP cells were transfected with indicated siRNAs, treated and subjected to a migration assay (top) or western blot analysis (bottom) as in FIG. 7C. *, significant changes from control (siLacZ)-transfected cells. Quantification of the blots is presented in FIG. 12.
Figure 11:
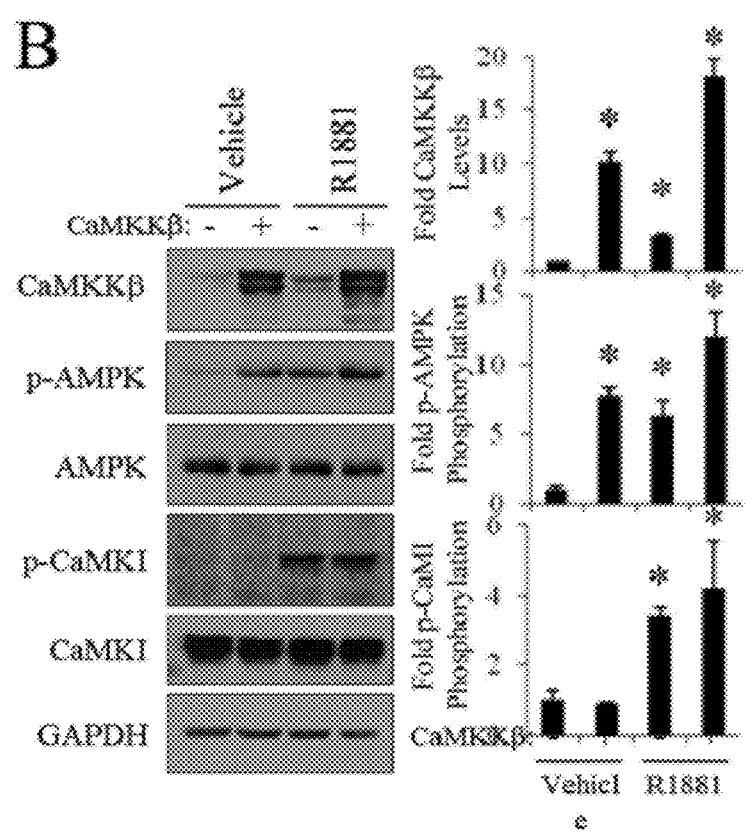
Figure 11:
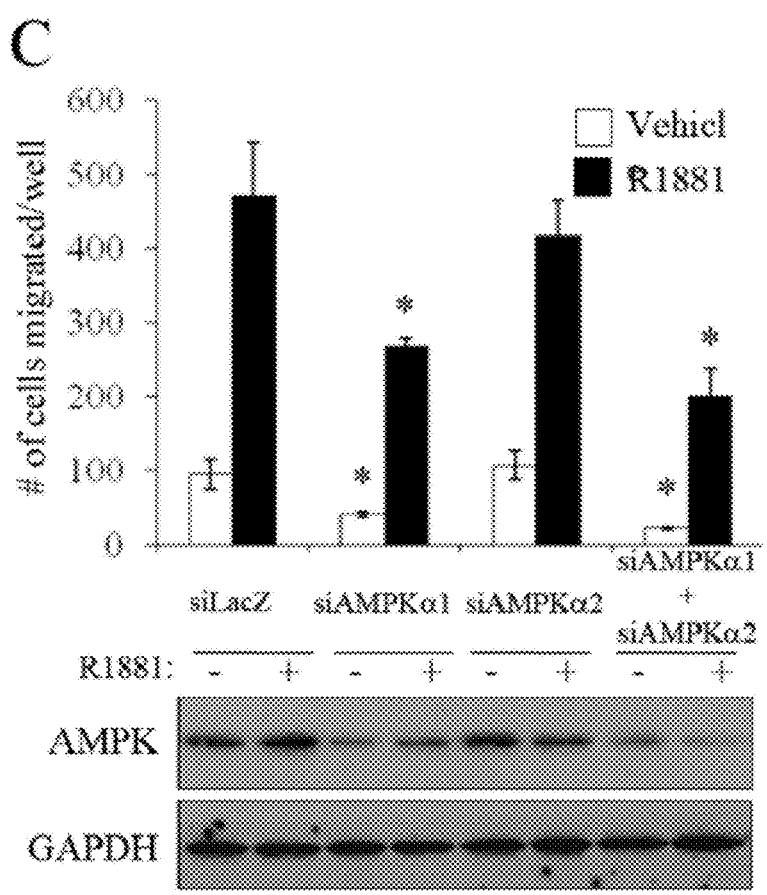
Figure 11:
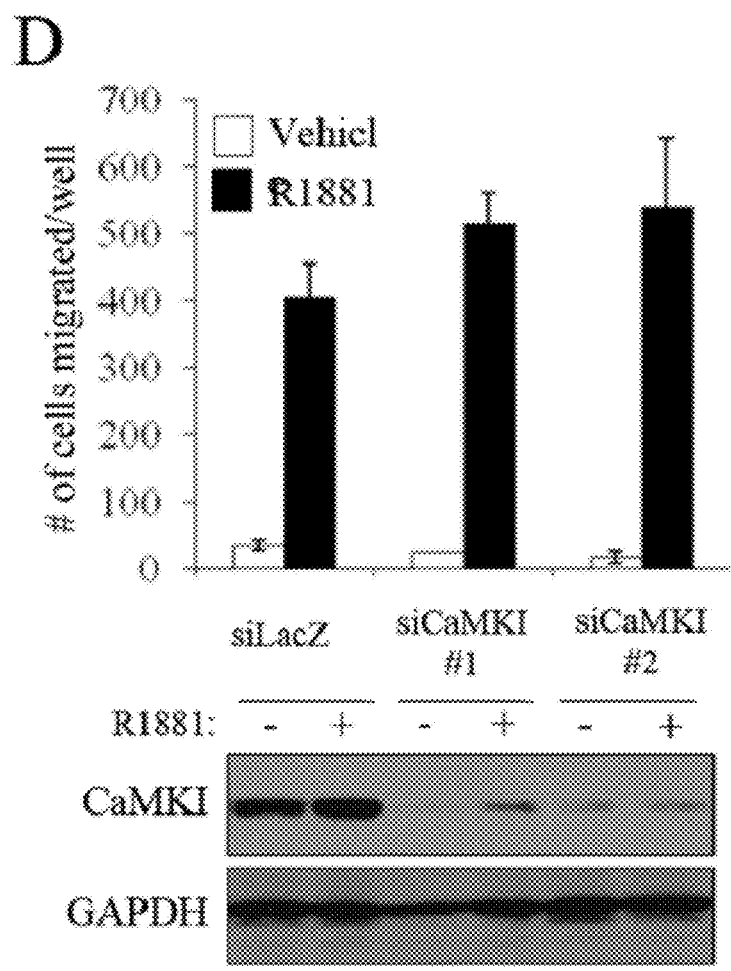
Figure 12:
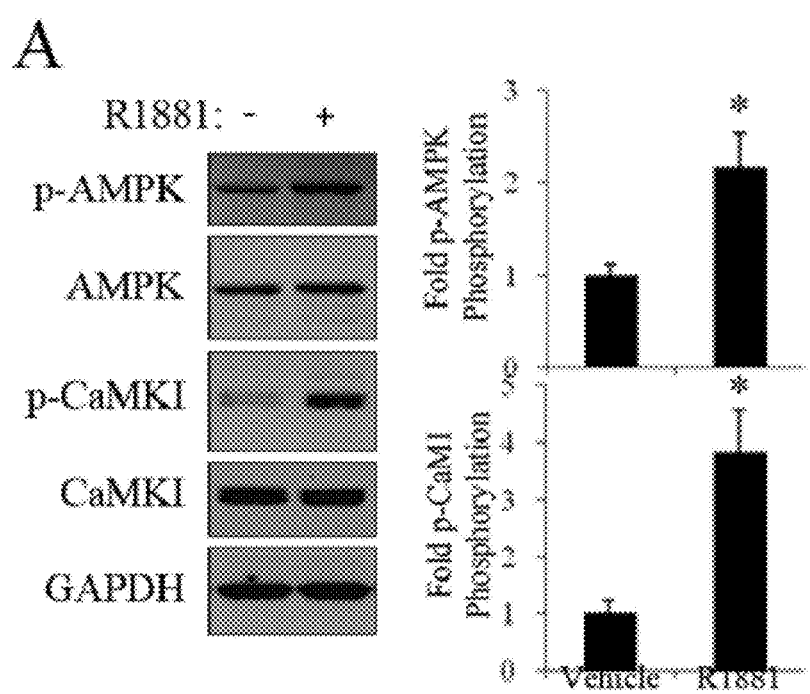
FIG. 12. Androgen-mediated migration occurs through a CaMKKβ-AMPK-dependent pathway. A, VCaP cells were treated for 24 h+/−10 nM R1881. Cell lysates were then subjected to western blot analysis and subsequent densitometry (right). Phospho-CaMKI (p-CaMKI) levels were normalized to total CaMKI. Phospho-AMPK (p-AMPK) levels were normalized to total AMPK. Results are expressed as fold induction/phosphorylation over vehicle-treated cells+SE (n=2). *, P<0.05 indicates significant changes from vehicle-treated cells. B, selection of optimal AMPKα1 and α2 siRNAs. LNCaP cells were transfected as described in FIG. 11 with mock or Stealth siRNAs targeting LacZ (negative control) or AMPKα1 or α2. The expression of AMPK was assessed using qPCR and normalized to 36B4 levels. Results are expressed as fold induction over mock-transfected cells+SE (n=2). *, P<0.05 indicates significant changes from mock-transfected cells. C and D, densitometry results for western blots in FIG. 11C and FIG. 11D, respectively. For AMPKa knockdown (C), siAMPKα1-#1 and siAMPKα2-#1 from B were selected since they produced the greatest knockdowns. *, P<0.05 indicates significant changes from control (siLacZ)-transfected cells.
Figure 12:
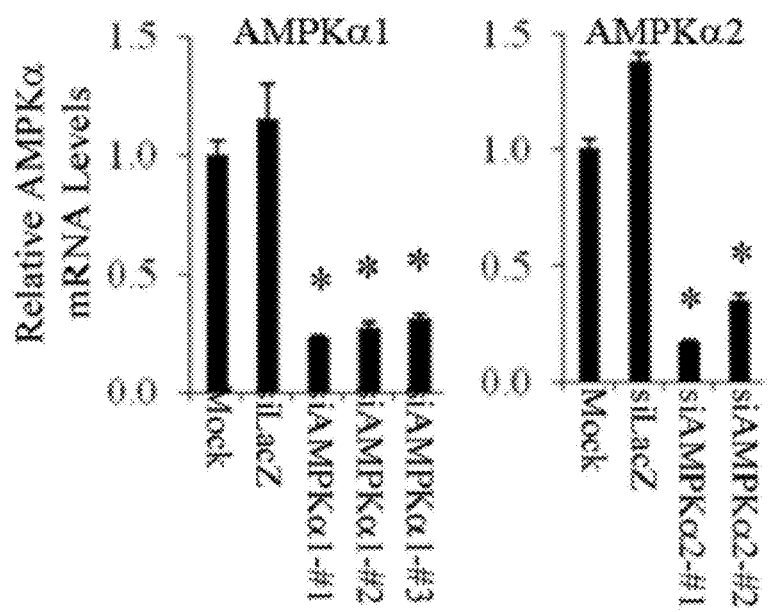
Figure 12:
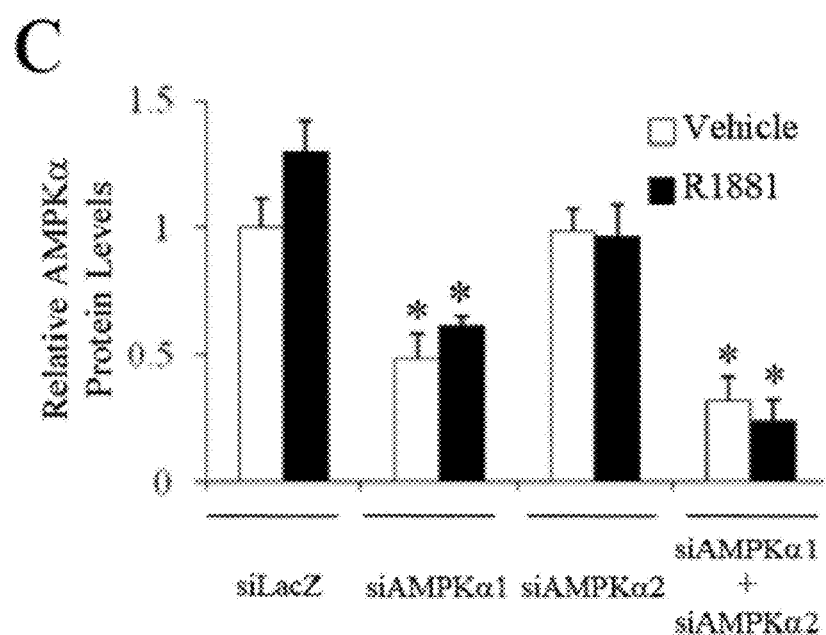
Figure 12:
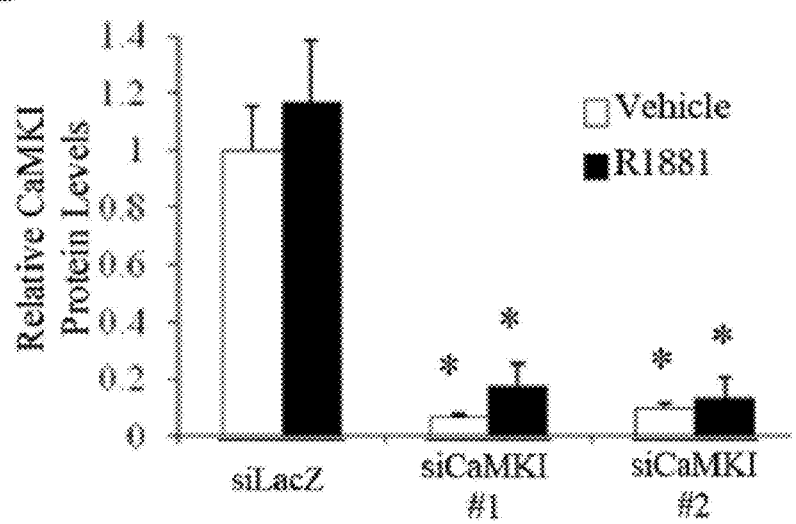
Figure 13:
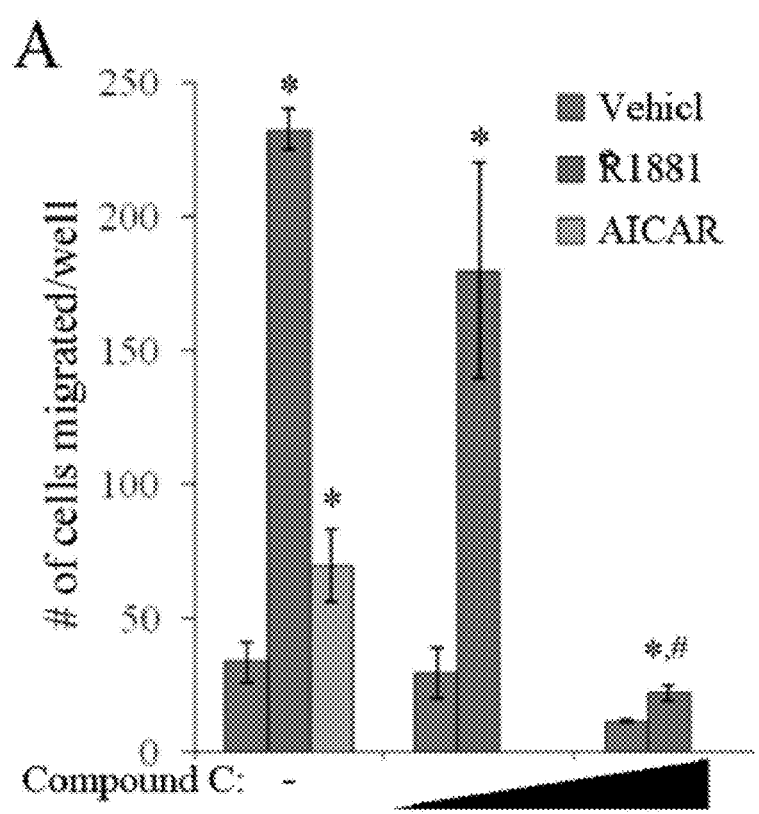
FIG. 13. AMPK and androgen-mediated prostate cancer cell migration. A, LNCaP cells were pretreated for 1 h with vehicle or increasing concentrations of compound C (10 or 40 mM) prior to overnight treatment+/−10 nM R1881 or 1 mM AICAR. Cells were then subjected to a migration assay as described in FIG. 7. The results are expressed as mean±SE (n=2). *, P<0.05 indicates significant changes from double vehicle-treated cells. #, P<0.05 indicates significant decreases from vehicle (no compound C)-treated cells. B, LNCaP cells were pretreated for 1 h with vehicle, 1, 10 or 40 mM compound C prior to overnight treatment+/−10 nM R1881. Cell lysates were then subjected to western blot analysis and subsequent densitometry (top). ACC is a direct target of AMPK and thus, was used as a readout of AMPK catalytic activity. Phospho-ACC (p-ACC) levels were normalized to total ACC. Results are expressed as fold induction/phosphorylation over double vehicle-treated cells+SE (n=2). *, P<0.05 indicates significant changes from double vehicle-treated cells. C, LNCaP cells were treated overnight+/−1 mM AICAR and then subjected to western blot analysis and densitometry (top) as in B. Phospho-AMPK (p-AMPK) levels were normalized to total AMPK. *, P<0.05 indicates significant changes from vehicle-treated cells.
Figure 13:
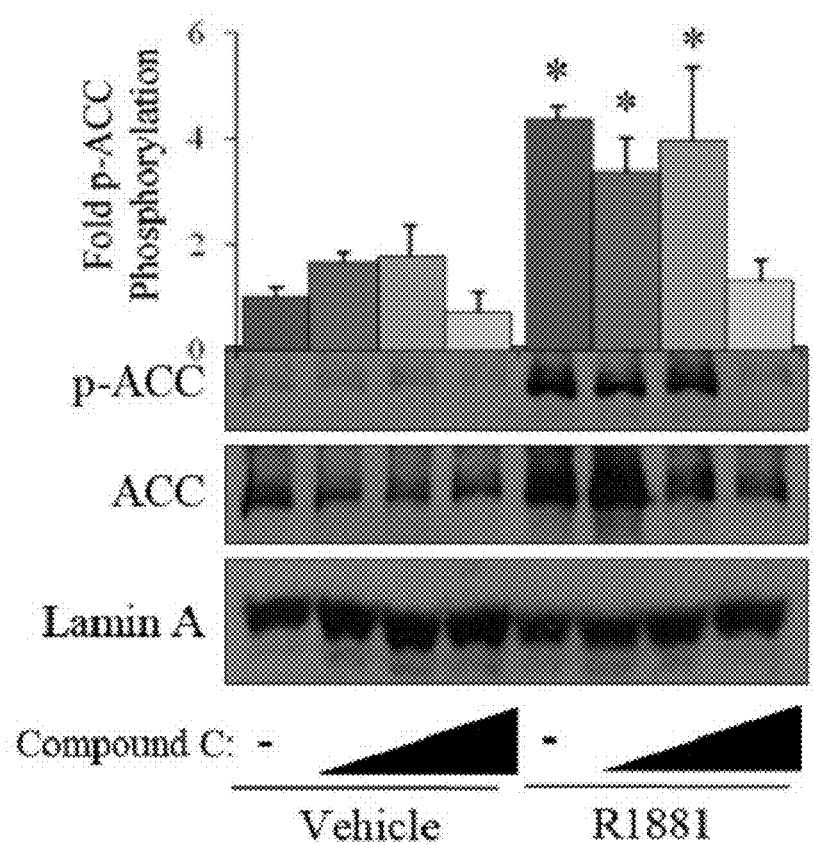
Figure 13:
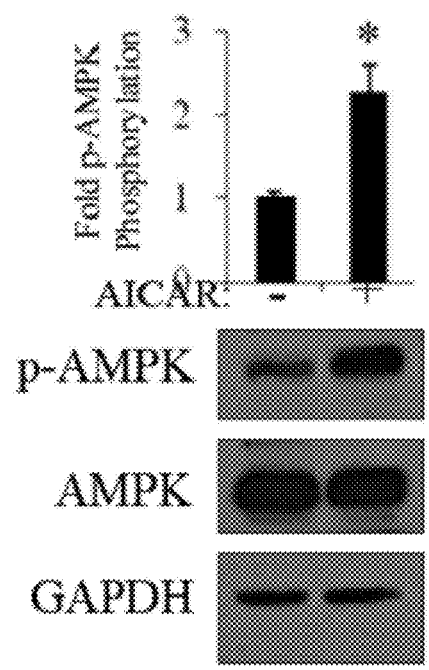

Example 5: Androgens Promote Prostate Cancer Cell Migration Through an AR-CaMKKβ-AMPK Signaling Axis CaMKI, CaMKIV and, more recently, AMPK have been shown to be downstream targets of CaMKKβ (24). Since CaMKIV is not expressed in the prostate (data not shown), we tested whether AR-CaMKKβ signaling led to increased CaMKI and/or AMPK signaling. Western blot analysis revealed that androgens increased the phosphorylation of both CaMKI and AMPK at their CaMKKβ activation loop target sites (T177 and T172 respectively) in both LNCaP and VCaP cells, an effect that was reversed by pretreatment with STO-609 (FIG. 11A and FIG. 12A). Interestingly, we found that overexpression of CaMKKβ alone was sufficient to increase the phosphorylation/activity of AMPK, but not CaMKI (FIG. 11B). These findings indicated that AMPK, rather than CaMKI, could be regulating cell migration because CaMKKβ overexpression alone was also sufficient to increase migration (FIG. 7D). To verify this, we used our most efficacious siRNAs (FIG. 12B) to knockdown both isoforms of the catalytic subunit of AMPK (FIG. 11C, bottom and FIG. 12C) or CaMKI (FIG. 11D, bottom and FIG. 12D). In this manner, it was demonstrated that loss of AMPK, but not CaMKI, resulted in decreased prostate cancer cell migration (FIG. 11C and FIG. 11D). In support of these findings, cotreatment of cells with the AMPK antagonist compound C, at a concentration that inhibited its kinase activity, completely abolished androgen-mediated cell migration (FIG. 13A and FIG. 13B). Conversely, treatment of LNCaP cells with the AMP mimetic AICAR alone was sufficient to increase cell migration (FIG. 13A and FIG. 13C). These data highlight a central role for AMPK in prostate cancer cell migration. Definition of the mechanism(s) by which AMPK interfaces with the cellular processes responsible for migration and invasion is currently under investigation.

REFERENCES

The following references are incorporated herein by reference in their entireties.

1. Cancer Facts and Figures: American Cancer Society; 2007.
2. Isaacs J T, Isaacs W B. Androgen receptor outwits prostate cancer drugs. Nat Med 2004; 10: 26-7.
3. Chen C D, Welsbie D S, Tran C, et al. Molecular determinants of resistance to antiandrogen therapy. Nature Med 2004; 10: 33-9.
4. Frigo D E, Sherk A B, Wittmann B M, et al. Induction of Kruppel-like factor 5 expression by androgens results in increased CXCR4-dependent migration of prostate cancer cells in vitro. Mol Endocrinol 2009.
5. Sherk A B, Frigo D E, Schnackenberg C G, et al. Development of a small molecule serum and glucocorticoid-regulated kinase 1 antagonist and its evaluation as a prostate cancer therapeutic. Cancer Res 2008; 68: 1-9.
6. Xu Y, Chen S Y, Ross K N, Balk S P. Androgens induce prostate cancer cell proliferation through mammalian target of rapamycin activation and post-transcriptional increases in cyclin D proteins. Cancer Res 2006; 66: 7783-92.
7. Migita T, Ruiz S, Fornari A, et al. Fatty acid synthase: a metabolic enzyme and candidate oncogene in prostate cancer. J Natl Cancer Inst 2009; 101: 519-32.
8. Balk S P, Knudsen K E. AR, the cell cycle, and prostate cancer. Nucl Recept Signal 2008; 6: e001.
9. Lawton C A, Winter K, Murray K, et al. Updated results of the phase III radiation therapy oncology group (RTOG) trial 85-31 evaluating the potential benefit of androgen suppression following standard radiation therapy for unfavorable prognosis carcinoma of the prostate. Int J Radiation Oncology Biol Phys 2001; 49: 937-46.
10. Bolla M, Collette L, Blank L, et al. Long-term results with immediate androgen suppression and external irradiation in patients with locally advanced prostate cancer (an EORTC study): a phase III randomised trial. The Lancet 2002; 360: 103-8.
11. Scher H I, Beer T M, Higano C S, et al. Antitumour activity of MDV3100 in castration-resistant prostate cancer: a phase 1-2 study. Lancet; 375: 1437-46.
12. Frigo D E, McDonnell D P. Differential effects of prostate cancer therapeutics on neuroendocrine transdifferentiation. Mol Cancer Ther 2008; 7: 659-69.
13. Kazmin D, Prytkova T, Cook C E, et al. Linking ligand-induced alterations in androgen receptor structure to differential gene expression: a first step in the rational design of selective androgen receptor modulators. Mol Endocrinol 2006; 20: 1201-17.
14. Lapointe J, Li C, Higgins J P, et al. Gene expression profiling identifies clinically relevant subtypes of prostate cancer. Proc Natl Acad Sci USA 2004; 101: 811-6.
15. Varambally S, Yu J, Laxman B, et al. Integrative genomic and proteomic analysis of prostate cancer reveals signatures of metastatic progression. Cancer Cell 2005; 8: 393-406.
16. Welsh J B, Sapinoso L M, Su A T, et al. Analysis of gene expression identifies candidate markers and pharmacological targets in prostate cancer. Cancer Res 2001; 61: 5974-8.
17. Yu Y P, Landsittel D, Jing L, et al. Gene expression alterations in prostate cancer predicting tumor aggression and preceding development of malignancy. J Clin Oncol 2004; 22: 2790-9.
18. Su A T, Welsh J B, Sapinoso L M, et al. Molecular classification of human carcinomas by use of gene expression signatures. Cancer Res 2001; 61: 7388-93.
19. Hsu L S, Chen G D, Lee L S, Chi C W, Cheng J F, Chen J Y. Human Ca2+/calmodulin-dependent protein kinase kinase beta gene encodes multiple isoforms that display distinct kinase activity. J Biol Chem 2001; 276: 31113-23.
20. Liao X, Thrasher J B, Pelling J, Holzbeierlein J, Sang Q X, Li B. Androgen stimulates matrix metalloproteinase-2 expression in human prostate cancer. Endocrinology 2003; 144: 1656-63.
21. Kokubo M, Nishio M, Ribar T J, Anderson K A, West A E, Means A R. BDNF-mediated cerebellar granule cell development is impaired in mice null for CaMKK2 or CaMKIV. J Neurosci 2009; 29: 8901-13.
22. Saneyoshi T, Wayman G, Fortin D, et al. Activity-dependent synaptogenesis: regulation by a CaM-kinase kinase/CaM-kinase I/betaPIX signaling complex. Neuron 2008; 57: 94-107.
23. Wang Q, Li W, Zhang Y, et al. Androgen receptor regulates a distinct transcription program in androgen-independent prostate cancer. Cell 2009; 138: 245-56.
24. Means A R. The Year in Basic Science: calmodulin kinase cascades. Mol Endocrinol 2008; 22: 2759-65.
25. Attar R M, Takimoto C H, Gottardis M M. Castration-resistant prostate cancer: locking up the molecular escape routes. Clin Cancer Res 2009; 15: 3251-5.
26. Wayman G A, Lee Y S, Tokumitsu H, Silva A, Soderling T R. Calmodulin-kinases: modulators of neuronal development and plasticity. Neuron 2008; 59: 914-31.
27. Hawley S A, Pan D A, Mustard K J, et al. Calmodulin-dependent protein kinase kinase-beta is an alternative upstream kinase for AMP-activated protein kinase. Cell Metab 2005; 2: 9-19.
28. Woods A, Dickerson K, Heath R, et al. Ca2+/calmodulin-dependent protein kinase kinase-beta acts upstream of AMP-activated protein kinase in mammalian cells. Cell Metab 2005; 2: 21-33.
29. Hurley R L, Anderson K A, Franzone J M, Kemp B E, Means A R, Witters L A. The Ca2+/calmodulin-dependent protein kinase kinases are AMP-activated protein kinase kinases. J Biol Chem 2005; 280: 29060-6.
30. Salt I, Celler J W, Hawley S A, et al. AMP-activated protein kinase: greater AMP dependence, and preferential nuclear localization, of complexes containing the alpha2 isoform. Biochem J 1998; 334 (Pt 1): 177-87.
31. Berglund L, Bjorling E, Oksvold P, et al. A genecentric Human Protein Atlas for expression profiles based on antibodies. Mol Cell Proteomics 2008; 7: 2019-27.
32. Park H U, Suy S, Danner M, et al. AMP-activated protein kinase promotes human prostate cancer cell growth and survival. Mol Cancer Ther 2009; 8: 733-41.
33. Zhou J, Huang W, Tao R, et al. Inactivation of AMPK alters gene expression and promotes growth of prostate cancer cells. Oncogene 2009; 28: 1993-2002.
34. Ben Sahra I, Laurent K, Loubat A, et al. The antidiabetic drug metformin exerts an antitumoral effect in vitro and in vivo through a decrease of cyclin D1 level. Oncogene 2008; 27: 3576-86.

35. Xiang X, Saha A K, Wen R, Ruderman N B, Luo Z. AMP-activated protein kinase activators can inhibit the growth of prostate cancer cells by multiple mechanisms. Biochem Biophys Res Commun 2004; 321: 161-7.
36. Nagata D, Mogi M, Walsh K. AMP-activated protein kinase (AMPK) signaling in endothelial cells is essential for angiogenesis in response to hypoxic stress. J Biol Chem 2003; 278: 31000-6.
37. Levine Y C, Li G K, Michel T. Agonist-modulated regulation of AMP-activated protein kinase (AMPK) in endothelial cells. Evidence for an AMPK→Rac1→Akt→endothelial nitric-oxide synthase pathway. J Biol Chem 2007; 282: 20351-64.
38. Kou R, Sartoretto J, Michel T. Regulation of Rac1 by simvastatin in endothelial cells: differential roles of AMP-activated protein kinase and calmodulin-dependent kinase kinase-beta. J Biol Chem 2009; 284: 14734-43.
39. Jaffe A B, Hall A. Rho GTPases: biochemistry and biology. Annu Rev Cell Dev Biol 2005; 21: 247-69.
40. Knight-Krajewski S, Welsh C F, Liu Y, et al. Deregulation of the Rho GTPase, Rac1, suppresses cyclin-dependent kinase inhibitor p21(CIP1) levels in androgen-independent human prostate cancer cells. Oncogene 2004; 23: 5513-22.
41. Kobayashi T, Inoue T, Shimizu Y, et al. Activation of Rac1 is closely related to androgen-independent cell proliferation of prostate cancer cells both in vitro and in vivo. Mol Endocrinol 2010; 24: 722-34.
42. Butler L M, Wong A S, Koh W P, Wang R, Yuan J M, Yu M C. Calcium intake increases risk of prostate cancer among Singapore Chinese. Cancer Res 2010; 70: 4941-8.
43. Yang S, Zhang J J, Huang X Y. Orai1 and STIM1 are critical for breast tumor cell migration and metastasis. Cancer Cell 2009; 15: 124-34.
44. Monet M, Lehen'kyi V, Gackiere F, et al. Role of cationic channel TRPV2 in promoting prostate cancer migration and progression to androgen resistance. Cancer Res 2010; 70: 1225-35.
45. Kampa M, Papakonstanti E A, Alexaki V I, Hatzoglou A, Stournaras C, Castanas E. The opioid agonist ethylketocyclazocine reverts the rapid, non-genomic effects of membrane testosterone receptors in the human prostate LNCaP cell line. Exp Cell Res 2004; 294: 434-45.
46. Papakonstanti E A, Kampa M, Castanas E, Stournaras C. A rapid, nongenomic, signaling pathway regulates the actin reorganization induced by activation of membrane testosterone receptors. Mol Endocrinol 2003; 17: 870-81.
47. Wang Q, Li W, Liu X S, et al. A hierarchical network of transcription factors governs androgen receptor-dependent prostate cancer growth. Mol Cell 2007; 27: 380-92.

We claim:

1. A method of decreasing prostate cancer cell migration and invasion in a subject, the method comprising:
administering to the subject an effective amount of a compound that inhibits activity of at least one of CaMKKβ, CaMKKβ splice variant 2, and CaMKKβ splice variant 7, wherein the compound is according to Formula III:

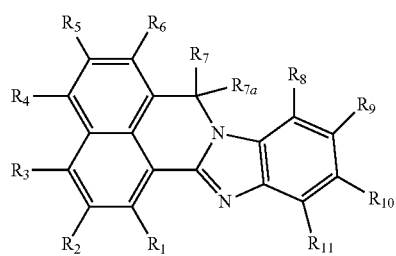

Formula III wherein $R_1$, $R_2$, $R_3$, $R_4$, $R_5$, $R_6$, $R_7$, $R_{7a}$, $R_8$, $R_9$, $R_{10}$, and $R_{11}$ are each independently selected from the group consisting of H, alkyl, alkenyl, alkynyl, cycloalkyl, cycloalkylalkyl, cycloalkylalkenyl, cycloalkylalkynyl, heterocyclo, heterocycloalkyl, heterocycloalkenyl, heterocycloalkynyl, aryl, arylalkyl, arylalkenyl, arylalkynyl, heteroaryl, heteroarylalkyl, heteroarylalkenyl, heteroarylalkynyl, alkoxy, halo, mercapto, azido, cyano, formyl, carboxylic acid, hydroxyl, nitro, acyl, aryloxy, alkylthio, amino, alkylamino, arylalkylamino, disubstituted amino, acylamino, acyloxy, ester, amide, sulfoxyl, sulfonyl, sulfonate, sulfonic acid, sulfonamide, urea, alkoxylacylamino, and aminoacyloxy; or a pharmaceutically acceptable salt or prodrug thereof.

2. The method of claim 1, wherein the compound inhibits the kinase activity of at least one of CaMKKβ, CaMKKβ splice variant 2, and CaMKKβ splice variant 7.

3. The method of claim 1, wherein the method decreases the activity of CaMKKβ and decreases the phosphorylation of AMPK.

4. The method of claim 1, wherein the compound inhibits the activity of CaMKKβ splice variant 2 or CaMKKβ splice variant 7.

5. The method of claim 1, wherein the compound specifically binds to CaMKKβ splice variant 2 or CaMKKβ splice variant 7.

6. The method of claim 1, wherein the compound is STO-609.

7. The method of claim 1, wherein the compound specifically binds to a C-terminal portion of CaMKKβ splice variant 2 polypeptide.

8. The method of claim 7, wherein the C-terminal portion of CaMKKβ splice variant 2 polypeptide is different from the C-terminal portion of splice variant 1 polypeptide.

9. The method of claim 1, wherein the compound specifically binds to a C-terminal portion of CaMKKβ splice variant 7 polypeptide.

10. The method of claim 9, wherein the C-terminal portion of CaMKKβ splice variant 7 polypeptide is different from the C-terminal portion of splice variant 1 polypeptide.

11. The method of claim 1, wherein the compound specifically binds to a portion of CaMKKβ splice variant 2 polypeptide encoded by exon 18.

12. The method of claim 1, wherein the compound specifically binds to a portion of CaMKKβ splice variant 7 polypeptide encoded by exon 18.

* * * * *